(12) United States Patent
Choi et al.

(10) Patent No.: US 7,879,852 B2
(45) Date of Patent: Feb. 1, 2011

(54) MELANOCORTIN RECEPTOR AGONISTS

(75) Inventors: Sung Pil Choi, Daejeon (KR); In Ae Ahn, Daejeon (KR); Sang Hyup Lee, Daejeon (KR); Sang Dae Lee, Daejeon (KR); Mi Sook Shin, Daejeon (KR); Koo Lee, Daejeon (KR); Deog Young Choi, Daejeon (KR); Dong Sup Shim, Daejeon (KR); Hyeon Joo Yim, Daejeon (KR); Min Kyung Yoon, Daejeon (KR); Soo Yong Chung, Daejeon (KR); Jung Ae Lee, Daejeon (KR); Yong Hwa Ha, Daejeon (KR); Young Kwan Kim, Daejeon (KR); Oeuk Park, Daejeon (KR); Hyun Min Lee, Daejeon (KR); Youn Hoa Kim, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 108 days.

(21) Appl. No.: 12/305,935

(22) PCT Filed: Jul. 13, 2007

(86) PCT No.: PCT/KR2007/003429

§ 371 (c)(1),
(2), (4) Date: Dec. 19, 2008

(87) PCT Pub. No.: WO2008/007930

PCT Pub. Date: Jan. 17, 2008

(65) Prior Publication Data

US 2009/0298829 A1  Dec. 3, 2009

(30) Foreign Application Priority Data

Jul. 14, 2006 (KR) .............. 10-2006-0066598
Jul. 14, 2006 (KR) .............. 10-2006-0066610

(51) Int. Cl.
| | |
|---|---|
| A61K 31/401 | (2006.01) |
| A61K 31/4025 | (2006.01) |
| A61K 31/422 | (2006.01) |
| A61K 31/427 | (2006.01) |
| A61K 31/4439 | (2006.01) |
| A61K 31/5377 | (2006.01) |
| C07D 207/14 | (2006.01) |
| C07D 213/72 | (2006.01) |
| C07D 263/48 | (2006.01) |
| C07D 277/54 | (2006.01) |
| C07D 295/28 | (2006.01) |

(52) U.S. Cl. ............ 514/235.5; 514/343; 514/422; 544/141; 546/279.1; 548/518; 548/235; 548/202

(58) Field of Classification Search ............ None
See application file for complete search history.

(56) References Cited

FOREIGN PATENT DOCUMENTS

| WO | WO-00/74679 A1 | 12/2000 |
|---|---|---|
| WO | WO-01/70708 A1 | 9/2001 |
| WO | WO-02/059107 A1 | 8/2002 |
| WO | WO-02/068388 A2 | 9/2002 |
| WO | WO-03/007949 A1 | 1/2003 |
| WO | WO-2005/047251 A1 | 5/2005 |

OTHER PUBLICATIONS

Tian, J. Med. Chem. 49:4745 (2006).*

* cited by examiner

*Primary Examiner*—Yong Chu
*Assistant Examiner*—Michael Barker
(74) *Attorney, Agent, or Firm*—Birch, Stewart, Kolasch & Birch, LLP

(57) ABSTRACT

The present invention relates to a compound of the following formula 1, pharmaceutically acceptable salt and isomer thereof effective as agonist of melanocortin receptor, and an agonistic composition of melanocortin receptor comprising the same as active ingredient.

19 Claims, No Drawings

MELANOCORTIN RECEPTOR AGONISTS

TECHNICAL FIELD

The present invention relates to a compound of the following formula 1, pharmaceutically acceptable salt or isomer thereof effective as an agonist for melanocortin receptor:

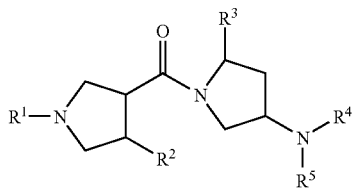

wherein $R^1$, $R^2$, $R^3$, $R^4$ and $R^5$ are as defined below.

The present invention also relates to a process for preparing a compound of the above formula 1.

The present invention also relates to a melanocortin receptor agonistic composition comprising a compound of the above formula 1 as active ingredient, in particular, a composition for the prevention and treatment of obesity, diabetes, inflammation or erectile dysfunction.

BACKGROUND ART

Five subtypes of receptors have been cloned and characterized in the melanocortin family. These G-protein coupled receptors (GPCR) stimulate the cAMP signal transduction pathway in many different tissues, mediating a wide range of physiological functions. Melanocortin 1 receptor (MC1R) is mainly expressed in melanocytes, monocytes, and mast cells, to mediate pigmentation of the hair and skin and to block inflammation. MC2R is expressed in adipocytes and adrenal cells, to mediate steroidogenesis in the adrenal gland. MC3R is present in the brain, hypothalamus, heart, gut, and placenta, and has been associated with energy homeostasis and inflammation. MC4R is uniquely expressed in the brain, and controls feeding behavior, energy homeostasis, and erectile function. MC4R knock-out mice revealed the phenotype of hyperphasia and obesity. MC5R is found in a wide range of tissues and is considered to play a role for the exocrine gland system.

With a plethora of physiological functions of melanocortin receptors, a large number of compounds have been designed and synthesized in search for potent agonists and antagonists. Early examples are synthetic peptides and peptide analogues that have been identified on the basis of endogenous agonist such as MSH. These peptide agonists have been used to characterize the function of these receptors. NDP-MSH is a highly potent and nonselective agonist of MC1R, 3R, 4R and 5R, and has been reported to attenuate food intake and body weight gain in rat models. A cyclic heptapeptide MT-II is an agonist with a similar non-selective profile, and its therapeutic use has been proven in clinical trials for the treatment of erectile dysfunction.

Small molecule agonists for the melanocortin receptors have been reported to have significant activity in drug trials for the treatment of obesity, sexual dysfunction or inflammation. For example, a series of potent and selective MC4R agonists has been identified, one of which demonstrated significant effect for augmenting erectile response in mice (*J. Med. Chem.* 2002, 45, 4849). A number of MC4R agonists have also been identified, which displayed hyphophasic activity and anti-obesity effect in the rat model (*Bioorg. Med. Chem. Lett.* 2005, 15, 171, *Bioorg. Med. Chem. Lett.* 2005, 15, 3430, *Bioorg. Med. Chem. Letu.* 2005, 15, 3501). A highly potent and selective MC1R agonist has been discovered, which showed efficacy in an acute mouse model of inflammation (*J. Med. Chem.* 2003, 46, 1123). In addition, a variety of small molecules as MCR agonists have been described in the patent applications (WO 01/55109, WO 01/70337, WO 01/70708, WO 02/018327, WO 02/059095, WO 02/059107, WO 02/059117, WO 02/059108, WO 02/081443, WO 02/085925, WO 02/15909, WO 02/067869, WO 02/068387, WO 02/068388, WO 03/009847, WO 03/009850, WO 2004/087159, WO 2004/078716, WO 2004/078717, WO 2005/040109, WO 2005/047251, WO 2005/077935, WO 2005/077935, WO 2006/019787, WO 2006/020277, WO 2007/041052, WO 2007/041061, WO 2007/047496, WO 2006/072393, WO 2007/015157, WO 2007/015162).

In view of the unresolved deficiencies of the various pharmaceutical compounds as discussed above, there is continuing need in the art for small molecule MCR agonists and pharmacological compositions that have improved pharmacological profiles. It is, therefore, an object of the present invention to provide novel compounds that are useful for the treatment of obesity, diabetes, sexual dysfunction, and inflammation.

DISCLOSURE OF INVENTION

Technical Solution

The present invention provides a compound of formula 1 having agonistic effect against MCRs, in particular, selective agonistic effect against MC4R, pharmaceutically acceptable salt or isomer thereof.

Another object of the present invention is to provide a process for preparing the compound of formula 1.

Another object of the present invention is to provide a melanocortin receptor agonistic composition comprising the compound of the formula 1, pharmaceutically acceptable salt or isomer thereof as active ingredients, together with a pharmaceutically acceptable carrier.

In particular, the composition according to the present invention has potent effect for the prevention and treatment of obesity, diabetes, inflammation or erectile dysfunction.

MODE FOR THE INVENTION

The present invention relates to a compound of the following formula 1, pharmaceutically acceptable salt or isomer thereof:

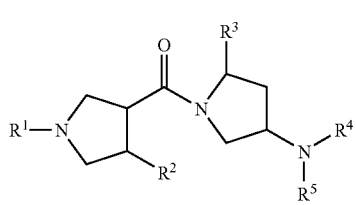

wherein $R^1$ represents hydrogen, amidino, $C_1$-$C_4$-alkylamidino, $C_1$-$C_4$-alkanoylamidino, $C_1$-$C_{10}$-alkyl, $C_3$-$C_7$-cycloalkyl, $C_6$-$C_{10}$-aryl, heterocycle, heteroaryl, $C_1$-$C_6$-alkylcarbonyl, $C_1$-$C_7$-cycloalkylcarbonyl, $C_1$-$C_4$-alkoxycarbonyl, $C_6$-$C_{10}$- aryl-$C_1$-$C_4$-alkoxycarbonyl, —$SO_2$—$C_1$-$C_4$-alkyl, —C(O)—N($R^6$)($R^7$) or —C(S)—N($R^6$)($R^7$), wherein, $R^6$ and $R^7$ each independently represents hydrogen, $C_1$-$C_6$-alkyl or $C_3$-$C_7$-cycloalkyl, alkyl, cycloalkyl, heterocycle, aryl or heteroaryl is unsubstituted or substituted with one or more substituents independently selected from the group consisting of halogen, amino, $C_1$-$C_4$-alkyl, trifluoromethyl, hydroxy, $C_1$-$C_4$-alkoxy and oxo, $R^2$ represents $C_6$-$C_{10}$-aryl or heteroaryl, each of which is unsubstituted or mono- or di-substituted with a substituent selected from the group consisting of halogen, hydroxy, $C_1$-$C_4$-alkyl, $C_1$-$C_4$-alkoxy, cyano and amino, $R^3$ represents hydrogen, cyano, $C_1$-$C_6$-alkyl, $C_3$-$C_7$-cycloalkyl, $C_2$-$C_6$-alkenyl, monocyclic heterocycle, monocyclic heteroaryl, —C(O)$R^8$ or —C(S)—$R^8$, wherein, $R^8$ represents hydroxy, $C_1$-$C_4$-alkyl, $C_1$-$C_4$-alkyloxy or N($R^9$)($R^{10}$), $R^9$ and $R^{10}$ each independently represents hydrogen, $C_1$-$C_6$-alkyl, $C_3$-$C_7$-cycloalkyl, $C_1$-$C_4$-alkyloxy, phenyl or heteroaryl, or $R^9$ and $R^{10}$ may combine each other to form single ring or two rings, or further comprise oxygen atom or sulfur atom, wherein, alkyl, cycloalkyl, heterocycle, phenyl or heteroaryl is unsubstituted or substituted with a substituent selected from the group consisting of methyl, trifluoromethyl, hydroxy, hydroxyimino, amino, acetylamino, ($C_1$-$C_4$-alkyl) amino and ($C_1$-$C_4$-alkyl)($C_1$-$C_4$-alkyl)amino, $R^4$ represents $C_3$-$C_8$-cycloalkyl, $C_6$-$C_{10}$-aryl, heteroaryl or heterocycle, wherein, $C_6$-$C_{10}$-aryl or heteroaryl is unsubstituted or mono- or poly-substituted with a substituent selected from the group consisting of halogen, hydroxy, $C_1$-$C_4$-alkyl, trifluoromethyl, $C_1$-$C_4$-alkoxy and amino, cycloalkyl or heterocycle is unsubstituted or mono- or poly-substituted with a substituent selected from the group consisting of halogen, hydroxy, $C_1$-$C_4$-alkyl, trifluoromethyl, $C_1$-$C_4$-alkoxy and oxo, $R^5$ represents hydrogen, $C_1$-$C_6$-alkyl, —C(O)—$R^{11}$, $C_1$-$C_6$-alkylsulfonyl, $C_6$-$C_{10}$-arylsulfonyl, —$(CH_2)_p$—$C_6$-$C_{10}$-aryl, —$(CH_2)_p$-heteroaryl or —$(CH_2)_p$—$C_3$-$C_8$-cycloalkyl, wherein, p represents 1 or 2, $R^{11}$ represents $C_1$-$C_{10}$-alkyl, $C_2$-$C_6$-alkenyl, $C_3$-$C_8$-cycloalkyl, $C_3$-$C_8$-cycloalkenyl, amino, $C_1$-$C_4$-alkylamino, ($C_1$-$C_4$-alkyl)($C_1$-$C_4$-alkyl)amino, $C_6$-$C_{10}$-aryl, heteroaryl, or heterocycle, wherein, alkyl is unsubstituted or substituted with one or more substituents independently selected from the group consisting of halogen, hydroxy, mercapto, $C_1$-$C_4$-alkoxy, $C_1$-$C_3$-alkylcarboxy, amino, dimethylamino, $C_1$-$C_4$-alkylcarbonylamino, cyano, carbamoyl, dimethylcarbamoyl, hydroxyimino and oxo, aryl or heteroaryl is unsubstituted or mono- or di-substituted with a substituent selected from the group consisting of halogen, hydroxy, $C_1$-$C_4$-alkyl, trifluoromethyl, $C_1$-$C_4$-alkoxy and amino, cycloalkyl, cycloalkenyl or heterocycle is unsubstituted or mono- or di-substituted with a substituent selected from the group consisting of halogen, hydroxy, amino, $C_1$-$C_4$-alkyl, trifluoromethyl, $C_1$-$C_4$-alkoxy and oxo.

In the radical definitions of the compound of formula (1) according to the present invention, the term "alkyl" means straight-chain or branched hydrocarbon radical when used alone or in combination with "alkyloxy". The term "cycloalkyl" represents unsaturated aliphatic ring including cyclohexyl.

The term "aryl" represents 6- to 10-membered aromatic group including phenyl, naphthyl, etc.

The term "heteroaryl" includes 1 to 2 heteroatom(s) selected from the group consisting of nitrogen atom, oxygen atom and sulfur atom, and represents aromatic 3- to 6-membered ring which can be fused with benzo or $C_3$-$C_8$-cycloalkyl. Examples of monocyclic heteroaryl are, but not limited to, thiazole, oxazole, thiophene, furane, pyrrole, imidazole, isoxazole, pyrazole, triazole, thiadiazole, tetrazole, oxadiazole, pyridine, pyridazine, pyrimidine, pyrazine, and similar group thereto. Examples of bicyclic heteroaryl are, but not limited to, indole, benzothiophene, benzofuran, benzimidazole, benzoxazole, benzisoxazole, benzthiazole, benzthiadiazole, benztriazole, quinoline, isoquinoline, purine, furopyridine, and similar group thereto The term "heterocycle" includes 1 to 2 heteroatom(s) from the group consisting of nitrogen atom, oxygen atom, and sulfur atom, and represents 4- to 8-membered ring which can be fused with benzo or $C_3$-$C_8$-cycloalkyl, and which is saturated or has 1 or 2 of double bond. Its examples are, but are not limited to, piperidine, morpholine, thiamorpholine, pyrrolidine, imidazolidine, tetrahydrofuran, piperazine, and similar group thereto.

Preferred compounds among the compounds of formula 1 above are those wherein i) $R^1$ represents hydrogen, amidino, $C_1$-$C_4$-alkylamidino, $C_1$-$C_4$-alkanoylamidino, $C_1$-$C_6$-alkyl, $C_3$-$C_7$-cycloalkyl, phenyl, monocyclic heterocycle, monocyclic heteroaryl, $C_1$-$C_6$-alkylcarbonyl, trifluoroacetyl, $C_1$-$C_4$-alkoxycarbonyl, $C_6$-$C_{10}$-aryl-$C_1$-$C_4$-alkoxycarbonyl, —$SO_2$—$C_1$-$C_4$-alkyl, carbamoyl, $C_1$-$C_6$-alkylcarbamoyl, ($C_1$-$C_6$-alkyl)($C_1$-$C_6$-alkyl)carbamoyl, thiocarbamoyl, $C_1$-$C_6$-alkylthiocarbamoyl or ($C_1$-$C_6$-alkyl)($C_1$-$C_6$-alkyl)thiocarbamoyl, more preferably, $R^1$ represents hydrogen, amidino, methylamidino, ethylamidino, acetylamidino, methyl, ethyl, trifluoroethyl, propyl, isopropyl, butyl, isobutyl, t-butyl, cyclopropyl, cyclobutyl, cyclopentyl, cyclohexyl, phenyl, oxazolynyl, imidazolynyl, thiazolynyl, piperidinyl, tetrahydropyranyl, imidazolyl, oxazolyl, thiazolyl, pyrazolyl, triazolyl, pyridinyl, acetyl, trifluoroacetyl, propionyl, butyryl, isobutyryl, pivaloyl, methoxycarbonyl, ethoxycarbonyl, benzyloxycarbonyl, methylsulfonyl, carbamoyl, methylcarbamoyl, ethylcarbamoyl, trifluoroethylcarbamoyl, propylcarbamoyl, isopropylcarbamoyl, butylcarbamoyl, t-butylcarbamoyl, thiocarbamoyl, methylthiocarbamoyl, ethylthiocarbamoyl or methylethylcarbamoyl, ii) $R^2$ represents phenyl unsubstituted or mono- or di-substituted with a substituent selected from the group consisting of F, Cl and methyl, more preferably, $R^2$ represents phenyl, 4-fluorophenyl, 4-chlorophenyl, 4-methylphenyl or 2,4-difluorophenyl, iii) $R^3$ represents hydrogen, cyano, $C_1$-$C_4$-alkyl, $C_1$-$C_4$-alkenyl, —$CH_2C(CH_3)_2CH_2OH$, oxazolyl, thiazolyl, oxazolynyl, thiazolynyl, carboxy, $C_1$-$C_4$-alkylcarbonyl, $C_1$-$C_4$-alkyloxycarbonyl, carbamoyl, thiocarbamoyl, $C_1$-$C_4$-alkylcarbamoyl, ($C_1$-$C_4$-alkyl)($C_1$-$C_4$-alkyl)carbamoyl, ($C_1$-$C_4$-alkyl)($C_1$-$C_4$-alkyloxy)carbamoyl, $C_1$-$C_4$-alkylthiocarbamoyl or ($C_1$-$C_4$-alkyl)($C_1$-$C_4$-alkyl)thiocarbamoyl, phenylcarbamoyl, heteroarylcarbamoyl, azetidinecarbonyl, pyrrolidinecarbonyl, piperidinecarbonyl or morpholinecarbonyl, wherein, alkyl is unsubstituted or substituted with a substituent selected from the group consisting of hydroxy, hydroxyimino, amino, ($C_1$-$C_4$-alkyl)amino and ($C_1$-$C_4$-alkyl)($C_1$-$C_4$-alkyl)amino, more preferably, $R^3$ represents hydrogen, cyano, methyl, ethyl, propyl, allyl, —CHNOH, hydroxymethyl, —CH($CH_3$)

OH, aminomethyl, dimethylaminomethyl, oxazolyl, thiazolyl, oxazolynyl, thiazolynyl, carboxy, acetyl, propanoyl, methoxycarbonyl, ethoxycarbonyl, isopropoxycarbonyl, t-butoxycarbonyl, carbamoyl, thiocarbamoyl, ethylcarbamoyl, t-butylcarbamoyl, dimethylcarbamoyl, methylethylcarbamoyl, methylmethoxycarbamoyl, dimethylthiocarbamoyl, phenylcarbamoyl, heteroarylcarbamoyl, —C(O)NH(CH$_2$)$_2$NH$_2$, azetidinecarbonyl, pyrrolidinecarbonyl, piperidinecarbonyl or morpholinecarbonyl.

iv) R$^4$ represents C$_4$-C$_7$-cycloalkyl or monocyclic heterocycle unsubstituted or mono- or poly-substituted with a substituent selected from the group consisting of halogen, hydroxy, C$_1$-C$_4$-alkyl, trifluoromethyl, C$_1$-C$_4$-alkoxy and oxo; or phenyl or monocyclic heteroaryl unsubstituted or mono- or di-substituted with a substituent selected from the group consisting of halogen, hydroxy, C$_1$-C$_4$-alkyl, trifluoromethyl, C$_1$-C$_4$-alkoxy and amino, more preferably, R$^4$ represents cyclobutyl, cyclopentyl, cyclohexyl, cycloheptyl, 4-methylcyclohexyl, 4,4-dimethylcyclohexyl, 4,4-difluorocyclohexyl, 4-trifluoromethylcyclohexyl, 3,4-tetramethylcyclopentyl, tetrahydropyranyl, pyridinyl, N-methylpyridinyl or phenyl, wherein, phenyl is unsubstituted or mono- or di-substituted with a substituent selected from the group consisting of F, Cl, methyl and methoxy.

v) R$^5$ represents hydrogen, C$_1$-C$_5$-alkyl, trifluoromethyl, C$_1$-C$_6$-alkylcarbonyl, trifluoroacetyl, acryloyl, methacryloyl, C$_3$-C$_8$-cycloalkylcarbonyl, C$_3$-C$_8$-cycloalkenylcarbonyl, carbamoyl, C$_1$-C$_4$-alkylcarbamoyl, (C$_1$-C$_4$-alkyl)(C$_1$-C$_4$-alkyl)carbamoyl, methanesulfonyl, ethanesulfonyl, propanesulfonyl, benzoyl, hydroxybenzoyl, aminobenzoyl, monocyclic heteroarylcarbonyl, heterocyclecarbonyl, benzyl, —CH$_2$-monocyclic heteroaryl, or —CH$_2$—C$_3$-C$_8$-cycloalkyl, more preferably, R$^5$ represents hydrogen, methyl, ethyl, propyl, isobutyl, hydroxyethyl, —CH$_2$C(CH$_3$)$_2$CH$_2$OH, —CH$_2$C(CH$_3$)$_2$CH(CH$_3$)OH, —CH$_2$CH$_2$NHC(O)CH$_3$, aminoethyl, acetyl, trifluoroacetyl, hydroxyacetyl, methoxyacetyl, ethoxyacetyl, propionyl, ethoxypropionyl, isobutyryl, cyanoisobutyryl, hydroxyisobutyryl, carbamoylisobutyryl, 3,3 dimethylbutanoyl, pivaloyl, fluoropivaloyl, difluoropivaloyl, hydroxypivaloyl, mercaptopivaloyl, dihydroxypivaloyl, methoxypivaloyl, ethoxypivaloyl, aminopivaloyl, dimethylaminopivaloyl, hydroxyiminopivaloyl, acetylisobutyryl, —C(O)C(CH$_3$)$_2$CH(CH$_3$)OH, —C(O)C(CH$_3$)$_2$C(CH$_3$)$_2$OH, acryloyl, methacryloyl, cyclopentanecarbonyl, cyclohexylenecarbonyl, carbamoyl, dimethylcarbamoyl, methanesulfonylcarbonyl, benzoyl, thiopenecarbonyl, furoyl, oxazolecarbonyl, thiazolecarbonyl, imidazolecarbonyl, pyrazolecarbonyl, tetrahydrofuroyl, dihydrofuroyl, tetrahydropyrancarbonyl, morpholinecarbonyl, methanesulfonyl, benzyl, furanmethyl, thiazolemethyl or imidazolemethyl.

The compounds according to the present invention also can form pharmaceutically acceptable salts. These pharmaceutically acceptable salts include acid-addition salts formed by acid which contains pharmaceutically acceptable anion to form non-toxic acid addition salt, for example, inorganic acids such as hydrochloric acid, sulfuric acid, nitric acid, phosphoric acid, hydrobromic acid, hydroiodic acid, and the like; organic carboxylic acid such as tartaric, formic, citric, acetic, trichloroacetic, trifluoroacetic, gluconic, benzoic, lactic, fumaric, maleic, and the like; sulfonic acid such as methanesulfonic acid, benzenesulfonic acid, p-toluenesulfonic acid or naphthalenesulfonic acid, and the like; and more preferably acid-addition salts formed by sulfuric acid, methansulfonic acid or hydrohalic acid, and the like. The compounds of formula 1 according to the present invention can be converted to its salts by conventional method.

Also, the compounds according to the present invention can have asymmetric carbon center, and so can be present as R or S isomeric forms, racemates, diastereomeric mixtures, and individual diasteromers. The present invention encompasses all these isomeric forms and mixtures.

Also, the present invention relates to a process for preparing the compound of formula 1 comprising amide coupling a compound of formula 2 with a compound of formula 3:

(2)

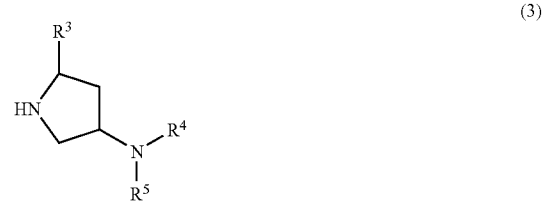

(3)

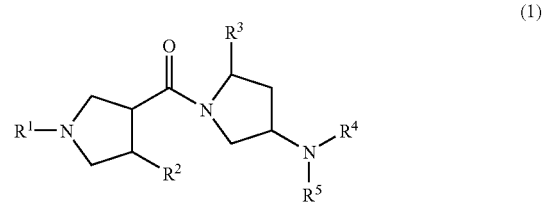

(1)

wherein, R$^1$, R$^2$, R$^3$, R$^4$ and R$^5$ are as defined above.

Also, the present invention relates to a process for preparing the compound of formula 1 comprising amide coupling a compound of formula 2' with a compound of formula 3 to form a compound of formula 1': and deprotecting the compound of formula 1':

(2')

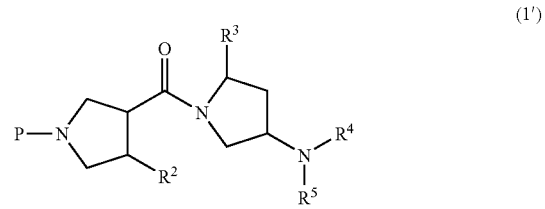

(1')

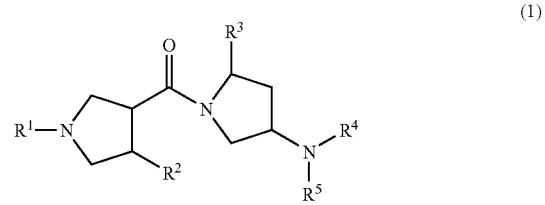

(1)

wherein, R¹ represents hydrogen,
R³, R⁴ and R⁵ are as defined above,
P represent amino protecting groups, preferably t-butoxycarbonyl (Boc), benzyloxycarbonyl (Cbz) or fluorenylmethoxycarbonyl (Fmoc).

Also, the present invention relates to a process for preparing the compound of formula 1 comprising deprotecting the compound of formula 1' in the above process followed by (i) amide coupling with $C_1$-$C_6$-alkyl-$CO_2H$, or (ii) reacting with isocyanate, $C_1$-$C_4$-alkylisocyanate, isothiocyanate or $C_1$-$C_4$-alkylisothiocyanate:

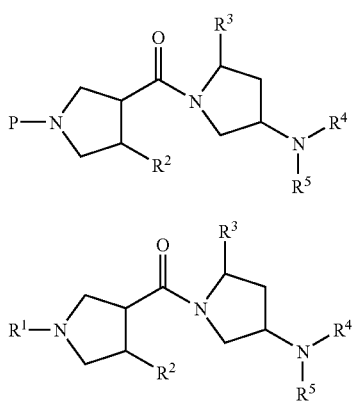

wherein, R¹ represents $C_1$-$C_6$-alkylcarbonyl, carbamoyl, thiocarbamoyl, $C_1$-$C_4$-alkylcarbamoyl or $C_1$-$C_4$-thiocarbamoyl, wherein, alkyl is unsubstituted or substituted with a substituent selected from the group consisting of halogen, amino, $C_1$-$C_4$-alkyl, trifluoromethyl, hydroxy, $C_1$-$C_4$-alkoxy and oxo;

R², R³, R⁴ and R⁵ are as defined above.

It is preferable to carry out each step of the above processes in conventional solvents which do not have significant deleterious effect to the reaction, and particularly preferable to use one or more kinds selected from the group consisting of, but not limited to, dimethylformamide, dimethylacetamide, tetrahydrofuran, methylene chloride, and chloroform.

Deprotection reaction for amino groups can be carried out in the presence of strong acid such as hydrochloric acid (HCl), trifluoroacetic acid (TFA), etc., in the presence of amine base such as triethylamine, diisopropylethylamine (DIPEA), etc., or by hydrogenation. Specific reaction conditions are described in T. W. Green & G. M. Wuts Protective Groups in Organic Synthesis, Chapter 7, pp 309-405.

Known coupling agents usable in coupling reaction are, but are not limited to, carbodiimides such as dicyclohexylcarbodiimide (DCC), 1-(3 dimethylaminopropyl)-3-ethylcarbodiimide (EDC), 1,1'-dicarbonyldiimidazole (CDI), etc. which are used in a mixture with 1-hydroxybenzotriazole (HOBT) or 1-hydroxy-7-azabenzotriazole (HOAT); bis-(2-oxo-3-oxazolidinyl)-phosphinic acid chloride (BOP-Cl), diphenylphosphorylazide (DPPA), N-[dimethylamino-1H-1,2,3-triazol[4,5-b]pyridine-1-ylmethylene]-N-methylmethaneaminum (HATU), etc.

The compounds of formula 1 prepared by the process of the present invention can be converted to its salts by conventional method.

After the above reactions according to the process of the present invention are completed, products can be separated and purified by conventional work-up methods, for example, chromatography, recrystallization, etc.

The compounds of the present invention have potent agonistic effect against melanocortin receptors, and so the present invention provides a melanocortin receptor agonistic composition comprising the compound of formula 1 as active ingredients together with pharmaceutically acceptable carrier. In particular, the composition according to the present invention has potent effect for the prevention and treatment of, but not limited to, diabetes, erectile dysfunction, obesity and inflammation.

When the compounds according to the present invention are administered for clinical purpose, a preferable daily dose would be within the range of 0.01~10 mg/kg body weight as unitary dosage or separated dosage. However, a dosage level specific to individual patients can be varied, depending upon specific compound to be used, weight, sex, health condition, diet, administration time and method of drug, excretion rate, drug mixing, and severity of disease condition.

Any route depending on purpose can administer the compounds according to the present invention. Injection, and oral and nasal administration are preferred, but administration may be made through dermal, intraperitoneal, retroperitoneal, and rectal route.

Injectable preparation, for example, aqueous or oily suspension for sterile injection, can be prepared according to known method by using proper dispersants, wetting agents or suspending agents. Solvents usable for this purpose are water, ringer's solution, and isotonic NaCl solution, and sterilized fixed oil is conventionally used as solvent or suspending media, too. Any non-irritable fixed oil including mono-, diglyceride can be used for this purpose, and aliphatic acid such as oleic acid can be used for injectable preparation.

Solid dosage forms for oral administrations are capsules, tablets, pills, powders and granules, and in particular, capsules and tablets are useful. Tablets and pills are preferable to be prepared as enteric coating. Solid dosage forms can be prepared by mixing the compounds of formula 1 according to the present invention with one or more inert diluents such as sucrose, lactose, starch, etc., and carriers, for example, lubricants like magnesium stearate, disintegrants, binding agents, etc.

Representative compounds of formula 1 according to the present invention include the following listed compounds:

(4S)-1-{[(3S,4R)-tert-butyl-4-(2,4-difluorophenyl)pyrrolidine-3-yl]carbonyl}-4-[(4,4-dimethylcyclohexyl)(2,2-dimethylpropanoyl)amino]-N,N-dimethyl-L-prolinamide (4S)-1-{[(3S,4R)-1-tert-butyl-4-{(4,4-chlorophenyl)pyrrolidine-3-yl]carbonyl}-4-{(4,4-dimethylcyclohexyl)[(2S)-tetrahydrofuran-2-ylcarbonyl]amino}-N,N-ethylmethyl-L-prolineamide (4S)-1-{[(3S,4R)-1-tert-butyl-4-(4-chlorophenyl)pyrrolidine-3-yl]carbonyl}-4-{(4,4-dimethylcyclohexyl)[(2S)-tetrahydrofuran-2-ylcarbonyl]amino}-N-ethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(3-hydroxy-2,2 dimethylpropanoyl)amino]-N-ethyl-N-methyl-L-prolineamide (4S)-1-{[(3S,4R)-1-tert-butyl-4-(4-chlorophenyl)pyrrolidine-3-yl]carbonyl)}-4-[(4,4-difluorocyclohexyl)(2,2-dimethylpropanoyl)amino]-N,N-dimethyl-L-prolineamide (4S)-1-{[(3S,4R)-1-tert-butyl-4-(4-chlorophenyl)pyrrolidine-3-yl]carbonyl)}-4-[(4,4-difluorocyclohexyl)(2,2-dimethylpropanoyl)amino]-N-ethyl-L-prolineamide (4S)-1-{[(3S,4R)-4-(4-chlorophenyl)-1-methylpyrrolidine-3-yl]carbonyl}-4-[(2,2-dimethylpropanoyl)(cis-4-methylcyclohexyl)amino]-L-prolineamide N-[(3S)-1-{[(3S,4R)-1-t-butyl-4-(4-chlorophenyl)pyrrolidine-3-yl]carbonyl}pyrrolidine-3-yl]-N-(4,4-dimethylcyclohexyl)-3-hydroxy-2,2-dimethylpropaneamide N-[(3S)-1-{[(3S,4R)-1-t-butyl-(4-chlorophenyl)pyrrolidine-3-yl]carbonyl}pyrrolidine-3-yl]-N-(4,4-dimethylcyclohexyl)-2,2-dimethylpropaneamide (4S)-1-{[(3S,4R)-1-tert-butyl-(2,4-fluorophenyl)pyrrolidine-3-yl]carbonyl}-4-[(4,4-dimethylcyclohexyl)(methylsulfonyl)amino]-N,N-dimethyl-L-prolineamide N-[(3S)-1-{[(3S,4R)-1-t-butyl-(4-chlorophenyl)pyrrolidine-3-yl]carbonyl}pyrrolidine-3-yl](4,4-dimethylcyclohexyl)amino-2,2-dimethylpropane-1-ol (3S)-1-{[(3S,4R)-1-tert-butyl(4-chlorophenyl)pyrrolidine-3-yl]carbonyl}-N-isobutyl-N-(cis-4-methylcyclohexyl)pyrrolidine-3-amine (4S)-1-{[(3S,4R)-1-tert-butyl-4-(4-chlorophenyl)pyrrolidine-3-yl]carbonyl}-4-[(cis-4,4-methylcyclohexyl)(tetrahydro-2H-pyran-4-ylcarbonyl)amino]-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(3-thienylcarbonyl)amino]-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(isobutyryl)amino]-N,N-dimethyl-L-prolineamide (4S)-1-{[(3S,4R)-1-tert-butyl-4-(4-chlorophenyl)pyrrolidine-3-yl]carbonyl}-[(4,4-dimethylcyclohexyl)(2,2,-dimethylpropanoyl)amino]-N,N-dimethyl-L-prolineamide (4S)-1-{[(3S,4R)-1-tert-butyl-(2,4-difluorophenyl)pyrrolidine-3-yl]carbonyl}-4-[(2,2-dimethylpropanoyl)(cis-4-methylcyclohexyl)amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(2,2,-dimethylpropanoyl)amino]-N-ethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(2,2-dimethylpropanoyl)amino]-N-ethyl-N-methyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(2,2,-dimethylpropanoyl)amino]-N-isopropyl-L-prolineamide N-[(3S,5S)-5-(azetidine-1-ylcarbonyl)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)-2,2-dimethyl propaneamide (4S)-1-{[(3S,4R)-1-tert-butyl-4-(2,4-difluorophenyl)pyrrolidine-3-yl]carbonyl}-4-[(2,5-dihydrofuran-3-ylcarbonyl)(4,4-dimethylcyclohexyl)amino]-N,N-dimethyl-L-prolineamide (4S)-1-{[(3S,4R)-1-tert-butyl-4-(4-chlorophenyl)pyrrolidine-3-yl]carbonyl}-4-[(4,4-dimethylcyclohexyl)(3-hydroxy-2,2,-dimethylpropanoyl)amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)[(2S)-tetrahydrofuran-2-ylcarbonyl]amino]-N,N-dimethyl-L-prolineamide (4S)-1-{[(3S,4R)-tert-butyl-4-(2,4-difluorophenyl)pyrrolidine-3-yl]carbonyl}-4-[(4,4-difluorocyclohexyl)(3-hydroxy-2,2,-dimethylpropanoyl)amino]-N,N-dimethyl-L-prolineamide (4S)-1-{[(3S,4R)-1-tert-butyl(2,4-difluorophenyl)pyrrolidine-3-yl]carbonyl}-4-[(4,4-dimethylcyclohexyl)(3-hydroxy-2,2,-dimethylpropanoyl)amino]-N-ethyl-N-methyl-L-prolineamide (4S)-1-{[(3S,4R)-1-tert-butyl(4-chlorophenyl)pyrrolidine-3-yl]carbonyl}-4-[(4,4-dimethylcyclohexyl)(3-furoyl)amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(3-furoyl)amino]-N-ethyl-N-methyl-L-prolineamide N-[(3S)-1-{[(3S,4R)-1-tert-butyl-4-(4-chlorophenyl)pyrrolidine-3-yl]carbonyl}pyrrolidine-3-yl]-N-[(4,4-difluorocyclohexyl)(3-hydroxy-2,2-dimethylpropanoyl)amino]-N-ethyl-N-methyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)[(2S)tetrahydrofuran-2-ylcarbonyl]amino]-N-ethyl-N-methyl-L-prolineamide (4S)-1-{[(3S,4R)-1-tert-butyl(4-chlorophenyl)pyrrolidine-3-yl]carbonyl}-4-[(4,4-difluorocyclohexyl)(2,2,-dimethylpropanoyl)amino]-N-ethyl-N-methyl-L-prolineamide (4S)-1-([(3S,4R)-1-tert-butyl-4-(4-chlorophenyl)pyrrolidine-3-yl]carbonyl)-N-ethyl-4-[(3-hydroxy-2,2,-dimethylpropanoyl)-cis-4-methylcyclohexylamino]-N-methyl-L-prolineamide N-[(3S,5S)-1-{[(3S,4R)-1-tert-butyl-4-(4-chlorophenyl)pyrrolidine-3-yl]carbonyl}-5-{([ethyl(methyl)amino]carbonyl}pyrrolidine-3-yl]-N-(4,4-dimethylcyclohexyl)-2,2-dimethylpropaneamide N-[(3S,5S)-1-{[(3S,4R)-1-tert-butyl-4-(4-chlorophenyl)pyrrolidine-3-yl]carbonyl}-5-(pyrrolidine-1-ylcarbonyl)pyrrolidine-3-yl]-N-(4,4-difluorocyclohexyl)-2,2-dimethylpropaneamide (4S)-1-{[(3S,4R)-1-tert-butyl-4-(4-chlorophenyl)pyrrolidine-3-yl]carbonyl}-[-N-ethyl-N-methyl-4-{spiro[2,5]oct-6-yl](2S)-tetrahydrofuran-2-ylcarbonyl]amino}-L-prolineamide N-[(3S,5S)-1-{[(3S,4R)-1-tert-butyl-4-(4-chlorophenyl)pyrrolidine-3-yl]carbonyl}-5-(pyrrolidine-4-ylcarbonyl)pyrrolidine-3-yl]-N-(4,4-dimethylcyclohexyl)acetamide (4S)-1-([(3S,4R)-1-tert-butyl-4-(4-chlorophenyl)pyrrolidine-3-yl]carbonyl)-[(4,4-dimethylcyclohexyl)[(2R)-tetrahydrofuran-2-ylcarbonyl]amino]-N-ethyl-N-methyl-L-prolineamide (4S)-1-{[(3S,4R)-1-tert-butyl-4-(4-chlorophenyl)pyrrolidine-3-yl]carbonyl}-4-[(4,4-dimethylcyclohexyl)(3-hydroxy-2,2-dimethylpropanoyl)amino]-N-ethyl-L-prolineamide (4S)-1-{[(3S,4R)-1-tert-butyl-4-(4-chlorophenyl)pyrrolidine-3-yl]carbonyl})[(4,4-dimethylcyclohexyl)(2,2,-dimethylpropanoyl)amino]-N-phenyl-L-prolineamide (2S)—N-[(3S)-1-{[(3S,4R)-1-tert-butyl(4-chlorophenyl)pyrrolidine-3-yl]carbonyl}pyrrolidine-3-yl]-N-(4,4-dimethylcyclohexyl)tetrahydrofuran-2-carboxamide N-[(3S)-1-{[(3S,4R)-1-tert-butyl-4-(4-chlorophenyl)pyrrolidine-3-yl]carbonyl}pyrrolidine-3-yl]-2-methyl-N-[cis-4-(trifluoromethyl)cyclohexyl]propaneamide (2S)—N-[(3S)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)tetrahydrofuran-2-carboxamide N-[(3S)-1-{[(3S,4R)-1-tert-butyl(2,4-difluorophenyl)pyrrolidine-3-yl]carbonyl}pyrrolidine-3-yl]-N-(4,4-dimethylcyclohexyl)tetrahydrofuran-3-carboxamide N-[(3S)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)-3-hydroxy-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-cycloheptyl-3-hydroxy-2,2-dimethylpropaneamide (4S)-1-{[(3S,4R)-1-tert-butyl-4-(4-chlorophenyl)pyrrolidine-3-yl]carbonyl}-4-{(4,4-dimethylcyclohexyl)[(methylsulfonyl)amino}-N-ethyl-N-methyl-L-prolineamide (3S)-1-{[(3S,4R)-1-tert-butyl(4-chlorophenyl)pyrrolidine-3-yl]carbonyl}-N-(4,4-dimethylcyclohexyl)-N-3-furylpyrrolidine-3-amine N-[(3S,5S)-1-{[(3S,4R)-1-tert-butyl(4-chlorophenyl)pyrrolidine-3-yl]carbonyl}-5-(4,5-dihydro-1,3-oxazole-2-yl)pyrrolidine-3-yl]-N-(4,4-dimethylcyclohexyl)-2,2-dimethylpropaneamide N-{(3S,5S)-1-{[(3S,4R)-1-tert-butyl-(4-chlorophenyl)pyrrolidine-3-yl]carbonyl}-5-[(dimethylamino)carbonothionyl]pyrrolidine-3-yl}-N-(4,4-dimethylcyclohexyl)-2-methylpropaneamide N-[(3S,5R)-1-{[(3S,4R)-1-tert-butyl-4-(2,4-difluorophenyl)pyrrolidine-3-yl]carbonyl}-5-(1,3-thiazole-2-yl)pyrrolidine-3-yl]-N-(4,4-dimethylcyclohexyl)-2,2-dimethylpropaneamide N-[(3S,5S)-1-{[(3S,4R)-1-tert-butyl-4-(4-chlorophenyl)pyrrolidine-3-yl]carbonyl}-5-(hydroxymethyl)pyrrolidine-3-yl]-N-(4,4-ethylcyclohexyl)-2,2-dimethylpropaneamide N-[(3S,5S)-1-{[(3S,4R)-1-tert-butyl(4-chlorophenyl)pyrrolidine-3-yl]carbonyl}-5-methylpyrrolidine-3-yl]-N-(4,4-dimethylcyclohexyl)-2,2-dimethylpropaneamide N-{(3S,5S)-1-{[(3S,4R)-1-tert-butyl(2,-difluorophenyl)pyrrolidine-3-yl]carbonyl}-5-[(E)-(hydroxyimino)methyl]pyrrolidine-3-yl}-N-(4,4-dimethylcyclohexyl)-2,2-dimethylpropaneamide N-[(3S,5S)-5-(aminoethyl)-1-{[(3S,4R)-1-tert-butyl(2,4-difluorophenyl)pyrrolidine-3-yl]carbonyl}pyrrolidine-3-yl]-N-(4,4-dimethylcyclohexyl)-2,2-dimethylpropaneamide N-[(3S,5S)-5-[(acetylamino)methyl]-1-{[(3S,4R)-1-tert-butyl-4-(2,4-dichlorophenyl)pyrrolidine-3-yl]carbonyl}pyrrolidine-3-yl]-N-(4,4-dimethylcyclohexyl)-2,2-dimethylpropaneamide N-[(3S,5S)-1-{[(3S,4R)-1-tert-butyl(2,4-dichlorophenyl)pyrrolidine-3-yl]carbonyl}-5-[(dimethylamino)methyl]pyrrolidine-3-yl]-N-(4,4-dimethylcyclohexyl)-2,2-dimethylpropaneamide N-[(3S,5S)-1-{[(3S,4R)-1-tert-butyl-4-(2,4-difluorophenyl)pyrrolidine-3-yl]carbonyl}-5-cyanopyrrolidine-3-yl]-2,2-dimethyl-N-(cis-4-methylcyclohexyl)propaneamide N-[(3S,5R)-5-acetyl-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethylpropaneamide N-[(3S)-1-{[(3S,4R)-1-tert-butyl-4-(4-chlorophenyl)pyrrolidine-3-yl]carbonyl}-5-(1-hydroxymethyl)pyrrolidine-3-yl]-N-(4,4-dimethylcyclohexyl)-2,2-dimethylpropaneamide (4S)-4-[acetyl(4,4-dimethylcyclohexyl)amino]-N-(2-aminoethyl)-1-{[(3S,4R)-1-tert-butyl-4-(2,4-difluorophenyl)pyrrolidine-3-yl]carbonyl}-L-prolineamide methyl(4S)-1-{[(3S,4R)-1-tert-butyl(4-chlorophenyl)pyrrolidine-3-yl]carbonyl}-4-[(4,4-dimethylcyclohexyl)(2,2-dimethylpropanoyl)amino]-L-prolinate (4S)-1-{[(3S,4R)-1-tert-butyl-4-(4-chlorophenyl)pyrrolidine-3-yl]carbonyl}-4-[(4,4-dimethylcyclohexyl)(2,2-dimethylpropanoyl)amino]-L-proline N-[(3S,5R)-5-(aminocarbothionyl-1-{[(3S,4R)-1-tert-butyl(2,4-difluorophenyl)pyrrolidine-3-yl]carbonyl}pyrrolidine-3-yl]-N-(4,4-dimethylcyclohexyl)-2,2-dimethylpropaneamide N-{(3S,5R)-1-{[(3S,4R)-1-tert-butyl-4-(2,4-difluorophenyl)pyrrolidine-3-yl]carbonyl}-5-[(dimethylamino)carbonothionyl]pyrrolidine-3-yl}-N-(4,4-dimethylcyclohexyl)-2,2-dimethylpropaneamide N-[(3S,5R)-1-{[(3S,4R)-1-tert-butyl-4-(2,4-difluorophenyl)pyrrolidine-3-yl]carbonyl}-5-propionylpyrrolidine-3-yl]-N-(4,4-dimethylcyclohexyl)-2,2-dimethylpropaneamide N-[(3S,5S)-1-{[(3S,4R)-1-tert-butyl-4-(4-chlorophenyl)pyrrolidine-3-yl]carbonyl}-5-propionylpyrrolidine-3-yl]-N-(4,4-difluorocyclohexyl)-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethylmalonamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-methoxy-2,2-dimethylpropaneamide (3E)-N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-(hydroxyimino)-2,2-dimethylpropaneamide N-[(3S)-1-{[(3S,4R)-1-tert-butyl(4-chlorophenyl)pyrrolidine-3-yl]carbonyl}pyrrolidine-3-yl]-N-(4,4-dimethylcyclohexyl)-3-hydroxy-2,2-dimethylbutaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethyl-3-oxobutaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxy-2,2,3-trimethylbutaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-fluoro-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3,3-difluoro-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-[(4,4-difluorocyclohexyl)(3-methoxy-2,2-dimethylpropanoyl)amino]-N-ethyl-N-methyl-L-prolineamide (4S)-4-[(3-amino-2,2-dimethylpropanoyl)(4,4-dimethylcyclohexyl)amino]-1-{[(3S,4R)-1-tert-butyl-4-(2,4-difluorophenyl)pyrrolidine-3-yl]carbonyl}-N,N-dimethyl-L-prolineamide (4S)-1-{[(3S,4R)-1-tert-butyl-4-(4-chlorophenyl)pyrrolidine-3-yl]carbonyl})-4-{[3-(dimethylamino)-2,2-dimethylpropanoyl](4,4-dimethylcyclohexyl)amino}-N,N-dimethyl-L-prolineamide N-{(3S,5S)-1-{[(3S,4R)-1-tert-butyl-4-(4-chlorophenyl)pyrrolidine-3-yl]carbonyl}-5-[(dimethylamino)carbonyl]pyrrolidine-3-yl}-N-(4,4-dimethylcyclohexyl)-2,2-diethyl malonamide S-(3-{[(3S,5S)-1-{[(3S,4R)-1-tert-butyl-4-(2,4-difluorophenyl)pyrrolidine-3-yl]carbonyl}-5-{[ethyl(methyl)amino]carbonyl}pyrrolidine-3-yl](4,4-ethylcyclohexyl)amino}-2,2-dimethyl-3-oxopropyl)ethanethioate (4S)-1-{[(3S,4R)-1-tert-butyl(2,4-difluorophenyl)pyrrolidine-3-yl]carbonyl}-4-[(4,4-dimethylcyclohexyl)(3-mercapto-2,2-dimethylpropanoyl)amino]-N-ethyl-N-methyl-L-prolineamide (4S)-1-{[(3S,4R)-1-tert-butyl-4-(4-chlorophenyl)pyrrolidine-3-yl]carbonyl}-4-[(4,4-difluorocyclohexyl)(3-methoxy-2,2,-dimethylpropanoyl)amino]-N,N-dimethyl-L-proline amide (4S)-1-{[(3S,4R)-1-tert-butyl-4-(4-chlorophenyl)pyrrolidine-3-yl]carbonyl}-4-[(4,4-difluorocyclohexyl)(3-ethoxy-2,2,-dimethylpropanoyl)amino]-N-ethyl-N-methyl-L-prolineamide (4S)-1-{[(3S,4R)-1-tert-butyl-4-(4-chlorophenyl)pyrrolidine-3-yl]carbonyl}-4-[(2,4-difluorophenyl)(2,2-dimethylpropanoyl)amino]-N,N-dimethyl-L-prolineamide (4S)-1-{[(3S,4R)-1-tert-butyl-(4-chlorophenyl)pyrrolidine-3-yl]carbonyl}-4-[(2,2,-dimethylpropanoyl)(4-methoxyphenyl)amino]-N,N-dimethyl-L-prolineamide (4S)-1-{[(3S,4R)-1-tert-butyl-4-(4-chlorophenyl)pyrrolidine-3-yl]carbonyl}-4 {(2,2,-dimethylpropanoyl)[4-(trifluoromethyl)phenyl]amino}-N,N-dimethyl-L-prolineamide (4S)-1-{[(3S,4R)-tert-butyl(4-chlorophenyl)pyrrolidine-3-yl]carbonyl}-4-[(2,2,-dimethylpropanoyl)(4-methylphenyl)amino]-N,N-diethyl-L-prolineamide (4S)-1-{[(3S,4R)-1-tert-butyl(4-chlorophenyl)pyrrolidine-3-yl]carbonyl})-4-{(2,4-difluorophenyl)[(2S)-tetrahydrofuran-2-ylcarbonyl]amino}-N,N-dimethyl-L-prolineamide (4S)-1-{[(3S,4R)-4-(4-chlorophenyl)pyrrolidine-3-yl]carbonyl}-4-[(4,4-dimethylcyclohexyl)(2,2-dimethylpropanoyl)amino]-N,N-diethyl-L-prolineamide (2S)—N-[(3S)-1-{[(3S,4R)-4-(4-chlorophenyl)pyrrolidine-3-yl]carbonyl}pyrrolidine-3-yl]-N-(4,4-dimethylcyclohexyl)tetrahydrofuran-2-carboxamide N-[(3S)-1-{[(3S,4R)-4-(4-chlorophenyl)pyrrolidine-3-yl]carbonyl}pyrrolidine-3-yl]-N-(cis-4-methylcyclohexyl)-3-furamide N-[(3S)-1-{[(3S,4R)-4-(4-chlorophenyl)pyrrolidine-3-yl]carbonyl}pyrrolidine-3-yl]-N-(cis-4-methylcyclohexyl)-2,2-dihydrofuran-3-carboxamide (4S)—N-1-{[(3S,4R)-4-(4-chlorophenyl)pyrrolidine-3-yl]carbonyl}-4-[(2,2,-dimethylpropanoyl)(cis-4-methylcyclohexyl)amino]-D-prolineamide N-[(3S)-1-{[(3S,4R)-4-(4-chlorophenyl)pyrrolidine-3-yl]carbonyl}-5-(1-hydroxymethyl)pyrrolidine-3-yl]-N-(4,4-diethylcyclohexyl)-2,2-dimethylpropaneamide (4S)-1-{[(3S,4R)-1-(aminocarbonyl)₄-(4-chlorophenyl)pyrrolidine-3-yl]carbonyl}-4-[(4,4-diethylcyclohexyl)(2,2-dimethylpropanoyl)amino]-N,N-dimethyl-L-prolineamide (3R,4S)-3-(4-chlorophenyl)-4-({(3S)-3-[(4,4-dimethylcyclohexyl)(3-hydroxy-2,2-dimethylpropanoyl)amino]pyrrolidine-1-yl}carbonyl)pyrrolidine-1-carboxamide (3R,4S)-3-(4-chlorophenyl)-4-({(3S)-3-[(4,4-dimethylcyclohexyl)(2,2-dimethylpropanoyl)amino]pyrrolidine-1-yl}carbonyl)pyrrolidine-1-carboxamide (4S)-1-({[(3S,4R)-4-(4-chlorophenyl)-1-(ethylamino)carbonyl]pyrrolidine-3-yl}carbonyl)-4-[(4,4-dimethylcyclohexyl)(2,2-dimethylpropanoyl)amino]-N,N-dimethyl-L-prolineamide N-[(3S)-1-{[(3S,4R)-4-(4-chlorophenyl)-1-[(ethylamino)carbonothionyl]pyrrolidine-3-yl]carbonyl}pyrrolidine-3-yl]-N-(4,4-difluorocyclohexyl)-3-hydroxy-2,2-dimethylpropaneamide (3R,4S)-3-(4-chlorophenyl)-4-({(3S)-3-[(4,4-dimethylcyclohexyl)(3-hydroxy-2,2-dimethylpropanoyl)amino]pyrrolidine-1-yl}carbonyl) N-ethylpyrrolidine-1-carboxamide (3R,4S-3-(4-chlorophenyl)-4-({(3S)-3-[(4,4-dimethylcyclohexyl)(2,2-dimethylpropanoyl)amino]pyrrolidine-1-yl}carbonyl)-N-ethylpyrrolidine-1-carboxamide (3R,4S)-3-(4-chlorophenyl-4-({(3S)-3-[(2,4-difluorophenyl)(2,2-dimethylpropanoyl)amino]pyrrolidine-1-yl}carbonyl)-N-ethylpyrrolidine-1-carboxamide (3R,4S)-3-(4-chlorophenyl)-N-ethyl-4-({(3S)-3-[isobutyryl(cis-4-methylcyclohexyl)amino]pyrrolidine-1-yl}carbonyl)-N-methylpyrrolidine-1-carboxamide (4S)-1-({[(3S,4R)-1-acetyl(4-chlorophenyl)pyrrolidine-3-yl]carbonyl})-4-[(4,4-dimethylcyclohexyl)(2,2-dimethylpropanoyl)amino]-N,N-dimethyl-L-propaneamide N-[(3S)-1-{[(3S,4R)(4-chlorophenyl)-1-isobutyrylpyrrolidine-3-yl]carbonyl}pyrrolidine-3-yl]-N-(4,4-dimethylcyclohexyl)-2,2-dimethylpropaneamide (4S)-1-{[(3S,4R)-4-(4-chlorophenyl)-1-isobutyrylpyrrolidine-3-yl]carbonyl}-4-[(4,4-dimethylcyclohexyl)(2,2-dimethylpropanoyl)amino]-L-prolineamide (4S)-1-({[(3S,4R)-4-(2,4-chlorophenyl)-1-cyclopropylpyrrolidine-3-yl]carbonyl}-4-[(4,4-dimethylcyclohexyl)(2,2-dimethylpropanoyl)amino]-N,N-dimethyl-L-prolineamide (4S)-1-{[(3S,4R)-4-(4-chlorophenyl)-1-(tetrahydro-2H-pyranyl)pyrrolidine-3-yl]carbonyl}-4-{(4,4-dimethylcyclohexyl)[(2S)-tetrahydrofuran-2-ylcarbonyl]amino}-N-ethyl-N-methyl-L-prolineamide N-[(3S)-1-{[(3S,4R)-4-(4-chlorophenyl)-1-(2,2,2-trifluoroethyl)pyrrolidine-3-yl]carbonyl}pyrrolidine-3-yl]-N-(4,4-dimethylcyclohexyl)-2,2-dimethylpropaneamide (4S)-1-{[(3S,4R)(2,4-difluorophenyl)-1-isobutyrylpyrrolidine-3-yl]carbonyl)}[(4,4-dimethylcyclohexyl)(3-hydroxy-2,2-dimethylpropanoyl)amino]-N,N-dimethyl-L-prolineamide (4S)-1-{[(3S,4R)-4-(4-chlorophenyl)-1-cyclobutylpyrrolidine-3-yl]carbonyl}-4-[(4,4-dimethylcyclohexyl)(3-hydroxy-2,2-dimethylpropanoyl)amino]-N,N-dimethyl-L-prolineamide (4S)-1-{[(3S,4R)-1-cyclopentyl-4-(2,4-difluorophenyl)pyrrolidine-3-yl]carbonyl}-4-[(4,4-ethylcyclohexyl)(2,2-dimethylpropanoyl)amino]-N,N-dimethyl-L-prolineamide N-{(3S,5S)-1-{[(3S,4R)-4-(2,4-difluorophenyl)-1-isobutyrylpyrrolidine-3-yl]carbonyl}-5-[(dimethylamino)carbonothio]pyrrolidine-3-yl}-N-(4,4-dimethylcyclohexyl)-2,2-dimethylpropaneamide N-[(3S)-1-{[(3S,4R)-4-(4-chlorophenyl)-1-(methylsulfonyl)pyrrolidine-3-yl]carbonyl}pyrrolidine-3-yl]-2-methyl-N-(cis-4-methylcyclohexyl)propaneamide (3R,4S)-3-(4-chlorophenyl)-4-({(3S)-3-[cis-8-methylcyclohexyl)(2-methylpropanoyl)amino]pyrrolidine-1-yl}carbonyl)-N-(2,2,2-trifluoroethyl)pyrrolidine-1-carboxamide (3R,4S)-3-(4-chlorophenyl)-4-({(3S)-3-[(4,4-dimethylcyclohexyl)(2,2-dimethylpropanoyl)amino]pyrrolidine-1-yl}carbonyl)-N-(2,2,2-trifluoromethyl)pyrrolidine-1-carboxamide methyl(3R,4S)-3-(4-chlorophenyl)-4-({(3S)-3-[(4,4-methylcyclohexyl)(3-hydroxy-2,2-dimethylpropanoyl)amino]pyrrolidine-1-yl}carbonyl)pyrrolidine-1-carboxylate N-[(3S)-1-{[(3S,4R)-1-[amino(imino)methyl]-4-(4-chlorophenyl)pyrrolidine-3-yl]carbonyl}pyrrolidine-3-yl]-2-methyl-N-(cis-4-methylcyclohexyl)propaneamide N-[(3S)-1-({(3S,4R)-4-(4-chlorophenyl)-1-[(ethylamino)(imino)methyl]pyrrolidine-3-yl}carbonyl)pyrrolidine-3-yl]2-methyl-N-(cis-4-methylcyclohexyl)propaneamide N-[(3S)-1-{[(3S,4R)-1-[(acetylamino)(imino)methyl]-4-(4-chlorophenyl)pyrrolidine-3-yl]carbonyl}pyrrolidine-3-yl]-2-methyl-N-(cis-4-methylcyclohexyl)propaneamide N-[(3S)-1-{[(3S,4R) (4-chlorophenyl)-1-phenylpyrrolidine-3-yl]carbonyl}pyrrolidine-3-yl]-N-(4,4-dimethylcyclohexyl)-propaneamide N-[(3S)-1-{[(3S,4R)-4-(4-chlorophenyl)-1-pyridine-2-ylpyrrolidine-3-yl]carbonyl}pyrrolidine-3-yl]-2,2-dimethyl-N-(cis-4-methylcyclohexyl)propaneamide N-[(3S)-1-{[(3S,4R)-4-(4-chlorophenyl)-1-(4,5-dihydro-1H-imidazole-2-yl)pyrrolidine-3-yl]carbonyl}pyrrolidine-3-yl]-N-(4,4-dimethylcyclohexyl)-3-hydroxy-2,2-dimethylpropaneamide N-[(3S)-1-{[(3S,4R)-4-(4-chlorophenyl)-1-(4,5-dihydro-1H-imidazole-2-yl)pyrrolidine-3-yl]carbonyl}pyrrolidine-3-yl]-N-(4,4-dimethylcyclohexyl)-3-hydroxy-2,2-dimethylpropaneamide.

The present invention is described in more detail by the exemplified compounds in the following Examples, but the scopes of the invention are not be construed to be limited thereby in any manner.

Abbreviations used in the following Preparation Examples and Examples are as follows:

| Ac | acetyl |
|---|---|
| AcOH | acetic acid |
| Bn | benzyl |
| n-Bu | n-butyl |
| t-Bu | t-butyl |
| BOP | (benzotriazol-1-yl-oxy)tris(dimethylamino-)-phosphonium hexafluorophosphate |
| Bu | butyl |
| CBZ(Cbz) | benzyloxycarbonyl |
| BOC(Boc) | t-butoxycarbonyl |
| CDI | N,N'-carbonyldiimidazole |
| c-Hex | cyclohexyl |
| c-Bu | cyclobutyl |
| c-Pen | cyclopentyl |
| c-Pr | cyclopropyl |
| DAST | diethylaminosulfur trifluoride |
| DCC | dicyclohexylcarbodiimide |
| DCE | dichloroethane |
| DCM | dichloromethane |
| diMe | dimethyl |
| diF | difluoro |
| DIPEA | diisopropylethylamine |
| DMAP | 4-dismethylaminopyridine |
| DMF | N,N-dimethylformamide |
| DMSO | dimethylsulfoxide |
| DPPA | diphenylphosphorylazide |
| EDC | 1-(3-dimethylaminopropyl)-3-ethylcarbodiimide hydrochloride |
| EDTA | ethylenediaminetetraacetic acid |
| Et | ethyl |
| EtOAc | ethylacetate |
| $Et_2O$ | diethylether |
| Fmoc | 9-fluorenylmethoxycarbonyl |
| Hex | normal hexane |
| HATU | N-[(dimethylarnino)(3H-1,2,3-triazolo[4,5-b]pyridine-3-yloxy) methylene]-N-methylenemethaneammonium hexafluorophosphate |
| HOAT | 1-hydroxy-7-azabenzotriazole |
| HOBT | hydroxybenzotriazole |
| HBTU | 2-(1H-benzotriazole-1-y1)-1,1,3,3-tetramethyluronium hexafluoro phosphate |
| i-Pr | isopropyl |
| i-Bu | isobutyl |
| KOCN | potassium cyanate |
| $K_2CO_3$ | potassium carbonate |
| $LiBH_4$ | lithium borohydride |
| Me | methyl |
| MeOH | methanol |
| MTBE | methyl t-butyl ether |
| $MgSO_4$ | magnesium sulfate |
| $NaBH_4$ | sodium borohydride |
| $NaBH(OAc)_3$ | sodium triacetoxyborohydride |
| NaOtBu | sodium t-butoxide |
| NaOH | sodium hydroxide |
| $NaN_3$ | sodium azide |
| NaH | sodium hydride |
| Pyr | pyridine |
| Ph | phenyl |
| Pr | propyl |
| TBAF | tetrabutylammonium fluoride |
| TEA | triethylamine |
| TFA | trifluoroacetic acid |
| TFAA | trifluoroacetic anhydride |
| THF | tetrahydrofuran |
| t-Bu | t-butyl |

The compounds of the present invention can be prepared according to the following procedures (Schemes A, B, C, D, E, etc.).

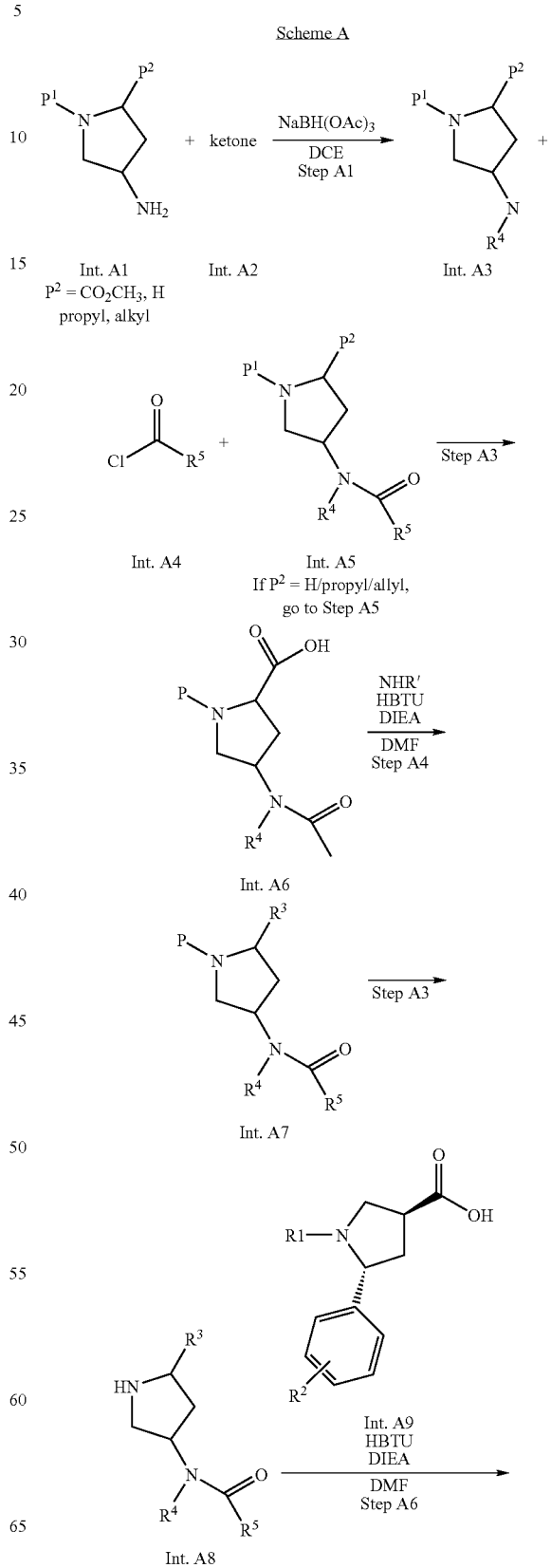

-continued

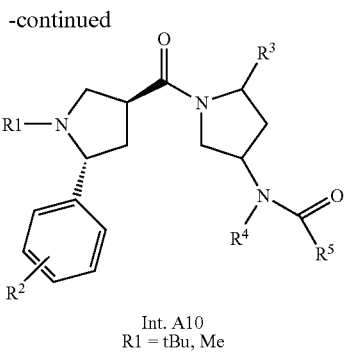

Int. A10
R1 = tBu, Me

Int. = intermediate

The Intermediate A1 compounds can be prepared as follows:

PREPARATION EXAMPLE A1-1

Methyl (2S,4S)-1-Boc-4-aminopyrrolidine-2-carboxylate

Step A: (4R)-1-Boc-4-hydroxy-L-proline

To a solution of (4R)-hydroxy-L-proline (5.08 g, 38.77 mmol) in 1N NaOH (40 ml) and 1,4-dioxane (40 ml) was added dropwise di-t-butyl dicarbonate (9.3 g, 42.6 mmol) at 0° C. The reaction mixture was stirred at rt for 8 h, concentrated in vacuo, acidified with 1N HCl, and extracted with EtOAc. The organic extracts were washed with brine, dried over $MgSO_4$, filtered, and concentrated in vacuo to give the title compound (8.8 g, 99%).
MS[M+H]=232 (M+1)

Step B: methyl (2S,4R)-1-Boc-4-hydroxypyrrolidine-2-carboxylate

To a solution of (4R)-1-Boc-4-hydroxy-L-proline (8 g, 34.63 mmol) prepared in Step A in DMF was added $K_2CO_3$ (14 g, 101 mmol) and methyliodide (2.6 ml, 51.9 mmol). The reaction mixture was stirred at rt for 5 h, concentrated in vacuo, and extracted with EtOAc. The organic extracts were washed with water and brine, dried over $MgSO_4$, filtered, and concentrated in vacuo to give the title compound (8.0 g, 95%).
MS[M+H]=246(M+1)

Step C: methyl (2S,4R)-1-Boc-4-[(methylsulfonyl)oxy]pyrrolidine-2-carboxylate

To a solution of methyl (2S,4R)-1-Bochydroxypyrrolidine-2-carboxylate (8 g, 32.65 mmol) prepared in Step B in DCM was added dropwise TEA (11.99 ml, 81.56 mmol) and methanesulfonyl chloride (3.77 ml, 48.9 mmol) at m° C. After the reaction mixture was stirred at rt for 3 h, the organic extracts were washed with a saturated $NaHCO_3$ aqueous solution, 1N HCl and brine, dried over $MgSO_4$, filtered, and concentrated in vacuo to give the title compound (9.4 g, 90%).
MS[M+H]=324(M+1)

Step D: methyl (2S,4S)-1-Boc-4-azidopyrrolidine-2-carboxylate

To a solution of methyl (2S,4R)-1-Boc-4-[(methylsulfonyl)oxy]pyrrolidine-2-carboxylate (9 g, 27.86 mmol) prepared in Step C in DMF was added $NaN_3$ (2.7 g, 41.79 mmol), and stirred at 90° C. for 10 h. The reaction mixture was concentrated in vacuo, extracted with EtOAc. The organic extracts were washed with brine, dried over $MgSO_4$, filtered, and concentrated in vacuo. The residue was purified by column chromatography (eluent, EtOAc/Hex=1/4) to give the title compound (6 g, 80%).
MS[M+H]=271(M+1)

Step E: methyl (4S,4S)-1-Boc-4-aminopyrrolidine-2-carboxylate

To a solution of methyl (2S,4S)-1-Boc-4-azidopyrrolidine-2-carboxylate (6 g, 22.22 mmol) prepared in Step D in dioxane (10 mL) was added Pd/C (800 mg). The reaction mixture was stirred under hydrogen condition for 24 h, filtered through Celite, and the filtrate was concentrated in vacuo to give the title compound as an oil (5.34 g, 98.5%).
MS[M+H]=245(M+1)

PREPARATION EXAMPLE A1-2

Methyl (2S,4R)-1-Boc-4-aminopyrrolidine-2-carboxylate

The title compound was prepared according to the procedure described in Preparation Example A1-1 using (4S)-hydroxy-1-proline.
MS[M+H]=245(M+1)

PREPARATION EXAMPLE A1-3

Methyl (2R,4S)-1-Boc-4-aminopyrrolidine-2-carboxylate

The title compound was prepared according to the procedure described in Preparation Example A1-1 using (4R)hydroxy-D-proline.
MS[M+H]=245(M+1)

PREPARATION EXAMPLE A1-4

(2S,4S)-1-Boc-2-allyl-4-aminopyrrolidine

Step A: (2S,4R)-1-Boc-2-allyl-4-hydroxypyrrolidine (3R)-1-BOC-3-hydroxypyrrolidine (1 g, 5.34 mmol) was dissolved in diethylether (50 ml), and filled with nitrogen. The reaction mixture was cooled to −78° C., N,N,N,N'-tetramethylethylenediamine (620 mg, 5.34 mmol) was added, and sec-butyllithium (1.4M cyclohexane solution 4.45 ml, 6.23 mmol) was slowly added. After being stirred for 30 min at the same temperature, dimethylsulfate (1.44 g, 10.68 mmol) was dissolved in diethylether (10 ml). The reaction solution was slowly heated to rt, diluted with water (12 ml), and extracted with diethylether. The organic extracts were dried over $MgSO_4$, and the residue was purified by column chromatography (eluent, EtOAc/Hex=1/4) to give the title compound (840 mg, 70%).
MS[M+H]=228(M+1)

Step B: (2S,4S)-1-Boc-2-allyl-4-azidopyrrolidine

The title compound was prepared according to the procedure described in Steps C~D of Preparation Example A1-1 using (2S,4S)-1-Boc-2-allyl-4-hydroxypyrrolidine prepared in Step A.
MS[M+H]=253(M+1)

Step C: (2S,4R)-1-Boc-2-allyl-4-aminopyrrolidine

To a solution of (2S,4R)-1-Boc-2-allyl-4-azidopyrrolidine (450 mg, 1.78 mmol) prepared in Step B in THF was added dropwise trimethylphosphine (135 mg, 1.78 mmol). After the reaction mixture was stirred at rt for 5 h, water (0.03 ml) was added, and stirred for additional 20 min. The reaction mixture was concentrated in vacuo, extracted with EtOAc, washed with water and brine, and concentrated in vacuo. The residue was purified by column chromatography(eluent, MeOH/DCM=1/9) to give the title compound (280 mg, 70%).
MS[M+H]=227(M+1)

PREPARATION EXAMPLE A1-5

(2S,4S)-1-Boc-2-propyl-4-aminopyrrolidine

To a solution of (2S,4S)-1-Boc-2-allyl-4-aminopyrrolidine (450 mg, 1.78 mmol) prepared in Preparation Example A1-4 in dioxane (5 mL) was added Pd/C (40 mg). The reaction mixture was stirred under hydrogen condition for 24 h, filtered through Celite, and the filtrate was concentrated in vacuo to give the title compound as an oil (390 mg, 98.5%).
MS[M+H]=229(M+1)

PREPARATION EXAMPLE A1-6

(2R,4S)-1-Boc-2-propyl-4-aminopyrrolidine

The title compound was prepared according to the procedure described in Preparation Example A1-5 using (2R,4R)-1-Boc-2-allyl-4-hydroxypyrrolidine as starting material.
MS[M+H]=229(M+1)

The Intermediate A2 compounds can be prepared as follows:

PREPARATION EXAMPLE A2-1

4,4-dimethyl-cyclohexanone 4,4-Dimethyl-cyclohexene-1-one (5 g, 40.3 mmol) and n-pentane (15 ml) were placed in a hydrogen reaction vessel, and Pd/C (500 mg) was added. The hydrogen reaction vessel was pressurized with hydrogen (25 psi), and reacted for 30 min. After the reaction finished, the reaction mixture was filtered through Celite, and the filtrate was concentrated in vacuo to give the title compound (5 g, 98%).
MS[M+H]=127(M+1)

PREPARATION EXAMPLE A2-2

4-trifluoromethylcyclohexanone

Step A: 4-trifluoromethyl-cyclohexanol

4-Hydroxybenzotrifluoride (5 g, 30.8 mmol) was placed in a hydrogen reaction vessel, dissolved in acetic acid (15 ml), and $Pt_2O$ (500 mg) was added. The hydrogen reaction vessel was pressurized with hydrogen (50 psi), and reacted for 16 h. After the reaction finished, the reaction mixture was filtered through Celite, and to the filtrate was added 1N-NaOH, extracted with diethylether, dried over $MgSO_4$, and concentrated in vacuo at rt to give the title compound (4.5 g, 87%).
MS[M+H]=169(M+1)

Step B: 4-trifluoromethylcyclohexanone

To a solution of 4-Trifluoromethylcyclohexanol (4.5 g, 26.7 mmol) in DCM (100 ml) was added Dess-Martin periodinane (13.6 g, 32 mmol), and stirred at rt for 2 h. After the reaction finished, the reaction mixture was concentrated in vacuo, sodium thiosulfate aqueous solution and diethylether were added and stirred at rt for 30 min, and extracted with diethylether. The organic layer was dried over $MgSO_4$, concentrated in vacuo at rt to give the title compound (4.2 g, 94.6%).
MS[4+H]=167(M+1)

PREPARATION EXAMPLE A2-3

4,4-difluoro cyclohexanone

Step A: 8,8-difluoro-1,4-dioxospiro-[4,5-]decane

To a solution of commercially available 1,4-cyclohexanedione-mono-ethylene ketal (25 g, 160 mmol) in DCM (500 ml) was added dropwise DAST (52 g, 2.0 mmol) at 0° C. The reaction mixture was slowly heated up to rt, and stirred until the reaction finished. After confirming that all the reaction mixture was disappeared, the reaction solution was added to a saturated $NaHCO_3$ aqueous solution (700 ml) to finish the reaction, and extracted with DCM. The organic extracts were washed with a saturated $NaHCO_3$ aqueous solution and brine, dried over $MgSO_4$, filtered, and concentrated in vacuo. The obtained residue was used in the next reaction without further purification.

Step B: 4,4-difluoro cyclohexanone

The product of Step A, 8,8-difluoro-1,4-dioxospiro[4.5]decane was dissolved in acetone (90 ml) and 3N HCl (900 ml), and stirred until the reaction finished. Then, the reaction mixture was extracted with DCM, washed with brine, dried over $MgSO_4$, filtered, and concentrated in vacuo. The obtained residue was used in the next reaction without further purification.

PREPARATION EXAMPLE A2-4 spiro[2,5]octane-6-one

Step A: 4,4-methylene-1,1-ethyleneketal-4-spiro[2,5]octane

To a solution of DMSO (15 mL), filled with nitrogen, was added NaH (60% suspension in mineral oil, 0.42 g, 10.50 mmol), and the reaction mixture was stirred at 50-60° C. for 2 h, methyltriphenylphosphonium bromide ($MeP(Ph)_3Br$) (3.76 g, 10.50 mmol) was added, and stirred at rt for 1 h. Cyclohexanedione monoethyleneketal (1 g, 6.40 mmol) was added, and stirred at 40° C. for 2 h. The reaction solution was cooled to rt, an ice water was added, and extracted with $Et_2O$. The organic extracts were dried over $MgSO_4$, filtered, and concentrated in vacuo. The residue was purified by column chromatography (eluent, EtOAc/Hex=1/5) to give the title compound (0.74 g, 74.95%).

Step B: spiro[2.5]octane-one

The product of Step A, 4,4-methylene-1,1-ethyleneketal-4-spiro[2,5]octane (0.74 g, 4.80 mmol) and diiodomethane (1.93 mL, 24.00 mmol) were placed in $Et_2O$ (45 mL), Zn—Cu (1.96 g, 30 mmol) was added, and refluxed for 12 h. The reaction solution was cooled to rt, diiodomethane (1.93 mL, 24.00 mmol) and Zn—Cu (1.96 g, 30 mmol) were added again, and refluxed for 20 h. The reaction solution was cooled to rt, filtered, and washed with Et$_2$O. To the filtrate was added 1M HCl (100 mL), reacted at rt for 1 h, and extracted for four (4) times with Et$_2$O. The organic extracts were dried over MgSO$_4$, filtered, and concentrated in vacuo (0.28 g, 46.99%).

The Intermediate A4 compounds can be prepared as follows:

PREPARATION EXAMPLE A4-1

2,2-dimethyl-3-acetyloxypropionyl chloride

Step A: 2,2-dimethyl-3-acetyloxypropionic acid 2,2-Dimethyl-3-hydroxypropionic acid (11.8 g, 100 mmol) was dissolved in pyridine (30 mL), and the reaction solution was cooled to 0° C. Acetyl chloride (11.8 g, 15.0 mmol) was slowed added dropwise, the temperature was increased to rt, and the reaction solution was stirred at rt for 3 h. After the reaction finished, 1N HCl (30 mL) was added, pH adjusted to 3-4, the reaction mixture was extracted with EtOAc. The organic extracts were washed with 1N HCl for 4-5 times, dried over MgSO$_4$, concentrated in vacuo to give the title compound (15.2 g, 95.0%).

MS[M+H]=161(M+1)

Step B: 2,2-dimethyl-3-acetyloxypropionyl chloride

The product of Step A, 2,2-dimethyl-3-acetyloxypropionic acid (11.76 g, 80 mmol) was dissolved in benzene (100 mL), the reaction solution was cooled 0° C., oxalyl chloride (15.0 g, 120 mmol) was slowly added dropwise. After 3 h, the solvent was removed in vacuo, and distilled in vacuo to give the title compound.

MS[M+H]=179(M+1)

PREPARATION EXAMPLE A4-2

2,5-dihydrofuran-3-carboxyl chloride

Step A: t-butyl 4-oxotetrahydrofuran-3-carboxylic acid

Sodium hydride (55% suspension in mineral oil, 0.5 g, 11.46 mmol) was placed in anhydride Et$_2$O (8 mL), and stirred, and ethyl glycolate (0.9 mL, 9.61 mmol) was added dropwise at rt. The reaction solution was stirred for 1 h, concentrated in vacuo, and t-butyl acrylate (1.68 mL, 11.46 mmol) in anhydride DMSO (8 mL) was added at 0-5° C. The reaction solution was stirred for 15 min at 0-5° C., stirred at rt for additional 1 h, and filtered. At 0-5° C., the filtrate was placed in a sulfuric acid solution (5%, 5.6 mL), and extracted with Et$_2$O for 3 times. The organic extracts were washed with brine, dried over MgSO$_4$, filtered, and concentrated in vacuo. The residue was purified by column chromatography (eluent, EtOAc/Hex=1/5) to give the title compound (0.95 g, 53.11%).

Step B: t-butyl 4-hydroxytetrahydrofuran-3-carboxylate

The product of Step A, tert-butyl 4-oxotetrahydrofuran-3-carboxylate (0.95 g, 5.10 mmol) was placed in isopropylalcohol (14 mL) at 0-5° C., NaBH$_4$ (77 mg, 2.04 mmol) was added, and stirred for 2 h. NaBH (77 mg, 2.04 mmol) was added again, and stirred at rt for 1 h, NaBH$_4$ (39 mg, 1.02 mmol) was added, and stirred for 30 min. The reaction mixture was treated with Et$_2$O to dilute, washed with brine, and extracted with Et$_2$O twice. The organic layer was collected, extracted with a NaHCO$_3$ aqueous solution, dried over MgSO$_4$, filtered, and concentrated in vacuo. The residue was purified by column chromatography (eluent, EtOAc/Hex=1/3) to give the title compound (0.83 g, 86.56%).

Step C: t-butyl 2,5-dihydrofuran-3-carboxylate

The product of Step B, t-butyl 4-hydroxytetrahydrofuran-3-carboxylate (0.83 g, 4.41 mmol) and PPh3 (1.74 g, 6.63 mmol) were placed in THF (5 mL), the solution was cooled to 0-5° C., and DIAD (1.13 mL, 5.74 mmol) was added dropwise. After reacting at rt for 12 h, the reaction mixture was filtered, washed with a solution of EtOAc/Hex=1/4, and the filtrate concentrated in vacuo The residue was purified by column chromatography (eluent, EtOAc/Hex=1/7) to give the title compound (0.39 g, 51.34%).

Step D: 2,5-dihydrofuran-3-carboxylic acid

To a solution of t-butyl 2,5-dihydrofuran-3-carboxylate (0.39 g, 2.29 mmol) prepared in Step C in DCM (2 mL) was added TFA (6 mL), and stirred at rt for 12 h. The reaction solution was concentrated in vacuo, the residue was treated with n-Hexane, stirred at rt for 30 min, and filtered to give the title compound (0.19 g, 72.3%).

Step E: 2,5-dihydrofuran-3-carboxyl chloride

The product of Step D, 2,5-dihydrofuran-3-carboxylic acid (0.19 g, 1.66 mmol) was dissolved in benzene (3 mL), the reaction solution was cooled to 0° C., and oxalyl chloride (0.4 g, 3.32 mmol) was slowly added dropwise. After 3 h, the solvent was removed in vacuo, and distilled in vacuo to give the title compound.

PREPARATION EXAMPLE A4-3

2-cyano-2-methylpropanoyl Chloride

To a solution of commercially available ethyl-2-cyano-2-methylpropanoate (3.5 g, 24.8 mmol) in methanol (10 ml) was added LiOH (900 mg, 37.2 mmol) and water (0.5 ml), and reacted at rt for 1 h. After the reaction finished, the solvent was concentrated in vacuo, 1N-HCl (50 ml) was added, and extracted with EtOAc. The extracted organic layer was dried over MgSO$_4$, concentrated in vacuo to give 2-cyano-2-methylpropionic acid (2.67 g, 95%). This compound (2.5 g, 22 mmol) was dissolved in DCM (7 ml), and reacted according to the procedure described in Step B of Preparation Example A4-1 to give the title compound (2.5 g, 86.3%).

MS[M+H]=132 (M+1)

PREPARATION EXAMPLE A4-4~9

The acylchlorides in the following table were prepared according to the procedure described in Preparation Example A4-1 or A4-3 using commercially available carboxylic acid.

TABLE 1

[Structure: Cl-C(=O)-R⁵]

| Preparation Example | R⁵ | MS(M + 1) |
|---|---|---|
| A4-4 | (tetrahydrofuran-3-yl) | 135 |
| A4-5 | (tetrahydrofuran-2-yl, H) | 135 |
| A4-6 | (tetrahydropyran-4-yl) | 149 |
| A4-7 | (thiophen-3-yl) | 147 |
| A4-8 | (tetrahydrofuran-2-yl, H dashed) | 135 |
| A4-9 | (furan-3-yl) | 131 |

PREPARATION EXAMPLE A9-1

(3S,4R)-1-t-butyl-4-(2,4-difluorophenyl)pyridine-3-carboxylic acid

The title compound was prepared according to the procedure described in WO 2004/09126.

PREPARATION EXAMPLE A9-2~7

The compounds in the following table were prepared according to the procedure described in Preparation Example A9-1 using commercially available alpha-halo ketone compounds.

TABLE 2

[Structure: HO₂C-CH-CH₂-N(Me)-A, with benzyl group bearing R²']

| Preparation Example | A | R²' | M + 1 |
|---|---|---|---|
| A9-2 | t-Bu | 4-Cl | 282 |
| A9-3 | t-Bu | 4-Me | 262 |
| A9-4 | t-Bu | 4-F | 266 |
| A9-6 | Me | 4-Cl | 240 |
| A9-7 | Me | 2,4-diF | 242 |

PREPARATION EXAMPLE A9-8

(3S,4R)-1-Boc-4-(2,4-difluorophenyl)pyrrolidine-3-carboxylic acid

Step A: (4R)-4-(2,4-difluorophenyl)pyrrolidine-3-carbonitrile

To a solution of (4R)-1-t-butyl-4-(2,4-difluorophenyl)pyrrolidine-3-carbonitrile (4 g, 15.15 mmol) prepared according to the procedure described in WO 2004/09126 in DCE (10 ml) was added dropwise 1-chloroethyl chloroformate (2.45 ml, 22.68 mmol) at 0° C. The reaction solution was heated to 70° C., and maintaining this temperature, 1.8-bis(dimethylamino)naphthalene (4.87 g, 22.72 mmol) in DCE (10 ml) was added dropwise for 2 h. After the reaction finished, methanol (10 ml) was added, and maintaining the temperature, the reaction mixture was stirred for additional 1 h, concentrated in vacuo, and the next reaction was carried out without further purification.
MS[M+1]=209(M+1)

Step B: (4R)-1-BOC-4-(2,4-difluorophenyl)pyrrolidine-3-carbonitrile

To a solution of (4R)-4-(2,4-difluorophenyl)pyrrolidine-3-carbonitrile prepared in Step A, DMAP (1.8 g, 15.15 mmol) and TEA (5.56 ml, 15.15 mmol) in DCM (10 ml) was added dropwise di-t-butyl dicarbonate (4.9 g, 22.7 mmol) at 0° C. The reaction mixture was stirred at rt for 8 h, concentrated in vacuo, and extracted with EtOAc. The organic extracts were washed with 1N-HCl and brine, dried over MgSO₄, concentrated in vacuo, and purified by column chromatography (eluent: EtOAc/Hex=1/6) to give the title compound (3.3 g, total of Step A and B: 72%).
MS[M+H]=309 (M+1)

Step C: (3S,4R)-1-Boc-4-(2,4-difluorophenyl)pyrrolidine-3-carboxylic acid

To a solution of (4R)-1-BOC-4-(2,4-difluorophenyl)pyrrolidine-3-carbonitrile (3.3 g, 10.6 mmol) prepared in Step B in ethanol (10 ml) was added 6N NaOH solution (5 ml), and stirred at 70° C. for 4 h. After the reaction finished, the solvent was removed, the reaction mixture diluted with ether, the organic solution was sufficiently acidified with 6N HCl, and washed. The organic solution was washed with brine, dried over MgSO₄, and concentrated in vacuo to give the title compound (3.43 g, 99.0%).
MS[M+1]=328(M+1)

PREPARATION EXAMPLE A9-9~11

The compounds in the following table were prepared according to the procedure described in Preparation Example A9-8 using phenylpyrrolidine-3-carbonitrile intermediates obtained in Preparation Example A9-2~4.

TABLE 3

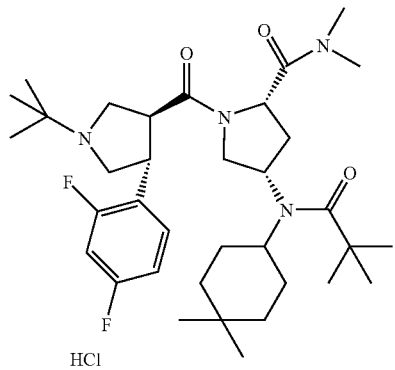

| Preparation Example | R²' | M + 1 |
|---|---|---|
| A9-9 | 4-Cl | 326 |
| A9-10 | 4-Me | 306 |
| A9-11 | 4-F | 310 |

The Examples synthesized by the procedure of Scheme A are as follows.

EXAMPLE A1

(4S)-1-{[(3S,4R)-1-tert-butyl-4-(2,4-difluorophenyl)pyrrolidine-3-yl]carbonyl}-4-[(4,4-dimethylcyclohexyl)(2,2-dimethylpropanoyl)amino]-N,N-dimethyl-L-prolineamide HCl salt

Step A: methyl-(2S,4S)-1-BOC-4-[(4,4-dimethylcyclohexyl)amino]pyrrolidine-2-carboxylate To methyl (2S,4S)-1-Boc-4-aminopyrrolidine-2-carboxylate (1.07 g, 4.38 mmol) and dimethylcyclohexanone (0.66 g, 5.25 mmol) in DCE (20 mL) was added dropwise NaBH(OAc) (1.39 g, 6.57 mmol) at rt. The reaction mixture was stirred at rt for 4 h, a saturated NaHCO₃ aqueous solution was added, and extracted with DCM (50 mL×2) and EtOAc. The organic extracts were washed with brine, dried over MgSO₄, filtered, and concentrated in vacuo. The obtained residue was purified by column chromatography (eluent, EtOAc/Hex=1/2) to give the title compound (1.16 g, 75%).

MS[M+H]=355(M+1)

Step B: 1-BOC-2-methyl-(2S,4S)-4-[(4,4-dimethyl-cyclohexyl)(2,2-dimethylpropanoyl)amino]pyrrolidine-2-carboxylate To a solution of methyl (2S,4S)-1-BOC-4-[(4,4-dimethylcyclohexyl)amino]pyrrolidine-2-carboxylate (1.01 g, 2.84 mmol) prepared in Step A in DCE (5 mL) was added dropwise TEA (5 mL) and DMAP (0.34 g, 2.84 mmol), and added commercially available pivaloyl chloride (1.01 g, 8.52 mmol). The reaction solution was heated to 90° C., and stirred for 24 h. After the reaction finished, the solvent was removed in vacuo, the residue treated with a saturated NaHCO₃ aqueous solution, and extracted with EtOAc. The organic extracts were washed with 1N HCl, dried over MgSO₄, concentrated in vacuo, and purified by column chromatography (eluent: EtOAc/Hex=1/4) to give the title compound (1.02 g, 82%).

MS[M+H]=439(M+1)

Step C: (4S)-1-BOC-4-[(4,4-dimethylcyclohexyl)(2,2-dimethylpropanoyl)amino]-L-proline To a solution of 1-BOC 2-methyl (2S,4S)-4-[(4,4-dimethylcyclohexyl)(2,2-dimethylpropanoyl)amino]pyrrolidine-2-carboxylate (1.02 g, 2.32 mmol) prepared in Step B in methanol (7 ml) and water (7 ml) was added LiOH (0.15 g, 6.99 mmol). The reaction mixture was stirred at rt for 3 h, concentrated in vacuo, and extracted with EtOAC. The organic extracts were washed with brine, dried over MgSO₄, and concentrated in vacuo to give the title compound (0.93 g, 95%).

MS[M+H]=425(M+1)

Step D: BOC(2S,4S)-2-[(dimethylamino)carbonyl]-4-[(4,4-dimethylcyclohexyl)(2,2-dimethylpropanoyl)amino]pyrrolidine To a solution of (4S)-1-BOC-4-[(4,4-dimethylcyclohexyl)(2,2-dimethylpropanoyl)amino]-L-proline (0.93 g, 2.2 mmol) prepared in Step C in DMF (10☐) was added dropwise DIPEA (0.95☐, 5.5 mmol) followed by dimethylamine-HCl salt (0.21 g, 2.57 mmol) and HBTU (0.83 g, 2.2 mmol). The reaction solution was stirred at rt for 2 h, and concentrated in vacuo. The residue was diluted with EtOAc, washed with a saturated NaHCO₃ aqueous solution, water and 1N HCl. The organic solution was dried over MgSO₄, concentrated in vacuo, and the residue was purified by column chromatography (eluent: EtOAc:Hex=2/1) to give the title compound (0.92 g, 93%).

MS[M+H]=452(M+1)

Step E: (4S)-4-[(4,4-diethylcyclohexyl)(2,2-dimethylpropanoyl)amino]-N,N-dimethyl-L-prolineamide To a solution of BOC(2S,4S)-2-[(dimethylamino)carbonyl]-4-[(4,4-dimethyl-cyclohexyl)(2,2-dimethylpropanoyl)amino]pyrrolidine (0.92 g, 2.0 mmol) prepared in Step D in DCM (1☐) was added dropwise 4M HCl (1☐). The reaction mixture was stirred at rt for 1 h, and concentrated in vacuo. The residue was concentrated in vacuo to give the title compound (705 mg, 99.9%).

MS[M+H]=352(M+1)

Step F: (4S)-1-{[(3S,4R)-1-tert-butyl-4-(2,4-difluorophenyl)pyrrolidine-3-yl]carbonyl}-4-[(4,4-dimethylcyclohexyl)(2,2-dimethylpropanoyl)amino]-N,N-dimethyl-L-prolineamide TFA salt To a solution of (4S)-4-[(4,4-dimethylcyclohexyl)(2,2-dimethylpropanoyl)amino]-N,N-dimethyl-L-prolineamide (0.70 g, 2.0 mmol) prepared in Step E in DMF (5☐) was added dropwise DIPEA (0.95☐, 5.5 mmol). Then, (3S,4R)-1-t-butyl-4-(2,4-difluorophenyl)pyrrolidine-3-carboxylic acid (0.57 g, 2.0 mmol) prepared in Preparation Example A-9-1 was added dropwise followed by HBTU (0.76 g, 2.0 mmol). The reaction mixture was stirred at rt for 2 h, and the solution was concentrated in vacuo. The residue was diluted with EtOAc, and washed with a saturated NaHCO₃ aqueous solution and water. The organic solution was dried over MgSO₄, concentrated in vacuo, and the residue was purified by HPLC to give the title compound (TFA salt, 1.04 g, 85%).
MS[M+H]=617(M+1)

Step G: (4S)-1-{[(3S,4R)-1-tert-butyl-4-(2,4-difluorophenyl)pyrrolidine-3-yl]carbonyl}-4-[(4,4-dimethylcyclohexyl)(2,2-dimethylpropanoyl)amino]-N,N-dimethyl-L-prolineamide HCl salt TFA salt of the compound prepared in Step F was basified with 1N NaOH, and extracted with EtOAc. The organic solution was dried over MgSO₄, concentrated in vacuo, treated with 4M HCl/dioxane, and stirred at rt for 1 h. The reaction solution was concentrated in vacuo without further purification to give HCl salt.
1H NMR (400 MHz, CDCl3) 8.10-8.04 (m, 1H), 6.97-6.93 (m, 1H), 6.79-6.74 (m, 1H), 4.70 (t, 1H), 4.35-4.22 (m, 2H), 3.95-3.90 (m, 2H), 3.81-3.69 (m, 1H), 3.67-3.54 (m, 2H), 3.42-3.29 (m, 2H), 3.22-3.11 (m, 1H), 2.99 (s, 3H), 2.95 (s, 3H), 2.82-2.68 (m, 1H), 2.19-1.97 (m, 1H), 1.61-1.39 (m, 4H), 1.49 (s, 9H), 1.31-1.15 (m, 4H), 1.22 (s, 9H), 0.95 (s, 3H), 0.91 (s, 3H)

EXAMPLE A2

(4S)-1-[(3S,4R)-1-tert-butyl-4-(4-chlorophenyl)pyrrolidine-3-yl]carbonyl)-4-{(4,4-dimethylcyclohexyl)[(2S)-tetrahydrofuran-2-ylcarbonyl]amino}-N,N-ethylmethyl-L-prolineamide HCl salt

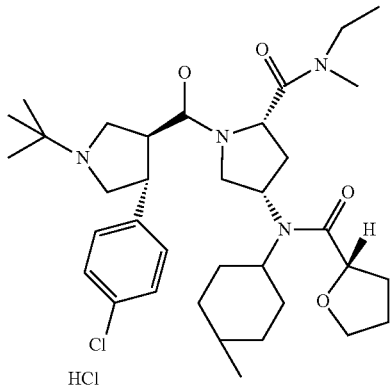

Step A: 1-boc-2-methyl (2S,4S)-4-{(4,4-dimethylcyclohexyl)[(2S)-tetrahydrofuran-2-ylcarbonyl]amino}pyrrolidine2-carboxylate To a solution of methyl-(2S,4S)-1-BOCA-4-[(4,4-dimethylcyclohexyl)amino]pyrrolidine-2-carboxylate (1.01 g, 2.84 mmol) prepared in Step A in Example A1 in DCE (5 mL) was added dropwise TEA (5 mL) and DMAP (0.34 g, 2.84 mmol). Then, (S)-tetrahydrofuran-2-carbonyl chloride (1.14 g, 8.52 mmol) prepared in Preparation Example A4-5, was added. The reaction solution was heated 90° C., and stirred for 24 h. After the reaction finished, the solvent was removed in vacuo, and to the residue was added a saturated aqueous NaHCO₃ solution, and extracted with EtOAc. The organic extracts were washed with 1N HCl, dried over MgSO₄, concentrated in vacuo, and purified by column chromatography (eluent: EtOAc/Hex=1/4) to give the title compound (1.05 g, 82%).
MS[M+H]=453(M+1)

Step B: (4S)-1-BOC-4-{(4,4-dimethylcyclohexyl)[(2S)-tetrahydrofuran-2-ylcarbonyl]amino}-L-proline The title compound was prepared according to the procedure described in Step C of Example A1, using 1-BOC-2-methyl(2S,4S)-4-{(4,4-dimethylcyclohexyl)[(2S)-tetrahydrofuran-2-ylcarbonyl]amino}pyrrolidine2-carboxylate (1.05 g, 2.32 mmol) prepared in Step A (0.96 g, 95%).
MS[M+H]=439(M+1)

Step C: BOC-(2S,4S)-4-{(4,4-dimethylcyclohexyl)[(2S)tetrahydrofuran-2-ylcarbonyl]amino}-2-{[ethyl(methyl)amino]carbonyl}pyrrolidine The title compound was prepared according to the procedure described in Step D of Example A1, using (4S)-1-BOC-4-{(4,4-dimethylcyclohexyl)[(2S)-tetrahydrofuran-2-ylcarbonyl]amino}-L-proline (0.96 g, 2.2 mmol) prepared in Step B and commercially available N-methylethylamine (0.92 g, 93%).
MS[M+H]=480(M+1)

Step D: (4S)-4-[4,4-dimethylcyclohexyl)(tetrahydrofuran-2-ylcarbonyl)amino]-N-ethyl-N-methyl-L-prolineamide To a solution of BOC-(2S,4S)-4-{(4,4-dimethylcyclohexyl)[(2S)-tetrahydrofuran-2-ylcarbonyl]amino}-2-{[ethyl(methyl)amino]carbonyl}pyrrolidine (0.92 g, 2.0 mmol) prepared in Step C in DCM (1☐) was added dropwise 4M HCl (1☐). The reaction mixture was stirred at rt for 1 h, and concentrated in vacuo. The residue was concentrated in vacuo to give the title compound (750 mg, 99.9%).
MS[M+H]=380(M+1)

Step E: (4S)-1-{[(3S,4R)-1-tert-butyl-4-(4-chlorophenyl)pyrrolidine-3-yl]carbonyl}-4-{(4,4-dimethylcyclohexyl)[(2S)-tetrahydrofuran-2-ylcarbonyl]amino}-N,N-ethylmethyl-L-prolineamide HCl salt To a solution of (4S)-4-[(4,4-dimethylcyclohexyl)(tetrahydrofuran-2-ylcarbonyl)amino]-N-ethyl-N-methyl-L-prolineamide (0.76 g, 2.0 mmol) prepared in Step D in DMF (5☐) was added dropwise DIPEA (0.95☐, 5.5 mmol). Then, the product of Preparation Example A9-2, (3S,4R)-1-t-butyl-4-(4-chlorophenyl)pyrrolidine-3-carboxylic acid (0.56 g, 2.0 mmol) was added dropwise followed by HBTU (0.76 g, 2.0 mmol). The reaction mixture was stirred at rt for 2 h, the solution was concentrated in vacuo. The residue was diluted with EtOAc, and washed with a saturated aqueous NaHCO₃ solution and water. The organic solution was dried over MgSO₄, concentrated in vacuo, and the residue was purified by HPLC to give TFA salt of the compound (1.09 g, 85%).

This compound was treated according to the procedure described in Step G of Example A1 to give the title compound.

MS[M+H]=643(M+1)

1H NMR (400 MHz, CDCl3) 7.51 (d, 21), 7.33 (d, 2H), 4.68 (t, 1H), 4.48 (t, 1M), 4.40-4.21 (m, 1H), 4.03-3.90 (m, 3H), 3.90-3.81 (m, 2H), 3.80-3.70 (m, 2H), 3.66-3.46 (m, 3H), 3.45-3.12 (m, 3H), 2.97 (d, 3H), 2.86-2.62 (m, 1H), 2.41-2.28 (m, 1H), 2.13-1.82 (m, 4H), 1.64-1.40 (m, 4H), 1.52 (s, 9H), 1.40-1.22 (m, 2H), 1.26 (t, 3H), 1.20-1.08 (m, 2H), 0.97 (s, 3H), 0.94 (s, 3H)

EXAMPLE A3

(4S)-1-{[(3S,4R)-1-tert-butyl-4-(4-chlorophenyl)pyrrolidine-3-yl]carbonyl}-4-{(4,4-dimethylcyclohexyl)[(2S)-tetrahydrofuran-2-ylcarbonyl]amino}-N-ethyl-L-prolineamide HCl salt

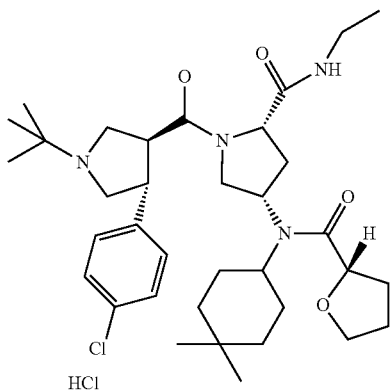

HCl

Step A: 1-BOC-(2S,4S)-4-{(4,4-dimethylcyclohexyl)[(2S)-tetrahydrofuran-2-ylcarbonyl]amino}-2-[(ethylamino)carbonyl)pyrrolidine The title compound was prepared according to the procedure described in Step D of Example A1, using (4S)-1-BOC-4-{(4,4-dimethylcyclohexyl)[(2S)-tetrahydrofuran-2-ylcarbonyl]amino}-L-proline (0.96 g, 2.2 mmol) prepared in Step B of Example A2 and commercially available ethylamine (0.95 g, 93%).

MS[M+H]=466 (M+1)

Step B: (4S)-4-[(4,4-dimethylcyclohexyl)(tetrahydrofuran-2-ylcarbonyl)amino]-N-ethyl-L-prolineamide To a solution of 1-BOC-(2S,4S)-4-{(4,4-dimethylcyclohexyl)[(2S)-tetrahydrofuran-2-ylcarbonyl]amino}-2-[(ethylamino)carbonyl)pyrrolidine (0.95 g, 2.0 mmol) prepared in Step A in DCM (1□) was added dropwise 4M HCl (1□). The reaction mixture was stirred at rt for 1 h, and concentrated in vacuo. The residue was concentrated in vacuo to give the title compound (730 mg, 99.9%).

MS[M+H]=366(M+1)

Step, C: (4S)-1-{[(3S,4R)-1-tert-butyl-4-(4-chlorophenyl)pyrrolidine-3-yl]carbonyl}-4-{(4,4-dimethylcyclohexyl)[(2S)-tetrahydrofuran-2-ylcarbonyl]amino}-N-ethyl-L-prolineamide HCl salt To a solution of (4S)-4-[(4,4-dimethylcyclohexyl)(tetrahydrofuran-2-ylcarbonyl)amino]-N-ethyl-L-proline amide (0.73 g, 2.0 mmol) prepared in Step B in DMF (5□) was added dropwise DIPEA (0.95□, 5.5 mmol). Then, the product of Preparation Example A9-2, (3S,4R)-1-t-butyl-4-(4-(dichlorophenyl)pyrrolidine-3-carboxylic acid (0.56 g, 2.0 mmol) was added dropwise followed by HBTU (0.76 g, 2.0 mmol). The reaction mixture was stirred at rt for 2 h, and the solution was concentrated in vacuo. The residue was diluted with EtOAc, and washed with a saturated aqueous NaHCO3 solution and water. The organic solution was dried over MgSO4, concentrated in vacuo, and the residue was purified by HPLC to give TFA salt of the compound (1.06 g, 85%). This compound was treated according to the procedure described in Step G of Example A1 to give the title compound.

MS[M+H]=629(M+1)

1H NMR (400 MHz, CDCl3) 7.55 (d, 2H), 7.33 (d, 2H), 4.51-4.43 (m, 1H), 4.26 (t, 1H), 4.06-3.98 (m, 1H), 3.97-3.56 (m, 7H), 3.49-3.02 (m, 4H), 2.83-2.74 (m, 1H), 2.49-2.38 (m, 1H), 2.32-2.22 (m, 1H), 2.21-2.11 (m, 1H), 2.02-1.82 (m, 4H), 1.61-1.15 (m, 8H), 1.49 (s, 9H), 1.10 (t, 3H), 0.93 (s, 3H), 0.91 (s, 3H)

EXAMPLE A4

(4S)-1-{[(3S,4R)-1-tert-butyl-4-(4-chlorophenyl)pyrrolidine-3-yl]carbonyl}-4-[(4,4-dimethylcyclohexyl)(3-hydroxy-2,2-dimethylpropanoyl)amino]-N-ethyl-N-methyl-L-prolineamide HCl salt

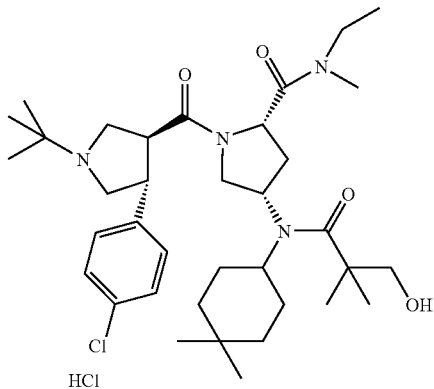

HCl

Step A: 1-boc-2-methyl-(2S,4S)-4-{[3-(acetyloxy)-2,2-dimethylpropanoyl](4,4-dimethylcyclohexyl)amino}pyrrolidine-2-carboxylate To a solution of methyl-(2S,4S)-1-BOC-4-[(4,4-dimethylcyclohexyl)amino]pyrrolidine-2-carboxylate (1.01 g, 2.84 mmol) prepared in Step A of Example A1 in DCE (5 mL) was added dropwise TEA (5 mL) and DMAP (0.34 g, 2.84 mmol). Then, the product of Preparation Example A4-1, 2,2-dimethyl-3-acetyloxypropionyl chloride (1.01 g, 5.68 mmol) was added. The reaction solution was heated to 90° C., and stirred for 48 h. After the reaction finished, the solvent was removed in vacuo, to the residue was added a saturated aqueous NaHCO₃ solution, and extracted with EtOAc. The organic extracts were washed with 1N HCl, dried over MgSO₄, concentrated in vacuo, and purified by column chromatography (eluent: EtOAc/Hex=1/4) to give the title compound (0.88 g, 63%).

MS[M+H]=497(M+1)

Step B: (4S)-1-BOC-4-[(4,4-dimethylcyclohexyl)(3-hydroxy-2,2-dimethylpropanoyl)amino]-L-proline To a solution of 1-BOC-2-methyl-(2S,4S)-4-{[3-(acetyloxy)-2,2-dimethylpropanoyl](4,4-methylcyclohexyl)amino}pyrrolidine-2-carboxylate (1.02 g, 2.05 mmol) prepared in Step A in methanol (10 ml) and water (10 ml), was added NaOH (246 mg, 6.15 mmol), and stiffed for 12 h. After the reaction finished, the reaction solution was concentrated in vacuo, acidified with 1N HCl, and extracted with EtOAc. The organic extracts were washed with 1N HCl, dried MgSO₄, and concentrated in vacuo to give the title compound (0.85 g, 95%).

MS[M+H]=441(M+1)

Step C: BOC-(2S,4S)-4-[(4,4-dimethylcyclohexyl)(3-hydroxy-2,2-dimethylpropanoyl)amino]-2-{[ethyl(methyl)amino]carbonyl}pyrrolidine The title compound was prepared according to the procedure described in Step D of Example A1 using (4S)-1-BOC-4-[(4,4-dimethylcyclohexyl)(3-hydroxy-2,2-dimethylpropanoyl)amino]-L-pr oline (0.85 g, 1.94 mmol) prepared in Step B and commercially available N-methylethylamine (0.86 g, 93%).

MS[M+H]=482(M+1)

Step D: (4S)-4-[(4,4-dimethylcyclohexyl)(3-hydroxy-2,2-dimethylpropanoyl)amino]-N-ethyl-N-methyl-L-prolineamide The title compound was prepared according to the procedure described in Step E of Example A1 using BOC-(2S,4S)-4-[(4,4-dimethylcyclohexyl)(3-hydroxy-2,2-dimethylpropanoyl)amino]-2-{[ethyl(methyl)amino]carbonyl}pyrrolidine (0.86 g, 1.8 mmol) prepared in Step C (0.68 g, 99.9

MS[M+H]=382(M+1)

Step E: (4S)-1-{[(3S,4R)-1-tert-butyl-4-(chlorophenyl)pyrrolidine-3-yl]carbonyl}-4-[(4,4-dimethylcyclohexyl)(3-hydroxy-2,2-dimethylpropanoyl)amino]-N-ethyl-N-methyl-L-prolineamide HCl salt TFA salt of the compound was prepared according to the procedure described in Step G of Example A1 using (4S)-4-[(4,4-dimethylcyclohexyl)(3-hydroxy-2,2-dimethylpropanoyl)amino]-N-ethyl-N-m ethyl-L-prolineamide (0.68 g, 2.0 mmol) prepared in Step D (1 g, 89%). This compound was treated according to the procedure described in Step G of Example A1 to give the title compound.

MS[M+H]=645(M+1)

1H NMR (400 MHz, CDCl3) 7.62 (d, 2H), 7.31 (d, 2H), 4.68 (t, 1H), 4.36-4.19 (m, 1H), 3.96-3.79 (m, 3H), 3.77-3.52 (m, 4H), 3.43-3.08 (m, 6H), 2.94 (s, 3H), 2.74-2.62 (m, 1H), 2.11-1.97 (m, 1H), 1.67-1.36 (m, 14H), 1.35-1.15 (m, 9H), 1.10 (t, 3H), 0.95 (s, 3H), 0.92 (s, 3H)

EXAMPLE A5

(4S)-1-{[(3S,4R)-1-tert-butyl-4-(4-chlorophenyl)pyrrolidine-3-yl]carbonyl}-4-[(4,4-difluorocyclohexyl)(2,2-dimethylpropanoyl)amino]-N,N-dimethyl-L-prolineamide HCl salt

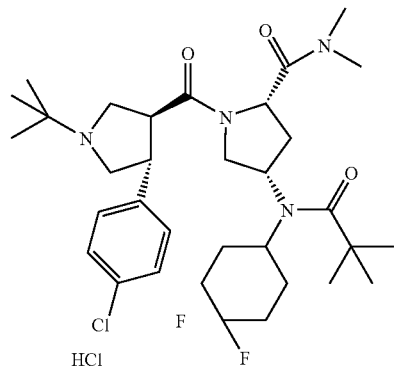

Step A: 2-methyl-(2S,4S)-1-BOC-4-[(4,4-difluorocyclohexyl)amino]pyrrolidine-carboxylate To a solution of 4,4-Difluoro cyclohexanone prepared in Preparation Example A2-3, and methyl (2S,4S)-1-Boc-4-aminopyrrolidine-2-carboxylate (29 g, 120 mmol) prepared in Preparation Example A1-1 in DCE was added NaBH(OAc)₃ (37 g, 180 mmol), and stirred at rt for 6 h. After the reaction finished, the solvent was concentrated in vacuo, NaHCO₃ aqueous solution was added, extracted with EtOAc, and the organic layer was dried over MgSO₄, concentrated in vacuo. The residue was purified by column chromatography (eluent: EtOAc/Hex=1/4) to isolate 2-methyl-(2S,4S)-1-BOC-4-[(4-fluorocyclohex-3-ene-1-yl)amino]pyrrolidine-carboxylate, whereby to give the title compound (23 g, 55%).

MS[M+H]=363 (M+1)

Step B: 1-BOC 2-methyl (2S,4S)-4-[(4,4-difluorocyclohexyl)(2,2-dimethylpropanoyl)amino]pyrrolidine-2-carboxylate The title compound was prepared according to the procedure described in Step B of Example A1 using 2-methyl-(2S,4S)-1-BOC-4-[(4,4-difluorocyclohexyl)amino]pyrrolidine-carboxylate (1.03 g, 2.84 mmol) prepared in Step A (1.02 g, 82%).

MS[M+H]=447(M+1)

Step C: (4S)-1-BOC-4-[(4,4-difluorocyclohexyl(2,2-dimethylpropanoyl)amino]-L-proline The title compound was prepared according to the procedure described in Step C of Example A1 using 1-BOC 2-methyl (2S,4S)-4-[(4,4-difluorocyclohexyl)(2,2-dimethylpropanoyl)amino]pyrrolidine-2-carboxylate (1.02 g, 2.32 mmol) prepared in Step B (0.95 g, 95%).

MS[M+H]=433(M+1)

Step D: BOC-(2S,4S)-4-[(4,4-difluorocyclohexyl)(2,2-dimethylpropanoyl)amino]-2-[(dimethylamino)carbonyl]pyrrolidine The title compound was prepared according to the procedure described in Step D of Example A1 using (4S)-1-BOC-4-[(4,4-difluorocyclohexyl)(2,2-dimethylpropanoyl)amino]-L-proline (0.95 g, 2.2 mmol) prepared in Step C (0.93 g, 93%).
MS[M+H]=460 (M+1)

Step E: (4S)-4-[(4,4-difluorocyclohexyl)(2,2-dimethylpropanoyl)amino]-N,N-diethyl-L-prolineamide The title compound was prepared according to the procedure described in Step E of Example A1 using BOC-(2S,4S)-4-[(4,4-difluorocyclohexyl)(2,2-dimethylpropanoyl)amino]-2-[(dimethylamino)carbonyl]pyrrolidine (0.93 g, 2.0 mmol) prepared in Step D (710 mg, 99.9%).
MS[M+H]=360(M+1)

Step F: (4S)-1-{[(3S,4R)-1-tert-butyl-4-(4-chlorophenyl)pyrrolidine-3-yl]carbonyl}-4-[(4,4-difluorocyclohexyl)(2,2-dimethylpropanoyl)amino]-N,N-dimethyl-L-prolineamide HCl salt The title compound was prepared according to the procedure described in Step F-G of Example A1, using (4S)-4-[(4,4-difluorocyclohexyl)(2,2-dimethylpropanoyl)amino]-N,N-dimethyl-L-prolineamide (0.70 g, 2.0 mmol) prepared in Step E and (3S,4R)-1-t-butyl(4-dichlorophenyl)pyrrolidine-3-carboxylic acid prepared in Preparation Example A9-2 (1.06 g, 85%).
MS[M+H]=623(M+1)
1H NMR (400 MHz, CDCl3) 7.60 (d, 2H), 7.31 (d, 2H), 4.69 (t, 1H), 4.33-4.11 (m, 1H), 4.00-3.51 (m, 6H), 3.37-3.08 (m, 3H), 2.99 (d, 6H), 2.45-1.96 (m, 5H), 1.90-1.56 (m, 5H), 1.48 (s, 9H), 1.21 (s, 9H)

EXAMPLE A6

(4S)-1-{[(3S,4R)-1-tert-butyl-4-(4-chlorophenyl)pyrrolidine-3-yl]carbonyl}-4-[(4,4-difluorocyclohexyl)(2,2-dimethylpropanoyl)amino]-N-ethyl-L-prolineamide HCl salt

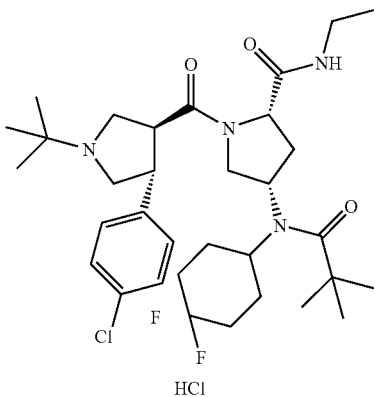

Step A: BOC-(2S,4S)-4-[(4,4-difluorocyclohexyl)(2,2-dimethylpropanoyl)amino]-2-[(ethylamino)carbonyl]pyrrolidine The title compound was prepared according to the procedure described in Step D of Example A1 using (4S)-1-BOC-4-[(4,4-difluorocyclohexyl)(2,2-dimethylpropanoyl)amino]-L-proline (0.95 g, 2.2 mmol) prepared in Step C of Example A5 and commercially available ethylamine (0.93 g, 93%).
MS[M+H]=460 (M+1)

Step B: (4S)-4-[(4,4-difluorocyclohexyl)(2,2-dimethylpropanoyl)amino]-N-ethyl-L-prolineamide The title compound was prepared according to the procedure described in Step E of Example A1 using BOC-(2S,4S)-4-[(4,4-difluorocyclohexyl)(2,2-dimethylpropanoyl)amino]-2-[(ethylamino)carbonyl]pyrrolidine (0.93 g, 2.0 mmol) prepared in Step A (710 mg, 99.9%).
MS[M+H]=360(M+1)

Step C: (4S)-1-{[(3S,4R)-1-tert-butyl-4-(4-chlorophenyl)pyrrolidine-3-yl]carbonyl}-4-[(4,4-difluorocyclohexyl)(2,2-dimethylpropanoyl)amino]-N-ethyl-L-prolineamide HCl salt The title compound was prepared according to the procedure described in Step F-G of Example A1, using (4S)-4-[(4,4-fluorocyclohexyl)(2,2-dimethylpropanoyl)amino]-N-ethyl-L-prolineamide (0.70 g, 2.0 mmol) prepared in Step B and (3S,4R)-1-t-butyl-4-(4-dichlorophenyl)pyrrolidine-3-carboxylic acid prepared in Preparation Example A9-2 (1.06 g, 85%).
MS[M+H]=623(M+1)
1H NMR (400 MHz, CDCl3) 7.56 (d, 2H), 7.35 (d, 2H), 4.26 (t, 1H), 4.04-3.57 (m, 61H), 3.57-3.40 (m, 1H), 3.40-3.05 (m, 3H), 2.70-2.50 (m, 1H), 2.43-2.15 (m, 3H), 1.95-1.22 (m, 8H), 1.49 (s, 9H), 1.22 (s, 9H), 1.11 (t, 3H)

EXAMPLE A7

(4S)-1-{[(3S,4R)-4-(4-Chlorophenyl)-1-methylpyrrolidine-3-yl]carbonyl}-4-[(2,2-dimethylpropanoyl)(cis-4-methylcyclohexyl)amino]-L-prolineamide HCl salt

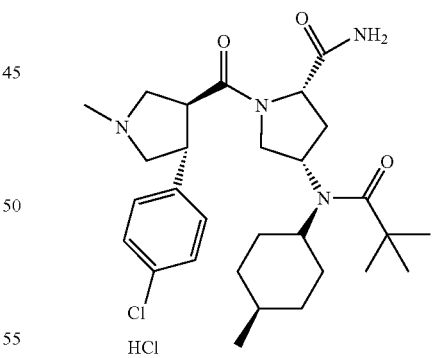

Step A: 1-BOC 2-methyl(2S,4S)-4-[(cis-4-methylcyclohexyl)amino]pyrrolidine-2-carboxylate To a solution of methyl (2S,4S)-1-Boc-4-aminopyrrolidine-2-carboxylate (1.07 g, 4.38 mmol) prepared in Preparation Example A1-1 and 4-methylcyclohexanone in DCE (30 ml) was added dropwise NaBH(OAc) (1.39 g, 6.57 mmol) at rt. The reaction mixture was stirred at rt for 4 h, a saturated NaHCO3 aqueous solution was added, and extracted with DCM (50 mL×2) and EtOAc. The organic extracts were washed with brine, dried over MgSO₄, filtered, and concentrated in vacuo. The residue was purified by column chromatography (eluent, EtOAc/Hex=1/2) to isolate cis and trans compounds, whereby to give the title compound (0.84 g, 57%).

MS[M+11]=341 (M+1)

Step B: 1-BOC 2-methyl(2S,4S)-4-[(2,2-dimethyl-propanoyl)(cis-4-methyl-cyclohexyl)amino]pyrrolidine-2-carboxylate The title compound was prepared according to the procedure described in Step B of Example A1 using 1-BOC 2-methyl(2S,4S)-4-[(cis-4-methylcyclohexyl)amino]pyrrolidine-2-carboxylate (0.84 g, 2.49 mmol) prepared in Step A (0.92 g, 87%).

MS[M+H]=425(M+1)

Step C: (4S)-1-BOC-4-[(2,2-dimethylpropanoyl)(cis-4-methylcyclohexyl)amino]-L-proline The title compound was prepared according to the procedure described in Step C of Example A1 using 1-BOC 2-methyl(2S,4S)-4-[(2,2-dimethylpropanoyl)(cis-4-methyl-cyclohexyl)amino]pyrrolidine-2-carboxylate (0.92 g, 2.16 mmol) prepared in Step B (0.84 g, 95%).

MS[M+H]=411(M+1)

Step D: BOC-(2S,4S)-2(aminocarbonyl)-4-[(2,2-dimethylpropanoyl)(cis-4-methylcyclohexyl)amino]pyrrolidine To a solution of (4S)-1-BOC-4-[(2,2-dimethylpropanoyl)(cis-4-methyl-cyclohexyl)amino]-L-proline (0.83 g, 2.05 mmol) prepared in Step C in THF was added dropwise TEA (0.32 ml, 2.27 mmol). Then, ethylchloroformate (0.24 g, 2.27 mmol) was slowly added dropwise at 0° C., and the reaction solution was stirred at the same temperature for 1 h. 28% Ammonia water (1 equivalent) was slowly added dropwise at 0° C., and stirred at the same temperature for additional 1 h. After the reaction finished, the reaction mixture was concentrated in vacuo, and extracted with EtOAC. The organic extracts were washed with brine, dried over MgSO₄, concentrated in vacuo, and purified by column chromatography (eluent: EtOAc/Hex=2/1) to give the title compound (0.62 g, 74%).

MS[M+H]=410(M+1)

Step E: (4S)-4-[(2,2-dimethylpropanoyl)(cis-4-methylcyclohexyl)amino]L-prolineamide The title compound was prepared according to the procedure described in Step E of Example A1 using BOC-(2S,4S)-2(aminocarbonyl)-4-[(2,2-dimethylpropanoyl)(cis-4-methylcyclohexyl)amino]pyrrolidine (0.62 g, 1.53 mmol) prepared in Step D (0.45 g, 95%).

MS[M+H]=310(M+1)

Step F: (4S)-1-{[(3S,4R)-4-(4-chlorophenyl)-1-methylpyrrolidine-3-yl]carbonyl}-4-[(2,2-dimethylpropanoyl)(cis-4-methylcyclohexyl)amino]-L-prolineamide HCl salt The title compound was prepared according to the procedure described in Step F-G of Example A1, using (4S)-4-[(2,2-dimethylpropanoyl)(cis-4-methylcyclohexyl)amino]L-prolineamide (0.45 g, 1.45 mmol) prepared in Step E and (3S,4R)-1-t-methyl-4-(4-chlorophenyl)pyrrolidine-3-carboxylic acid prepared in Preparation Example A9-6 (0.67 g, 88%).

MS[M+H]=531(M+1)

1H NMR (400 MHz, CDCl3) 7.51 (d, 2H), 7.33 (d, 2H), 4.69 (t, 1H), 4.35-4.22 (m, 2H), 3.95-3.90 (m, 2H), 3.81-3.69 (m, 1H), 3.67-3.54 (m, 2H), 3.42-3.29 (m, 2H), 3.22-3.11 (m, 1H), 2.82-2.68 (m, 1H), 2.68-2.56 (m, 3H), 2.19-1.97 (m, 1H), 1.61-1.39 (m, 5H), 1.31-1.15 (m, 4H), 1.22 (s, 9H), 0.90 (d, 3H)

EXAMPLE A8

N-[(3S)-1[(3S,4R)-1-T-butyl-4-(4-chlorophenyl)pyrrolidine-3-yl]carbonyl)pyrrolidine-3-yl]-N-(4,4-dimethylcyclohexyl)-3-hydroxy-2,2-dimethylpropaneamide HCl salt

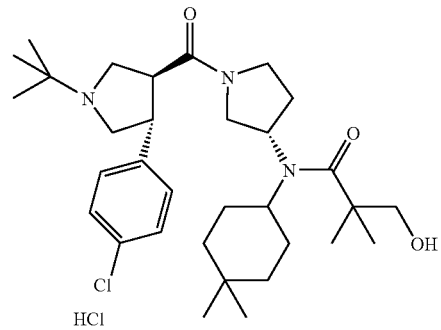

Step A: (3S)-1-Boc-3-[(4,4-dimethylcyclohexyl)amino]pyrrolidine

To a solution of 4,4-dimethylcyclohexanone (3.8 g, 30 mmol) in DCM (200 ml) was added commercially obtained (3S)-1-Boc-3-aminopyrrolidine (5.6 g, 30 mmol), and NaBH(OAc) (12.7 g, 60 mmol) was added, and stirred at rt for 6 h. After the reaction finished, the solvent was concentrated in vacuo, a NaHCO₃ aqueous solution was added, and extracted with EtOAc. The organic layer was dried over MgSO₄, concentrated in vacuo, and purified by column chromatography (eluent: EtOAc/Hex=2/1) to give the title compound (8.4 g, 94.5%).

MS[M+H]=297 (M+1)

Step B: (3S)-1-Boc-3-[(4,4-dimethylcyclohexyl)(3-hydroxy-2,2-dimethylpropanoyl)amino]pyrrolidine To a solution of (3S)-1-Boc-3-[(4,4-dimethylcyclohexyl)amino]pyrrolidine (2 g, 6.7 mmol) prepared in Step A in anhydrous THF was added TEA (2.03 g, 20.1 mmol) and DMAP (818 mg, 6.7 mmol). Then, the product of Preparation Example A4-1, 2,2-dimethyl-3-acetyloxypropionyl chloride (3.6 g, 20.1 mmol) was added, and the solution was stirred at 80° C. for 14 h. After the reaction finished, the solvent was concentrated in vacuo, and the residue was diluted with EtOAc, and washed with 1N-NaOH and 1N-HCl. The organic layer was dried over MgSO₄, concentrated in vacuo, and purified by column chromatography (eluent: EtOAc/Hex=1/3) to give (3S)-1-Boc-3-({[3-(acetyloxy)-2,2-dimethylpropanoyl](4,4-dimethylcyclohexyl)amino}pyrrolidine (2.3 g, 78%). This compound was dissolved in methanol (10 ml), and LiOH (187 mg, 7.8 mmol) and water (0.3 ml) were added, and stirred at rt for 3 h. After the reaction finished, the solvent was removed in vacuo, diluted with water (50 ml), and extracted with EtOAc. The organic layer was washed with 1N-HCl, dried over MgSO4, concentrated in vacuo to give the title compound (1.95 g, 94.5%).
MS[M+H]=397 (M+1)

Step C: N-(4,4-dimethylcyclohexyl)-3-hydroxy-2,2-dimethyl-N-[(3S)pyrrolidine-3-yl]propaneamide The title compound was prepared according to the procedure described in Step E of Example A1 using (3S) 1-Boc-3-[(4,4-dimethylcyclohexyl)(3-hydroxy-2,2-dimethylpropanoyl)amino]pyrrolidine (484 mg, 1.22 mmol) prepared in Step B (500 mg, 99.9%).

Step D: N-[(3S)-1-{[(3S,4R)-1-t-butyl-4-(4-chlorophenyl) pyrrolidine-3-yl]carbonyl}pyrrolidine-3-yl]-N-(4,4-dimethylcyclohexyl)-3-hydroxy-2,2-dimethylpropaneamide HC salt The title compound was prepared according to the procedure described in Step F-G of Example A1, using N-(4,4-dimethylcyclohexyl)-3-hydroxy-2,2-dimethyl-N-[(3S)-pyrrolidine-3-yl]propaneamide (500 mg, 1.21 mmol) prepared in Step B and (3S,4R)-1-t-butyl-4-(4-chlorophenyl)pyrrolidine-3-carboxylic acid prepared in Preparation Example A9-2 (672 mg, 91.9%).
MS[M+H]=560(M+1)
1H NMR (500 MHz, CDCl3) 7.55-7.48 (m, 2H), 7.36-7.28 (m, 2H), 3.95-3.20 (m, 12H), 3.01-2.93 (m, 0.5H), 2.75-2.68 (m, 0.5H), 2.48-2.38 (m, 0.5H), 2.18-2.08 (m, 0.5H), 1.86-1.68 (m, 1H), 1.67-1.53 (m, 6H), 1.53-1.35 (m, 10H), 1.32-1.14 (m, 8H), 0.94 (s, 3H), 0.91 (s, 3H)

EXAMPLE A9

N-[(3S,4R)-1-{[(3S,4R)-1-T-butyl-4-(4-chlorophenyl)pyrrolidine-3-yl]carbonyl}pyrrolidine-3-yl]-N-(4,4-dimethylcyclohexyl)-2,2-dimethylpropaneamide HCl salt

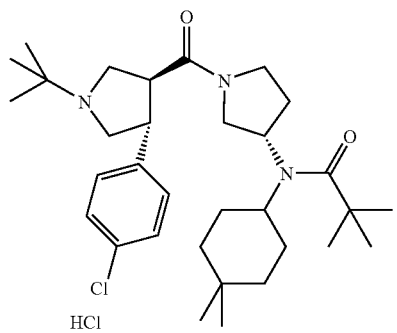

Step A: (3S)-1-Boc-3-[(4,4-dimethylcyclohexyl)(2,2-dimethylpropanoyl)amino]pyrrolidine The title compound was prepared according to the procedure described in Step B of Example A1 using (3S)-1-Boc-3-[(4,4-dimethylcyclohexyl)amino]pyrrolidine (2 g, 6.7 mmol) prepared in Step A of Example A8 (2.4 g, 94.5%).
MS[M+H]=381 (M+1)

Step B: N-(4,4 dimethylcyclohexyl)-2,2-dimethyl-N-[(3S)-pyrrolidine-3-yl]propaneamide The title compound was prepared according to the procedure described in Step E of Example A1 using (3S)-1-Boc-3-[(4,4-dimethylcyclohexyl)(2,2-dimethylpropanoyl)amino]pyrrolidine (460 mg, 1.22 mmol) prepared in Step A (0.33 g, 97%).
MS[M+H]=281(M+1)

Step C: N-[(3S)-1-{[(3S,4R)-1-t-butyl-4-(chlorophenyl)pyrrolidine-3-yl]-carbonyl}pyrrolidine-3-yl]-N-(4,4-dimethylcyclohexyl)-2,2-dimethylpropaneamide HCl salt The title compound was prepared according to the procedure described in Step F-G of Example A1, using N-(4,4-dimethylcyclohexyl)-2,2-dimethyl-N-[(3S)-pyrrolidine-3-yl]propaneamide (300 mg, 1.06 mmol) prepared in Step B and (3S,4R)-1-t-butyl-4-(4-chlorophenyl)pyrrolidine-3-carboxylic acid prepared in Preparation Example A9-2 (510 mg, 90%).
MS[M+H]=544(M+1)
1H NMR (400 MHz, CDCl3) 7.58-7.47 (m, 2H), 7.37-7.30 (m, 2H), 3.92-3.48 (m, 7H), 3.47-3.22 (m, 3H), 2.77-2.69 (m, 1H), 2.53-2.33 (m, 1H), 1.78-1.57 (m, 8H), 1.52-1.38 (m, 10H), 1.32-1.20 (m, 10H), 0.94 (s, 3H), 0.92 (s, 3H)

EXAMPLE A10

(4S)-1-{[(3S,4R)-1-tert-butyl-4-(2,4-difluorophenyl)pyrrolidine-3-yl]carbonyl}-4-[(4,4-dimethylcyclohexyl)(methylsulfonyl)amino]-N,N-dimethyl-L-prolineamide HCl salt

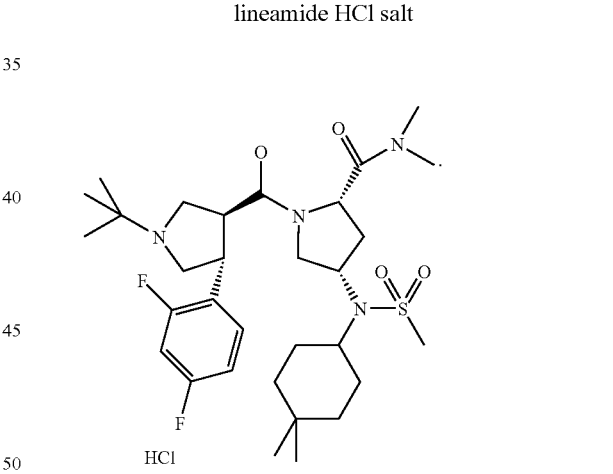

Step A: methyl (2S,4S)-1-BOC-4-[(4,4-dimethylcyclohexyl)(methylsulfonyl)amino]pyrrolidine-2-carboxylate To a solution of methyl (2S,4S)-1-BOC-4-[(4,4-dimethylcyclohexyl)amino]pyrrolidine-2-carboxylate (2.37 g, 6.7 mmol) prepared in Step A of Example A1 in DCM (10 ml) was added TEA (1.36 g, 13.4 mmol), slowly added dropwise methanesulfonylchloride (104 mg, 0.91 mmol) at 0° C., and stirred at rt for 30 min. After the reaction finished, the solvent was concentrated in vacuo, the residue was extracted with water and EtOAc. The organic layer was dried over MgSO4, concentrated in vacuo, and purified by column chromatography (eluent: EtOAc/Hex =1/1) to give the title compound (2.08 g, 72%).
MS[M+H]=433 (M+1)

Step B: (4S)-1-BOC-4-[(4,4-dimethylcyclohexyl)(methylsulfonyl)amino]-L-proline The title compound was prepared according to the procedure described in Step C of Example A1 using methyl (2S,4S)-1-BOC-4-[(4,4-dimethylcyclohexyl)(methylsulfonyl)amino]pyrrolidine-2-carb oxylate (500 mg, 1.19 mmol) prepared in Step A (470 mg, 95%).
MS[M+H]=419(M+1)

Step C: 1-BOC-(2S,4S)-2-[(dimethylaminocarbonyl)-4-[(4,4-dimethylcyclohexyl)(methylsulfonyl)amino]pyrrolidine The title compound was prepared according to the procedure described in Step D of Example A1 using (4S)-1-BOC-4-[(4,4-dimethylcyclohexyl)(methylsulfonyl)amino]-L-proline (470 mg, 1.13 mmol) prepared in Step B (402 mg, 80%).
MS[M+H]=446 (M+1)

Step D: (4S)-4-[(4,4-dimethylcyclohexyl)(methylsulfonylamino]-N,N-dimethyl-L-prolineamide The title compound was prepared according to the procedure described in Step E of Example A1 using 1-BOC-(2S,4S)-2-[(dimethylaminocarbonyl)-4-[(4,4-dimethylcyclohexyl)(methylsulfonyl)amino]pyrrolidine (402 mg, 0.90 mmol) prepared in Step C (310 mg, 97%).
MS[M+H]=346(M+1)

Step E: (4S)-1-{[(3S,4R)-1-tert-butyl-4-(2,4-difluorophenylpyrrolidine-3-yl]carbonyl}-4-[(4,4-dimethylcyclohexyl)(methylsulfonyl)amino]-N,N-dimethyl-L-prolineamide HCl salt The title compound was prepared according to the procedure described in Step F-G of Example A1 using (4S)-4-[(4,4-dimethylcyclohexyl)(methylsulfonyl)amino]-N,N-dimethyl-L-prolineamide (300 mg, 0.86 mmol) prepared in Step D (370 mg, 70%).
MS[M+H]=611(M+1)
1H NMR (400 MHz, CDCl3) 7.85-7.76 (m, 1H), 6.96-6.92 (m, 1H), 6.85-6.79 (m, 11H), 4.66 (t, 11H), 4.21-4.00 (m, 2H), 4.00-3.80 (m, 2H), 3.71-3.52 (m, 2H), 3.48-3.29 (m, 2H), 3.08 (s, 3H), 2.99 (s, 3H), 2.86 (s, 3H), 2.43-2.33 (m, 1H), 2.22-2.11 (m, 1H), 1.99-1.78 (m, 2H), 1.57-1.18 (m, 8H), 1.48 (s, 9H), 0.91 (s, 6H)

EXAMPLE A11

N-[(3S)-1-{[(3S,4R)-1-T-BUTYL-4-(4-chlorophenyl)pyrrolidine-3-yl]carbonyl}pyrrolidine-3-yl](4,4-dimethylcyclohexyl)amino}-2,2-dimethylpropane-1-ol HCl salt

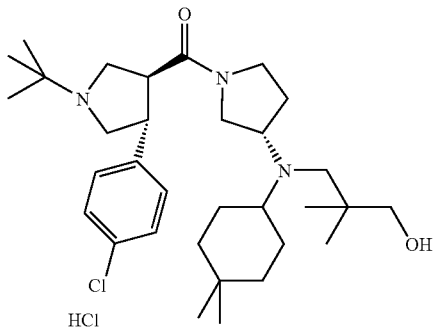

Step A: (3S) 1-Boc-3-[(4,4-dimethylcyclohexyl)(3-hydroxy-2,2-dimethylpropyl)amino]pyrrolidine To a solution of (3S)-1-Boc-3-[(4,4-dimethylcyclohexyl)(3-hydroxy-2,2-dimethylpropanoyl)amino]pyrrolidine (210 mg, 0.53 mmol) prepared in Step B of Example A8 in THF was added dropwise borane-methylsulfide complex (in THF, 2.0M, 0.4 ml, 0.8 mmol), and stirred at 80° C. for 3 h. After the reaction finished, the solvent was concentrated in vacuo, water added, extracted with EtOAc. The organic layer was dried over MgSO$_4$, concentrated in vacuo, and purified by column chromatography (eluent: DCM/MeOH=9/1) to give the title compound (140 mg, 75%).
MS[M+H]=382 (M+1)

Step B: N-[(3S)-1-{[(3S,4R)-1-t-butyl-4-(4-chlorophenyl)pyrrolidine-3-yl]carbonyl}pyrrolidine-3-yl](4,4-dimethylcyclohexyl)amino}-2,2-dimethylpropane-1-ol HCl salt The title compound was prepared according to the procedure described in Step E~G of Example A1 using (3S)-Boc-3-[(4,4-dimethylcyclohexyl)(3-hydroxy-2,2-dimethylpropyl)amino]pyrrolidine (140 mg, 0.36 mmol) prepared in Step A (156 mg, 78%).
MS[M+H]=546 (M+1)
1H NMR (500 MHz, CDCl3) 7.55-7.48 (m, 2H), 7.36-7.28 (m, 2H), 3.95-3.15 (m, 11H), 2.85-2.78 (m, 1H), 2.58-2.38 (m, 2H), 2.28-2.08 (m, 2H), 1.85-1.53 (m, 7H), 1.53-1.35 (m, 10H), 1.32-1.14 (m, 8H), 0.94 (s, 3H), 0.91 (s, 3H)

EXAMPLE A12

(3S)-1-{[(3S,4R)-1-tert-butyl-4-(4-chlorophenyl)pyrrolidine-3-yl]carbonyl}-N-isobutyl-N-(cis-4-methylcyclohexyl)pyrrolidine-3-amine HCl salt

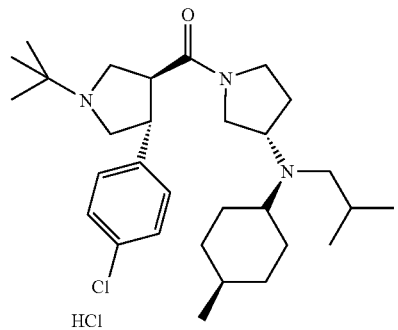

Step A: (3S)-1-Boc-3-[isobutyl(cis-4-methylcyclohexyl)amino]pyrrolidine

Commercially obtained (3S)-1-Boc-3-aminopyrrolidine (5.6 g, 30 mmol) was reacted according to the procedure described in Step A of Example A7 to give (3S)-1-Boc-3-cis-(4'-methylcyclohexyl)aminopyrrolidine. Then, the title compound was prepared from this compound and isobutylaldehyde via reductive amination as described in Step A of Example A1.
MS[M+H]=339 (M+1)

Step B: (3S)-1-{[(3S,4R)-1-tert-butyl-4-(4-chlorophenyl)pyrrolidine-3-yl]carbonyl}-N-isobutyl-N-(cis-4-methylcyclohexyl)pyrrolidine-3-amine HCl salt The title compound was prepared according to the procedure described in Steps E, F, G of Example A1 using (3S)-1-Boc-3-[isobutyl(cis-4-methylcyclohexyl)amino]pyrrolidine (100 mg, 0.30 mmol) prepared in Step A (115 mg, 78%).
MS[M+H]=502 (M+1)

1H NMR (400 MHz, CDCl3) 7.59-7.48 (m, 2H), 7.35-7.28 (m, 2H), 3.91-3.47 (m, 7H), 3.47-3.22 (m, 3H), 2.80-2.69 (m, 2H), 2.53-2.33 (m, 1H), 1.78-1.57 (m, 8H), 1.52-1.38 (m, 111H), 1.28-1.18 (m, 7H), 0.95 (d, 3H)

EXAMPLE A13~172

The following Examples were prepared according to the procedure described in Example A1~A7, A9, using appropriate compounds among Preparation Example A1, A2, A4, A9 and commercially available amine.

TABLE 4

| Example | R$^1$ | R$^{2'}$ | R$^{3'}$ | R$^4$ | R$^{5'}$ | * | ** | MS (M + 1) |
|---|---|---|---|---|---|---|---|---|
| A13 | t-Bu | 4-Cl | C(O)NH$_2$ | cis-4-Me-c-Hex | t-Bu | S | S | 573 |
| A14 | t-Bu | 2,4-diF | C(O)NH$_2$ | 4,4-diMe-c-Hex | t-Bu | S | S | 589 |
| A15 | t-Bu | 4-Cl | C(O)NH$_2$ | c-Hex | Me | S | S | 517 |
| A16 | t-Bu | 4-H | C(O)NH$_2$ | cis-4-Me-c-Hex | t-Bu | S | S | 539 |
| A17 | t-Bu | 4-Me | C(O)NH$_2$ | cis-4-Me-c-Hex | t-Bu | S | S | 553 |
| A18 | t-Bu | 4-F | C(O)NH$_2$ | cis-4-Me-c-Hex | t-Bu | S | S | 557 |
| A19 | t-Bu | 2,4-diF | C(O)NH$_2$ | 4,4-diMe-c-Hex | CH(CH$_3$)$_2$ | S | S | 575 |
| A20 | t-Bu | 2,4-diF | C(O)NH$_2$ | 4,4-diMe-c-Hex | CH(CH$_3$)$_2$ | S | R | 575 |
| A21 | t-Bu | 4-Cl | C(O)NH$_2$ | 4,4-diMe-c-Hex | CH(CH$_3$)$_2$ | S | S | 573 |
| A22 | t-Bu | 4-Cl | C(O)NH$_2$ | | CH(CH$_3$)$_2$ | S | S | 547 |
| A23 | t-Bu | 4-Cl | C(O)NH$_2$ | c-Pen | CH(CH$_3$)$_2$ | S | S | 531 |
| A24 | t-Bu | 2,4-diF | C(O)NH$_2$ | cis-4-Me-c-Hex | t-Bu | S | S | 575 |
| A25 | t-Bu | 2,4-diF | C(O)NH$_2$ | 4,4-diMe-c-Hex | | S | S | 573 |
| A26 | t-Bu | 2,4-diF | C(O)NH$_2$ | 4,4-diMe-c-Hex | | S | S | 603 |
| A27 | t-Bu | 4-Cl | C(O)NH$_2$ | cis-4-Me-c-Hex | | S | S | 601 |
| A28 | t-Bu | 2,4-diF | C(O)NH$_2$ | cis-4-Me-c-Hex | | S | S | 585 |
| A29 | t-Bu | 2,4-diF | C(O)NH$_2$ | 4,4-diMe-c-Hex | | S | S | 615 |

TABLE 4-continued

| Example | R¹ | R²' | R³' | R⁴ | R⁵' | * | ** | MS (M+1) |
|---|---|---|---|---|---|---|---|---|
| A30 | t-Bu | 2,4-diF | C(O)NH₂ | 4,4-diMe-c-Hex | (S)-tetrahydrofuran-2-yl | S | S | 603 |
| A31 | t-Bu | 2,4-diF | C(O)NH₂ | 4,4-diMe-c-Hex | (R)-tetrahydrofuran-2-yl | S | S | 603 |
| A32 | t-Bu | 2,4-diF | C(O)NH₂ | 4,4-diMe-c-Hex | furan-2-yl | S | S | 599 |
| A33 | t-Bu | 4-Cl | C(O)N(CH₃)₂ | c-Hex | Me | S | S | 545 |
| A34 | t-Bu | 4-Cl | C(O)N(CH₃)₂ | cis-4-Me-c-Hex | tetrahydrofuran-2-yl | S | S | 615 |
| A35 | t-Bu | 4-Cl | C(O)NHEt | c-Hex | Me | S | S | 545 |
| A36 | t-Bu | 4-Cl | C(O)NHEt | cis-4-Me-c-Hex | t-Bu | S | S | 601 |
| A37 | t-Bu | 2,4-diF | C(O)NHt-Bu | c-Hex | Me | S | S | 575 |
| A38 | t-Bu | 2,4-diF | C(O)NHt-Bu | cis-4-Me-c-Hex | t-Bu | S | R | 631 |
| A39 | t-Bu | 2,4-diF | C(O)NH₂ | 4,4-diF-c-Hex | t-Bu | S | S | 597 |
| A40 | t-Bu | 4-Cl | C(O)NH₂ | 4,4-diF-c-Hex | t-Bu | S | S | 595 |
| A41 | t-Bu | 4-Cl | C(O)NH₂ | 4,4-diF-c-Hex | CH(CH₃)₂ | S | S | 581 |
| A42 | t-Bu | 2,4-diF | C(O)N(CH₃)₂ | 4,4-diF-c-Hex | CH(CH₃)₂ | S | S | 611 |
| A43 | t-Bu | 2,4-diF | C(O)N(CH₃)₂ | 4,4-diF-c-Hex | t-Bu | S | S | 625 |
| A44 | t-Bu | 2,4-diF | C(O)N(CH₃)₂ | 4,4-diMe-c-Hex | CH(CH₃)₂ | S | S | 603 |
| A45 | t-Bu | 2,4-diF | C(O)NH₂ | cis-4-Me-c-Hex | t-Bu | S | R | 575 |
| A46 | t-Bu | 4-Cl | C(O)N(CH₃)₂ | 4,4-diMe-c-Hex | tetrahydrofuran-2-yl | S | S | 629 |
| A47 | t-Bu | 4-Cl | C(O)NHEt | 4,4-diMe-c-Hex | t-Bu | S | S | 615 |
| A48 | t-Bu | 4-Cl | C(O)N(CH₃)₂ | 4,4-diMe-c-Hex | t-Bu | S | S | 615 |
| A49 | t-Bu | 4-Cl | C(O)N(CH₃)₂ | cis-4-Me-c-Hex | t-Bu | S | S | 601 |
| A50 | t-Bu | 2,4-diF | C(O)N(CH₃)₂ | cis-4-Me-c-Hex | t-Bu | S | S | 603 |
| A51 | t-Bu | 4-Cl | C(O)NH₂ | 4,4-diMe-c-Hex | t-Bu | S | S | 587 |
| A52 | t-Bu | 2,4-diF | C(O)NHEt | 4,4-diMe-c-Hex | t-Bu | S | S | 617 |
| A53 | t-Bu | 2,4-diF | C(O)NMeEt | 4,4-diMe-c-Hex | t-Bu | S | S | 631 |
| A54 | t-Bu | 2,4-diF | C(O)NHiPr | 4,4-diMe-c-Hex | t-Bu | S | S | 631 |
| A55 | t-Bu | 2,4-diF | azetidin-1-yl-carbonyl | 4,4-diMe-c-Hex | t-Bu | S | S | 629 |
| A56 | t-Bu | 2,4-diF | C(O)N(CH₃)₂ | 4,4-diMe-c-Hex | furan-3-yl | S | S | 627 |

TABLE 4-continued

| Example | R¹ | R²' | R³' | R⁴ | R⁵' | * | ** | MS (M + 1) |
|---|---|---|---|---|---|---|---|---|
| A57 | t-Bu | 2,4-diF | C(O)N(CH₃)₂ | 4,4-diMe-c-Hex | tetrahydrofuran-3-yl | S | S | 631 |
| A58 | t-Bu | 2,4-diF | C(O)N(CH₃)₂ | 4,4-diMe-c-Hex | C(CH₃)₂CH₂OH | S | S | 633 |
| A59 | i-Pr | 2,4-diF | C(O)N(CH₃)₂ | 4,4-diF-c-Hex | t-Bu | S | S | 611 |
| A60 | t-Bu | 2,4-diF | C(O)N(CH₃)₂ | 4,4-diMe-c-Hex | 2,5-dihydrofuran-3-yl | S | S | 629 |
| A61 | t-Bu | 2,4-diF | C(O)N(CH₃)₂ | 4,4-diMe-c-Hex | t-Bu | S | R | 617 |
| A62 | t-Bu | 4-Cl | C(O)N(CH₃)₂ | 4,4-diMe-c-Hex | C(CH₃)₂CH₂OH | S | S | 631 |
| A63 | t-Bu | 2,4-diF | C(O)N(CH₃)₂ | 4,4-diMe-c-Hex | (S)-tetrahydrofuran-2-yl | S | S | 631 |
| A64 | t-Bu | 2,4-diF | C(O)N(CH₃)₂ | 4,4-diMe-c-Hex | furan-2-yl | S | S | 627 |
| A65 | t-Bu | 2,4-diF | C(O)N(CH₃)₂ | 4,4-diF-c-Hex | C(CH₃)₂CH₂OH | S | S | 641 |
| A66 | t-Bu | 2,4-diF | C(O)N(CH₃)₂ | 4,4-diMe-c-Hex | (R)-tetrahydrofuran-2-yl | S | S | 631 |
| A67 | t-Bu | 2,4-diF | C(O)NMeEt | 4,4-diMe-c-Hex | C(CH₃)₂CH₂OH | S | S | 647 |
| A68 | t-Bu | 4-Cl | C(O)NMeEt | 4,4-diMe-c-Hex | furan-2-yl | S | S | 639 |
| A69 | t-Bu | 2,4-diF | C(O)NMeEt | 4,4-diMe-c-Hex | furan-2-yl | S | S | 641 |
| A70 | t-Bu | 2,4-diF | C(O)N(CH₃)₂ | 3,3-4,4-tetraMe-c-Pen | t-Bu | S | S | 631 |
| A71 | t-Bu | 4-Cl | C(O)N(CH₃)₂ | 4,4-diF-c-Hex | C(CH₃)₂CH₂OH | S | S | 639 |
| A72 | t-Bu | 4-Cl | C(O)NMeEt | 4,4-diF-c-Hex | C(CH₃)₂CH₂OH | S | S | 653 |
| A73 | t-Bu | 2,4-diF | C(O)NMeEt | 4,4-diMe-c-Hex | tetrahydrofuran-2-yl | S | S | 645 |
| A74 | t-Bu | 4-Cl | C(O)N(CH₃)₂ | 3,3-4,4-tetraMe-c-Pen | t-Bu | S | S | 629 |
| A75 | t-Bu | 4-Cl | C(O)NMeEt | 4,4-diF-c-Hex | t-Bu | S | S | 637 |

TABLE 4-continued

| Example | R¹ | R²' | R³' | R⁴ | R⁵' | * | ** | MS (M + 1) |
|---|---|---|---|---|---|---|---|---|
| A76 | t-Bu | 4-Cl | C(O)N(CH₃)₂ | 4,4-diF-c-Hex | (tetrahydrofuran-2-yl, H) | S | S | 637 |
| A77 | t-Bu | 4-Cl | C(O)NMeEt | 4,4-diF-c-Hex | (tetrahydrofuran-2-yl, H) | S | S | 651 |
| A78 | t-Bu | 4-Cl | C(O)N(CH₃)₂ | cis-4-Me-c-Hex | C(CH₃)₂CH₂OH | S | S | 617 |
| A79 | t-Bu | 4-Cl | C(O)NMeEt | cis-4-Me-c-Hex | C(CH₃)₂CH₂OH | S | S | 631 |
| A80 | t-Bu | 4-Cl | C(O)N(CH₃)₂ | 4,4-diF-c-Hex | CH(CH₃)₂ | S | S | 609 |
| A81 | t-Bu | 4-Cl | C(O)NMeEt | 4,4-diF-c-Hex | CH(CH₃)₂ | S | S | 623 |
| A82 | t-Bu | 4-Cl | C(O)NHtBu | 4,4-diMe-c-Hex | t-Bu | S | R | 643 |
| A83 | t-Bu | 4-Cl | C(O)NMeEt | 4,4-diMe-c-Hex | C(CH₃)₂C(O)NH₂ | S | S | 658 |
| A84 | t-Bu | 4-Cl | C(O)N(CH₃)₂ | 4,4-diMe-c-Hex | (tetrahydrofuran-2-yl, H) | S | S | 629 |
| A85 | t-Bu | 4-Cl | C(O)NMeEt | 4,4-diMe-c-Hex | (tetrahydrofuran-3-yl) | S | S | 643 |
| A86 | t-Bu | 4-Cl | pyrrolidine-1-carbonyl | 4,4-diF-c-Hex | t-Bu | S | S | 649 |
| A87 | t-Bu | 4-Cl | C(O)N(CH₃)₂ | 4,4-diF-c-Hex | cBu | S | S | 621 |
| A88 | t-Bu | 4-Cl | C(O)N(CH₃)₂ | 4,4-diF-c-Hex | CH₂OCH₃ | S | S | 611 |
| A89 | t-Bu | 4-Cl | C(O)N(CH₃)₂ | 4,4-diF-c-Hex | cPr | S | S | 607 |
| A90 | t-Bu | 4-Cl | C(O)NMeEt | spiro[2.5]octan-6-yl | (tetrahydrofuran-2-yl, H) | S | S | 641 |
| A91 | t-Bu | 4-Cl | C(O)N(CH₃)₂ | 4,4-diMe-c-Hex | CH₃ | S | S | 573 |
| A92 | t-Bu | 4-Cl | C(O)NMeEt | 4,4-Me-c-Hex | CH₃ | S | S | 587 |
| A93 | t-Bu | 4-Cl | CH₂-pyrrolidin-1-yl | 4,4-diMe-c-Hex | CH₃ | S | S | 599 |

TABLE 4-continued

| Example | R¹ | R²' | R³' | R⁴ | R⁵' | * | ** | MS (M + 1) |
|---|---|---|---|---|---|---|---|---|
| A94 | t-Bu | 4-Cl | C(O)-piperidinyl | 4,4-diMe-c-Hex | $CH_3$ | S | S | 613 |
| A95 | t-Bu | 2,4-diF | C(O)-morpholinyl | 4,4-diMe-c-Hex | $CH_3$ | S | S | 617 |
| A96 | t-Bu | 4-Cl | C(O)-morpholinyl | 4,4-diMe-c-Hex | $CH_3$ | S | S | 615 |
| A97 | t-Bu | 4-Cl | C(O)NMeEt | 4,4-diMe-c-Hex | tetrahydrofuran-2-yl | S | S | 643 |
| A98 | t-Bu | 4-Cl | C(O)NEt | 4,4-diMe-c-Hex | $C(CH_3)_2CH_2OH$ | S | S | 631 |
| A99 | t-Bu | 4-Cl | C(O)NHPh | 4,4-diMe-c-Hex | t-Bu | S | S | 663 |
| A100 | t-Bu | 4-Cl | C(O)NH-(pyridin-4-yl) | 4,4-diMe-c-Hex | t-Bu | S | S | 664 |
| A101 | t-Bu | 4-Cl | C(O)NH-(thiazol-2-yl) | 4,4-diMe-c-Hex | t-Bu | S | S | 670 |
| A102 | t-Bu | 4-Cl | $C(O)N(CH_3)_2$ | cis-4-Me-c-Hex | $C(CH_3)_2CH_2OH$ | R | S | 617 |
| A103 | Me | 4-Cl | $C(O)NH_2$ | cis-4-Me-c-Hex | t-Bu | S | S | 531 |
| A104 | Me | 4-Cl | $C(O)NH_2$ | 4,4-diMe-c-Hex | $CH(CH_3)_2$ | S | S | 531 |
| A105 | Me | 2,4-diF | $C(O)NH_2$ | 4,4-diMe-c-Hex | t-Bu | S | S | 547 |
| A106 | Me | 2,4-diF | $C(O)NH_2$ | cis-4-Me-c-Hex | tetrahydrofuran-3-yl | S | S | 547 |

TABLE 4-continued

| Example | R¹ | R²' | R³' | R⁴ | R⁵' | * | ** | MS (M + 1) |
|---|---|---|---|---|---|---|---|---|
| A107 | Me | 4-Cl | C(O)NH₂ | 4,4-diMe-c-Hex | (tetrahydrofuran-2-yl, H up) | S | S | 559 |
| A108 | Me | 2,4-diF | C(O)N(CH₃)₂ | cis-4-Me-c-Hex | (tetrahydrofuran-2-yl) | S | S | 575 |
| A109 | t-Bu | 4-Cl | CO₂CH₃ | 4,4-diMe-c-Hex | t-Bu | S | S | 602 |
| A110 | t-Bu | 4-Cl | CO₂H | 4,4-diMe-c-Hex | t-Bu | S | S | 588 |
| A111 | t-Bu | 4-Cl | H | 4,4-diF-c-Hex | C(CH₃)₂CH₂OH | S | | 568 |
| A112 | t-Bu | 4-Cl | H | 4,4-diMe-c-Hex | CH(CH₃)₂ | S | | 530 |
| A113 | t-Bu | 4-Cl | H | 4,4-diMe-c-Hex | CH₂C(CH₃)₃ | S | | 558 |
| A114 | t-Bu | 4-Cl | H | 4,4-diMe-c-Hex | Ph | S | | 564 |
| A115 | t-Bu | 4-Cl | H | 4,4-diMe-c-Hex | (tetrahydrofuran-2-yl, H dashed) | S | | 558 |
| A116 | t-Bu | 4-Cl | H | 4,4-diMe-c-Hex | (tetrahydrofuran-2-yl, H wedge) | S | | 558 |
| A117 | t-Bu | 4-Cl | H | 4,4-diMe-c-Hex | (tetrahydrofuran-3-yl) | S | | 558 |
| A118 | t-Bu | 4-Cl | H | 4,4-diMe-c-Hex | (tetrahydropyran-4-yl) | S | | 572 |
| A119 | t-Bu | 4-Cl | H | 4,4-diMe-c-Hex | (2,5-dihydrofuran-3-yl) | S | | 556 |
| A120 | t-Bu | 4-Cl | H | 4,4-diMe-c-Hex | (cyclohex-1-en-1-yl) | S | | 568 |
| A121 | t-Bu | 4-Cl | H | 4,4-diMe-c-Hex | (isopropenyl) | S | | 528 |
| A122 | t-Bu | 4-Cl | H | cis-4-Me-c-Hex | CH₃ | S | | 488 |

TABLE 4-continued

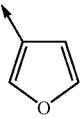

salt

| Example | R¹ | R²' | R³' | R⁴ | R⁵' | * | ** | MS (M + 1) |
|---|---|---|---|---|---|---|---|---|
| A123 | t-Bu | 4-Cl | H | 4,4-diMe-c-Hex | 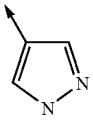 | | S | 554 |
| A124 | t-Bu | 4-Cl | H | 4,4-diMe-c-Hex |  | | S | 554 |
| A125 | t-Bu | 4-Cl | H | 4,4-diMe-c-Hex | 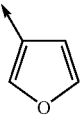 | | S | 571 |
| A126 | t-Bu | 4-Cl | H | 4,4-diMe-c-Hex | CH₂OCH₃ | | S | 532 |
| A127 | t-Bu | 4-Cl | H | 4,4-diMe-c-Hex | CH₂OCH₂CH₃ | | S | 546 |
| A128 | t-Bu | 4-Cl | H | 4,4-diMe-c-Hex | C(CH₃)₂OH | | S | 546 |
| A129 | t-Bu | 4-Cl | H | cis-4-Me-c-Hex | CH₂CH₃ | | S | 502 |
| A130 | t-Bu | 4-Cl | H | cis-4-Me-c-Hex | CH₂OCH₃ | | S | 518 |
| A131 | t-Bu | 4-Cl | H | cis-4-Me-c-Hex | t-Bu | | S | 530 |
| A132 | t-Bu | 4-Cl | H | cis-4-Me-c-Hex | cyclopentyl | | S | 542 |
| A133 | t-Bu | 4-Cl | H | cis-4-Me-c-Hex | 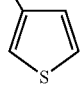 | | S | 540 |
| A134 | t-Bu | 4-Cl | H | cis-4-Me-c-Hex |  | | S | 556 |
| A135 | t-Bu | 4-Cl | H | cis-4-Me-c-Hex | C(CH₃)₂CH₂OH | | S | 546 |
| A136 | t-Bu | 4-Cl | H | cis-4-Me-c-Hex | C(CH₃)₂CH(CH₃)OH | | S | 560 |
| A137 | t-Bu | 4-Cl | H | cis-4-Me-c-Hex | C(CH₃)₂C(CH₃)₂OH | | S | 574 |
| A138 | t-Bu | 4-Cl | H | cis-4-Me-c-Hex | C(CH₃)₂CN | | S | 541 |
| A139 | t-Bu | 4-Cl | H | cis-4-Me-c-Hex | 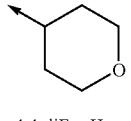 | | S | 514 |
| A140 | t-Bu | 4-Cl | H | cis-4-Me-c-Hex | CH₂C(CH₃)₃ | | S | 544 |
| A141 | t-Bu | 4-Cl | H | Trans-4-Me-c-Hex | CH(CH₃)₂ | | S | 516 |
| A142 | t-Bu | 4-Cl | H | Trans-4-Me-c-Hex | t-Bu | | S | 530 |
| A143 | t-Bu | 2,4-diF | H | Trans-4-Me-c-Hex | t-Bu | | S | 532 |
| A144 | t-Bu | 4-Cl | H | cyclopentyl | C(CH₃)₂CH₂OH | | S | 518 |
| A145 | t-Bu | 4-Cl | H |  | C(CH₃)₂CH₂OH | | S | 534 |
| A146 | t-Bu | 4-Cl | H | 4,4-diF-c-Hex | CH(CH₃)₂ | | S | 538 |

TABLE 4-continued

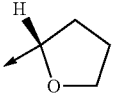

salt

| Example | R¹ | R²' | R³' | R⁴ | R⁵' | * | ** | MS (M + 1) |
|---|---|---|---|---|---|---|---|---|
| A147 | t-Bu | 4-Cl | H | 4,4-diF-c-Hex | t-Bu | | S | 552 |
| A148 | t-Bu | 4-Cl | H | 4,4-diF-c-Hex | 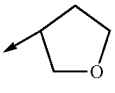 | | S | 566 |
| A149 | t-Bu | 4-Cl | H | 4,4-diF-c-Hex | 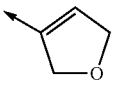 | | S | 566 |
| A150 | t-Bu | 4-Cl | H | 4,4-diF-c-Hex | CH₃ | | | 510 |
| A151 | t-Bu | 4-Cl | H | Cis-4-CF₃-c-Hex | CH(CH₃)₂ | | S | 570 |
| A152 | t-Bu | 4-Cl | H | Cis-4-CF₃-c-Hex | t-Bu | | S | 584 |
| A153 | t-Bu | 4-Cl | H | Trans-4-CF₃-c-Hex | t-Bu | | S | 584 |
| A154 | t-Bu | 2,4-diF | H | 4,4-diMe-c-Hex | CH(CH₃)₂ | | S | 532 |
| A155 | t-Bu | 2,4-diF | H | 4,4-diMe-c-Hex | t-Bu | | S | 546 |
| A156 | t-Bu | 2,4-diF | H | 4,4-diMe-c-Hex | 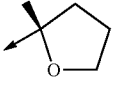 | | S | 558 |
| A157 | t-Bu | 2,4-diF | H | 4,4-diMe-c-Hex | 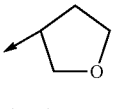 | | S | 560 |
| A158 | t-Bu | 2,4-diF | H | 4,4-diMe-c-Hex |  | | S | 560 |
| A159 | t-Bu | 2,4-diF | H | 4,4-diMe-c-Hex | C(CH₃)₂CH₂OH | | S | 562 |
| A160 | t-Bu | 2,4-diF | H | 4,4-diMe-c-Hex | CH₂CH₂OCH₂CH₃ | | S | 562 |
| A161 | t-Bu | 2,4-diF | H | cis-4-Me-c-Hex | t-Bu | | S | 532 |
| A162 | t-Bu | 2,4-diF | H | cis-4-Me-c-Hex | 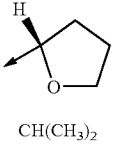 | | S | 542 |
| A163 | t-Bu | 2,4-diF | H | 4,4-diF-c-Hex | C(CH₃)₃ | | S | 554 |
| A164 | t-Bu | 2,4-diF | H | 4,4-diF-c-Hex | C(CH₃)₂CH₂OH | | S | 570 |
| A165 | t-Bu | 2,4-diF | H | 4,4-diF-c-Hex | 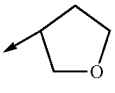 | | S | 568 |
| A166 | t-Bu | 4-F | H | Cis-4-Me-c-Hex | CH(CH₃)₂ | | S | 500 |
| A167 | t-Bu | 4-Me | H | 4,4-diMe-c-Hex | t-Bu | | S | 524 |
| A168 | t-Bu | 4-Cl | H | cyclobutyl | C(CH₃)₂CH₂OH | | S | 504 |
| A169 | t-Bu | 4-Cl | H | cycloheptyl | C(CH₃)₂CH₂OH | | S | 546 |

TABLE 4-continued

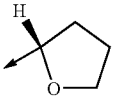

salt

| Example | R¹ | R²' | R³' | R⁴ | R⁵' | * | ** | MS (M + 1) |
|---|---|---|---|---|---|---|---|---|
| A170 | Me | 4-Cl | H | 4,4-diMe-c-Hex | 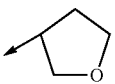 | | S | 516 |
| A171 | Me | 4-Cl | H | 4,4-diMe-c-Hex | 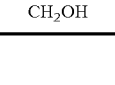 | | S | 516 |
| A172 | t-Bu | 4-Cl | H | 4,4-diMe-c-Hex | CH₂OH | | S | 518 |

(A44) (TFA Salt)
1H NMR (500 MHz, CDCl3) 7.60-7.52 (m, 1H), 6.92-6.85 (m, 1H), 6.82-6.74 (m, 1H), 4.72 (t, 1H), 4.23-4.10 (m, 2H), 4.06-3.93 (m, 2H), 3.74-3.40 (m, 5H), 3.35-3.25 (m, 1H), 2.99 (s, 3H), 2.95 (s, 3H), 2.81-2.66 (m, 2H), 2.17-2.06 (m, 1H), 1.68-1.14 (m, 611), 1.44 (s, 9H), 1.14-1.00 (m, 2H), 1.07 (dd, 6H), 0.95 (s, 3H), 0.92 (s, 3H)

(A50) (TFA Salt)
1H NMR (500 MHz, CDCl3) 7.61-7.54 (m, 1H), 6.92-6.86 (m, 1H), 6.81-6.75 (m, 1H), 4.71 (t, 1H), 4.25-4.07 (m, 2H), 4.04-3.93 (m, 2H), 3.84-3.71 (m, 1H), 3.70-3.55 (m, 2H), 3.55-3.45 (m, 1H), 3.45-3.35 (m, 1H), 3.35-3.25 (m, 1H), 3.11 (s, 6H), 2.81-2.70 (m, 1H), 2.01-1.90 (T, 1H), 1.60-1.39 (m, 5H), 1.44 (s, 9H), 1.28-1.13 (m, 4H), 1.21 (s, 9H), 0.97 (d, 3H)

(A52) (HCl Salt)
1H NMR (400 MHz, CDCl3) 8.10-8.04 (m, 1H), 6.97-6.93 (m, 1H), 6.79-6.74 (m, 1H), 4.70 (t, 1H), 4.35-4.22 (m, 2H), 3.95-3.40 (m, 2H), 3.81-3.69 (m, 1H), 3.67-3.54 (m, 2H), 3.42-3.29 (m, 2H), 3.26-3.11 (m, 3H), 2.82-2.68 (m, 1H), 2.19-1.97 (m, 1H), 1.61-1.39 (m, 4H), 1.49 (s, 9H), 1.32-1.15 (m, 7H), 1.22 (s, 9H), 0.95 (s, 3H), 0.91 (s, 3H)

(A53) (HCl Salt)
1H NMR (400 MHz, CDCl3) 8.10-8.04 (m, 1H), 6.97-6.93 (m, 1H), 6.79-6.74 (m, 1H), 4.70 (t, 1H), 4.35-4.22 (m, 2H), 3.95-3.40 (m, 2H), 3.81-3.69 (m, 1H), 3.67-3.54 (m, 2H), 3.42-3.29 (m, 2H), 3.26-3.11 (m, 3H), 2.99 (s, 3H), 2.82-2.68 (m, 1H), 2.19-1.97 (m, 1H), 1.61-1.39 (m, 4H), 1.49 (s, 9H), 1.32-1.15 (m, 7H), 1.22 (s, 9H), 0.95 (s, 3H), 0.91 (s, 3H)

(A54) (HCl Salt)
1H NMR (400 MHz, CDCl3) 8.10-8.04 (m, 1H), 6.97-6.93 (m, 1H), 6.79-6.74 (m, 1H), 4.70 (t, 1H), 4.35-4.22 (m, 2H), 3.98-3.93 (m, 1H), 3.95-3.81 (m, 2H), 3.81-3.69 (m, 1H), 3.67-3.54 (m, 2H), 3.42-3.29 (m, 2H), 3.26-3.11 (m, 3H), 2.82-2.68 (m, 1H), 2.19-1.97 (m, 1H), 1.61-1.39 (m, 4H), 1.49 (s, 9H), 1.34-1.15 (m, 10H), 1.22 (s, 9H), 0.95 (s, 3H), 0.91 (s, 3H)

(A55) (HCl Salt)
1H NMR (400 MHz, CDCl3) 8.10-8.04 (m, 1H), 6.97-6.93 (m, 1H), 6.79-6.74 (m, 1H), 4.70 (t, 1H), 4.35-4.22 (m, 2H), 3.97-3.81 (m, 6H), 3.81-3.69 (m, 1H), 3.67-3.54 (m, 2H), 3.42-3.29 (m, 2H), 3.22-3.11 (m, 1H), 2.82-2.68 (m, 1H), 2.35-2.20 (m, 2H), 2.19-1.97 (m, 1H), 1.61-1.39 (m, 4H), 1.49 (s, 9H), 1.31-1.15 (m, 4H), 1.22 (s, 9H), 0.95 (s, 3H), 0.91 (s, 3H)

(A60) (HCl Salt)
1H NMR (400 MHz, CDCl3) 8.14-8.00 (m, 1H), 7.03-6.91 (m, 1H), 6.83-6.72 (m, 1H), 5.94 (s, 1H), 4.89-4.66 (m, 5H), 4.30-4.12 (m, 2H), 4.12-3.99 (m, 1H), 3.99-3.88 (m, 1H), 3.74-3.47 (m, 4H), 3.42-3.26 (m, 2H), 3.00 (s, 3H), 2.95 (s, 3H), 2.76-2.52 (m, 1H), 2.24-2.09 (m, 1H), 1.57-1.34 (m, 4H), 1.49 (s, 9H), 1.34-1.16 (m, 4H), 0.93 (s, 3H), 0.90 (s, 3H)

A62) (HCl Salt)
1H NMR (400 MHz, CDCl3) 7.62 (d, 2H), 7.31 (d, 2H), 4.70 (t, 1H), 4.36-4.19 (m, 1H), 3.97-3.80 (m, 3H), 3.78-3.64 (m, 2H). 3.63-3.52 (m, 2H), 3.39-3.21 (m, 3H), 3.19-3.10 (m, 1H), 2.99 (s, 6H), 2.74-2.62 (m, 1H), 2.11-1.97 (m, 1H), 1.67-1.36 (m, 14H), 1.35-1.15 (m, 9H), 0.95 (s, 3H), 0.92 (s, 3H)

(A63) (HCl Salt)
1H NMR (400 MHz, CDCl3) 8.08-8.02 (m, 1H), 6.96-6.92 (m, 1H), 6.78-6.73 (m, 1H), 4.68 (t, 1H), 4.48 (t, 1H), 4.40-4.21 (m, 1H), 4.04-3.81 (m, 5H), 3.80-3.71 (m, 2H), 3.66-3.46 (m, 3H), 3.22-3.12 (m, 1H), 2.97 (s, 6H), 2.86-2.62 (m, 1H), 2.41-2.28 (m, 1H), 2.13-1.82 (m, 4H), 1.64-1.39 (m, 4H), 1.49 (s, 9H), 1.39-1.22 (m, 2H), 1.20-1.08 (m, 2H), 0.97 (s, 3H), 0.94 (s, 3H)

(A67) (HCl Salt)
1H NMR (400 MHz, CDCl3) 8.10-8.04 (m, 1H), 6.97-6.93 (m, 1H), 6.79-6.74 (m, 1H), 4.69 (t, 1H), 4.38-4.19 (m, 2H), 4.03-3.80 (m, 2H), 3.76-3.50 (m, 4H), 3.43-3.08 (m, 4H), 2.94 (s, 3H), 2.74-2.62 (m, 1H), 2.11-1.97 (m, 1H), 1.67-1.36 (m, 14H), 1.35-1.15 (m, 9H), 1.10 (t, 3H), 0.95 (s, 3H), 0.92 (s, 3H)

(A68) (HCl Salt)
1H NMR (500 MHz, CDCl3) 8.13-8.03 (m, 1H), 7.62 (s, 1H), 7.40 (s, 1H), 6.99-6.92 (m, 1H), 6.78-6.71 (m, 1H), 6.43 (s, 1H), 4.75-4.67 (m, 1H), 4.31-4.18 (m, 2H), 4.11-4.01 (m, 1H), 3.96-3.89 (m, 1H), 3.78-3.66 (m, 1H), 3.66-3.48 (m, 4H), 3.42-3.24 (m, 4H), 2.93 (d, 3H), 2.23-2.12 (m, 1H), 1.88-1.06 (m, 8H), 1.48 (s, 9H), 1.20 (t, 3H), 0.91 (s, 3H), 0.90 (s, 3H)

(A72) (HCl Salt)
1H NMR (500 MHz, CDCl3) 7.64-7.56 (m, 2H), 7.35-7.29 (m, 2H), 4.70-4.61 (m, 1H), 4.32-4.16 (m, 1H), 3.97-3.50 (m, 7H), 3.41-3.14 (m, 5H), 2.93 (s, 3H), 2.76-2.56 (m, 1H), 2.40-2.28 (m, 1H), 2.23-2.12 (m, 1H), 1.70-1.14 (m, 8H), 1.48 (s, 9H), 1.30-1.16 (m, 6H), 1.10 (t, 3H)

(A73) (HCl Salt)
1H NMR (400 MHz, CDCl3) 8.08-8.02 (m, 1H), 6.96-6.92 (m, 1H), 6.78-6.73 (m, 1H), 4.68 (t, 1H), 4.48 (t, 1H), 4.40-4.21 (m, 1H), 4.04-3.81 (m, 51), 3.80-3.71 (m, 2H), 3.66-3.46 (m, 3H), 3.45-3.12 (m, 3H), 2.97 (d, 3H), 2.86-2.62 (m, 1H), 2.41-2.28 (m, 1H), 2.13-1.82 (m, 4H), 1.64-1.39 (m, 4H), 1.49 (s, 9H), 1.39-1.22 (m, 2H), 1.26 (t, 3H), 1.20-1.08 (m, 2H), 0.97 (s, 3H), 0.94 (s, 3H)

(A75) (HCl Salt)
1H NMR (400 MHz, CDCl3) 7.60 (d, 2H), 7.31 (d, 2H), 4.65 (t, 1H), 4.33-4.11 (m, 1H), 4.00-3.51 (m, 5H), 3.37-3.08 (m, 6H), 2.95 (d, 3H), 2.45-1.96 (m, 51), 1.90-1.56 (m, 5H), 1.48 (s, 9H), 1.21 (s, 9H), 1.10 (t, 3H)

(A83) (TFA Salt)
1H NMR (500 MHz, CDCl3) 7.36 (d, 2H), 7.29 (d, 2H), 4.60 (t, 1H), 4.38-4.25 (m, 1H), 4.25-4.14 (m, 1H), 3.92-3.78 (m, 1H), 3.72-3.27 (m, 8H), 3.19-3.12 (m, 1H), 2.96 (d, 3H), 2.85-2.68 (m, 1H), 2.13-1.99 (m, 1H), 1.62-1.11 (m, 1111), 1.43 (s, 9H), 1.39 (s, 3H), 1.33 (s, 3H), 0.90 (s, 3H), 0.87 (s, 3H)

(A90) (HCl Salt)
1H NMR (400 MHz, CDCl3) 7.50 (d, 2H), 7.32 (d, 2H), 4.68 (t, 1H), 4.48 (t, 1H), 4.40-4.21 (m, 1H), 4.03-3.90 (t, 3H), 3.90-3.81 (m, 2H), 3.80-3.70 (m, 2H), 3.66-3.46 (m, 3H), 3.45-3.12 (m, 3H), 2.97 (d, 3H), 2.86-2.62 (m, 1H), 2.41-2.28 (m, 1H), 2.13-1.82 (m, 4H), 1.64-1.40 (m, 4H), 1.52 (s, 9H), 1.40-1.22 (m, 2H), 1.26 (t, 3H), 1.20-1.08 (m, 2H), 0.39-0.11 (m, 4H)

(A96) (TFA Salt)
1H NMR (500 MHz, CDCl3) 7.40 (d, 2H), 7.29 (d, 2H), 4.69 (t, 1H), 4.12-4.00 (m, 2H), 3.89-3.75 (m, 2H), 3.74-3.53 (m, 9H), 3.51-3.30 (m, 4H), 3.28-3.18 (M, 1H), 2.72-2.63 (m, 1H), 2.07 (s, 3H), 1.60-1.38 (m, 15H), 1.32-1.21 (m, 3H), 0.92 (s, 3H), 0.90 (s, 3H)

(A97) (TFA Salt)
1H NMR (400 MHz, CDCl3) 7.40 (d, 2H), 7.31 (d, 2H), 4.66 (t, 1H), 4.51 (t, 1H), 4.26-4.13 (m, 1H), 4.09-3.96 (m, 1H), 3.96-3.65 (m, 5H), 3.65-3.21 (m, 7H), 2.94 (d, 3H), 2.88-2.27 (m, br, 2H), 2.19-1.82 (m, 4H), 1.62-1.39 (m, 4H), 1.44 (s, 9H), 1.35-1.12 (m, br, 2H), 1.23 (t, 3H), 1.12-1.06 (m, 2H), 0.94 (s, 3H), 0.91 (s, 3H)

(A98) (TFA Salt)
1H NMR (500 MHz, CDCl3) 7.37 (d, 2H), 7.32 (d, 2H), 4.34-4.21 (m, 1H), 4.02-3.86 (m, 2H), 3.85-3.12 (m, 1H), 2.95-2.83 (m, 1H), 2.53-2.40 (m, 1H), 2.31-2.19 (m, 1H), 1.60-1.14 (m, 8H), 1.44 (s, 9H), 1.21 (s, 6H), 1.11 (t, 3H), 0.94 (s, 3H), 0.91 (s, 3H)

(A99) (TFA Salt)
1H NMR (500 MHz, CDCl3) 7.66 (d, 2H), 7.39-7.22 (m, 6H), 7.06 (t, 1H), 4.34 (t, 1H), 3.93-3.84 (m, 2H), 3.84-3.75 (m, 2H), 3.74-3.35 (m, 4H), 3.32-3.23 (m, 1H), 3.04-2.96 (m, 1H), 2.56-2.46 (m, 1H), 2.35-2.25 (m, 1H), 1.68-1.17 (m, 8H), 1.40 (s, 9H), 1.25 (s, 9H), 0.95 (s, 3H), 0.93 (s, 3H)

(A158) (TFA Salt)
1H NMR (500 MHz, CDCl3) 7.57-7.41 (m, 1H), 6.95-6.86 (m, 1H), 6.86-6.75 (m, 1H), 4.17-3.72 (m, 9H), 3.72-3.36 (m, 6H), 3.36-3.26 (m, 1H), 3.26-3.09 (m, 2H), 2.55-2.41 (m, 1H), 2.22-1.98 (m, 2H), 1.94-1.77 (m, 1H), 1.73-1.23 (m, 7H), 1.44 (s, 9H), 0.95 (s, 3H), 0.92 (s, 3H)

EXAMPLE A173~177

The following Examples were prepared according to the procedure described in Example A10, using appropriate compounds among Preparation Example A1, A2, A4, A9 and commercially available amine.

TABLE 5

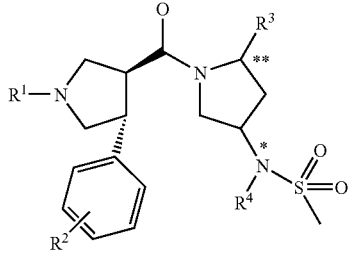

| Example | R¹ | R²' | R³ | R⁴ | * | ** | MS (M + 1) |
|---------|-----|-------|-----------------------|------------------|---|----|------------|
| A173    | t-Bu | 4-Cl | H                     | 4,4-diMe-c-Hex   | S |    | 538        |
| A174    | t-Bu | 4-Cl | H                     | cis-4-Me-c-Hex   | S |    | 524        |
| A175    | t-Bu | 2,4-diF | H                  | cis-4-Me-c-Hex   | S |    | 526        |
| A176    | t-Bu | 4-Cl | C(O)N(CH₃)₂           | 4,4-diMe-c-Hex   | S | S  | 609        |
| A177    | t-Bu | 4-Cl | C(O)NMeEt             | 4,4-diMe-c-Hex   | S | S  | 623        |

EXAMPLE A178~188

The following Examples were prepared according to the procedure described in Example A11, A12, using appropriate compounds of Preparation Example A1, A2, A4, A9 and commercially available amine.

TABLE 6

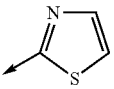

| Example | R¹ | R²' | R³' | R⁴ | R⁵ | * | MS (M + 1) |
|---------|-----|------|-----|----------------|----------------------|---|------------|
| A178 | t-Bu | 4-Cl | H | 4,4-diMe-c-Hex | $CH_2OH$ | S | 518 |
| A179 | t-Bu | 4-Cl | H | 4,4-diMe-c-Hex | 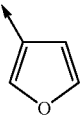 | S | 571 |
| A180 | t-Bu | 4-Cl | H | 4,4-diMe-c-Hex | Ph | S | 564 |
| A181 | t-Bu | 4-Cl | H | 4,4-diMe-c-Hex | 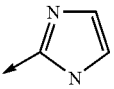 | S | 554 |
| A182 | t-Bu | 4-Cl | H | Cis-4-Me-c-Hex | $CH_2OH$ | S | 504 |
| A183 | t-Bu | 4-Cl | H | Cis-4-Me-c-Hex | $CH_2NH_2$ | S | 503 |
| A184 | t-Bu | 4-Cl | H | Cis-4-Me-c-Hex | $CH_2NHC(O)CH_3$ | S | 545 |
| A185 | t-Bu | 4-Cl | H | Cis-4-Me-c-Hex | Ph | S | 550 |
| A186 | t-Bu | 4-Cl | H | Cis-4-Me-c-Hex | 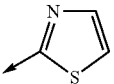 | S | 540 |
| A187 | t-Bu | 4-Cl | H | Cis-4-Me-c-Hex |  | S | 557 |
| A188 | t-Bu | 4-Cl | H | Cis-4-Me-c-Hex | 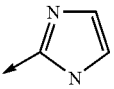 | S | 540 |

Scheme B

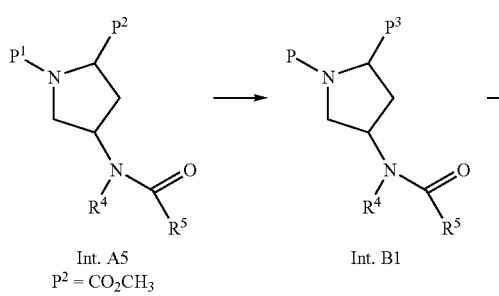

Int. A5
P² = CO₂CH₃

Int. B1

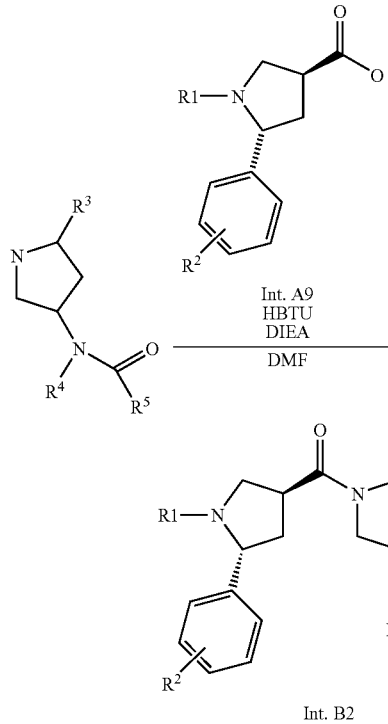

Int. = intermediate

The preparation process of the Intermediate B1 compounds, and the Examples synthesized by the procedure of Scheme B are as follows.

EXAMPLE B1

N-[(3S,5S)-1-{[(3S,4R)-1-tert-butyl-4-(4-chlorophenyl)pyrrolidine-3-yl]carbonyl}-5-(4,5-dihydro-1,3-oxazole-2-yl)pyrrolidine-3-yl]-N-(4,4-dimethylcyclohexyl)-2,2-dimethylpropaneamide HCl salt

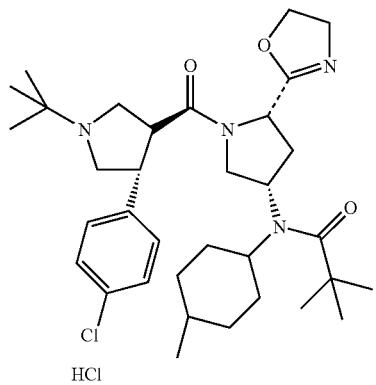

HCl

Step A (2S,4S)-1-Boc-2-{[(2-hydroxyethyl)amino]carbonyl}-4-[dimethylpropanoyl(4,4-dimethylcyclohexyl)amino]pyrrolidine The title compound was prepared according to the procedure described in Step D of Example A1 using (4S)-1-BOC-4-[(4,4-difluorocyclohexyl)(2,2-dimethylpropanoyl)amino]-L-proline (410 mg, 0.9 mmol) prepared in Step C of Example A1 and hydroxy ethyl amine (273 mg, 65%).
MS[M+H]=468 (M+1)

Step B: (2S,4S)-1-Boc-2-(4,5-dihydro-1,3-oxazole-2-yl)-4-[dimethylpropanoyl(4,4-dimethylcyclohexyl)amino]pyrrolidine The product of Step A, (2S,4S)-1-Boc-2-{[(2-hydroxyethyl)amino]carbonyl}-4-[dimethylpropanoyl(4,4-dimethylcyclohexyl)amino]pyrrolidine (410 mg, 0.58 mmol) together with DMAP (70.7 mg, 0.58 mmol) and DIPEA (0.39 ml, 2.32 mmol) were dissolved in toluene (3 ml), and phosgene (20% in toluene, 0.31 ml, 0.87 mmol) was added dropwise. After the reaction solution was stirred at 30~40° C. for 48 h, the solution was concentrated in vacuo. The residue was diluted with EtOAc, and washed with a saturated NaHCO₃ aqueous solution, water and 1N HCl. The organic solution was dried over MgSO₄, concentrated in vacuo, and the residue was purified by column chromatography (eluent: EtOAc) to give the title compound (160 mg, 62%).
MS[M+H]=450(M+1)

Step C: N-[(3S,5S)-1-{[(3S,4R)-1-tert-butyl-4-(4-chlorophenyl)pyrrolidine-3-yl]carbonyl}-5-(4,5-dihydro-1,3-oxazole-2-yl)pyrrolidine-3-yl]-N-(4,4-dimethylcyclohexyl)-2,2-dimethylpropaneamide HCl salt The title compound was prepared according to the procedure described in Step E-G of Example A1 using (2S,4S)-1-Boc-2-(4,5-dihydro-1,3-oxazole-2-yl)-4-[dimethylpropanoyl(4,4-dimethylcyclohexyl)amino]pyrrolidine (100 mg, 0.2 mmol) prepared in Step B (95 mg, 82%).
MS[M+H]=613(M+1)
1H NMR (400 MHz, CDCl3) 7.36 (d, 2H), 7.29 (d, 2H), 4.35-4.22 (m, 2H), 3.95-3.90 (m, 2H), 3.80-3.51 (m, 6H), 3.42-3.29 (m, 2H), 3.22-3.11 (m, 1H), 2.82-2.68 (m, 1H), 2.19-1.97 (m, 1H), 1.61-1.39 (m, 6H), 1.49 (s, 9H), 1.31-1.15 (m, 4H), 1.22 (s, 9H), 0.95 (s, 3H), 0.91 (s, 3H)

EXAMPLE B2

N-{(3S,5S)-1-{[(3S,4R)-1-tert-butyl-4-(4-chlorophenyl)pyrrolidine-3-yl]carbonyl}-5-[(dimethylamino)carbonothionyl]pyrrolidine-3-yl}-N-(4,4-dimethylcyclohexyl)-2-methylpropaneamide TFA salt

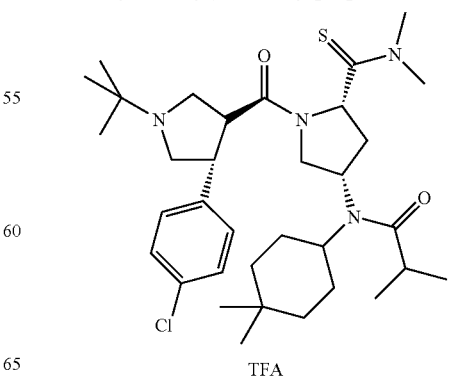

TFA

Step A: 1-BOC-2-methyl(2S,4S)-4-[(4,4-dimethylcyclohexyl)(isobutyryl)amino]pyrrolidine-2-carboxylate The title compound was prepared according to the procedure described in Step B of Example A1, using methyl-(2S,4S)-4-BOC-4-[(4,4-dimethylcyclohexyl)amino]pyrrolidine-2-carboxylate (1 g, 2.82 mmol) prepared in Step A of Example A1☐ Step A and isobutyryl chloride (1.1 g, 93%).
MS[M+H]=425(M+1)

Step B: (4S)-BOC-4-[(4,4-dimethylcyclohexyl)(isobutyryl)amino]-L-proline

The title compound was prepared according to the procedure described in Step C of Example A1 using 1-BOC-2-methyl(2S,4S)-4-[(4,4-dimethylcyclohexyl)(isobutyryl)amino]pyrolidine-2-carboxylate (1.1 g, 2.62 mmol) prepared in Step A (1.0 g, 93%).
MS[M+H]=411(M+1)

Step C: BOC-(2S,4S)-2-[(dimethylamino)carbonyl]-4-[(4,4-dimethylcyclohexyl)(isobutyryl)amino]pyrrolidine The title compound was prepared according to the procedure described in Step D of Example A1 using (4S)-1-BOC-4-[(4,4-dimethylcyclohexyl)(isobutyryl)amino]-L-proline (1.0 g, 2.43 mmol) prepared in Step B (0.97 g, 92%).
MS[M+H]=438(M+1)

Step D: BOC (2S,4S)$_2$-[(dimethylamino)carbonothionyl]-4-[(4,4-dimethylcyclohexyl)(isobutyryl)amino]pyrrolidine To a solution of BOC-(2S,4S)-2-[(dimethylamino)carbonyl]-4-[(4,4-dimethylcyclohexyl)(isobutyryl)amino]pyrrolidine (615 mg, 1.41 mmol) prepared in Step C in benzene (3 ml) was added Lawson s reagents (570 mg, 1.47 mmol). The reaction solution was heated to 80° C., and stirred for 1 h. After the reaction finished, the solution was concentrated in vacuo. The residue was diluted with EtOAc, and washed with brine. The organic solution was dried over MgSO$_4$, concentrated in vacuo, and the residue was purified by column chromatography (eluent: EtOAc:Hex=1/2) to give the title compound (409 mg, 64%).
MS[M+H]=454(M+1)

Step E: N-{(3S,5S)-5-[(dimethylamino)carbonothionyl]pyrrolidine-3-yl}-N-(4,4-dimethylcyclohexyl)-2-methylpropaneamide The title compound was prepared according to the procedure described in Step E of Example A1 using BOC (2S,4S)-2-[(dimethylamino)carbonothionyl]-4-[(4,4-dimethylcyclohexyl)(isobutyryl)amino]pyrrolidine (50 mg, 0.11 mmol) prepared in Step D (38 mg, 98%).
MS[M+H]=354 (M+1)

Step F: N-{(3S,5S)-1-{[(3S,4R)-1-tert-butyl-4-(4-chlorophenyl)pyrrolidine-3-yl]carbonyl}-5-[(dimethylamino)carbonothionyl]pyrrolidine-3-yl}-N-(4,4-dimethylcyclohexyl)-2-methylpropaneamide TFA salt The title compound was prepared according to the procedure described in Step F of Example A1 using N-{(3S,5S)-5-[(dimethylamino)carbonothionyl]pyrrolidine-3-yl}-N-(4,4-dimethylcyclohexyl)-2-methylpropaneamide (38 mg, 0.10 mmol) prepared in Step E and (3S,4R)-1-t-butyl-4-(4-chlorophenyl)pyrrolidine-3-carboxylic acid prepared in Preparation Example A9-2 (55 mg, 89%).
MS[M+H]=617(M+1)
1H NMR (500 MHz, CDCl3) 7.55-7.50 (m, 1H), 6.92-6.85 (m, 1H), 6.82-6.75 (m, 1H), 5.02-4.95 (t, 1H), 4.20-4.08 (m, 1H), 4.08-3.90 (m, 2H), 3.68-3.26 (m, 5H), 3.46 (s, 3H), 3.31 (s, 3H), 3.15-2.88 (m, 3H), 2.79-2.68 (m, 1H), 2.20-2.00 (m, 1H), 1.75-1.60 (m, 1H), 1.60-1.52 (m, 1H), 1.52-1.38 (m, 4H), 1.44 (s, 9H), 1.38-1.25 (m, 2H), 1.10 (dd, 6H), 0.94 (s, 3H), 0.92 (s, 3H)

EXAMPLE B3

N-[(3S,5R)-1-{[(3S,4R)-1-tert-butyl-4-(2,4-difluorophenyl)pyrrolidine-3-yl]carbonyl}-5-(1,3-thiazole-2-yl)pyrrolidine-3-yl]-N-(4,4-dimethylcyclohexyl)-2,2-dimethylpropanamide HCl salt

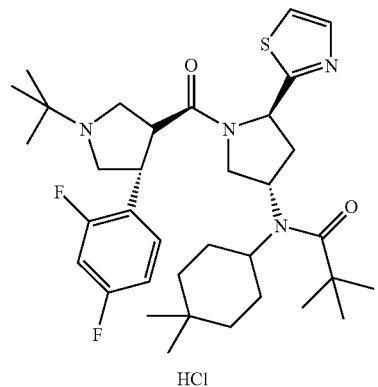

Step A: BOC (2R,4S)-2-(aminocarbonothionyl)-4-[(4,4-dimethylcyclohexy(2,2-dimethylproanoyl)amino pyrrolidine The title compound was prepared according to the procedure described in Step A-C of Example A1 and Step D of Example B2, using methyl (2R,4S)-1-Boc-4-aminopyrrolidine-2-carboxylate prepared in Preparation Example A1-3 as starting material (880 mg, 2 mmol).
MS[M+H]=440 (M+1)

Step B: BOC(2R,4S)-4-[(4,4-dimethylcyclohexyl)(2,2-dimethylpropanoyl)amino]-2-(1,3-thiazole-2-yl)pyrrolidine To a solution of BOC (2R,4S)-2-(aminocarbonothionyl)-4-[(4,4-dimethylcyclohexyl)(2,2-dimethylpropanoyl)amino pyrrolidine (880 mg, 2 mmol) prepared in Step A in dimethoxyethane (10 ml) was added 50 wt % chloroacetaldehyde (0.38 ml, 3 mmol) and NaHCO$_3$ (504 mg, 6 mmol), and stiffed at rt for 2 h. After the reaction finished, the reaction solution was concentrated in vacuo, and extracted with EtOAC. The organic extracts were washed with water and brine, dried over MgSO$_4$, concentrated in vacuo, and the residue was purified by column chromatography (eluent: EtOAc:Hex=1/1). This compound (510 mg, 1.24 mmol) was dissolved in pyridine (0.9 ml, 11.1 mmol), and TFAA (1.0 g, 4.96 mmol) was added dropwise at 0° C. At the same temperature, the solution was stirred for 1.5 h, concentrated in vacuo, and extracted with EtOAc. The organic extracts were washed with 0.5N HCl solution and brine, dried over MgSO$_4$, and concentrated in vacuo. The residue was purified by column chromatography (eluent: EtOAc/Hex=2/1) to give the title compound (249 mg, 51.0%).

MS[M+H]=464 (M+1)

Step C: N-(4,4-dimethylcyclohexyl)-2,2-dimethyl-N-[(3S,5R)-5-(1,3-thiazole-2-yl)pyrrolidine-3-yl]propaneamide The title compound was prepared according to the procedure described in Step E of Example A1 using BOC (2R,4S)-4-[(4,4-dimethylcyclohexyl)(2,2-dimethylpropanoyl)amino]-2-(1,3-thiazole-2-yl)pyrrolidine (80 mg, 0.17 mmol) prepared in Step B (60 mg, 98%).

MS[M+H]=364 (M+1)

Step D: N-[(3S,5R)-1-{[(3S,4R)-1-tert-butyl-4-(2,4-difluorophenyl)pyrrolidine-3-yl]carbonyl}-5-(1,3-thiazole-2-yl)pyrrolidine-3-yl]-N-(4,4-dimethylcyclohexyl)-2,2-dimethylpropaneamide HCl salt The title compound was prepared according to the procedure described in Step F, G of Example A1 using N-(4,4-dimethylcyclohexyl)-2,2-dimethyl-N-[(3S,5R)-5-(1,3-thiazole-2-yl)pyrrolidine-3-yl]propaneamide (60 mg, 0.16 mmol) prepared in Step C (55 mg, 89%).

MS[M+H]=629(M+1)

1H NMR (400 MHz, CDCl3) 8.10-8.04 (m, 1H), 7.92-7.86 (m, 1H), 7.21-7.15 (m, 1H), 6.97-6.93 (m, 1H), 6.79-6.74 (m, 1H), 4.94 (t, 1H), 4.35-4.22 (m, 2H), 3.95-3.90 (m, 2H), 3.81-3.69 (m, 1H), 3.67-3.54 (m, 2H), 3.42-3.29 (m, 2H), 3.22-3.11 (m, 1H), 2.82-2.68 (m, 1H), 2.19-1.97 (m, 1H), 1.61-1.39 (m, 4H), 1.49 (s, 9H), 1.31-1.15 (m, 4H), 1.22 (s, 9H), 0.95 (s, 3H), 0.91 (s, 3H)

EXAMPLE B4

N-[(3S,5S)-1-{[(3S,4R)-1-tert-butyl-4-(4-chlorophenyl)pyrrolidine-3-yl]carbonyl}-5-(hydroxymethyl)pyrrolidine-3-yl]-N-(4,4-dimethylcyclohexyl)-2,2-dimethylpropaneamide TFA salt

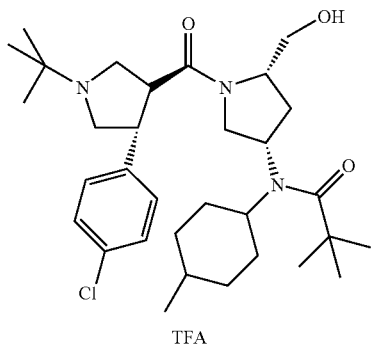

TFA

Step A: BOC(2S,4S)-4-[(4,4-dimethylcyclohexyl)(2,2-dimethylpropanoyl)amino]-2-(hydroxymethyl)pyrrolidine To a solution of 1-BOC-2-methyl-(2S,4S)-4-[(4,4-dimethylcyclohexyl)(2,2-dimethylpropanoyl)amino]pyrrolidine-2-carboxylate (1.18 g, 2.71 mmol) prepared in Step B of Example A1 in THF (10 ml) was added LiBH$_4$ (177 mg, 8.13 mmol). The solution was stirred at 70° C. for 2 h, concentrated in vacuo, and extracted with EtOAc. The organic extracts were washed with a saturated NaHCO$_3$ aqueous solution and brine, dried over MgSO$_4$, and concentrated in vacuo to give the title compound (0.88 g, 81%).

MS[M+H]=411(M+1)

Step B: N-(4,4-dimethylcyclohexyl)-N-[(3S,5S)-5-(hydroxymethyl)pyrrolidine-3-yl]-2,2-dimethylpropaneamide The title compound was prepared according to the procedure described in Step E of Example A1 using BOC (2S,4S)-4-[(4,4-dimethylcyclohexyl)(2,2-dimethylpropanoyl)amino]-2-(hydroxymethyl)pyrrolidine (120 mg, 0.29 mmol) prepared in Step A (89 mg, 98%).

MS[M+H]=311 (M+1)

Step C: N-[(3S,5S)-1-{[(3S,4R)-1-tert-butyl-4-(4-chlorophenyl)pyrrolidine-3-yl]carbonyl}-5-(hydroxymethyl)pyrrolidine-3-yl]-N-(4,4-dimethylcyclohexyl)-2,2-dimethylpropaneamide TFA salt The title compound was prepared according to the procedure described in Step F of Example A1, using N-(4,4-dimethylcyclohexyl)-N-[(3S,5S)-5-(hydroxymethyl)pyrrolidine-3-yl]-2,2-dimethylpropaneamide (60 mg, 0.28 mmol) prepared in Step B and (3S,4R)-1-t-butyl-4-(4-chlorophenyl)pyrrolidine-3-carboxylic acid prepared in Preparation Example A9-2 (144 mg, 90%).

MS[M+H]=574(M+1)

1H NMR (400 MHz, CDCl3) 7.49-7.21 (m, 4H), 4.28-3.21 (m, 12H), 3.17-3.04 (m, 1H), 2.46-2.29 (m, 1H), 2.06-1.92 (m, 1H), 1.72-1.04 (m, 8H), 1.45 (s, 9H), 1.21 (s, 9H), 0.93 (s, 3H), 0.90 (s, 3H)

EXAMPLE B5

N-[(3S,5S)-1-{[(3S,4R)-1-tert-butyl-4-(4-chlorophenyl)pyrrolidine-3-yl]carbonyl}-5-methylpyrrolidine-3-yl]-N-(4,4-dimethylcyclohexyl)-2,2-dimethylpropaneamide TFA salt

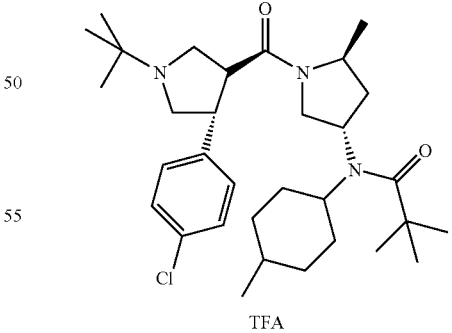

TFA

Step A: BOC-(2R,4S)-4-[(4,4-dimethylcyclohexyl)(2,2-dimethylpropanoyl)amino]-2-(hydroxymethyl)pyrrolidine The title compound (1.11 g) was prepared according to the procedure described in Step A~C of Example A1 and Step A of Example B4, using methyl (2R,4S)-1-Boc-4-aminopyrrolidine-2-carboxylate prepared in Preparation Example A1-3 as starting material.

MS[M+H]=411(M+1)

Step B: BOC-(2R,4S)-4-[(4,4-dimethylcyclohexyl)(2,2-dimethylpropanoyl)amino]-2-{[(methylsulfonyl)oxy]methyl}pyrrolidine The title compound was prepared according to the procedure described in Step C of Preparation Example A1-1A using BOC-(2R,4S)-4-[(4,4-dimethylcyclohexyl)(2,2-dimethylpropanoyl)amino]-2-(hydroxymethyl)pyrrolidine (1.11 g, 2.71 mmol) prepared in Step A (1.1 g, 85%).

MS[M+H]=489 (M+1)

Step C: BOC-(2R,4S)-4-[(4,4-dimethylcyclohexyl)(2,2-dimethylpropanoyl)amino]-2-methylpyrrolidine To a solution of BOC-(2R,4S)-4-[(4,4-dimethylcyclohexyl)(2,2-dimethylpropanoyl)amino]-2-{[(methylsulfonyl)oxy]methyl}pyrrolidine (580 mg, 1.19 mmol) prepared in Step B in THF (5 ml) was added dropwise LiBH$_4$ (77 mg, 3.57 mmol) at 70° C. The solution was stirred at 70° C. for 5 h, concentrated in vacuo, and extracted with EtOAC. The organic extracts were washed with a saturated NaHCO$_3$ aqueous solution and brine, dried over MgSO$_4$, and concentrated in vacuo. The residue was purified by column chromatography (eluent: EtOAc:Hex=1/4) to give the title compound (258 mg, 53%).

MS[M+H]=395(M+1)

Step D: N-(4,4-dimethylcyclohexyl)-2,2-dimethyl-N-[(3S,5S)-5-methylpyrrolidine-3-yl]propaneamide The title compound was prepared according to the procedure described in Step E of Example A1 using BOC-(2R,4S)-4-[(4,4-dimethyl-cyclohexyl)(2,2-dimethylpropanoyl)amino]-2-methylpyrrolidine (50 mg, 0.12 mmol) prepared in Step C (36 mg, 98%).

MS[M+H]=295(M+1)

Step E: N-[(3S,5S)-1-{[(3S,4R)-1-tert-butyl-4-(4-chlorophenyl)pyrrolidine-3-yl]carbonyl}-5-methylpyrrolidine-3-yl]-N-(4,4-dimethylcyclohexyl)-2,2-dimethylpropaneamide TFA salt The title compound was prepared according to the procedure described in Step F of Example A1, using N-(4,4-dimethylcyclohexyl)-2,2-dimethyl-N-[(3S,5S)-5-methylpyrrolidine-3-yl]propaneamide (36 mg, 0.12 mmol) prepared in Step D and (3S,4R)-1-t-butyl-4-(4-chlorophenyl)pyrrolidine-3-carboxylic acid prepared in Preparation Example A9-2 (144 mg, 90%).

MS[M+H]=558(M+1)

1H NMR (400 MHz, CDCl3) 7.48-7.20 (m, 4H), 4.28-3.25 (m, 10H), 3.17-3.04 (m, 1H), 2.46-2.29 (m, 1H), 2.06-1.92 (m, 1H), 1.72-1.04 (m, 8H), 1.45 (s, 9H), 1.27 (m, 3H), 1.21 (s, 9H), 0.93 (s, 3H), 0.90 (s, 3H)

EXAMPLE B6

N-{(3S,5S)-1-{[(3S,4R)-1-tert-butyl-4-(2,4-difluorophenyl)pyrrolidine-3-yl]carbonyl}-5-[(E)-(hydroxyimino)methyl]pyrrolidine-3-yl}-N-(4,4-dimethylcyclohexyl)-2,2-dimethylpropaneamide HCl salt

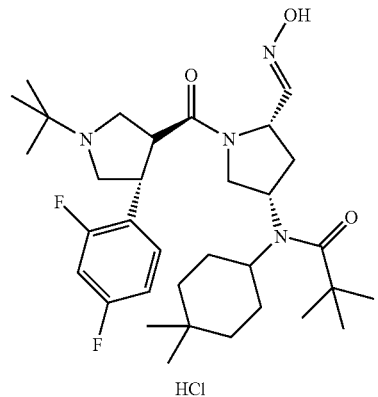

Step A: (2S,4S)-1-Boc-4-[(4,4-methylcyclohexyl)(2,2-dimethylpropanoyl)amino]-2-formylpyrrolidine To a solution of BOC (2S,4S)-4-[(4,4-dimethylcyclohexyl)(2,2-dimethylpropanoyl)amino]-2-(hydroxymethyl)pyrrolidine (602 mg, 1.47 mmol) prepared in Step A of Example B4 in DCM (5 ml) was added dropwise 15 wt % Dess-Martin/DCM reagent (2.2 mmol) at 70'. The solution was stirred at rt for 3 h, concentrated in vacuo, and extracted with EtOAC. The organic extracts were washed with water and brine, dried over MgSO$_4$, and concentrated in vacuo. The residue was purified by column chromatography (eluent: EtOAc:Hex=1/4) to give the title compound (312 mg, 60%).

MS[M+H]=423 (M+1)

Step B: BOC (2S,4S)-4-[(4,4-dimethylcyclohexyl)(2,2-dimethylpropanoyl)amino]-2-[(E)-(hydroxyimino)methyl]pyrrolidine To a solution of (2S,4S)-1-Boc-4-[(4,4-dimethylcyclohexyl)(2,2-dimethylpropanoyl)amino]-2-formylpyrrolidine (312 mg, 0.88 mmol) prepared in Step A in methanol (5 ml) and TEA (0.64 ml, 4.4 mmol) was added hydroxylamine hydrochloride (305 mg, 4.4 mmol), and stirred at rt for 2 h. After the reaction finished, the solution was concentrated in vacuo, and extracted with EtOAC. The organic extracts were washed with water and brine, dried over MgSO$_4$, and concentrated in vacuo. The residue was purified by column chromatography (eluent: EtOAc:Hex=1/2) to give the title compound (208 mg, 67%).

MS[M+H]=424 (M+1)

Step C: N-(4,4-dimethylcyclohexyl)-N-{(3S,5S)-5-[(E)-hydroxyimino)methyl]pyrrolidine-3-yl}-2,2-dimethylpropaneamide The title compound was prepared according to the procedure described in Step E of Example A1 using BOC (2S,4S)-4-[(4,4-dimethylcyclohexyl)(2,2-dimethylpropanoyl) amino]-2-[(E)-(hydroxyimino)methyl]pyrrolidine (200 mg, 0.47 mmol) prepared in Step B (150 mg, 98%).

MS[M+H]=324(M+1)

Step D: N-[(3S,5S)-1-{[(3S,4R)-1-tert-butyl-4-(2,4-difluorophenyl)pyrrolidine-3-yl]carbonyl}-5-[(E)-(hydroxyimino)methyl]pyrrolidine-3-yl]-N-(4,4-dimethylcyclohexyl)-2,2-dimethylpropaneamide HCl salt The title compound was prepared according to the procedure described in Step F, G of Example A1 using N-(4,4-dimethylcyclohexyl)-N-{(3S,5S)-5-[(E)-(hydroxyimino)methyl]pyrrolidine-3-yl}-2,2-dimethylpropaneamide (150 mg, 0.46 mmol) prepared in Step C (144 mg, 90%).

MS[M+H]=589(M+1)

1H NMR (500 MHz, CDCl3) 8.06-8.01 (m, 1H), 7.36-7.30 (m, 1H), 6.97-6.93 (m, 1H), 6.79-6.74 (m, If), 4.34-4.25 (m, 1H), 3.82-3.69 (m, 3H), 3.69-3.44 (m, 3H), 3.19-3.10 (m, 21), 3.08-2.98 (m, 1H), 2.88 (d, 1H), 2.34-2.25 (m, 1H), 2.13-2.03 (m, 1H), 1.61-1.37 (m, 4H), 1.45 (s, 9H), 1.36-1.17 (m, 4H), 1.23 (s, 91), 0.94 (s, 3H), 0.90 (s, 3H)

EXAMPLE B7

N-[(3S,5S)-5-(aminoethyl)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)-2,2-dimethylpropaneamide TFA salt

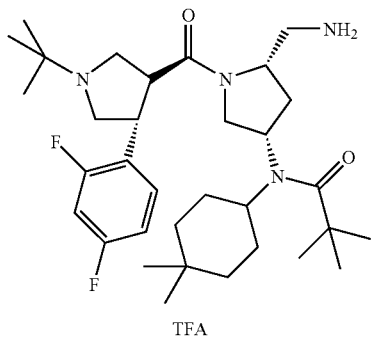

Step A: (2S,4S)-1-BOC-2-(aminomethyl)4-[(4,4-dimethylcyclohexyl)(2,2-dimethylpropanoyl)amino]pyrrolidine The title compound was prepared according to the procedure described in Step C-E of Preparation Example A1-1 using BOC (2S,4S)-4-[(4,4-dimethylcyclohexyl)(2,2-dimethylpropanoyl)amino]-2-(hydroxymethyl)pyrrolidine (2 g, 4.87 mmol) prepared in Step A of Example B40 Step A (1.69 g, 85%).

MS[M+H]=410 (M+1)

Step B: (2S,4S)-1-BOC-2-({[(benzyloxy)carbonyl]amino}methyl)-4-[(4,4-dimethylcyclohexyl)(2,2-dimethylpropanoyl)amino]pyrrolidine To a solution of (2S,4S)-1-BOC-2-(aminomethyl)-4-[(4,4-dimethylcyclohexyl)(2,2-dimethylpropanoyl)amino]pyrrolidine (410 mg, 1 mmol) prepared in Step A in DCM (10 ml) was slowly added dropwise benzyl chloroformate (200 mg, 1.2 mmol) at 0° C., and stirred at rt for 3 h. After the reaction finished, the solvent was concentrated in vacuo, the residue was extracted with water and EtOAc, and the organic layer was dried over MgSO4, concentrated in vacuo, and purified by column chromatography (eluent: EtOAc/Hex=1/1) to give the title compound (310 g, 72%).

MS[M+H]=544 (M+1)

Step C: benzyl({(2S,4S)-4-[(4,4-methylcyclohexyl)(2,2-dimethylpropanoyl)amino]pyrrolidine-2-yl}methyl)carbamate The title compound was prepared according to the procedure described in Step E of Example A1 using (2S,4S)-1-BOC-2-({[(benzyloxy)carbonyl]amino}methyl)-4-[(4,4-dimethylcyclohexyl)(2,2-dimethylpropanoyl)amino]pyrrolidine (150 mg, 0.27 mmol) prepared in Step B (120 mg, 98%).

MS[M+H]=444(M+1)

Step D: benzyl({(2S,4S)-1-{[(3S,4R)-1-tert-butyl-4-(2,4-difluorophenyl)pyrrolidine-3-yl]carbonyl}-4-[(4,4-dimethylcyclohexyl)(2,2-dimethylpropanoyl)amino]pyrrolidine-2-yl}methyl)carbamate The title compound was prepared according to the procedure described in Step F of Example A1 using benzyl({(2S,4S)-4-[(4,4-dimethylcyclohexyl)(2,2-dimethylpropanoyl)amino]pyrrolidine-2-yl}methyl)carbamate (120 mg, 0.27 mmol) prepared in Step C (170 mg, 90%). Only, the reaction proceeded to next step without further purification, and in Step E, HPLC was used for purification.

MS[M+H]=709(M+1)

Step E: N-[(3S,5S)-5-(aminoethyl)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)-2,2-dimethylpropaneamide TFA salt The title compound was prepared according to the procedure described in Step E of Preparation Example A1-1 using benzyl({(2S,4S)-1-{[(3S,4R)-1-tert-butyl-4-(2,4-fluorophenyl)pyrrolidine-3-yl]carbonyl}-4-[(4,4-dimethylcyclohexyl)(2,2-dimethylpropanoyl)amino]pyrrolidine-2-yl)methyl)carbamate (170 mg, 0.27 mmol) prepared in Step D, and purification via HPLC (108 mg, 70%).

MS[M+H]=575(M+1)

1H NMR (500 MHz, CDCl3) 7.61-7.54 (m, 1H), 6.92-6.86 (m, 1H), 6.81-6.75 (m, 1H), 4.34-4.24 (m, 1H), 3.84-3.69 (m, 4H), 3.69-3.54 (m, 2H), 3.19-3.10 (m, 2H), 3.08-2.90 (m, 3H), 2.88 (d, 1H), 2.34-2.25 (m, 1H), 2.13-2.03 (m, 1H), 1.61-1.37 (m, 4H), 1.45 (s, 9H), 1.36-1.17 (m, 4H), 1.23 (s, 9H), 0.94 (s, 3H), 0.90 (s, 3H)

EXAMPLE B8

N-[(3S,5S)-5-[(acetylamino)methyl]-1-{[(3S,4R)-1-tert-butyl-4-(2,4-dichlorophenyl)pyrrolidine-3-yl]carbonyl}pyrrolidine-3-yl]-N-(4,4-dimethylcyclohexyl)-2,2-dimethylpropaneamide TFA salt

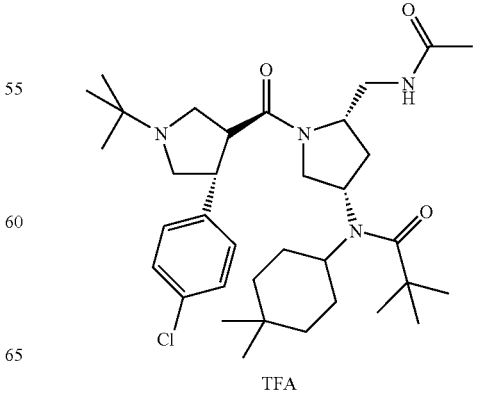

Step A: (2S,4S)-1-BOC-2-[(acetylamino)methyl]4-[(4,4-dimethylcyclohexyl)(2,2-dimethylpropanoyl)amino]pyrrolidine To a solution of (2S,4S)-t-BOC-2-(aminomethyl)-4-[(4,4-dimethylcyclohexyl)(2,2-dimethylpropanoyl)amino]pyrrolidine (500 mg, 1.21 mmol) prepared in Step A of Example B7 in DMF was added dropwise acetic acid (80 mg, 1.3 mmol), HBTU (490 mg, 1.28 mmol) and DIPEA (0.56 ml, 3.22 mmol) in order. After the reaction mixture was stirred at rt for 5 h, the solution was concentrated in vacuo. The residue was diluted with EtOAc, and washed with a saturated NaHCO$_3$ aqueous solution, water and 1N HCl. The organic solution was dried over MgSO$_4$, and concentrated in vacuo. The residue was purified by column chromatography (eluent: EtOAc:Hex=1/2) to give the title compound (508 mg, 93%).
MS[M+H]=452(M+1)

Step B: N-{(3S,5S)-5-[(acetylamino)methyl]pyrrolidine-3-yl}-N-(4,4-dimethylcyclohexyl)-2,2-dimethylpropaneamide The title compound was prepared according to the procedure described in Step E of Example A1 using (2S,4S)-1-BOC-2-[(acetylamino)methyl]-4-[(4,4-dimethylcyclohexyl)(2,2-dimethylpropanoyl)amino]pyrrolidine (100 mg, 0.22 mmol) prepared in Step A (75 mg, 98%).
MS[M+H]=352(M+1)

Step C: N-[(3S,5S)-5-[(acetylamino)methyl]-1-{[(3S,4R)-1-tert-butyl(2,4-dichlorophenyl)pyrrolidine-3-yl]carbonyl}pyrrolidine-3-yl]-N-(4,4-dimethylcyclohexyl)-2,2-dimethylpropaneamide TFA salt The title compound was prepared according to the procedure described in Step F of Example A1, using N-{(3S,5S)-5-[(acetylamino)methyl]pyrrolidine-3-yl}-N-(4,4-dimethylcyclohexyl)-2,2-dimethylpropaneamide (75 mg, 0.21 mmol) prepared in Step B and (3S,4R)-1-t-butyl-4-(4-chlorophenyl)pyrrolidine-3-carboxylic acid prepared in Preparation Example A9-2 (113 mg, 89%).
MS[M+H]=615(M+1)
1H NMR (500 MHz, CDCl3) 7.41 (d, 2H), 7.30 (d, 2H), 4.34-4.24 (m, 2H), 3.82-3.69 (m, 3H), 3.69-3.54 (m, 2H), 3.42-3.27 (m, 2H), 3.19-3.10 (m, 2H), 3.08-2.98 (m, 1H), 2.88 (d, 1H), 2.34-2.25 (m, 1H), 2.13-2.03 (m, 1H), 2.08 (s, 3H), 1.61-1.37 (m, 4H), 1.45 (s, 9H), 1.36-1.17 (m, 4H), 1.23 (s, 9H), 0.94 (s, 3H), 0.90 (s, 3H)

EXAMPLE B9

N-[(3S,5S)-1-{[(3S,4R)-1-tert-butyl-4-(2,4-dichlorophenyl)pyrrolidine-3-yl]carbonyl}-5-[(dimethylamino)methyl]pyrrolidine-3-yl]-N-(4,4-dimethylcyclohexyl)-2,2-dimethylpropaneamide HCl salt

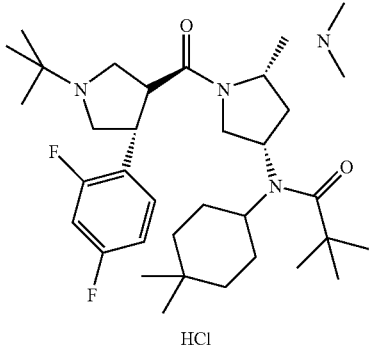

HCl

Step A: (2S,4S)-1-Boc 2-[(dimethylamino)methyl]-4-[(4,4-dimethylcyclohexyl)(2,2-dimethylpropanoyl)amino]pyrrolidine The title compound was prepared according to the procedure described in Step A of Example A1, using (2S,4S)-1-BOC-2-(aminomethyl)-4-[(4,4-dimethylcyclohexyl)(2,2-dimethylpropanoyl)amino]pyrrolidine (440 mg, 1 mmol) prepared in Step A of Example B7 and formaldehyde via reductive amination (300 mg, 70%).
MS[M+H]=438 (M+1)

Step B: N-{(3S,5S)-5-[(dimethylamino)methyl]pyrrolidine-3-yl}-N-(4,4-dimethylcyclohexyl)-2,2-dimethylpropaneamide The title compound was prepared according to the procedure described in Step E of Example A1 using (2S,4S)-1-Boc-2-[(dimethylamino)methyl]-4-[(4,4-dimethylcyclohexyl)(2,2-dimethylpropanoyl)amino]pyrrolidine (100 mg, 0.22 mmol) prepared in Step A (75 mg, 98%).
MS[M+H]=338(M+1)

Step C: N-[(3S,5S)-1-{[(3S,4R)-1-tert-butyl-4-(2,4-dichlorophenyl)pyrrolidine-3-yl]carbonyl}-5-[(dimethylamino)methyl]pyrrolidine-3-yl}-N-(4,4-dimethylcyclohexyl)-2,2 dimethylpropaneamide HCl salt The title compound was prepared according to the procedure described in Step F, G of Example A1 using N-{(3S,5S)-5-[(dimethylamino)methyl]pyrrolidine-3-yl}-N-(4,4-dimethylcyclohexyl)-2,2-dimethylpropaneamide (75 mg, 0.21 mmol) prepared in Step B (113 mg, 89%).
MS[M+H]=603(M+1)
1H NMR (500 MHz, CDCl3) 8.05-7.90 (m, 1H), 6.97-6.93 (m, 1H), 6.79-6.74 (m, 1H), 4.67-4.48 (m, 1H), 3.84-3.69 (m, 4H), 3.69-3.54 (m, 2H), 3.19-3.10 (m, 2H), 3.08-2.97 (m, 1H), 2.88-2.58 (m, 3H), 2.34-2.27 (m, 1H), 2.25 (s, 3H), 2.23 (s, 3H), 2.13-2.03 (m, 1H), 1.61-1.37 (m, 4H), 1.45 (s, 9H), 1.36-1.17 (m, 4H), 1.23 (s, 9H), 0.94 (s, 3H), 0.90 (s, 3H)

EXAMPLE B10

N-[(3S,5S)-1-{[(3S,4R)-1-tert-butyl-4-(2,4-difluorophenyl)pyrrolidine-3-yl]carbonyl}-5-cyanopyrrolidine-3-yl]-2,2-dimethyl-N-(cis-4-methylcyclohexyl)propaneamide HCl salt

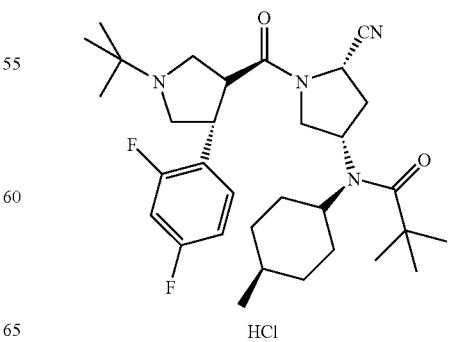

HCl

Step A: 1-BOC (2S,4S)-2-cyano-4-[(2,2-dimethyl-propanoyl)(cis-4-methylcyclohexyl)amino]pyrrolidine To a solution of BOC-(2S,4S)-2(aminocarbonyl)-4-[(2,2-dimethylpropanoyl)(cis-4-methylcyclohexyl)amino]pyrrolidine (576 mg, 1.41 mmol) prepared in Step D of Example A7 in DCM (5 ml) was added dropwise TFAA (0.2 ml, 1.41 mmol), and the solution was stirred at rt for 2 h. After the reaction finished, the solution was concentrated in vacuo. The residue was diluted with EtOAc, and washed with brine. The organic solution was dried over $MgSO_4$, and concentrated in vacuo. The residue was purified by column chromatography (eluent: EtOAc:Hex=1/2) to give the title compound (514 mg, 93%).
MS[M+H]=392 (M+1)

Step B: N-[(3S,5S)-5-cyanopyrrolidine-3-yl]-2,2-dimethyl-N-(cis-4-methylcyclohexyl)propaneamide The title compound was prepared according to the procedure described in Step E of Example A1 using 1-BOC (2S,4S)-2-cyano-4-[(2,2-dimethylpropanoyl)(cis-4-methylcyclohexyl)amino]pyrrolidine (50 mg, 0.13 mmol) prepared in Step A (37 mg, 98%).
MS[M+H]=292(M+1)

Step C: N-[(3S,5S)-1-{[(3S,4R)-1-tert-butyl-4-(2,4-difluorophenyl)pyrrolidine-3-yl]carbonyl}-5-cyanopyrrolidine-3-yl]-2,2-dimethyl-N-(cis-4-methylcyclohexyl)propaneamide HCl salt The title compound was prepared according to the procedure described in Step F, G of Example A1 using N-[(3S,5S)-5-cyanopyrrolidine-3-yl]-2,2-dimethyl-N-(cis-4-methylcyclohexyl)propaneamide (37 mg, 0.12 mmol) prepared in Step B (58 mg, 89%).
MS[M+H]=557(M+1)
1H NMR (400 MHz, CDCl3) 8.10-8.04 (m, 1H), 6.97-6.93 (m, 1H), 6.79-6.74 (m, 1H), 4.76 (t, 1H), 4.35-4.22 (m, 2H), 3.95-3.90 (m, 2H), 3.81-3.69 (m, 1H), 3.67-3.54 (m, 2H), 3.42-3.29 (m, 2H), 3.22-3.11 (m, 1H), 2.82-2.68 (m, 1H), 2.28-2.10 (m, 1H), 1.61-1.39 (m, 5H), 1.49 (s, 9H), 1.31-1.15 (m, 4H), 1.22 (s, 9H), 0.86 (d, 3H)

EXAMPLE B11

N-[(3S,5R)-5-acetyl-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethylpropaneamide TFA salt

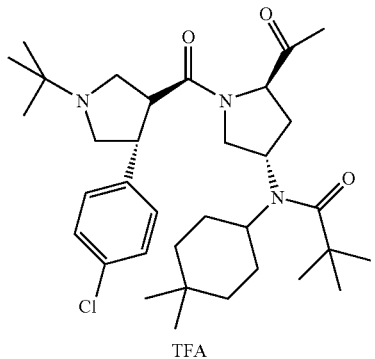

TFA

Step A: (4S)-1-BOC-4-[(4,4-dimethylcyclohexyl)(2,2-dimethylpropanoyl)amino]-D-proline The title compound was prepared according to the procedure described in Step A-C of Example A1 using Preparation Example A1-3 as starting material.

Step B: BOC (2R,4S)[(4,4-dimethylcyclohexyl)(2,2-dimethylpropanoyl)amino]-2-{[methoxy(methyl)amino]carbonyl}pyrrolidine To a solution of (4S)-1-BOC-4-[(4,4-dimethylcyclohexyl)(2,2-dimethylpropanoyl)amino]-D-proline (1.08 g, 2.57 mmol) prepared in Step A in DMF (10 D) was added dropwise DIPEA (1.15□, 6.70 mmol), and N,O-dimethylhydroxylamine hydrochloride (292 mg, 3 mmol) and HBTU (1.1 g, 3 mmol) were added dropwise in order. After the reaction mixture was stirred at rt for 1 h, the solution was concentrated in vacuo. The residue was diluted with EtOAc, and washed with a saturated $NaHCO_3$ aqueous solution, water and 1N HCl. The organic solution was dried over $MgSO_4$, and concentrated in vacuo. The residue was purified by column chromatography (eluent: EtOAc:Hex=3/1) to give the title compound (600 mg, 50%).
MS[M+H]=468(M+1)

Step C: 1-BOC-(2R,4S)-2-acetyl-4-[(4,4-dimethylcyclohexyl)(2,2-dimethylpropanoyl)amino]pyrrolidine To a solution of BOC (2R,4S)-4-[(4,4-dimethylcyclohexyl)(2,2-dimethylpropanoyl)amino]-2-{[methoxy(methyl)amino]carbonyl}pyrrolidine (670 mg, 1.44 mmol) prepared in Step B in THF (5 ml) was added methylmagnesium bromide 3M in ether solution (1.2 ml, 3.66 mmol), and the solution was stirred for 3 h. After the reaction finished, the solution was concentrated in vacuo. The residue was diluted with EtOAc, and washed with water and brine. The organic solution was dried over $MgSO_4$, and concentrated in vacuo. The residue was purified by column chromatography (eluent: EtOAc:Hex=3/1) to give the title compound (280 mg, 46%).
MS[M+H]=423(M+1)

Step D: N-[(3S,5R)-5-acetylpyrrolidine-3-yl]-N-(4,4-dimethylcyclohexyl)-2,2-dimethylpropaneamide The title compound was prepared according to the procedure described in Step E of Example A1 using 1-BOC-(2R,4S)-2-acetyl-4-[(4,4-dimethylcyclohexyl)(2,2-dimethylpropanoyl)amino]pyrrolidine (200 ng, 0.47 mmol) prepared in Step C (149 mg, 98%).
MS[M+H]=323(M+1)

Step E: N-[(3S,5R)-5-acetyl-1-{[(3S,4R)-tert-butyl-4-(4-chlorophenyl)pyrrolidine-3-yl]carbonyl}pyrrolidine-3-yl]-N-(4,4-dimethylcyclohexyl)-2,2-dimethylpropaneamide TFA salt The title compound was prepared according to the procedure described in Step F of Example A1, using N-[(3S,5R)-5-acetylpyrrolidine-3-yl]-N-(4,4-dimethylcyclohexyl)-2,2-dimethylpropaneamide (149 mg, 0.46 mmol) prepared in Step D and (3S,4R)-1-t-butyl(4-chlorophenyl)pyrrolidine-3-carboxylic acid prepared in Preparation Example A9-2 (230 mg, 89%).
MS[M+H]=587(M+1)

1H NMR (500 MHz, CDCl3) 7.44-7.37 (m, 2H), 7.36-7.28 (m, 2H), 4.80-4.74 (m, 1H), 4.01-3.26 (m, 10H), 2.81-2.71 (m, 1H), 2.64 (t, 1H), 2.11 (s, 3H), 1.70-1.13 (m, 8H), 1.45 (s, 9H), 1.20 (s, 9H), 0.93 (s, 3H), 0.91 (s, 3H)

EXAMPLE B12

N-[(3S)-1-{[(3S,4R)-1-tert-butyl-4-(4-chlorophenyl)pyrrolidine-3-yl]carbonyl}-5-(1-hydroxymethyl)pyrrolidine-3-yl]-N-(4,4-dimethylcyclohexyl)-2,2-dimethylpropaneamide TFA salt

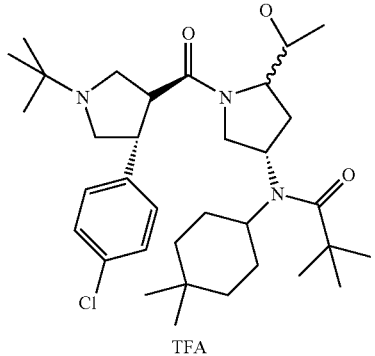

TFA

Step A: 1-boc-(4S)-4-[(4,4-dimethylcyclohexyl)(2,2-dimethylpropanoyl)amino]-2-(1-hydroxymethyl pyrrolidine To a solution of 1-BOC-(2R,4S)-2-acetyl-4-[(4,4-dimethylcyclohexyl)(2,2-dimethylpropanoyl)amino]pyrrolidine (270 mg, 0.66 mmol) prepared in Step C of Example B11 in methanol (5 ml) was added NaBH4 (49.9 mg, 1.32 mmol). The solution was stirred at rt for 2 h, concentrated in vacuo, and extracted with EtOAC. The organic extracts were washed with brine, dried over MgSO4, and concentrated in vacuo to give the title compound (225 mg, 80%).
MS[M+H]=425(M+1)

Step B: N-(4,4-dimethylcyclohexyl)-N-[(3S)-5-(1-hydroxyethyl)pyrrolidine-3-yl]-2,2-dimethylpropaneamide The title compound was prepared according to the procedure described in Step E of Example A1 using 1-boc-(4S)-4-[(4,4-dimethylcyclohexyl)(2,2-dimethylpropanoyl)amino]-2-(1-hydroxymethyl)pyrrolidine (100 mg, 0.23 mmol) prepared in Step A (75 mg, 98%).
MS[M+H]=325(M+1)

Step C: N-[(3S)-1-{[(3S,4R)-1-tert-butyl-4-(4-chlorophenyl)pyrrolidine-3-yl]carbonyl}-5-(1-hydroxymethyl)pyrrolidine-3-yl]-N-(4,4-dimethylcyclohexyl)-2,2-dimethylpropaneamide TFA salt The title compound was prepared according to the procedure described in Step F of Example A1, using N-(4,4-dimethylcyclohexyl)-N-[(3S)-5-(1-hydroxyethyl)pyrrolidine-3-yl]-2,2-dimethylpropaneamide (75 mg, 0.22 mmol) prepared in Step B and (3S,4R)-1-t-butyl-4-(4-chlorophenyl)pyrrolidine-3-carboxylic acid prepared in Preparation Example A9-2 (113 mg, 88%).
MS[M+H]=588(M+1)
1H NMR (400 MHz, CDCl3) 7.49-7.21 (m, 4H), 4.30-3.24 (m, 111H), 3.17-3.04 (m, 1H), 2.46-2.29 (m, 1H), 2.06-1.92 (m, 1H), 1.72-1.04 (m, 8H), 1.45 (s, 9H), 1.21 (s, 9H), 1.18 (d, 3H), 0.93 (s, 3H), 0.90 (s, 3H)

EXAMPLE B13

(4S)-4-[acetyl(4,4-dimethylcyclohexyl)amino]-N-(2-aminoethyl)-1-{[(3S,4R)-1-tert-butyl-4-(2,4-difluorophenyl)pyrrolidine-3-yl]carbonyl}-L-prolinamide TFA salt

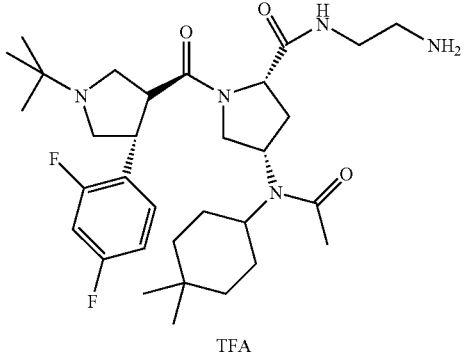

TFA

Step A: 1-BOC (2S,4S)-4-[acetyl(4,4-dimethylcyclohexyl)amino]-2-{[(2-{[(benzyloxy)carbonyl]amino}ethyl)amino]carbonyl}pyrrolidine Methyl-(2S,4S)-1-BOC-4-[(4,4-dimethylcyclohexyl)amino]pyrrolidine-2-carboxylate (1.77 g, 5 mmol) prepared in Step A of Example A1 and acetyl chloride were reacted according to the procedure described in Step B~C of Example A1, and then reacted according to the procedure described in Step D of Example A1 using CBZ-ethylamine to give the title compound (1.5 g, 55%).
MS[M+H]=559(M+1)

Step B: (4S)-4-[acetyl(4,4-dimethylcyclohexyl)amino]-N-(2-{[(benzyloxy)carbonyl]amino}ethyl)-1-{[(3S,4R)-1-tert-butyl-4-(2,4-difluorophenyl)pyrrolidine-3-yl]carbonyl}-L-prolinamide The title compound was prepared according to the procedure described in Step E-F of Example A1 using 1-BOC (2S,4S)-4-[acetyl(4,4-dimethylcyclohexyl)amino]-2-{[(2-{[(benzyloxy)carbonyl]amino}ethyl)amino]carbonyl}pyrrolidine (560 mg, 1 mmol) prepared in Step A (0.56 g, 78%).
MS[M+H]=724(M+1)

Step C: 4S)-4-[acetyl(4,4-dimethylcyclohexyl)amino]-N-(2-aminoethyl)-1-{[(3S,4R)-1-tert-butyl-4-(2,4-difluorophenyl)pyrrolidine-3-yl]carbonyl}-L-prolineamide TFA salt The title compound was prepared according to the procedure described in Step E of Preparation Example A1-1 using (4S)-4-[acetyl(4,4-dimethylcyclohexyl)amino]-N-(2-{[(benzyloxy)carbonyl]amino}ethyl)-1-{[(3S,4R)-1-tert-butyl-4-(2,4-difluorophenyl)pyrrolidine-3-yl]carbonyl}-L-prolineamide (100 mg, 0.13 mmol) prepared in Step B and purification via HPLC (65 mg, 80%).
MS[M+H]=590(M+1)
1H NMR (500 MHz, CDCl3) 7.71-7.61 (m, 1H), 6.99-6.79 (m, 2H), 4.67-4.48 (m, 1H), 4.22-3.94 (m, 2H), 3.94-3.84 (m, 1H), 3.83-3.00 (m, 1H), 2.59-2.29 (m, 2H), 1.99 (d, 3H), 1.69-1.17 (m, 8H), 1.43 (s, 9H), 0.94 (s, 3H), 0.91 (s, 3H)

EXAMPLE B14 methyl (4S)-1-{[(3S,4R)-1-tert-butyl-4-(4-chlorophenyl)pyrrolidine-3-yl]carbonyl}-4-[(4,4-dimethylcyclohexyl)(2,2-dimethylpropanoyl)amino]-L-prolinate HCl salt

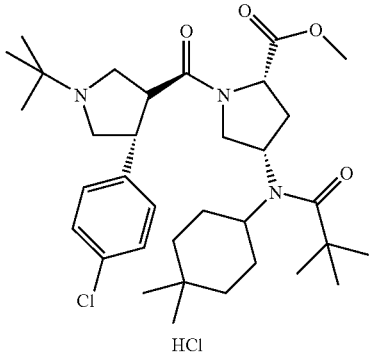

HCl

The title compound was prepared according to the procedure described in Step E-G of Example A1 using 1-BOC-2-methyl-(2S,4S)-4-[(4,4-dimethylcyclohexyl)(2,2-dimethylpropanoyl)amino]pyrrolidine-2-carboxylate (200 mg, 0.45 mmol) prepared in Step B of Example A1 (230 mg, 87%).

MS[M+H]=602(M+1)

1H NMR (500 MHz, CDCl3) 7.57 (d, 2H), 7.32 (d, 2H), 4.45 (t, 1H), 4.05-3.94 (m, 1H), 3.89-3.54 (m, 6H), 3.72 (s, 3H), 3.39-3.21 (m, 2H), 3.04-2.95 (m, 1H), 2.74-2.62 (m, 1H), 2.15-2.05 (m, 1H), 1.54-1.35 (m, 4H), 1.48 (s, 9H), 1.27-1.12 (m, 4H), 1.19 (s, 9H), 0.93 (s, 3H), 0.90 (s, 3H)

EXAMPLE B15

(4S)-1-{[(3S,4R)-1-tert-butyl-4-(4-chlorophenyl)pyrrolidine-3-yl]carbonyl}-4-[(4,4-dimethylcyclohexyl)(2,2-dimethylpropanoyl)amino]-L-proline TFA salt

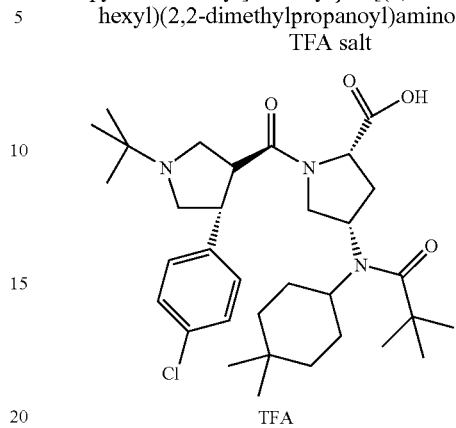

TFA

The title compound was prepared according to the procedure described in Step C of Example A1 using methyl (4S)-1-{[(3S,4R)-1-tert-butyl-4-(4-chlorophenyl)pyrrolidine-3-yl]carbonyl}-4-[(4,4-dimethylcyclohexyl)(2,2-dimethylpropanoyl)amino]-L-prolinate TFA salt prepared in Example B14 (230 mg, 82%).

MS[M+H]=588(M+1)

1H NMR (500 MHz, CDCl3) 7.38 (d, 2H), 7.30 (d, 2H), 4.37 (t, 1H), 4.10-3.56 (m, 8H), 3.36-3.18 (m, 2H), 2.51-2.42 (m, 1H), 2.40-2.30 (m, 1H), 1.61-1.37 (m, 5H), 1.50 (s, 9H), 1.32-1.08 (m, 3H), 1.22 (s, 9H), 0.94 (s, 3H), 0.90 (s, 3H)

EXAMPLE B16~41

The following Examples were prepared according to the procedure described in Example B1~15, using the intermediates which are prepared in a series of Example A by the reactions between appropriate compounds among Preparation Example A1, A2, A4, A9 and appropriate amines.

TABLE 7

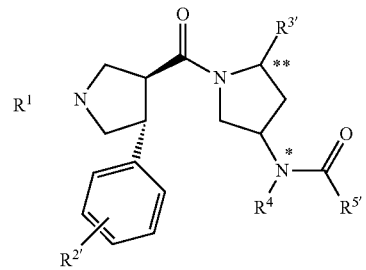

| Example | R¹ | R²' | R³' | R⁴ | R⁵' | * | ** | MS (M + 1) |
|---|---|---|---|---|---|---|---|---|
| B16 | t-Bu | 4-Cl | Me | c-Hex | Me | S | S | 488 |
| B17 | t-Bu | 2,4-diF | C(S)NH₂ | c-Hex | Me | S | R | 535 |
| B18 | t-Bu | 2,4-diF | C(S)NH₂ | cis-4-Me-c-Hex | (tetrahydrofuran) | S | R | 605 |
| B19 | t-Bu | 2,4-diF | CH₂OH | c-Hex | Me | S | S | 506 |
| B20 | t-Bu | 2,4-diF | CH₂OH | cis-4-Me-c-Hex | t-Bu | S | S | 562 |

TABLE 7-continued

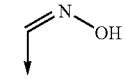

| Example | R¹ | R²' | R³' | R⁴ | R⁵' | * | ** | MS (M + 1) |
|---|---|---|---|---|---|---|---|---|
| B21 | t-Bu | 2,4-diF | 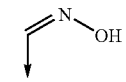 | c-Hex | Me | S | R | 519 |
| B22 | t-Bu | 2,4-diF |  | cis-4-Me-c-Hex | t-Bu | S | R | 575 |
| B23 | t-Bu | 2,4-diF | 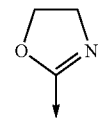 | cis-4-Me-c-Hex | CH(CH₃)₂ | S | R | 603 |
| B24 | t-Bu | 4-Cl | 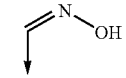 | cis-4-Me-c-Hex | CH(CH₃)₂ | S | S | 585 |
| B25 | t-Bu | 4-Cl | CH₂NH₂ | c-Hex | Me | S | S | 505 |
| B26 | t-Bu | 2,4-diF | CH₂N(CH₃)₂ | c-Hex | Me | S | S | 533 |
| B27 | t-Bu | 2,4-diF | Ac | cis-4-Me-c-Hex | t-Bu | S | R | 503 |
| B28 | t-Bu | 2,4-diF | C(S)NH₂ | cis-4-Me-c-Hex | t-Bu | S | R | 591 |
| B29 | t-Bu | 4-Cl | C(S)NH₂ | cis-4-Me-c-Hex | t-Bu | S | R | 589 |
| B30 | t-Bu | 2,4-diF | C(S)N(CH₃)₂ | 4,4-diMe-c-Hex | t-Bu | S | S | 633 |
| B31 | t-Bu | 2,4-diF | CH₂OH | 4,4-diMe-c-Hex | CH(CH₃)₂ | S | S | 562 |
| B32 | t-Bu | 2,4-diF | 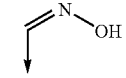 | 4,4-diMe-c-Hex | CH(CH₃)₂ | S | R | 575 |
| B33 | t-Bu | 2,4-diF | 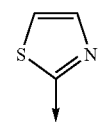 | 4,4-diMe-c-Hex | CH(CH₃)₂ | S | S | 575 |
| B34 | t-Bu | 2,4-diF | Ac | 4,4-diMe-c-Hex | CH(CH₃)₂ | S | S | 574 |
| B35 | t-Bu | 2,4-diF | Ac | 4,4-diMe-c-Hex | t-Bu | S | S | 588 |
| B36 | t-Bu | 4-Cl | C(S)N(CH₃)₂ | 4,4-diMe-c-Hex | t-Bu | S | S | 631 |
| B37 | t-Bu | 2,4-diF | C(S)N(CH₃)₂ | 4,4-diMe-c-Hex | t-Bu | S | R | 633 |
| B38 | t-Bu | 2,4-diF | C(O)Et | 4,4-diMe-c-Hex | t-Bu | S | R | 602 |
| B39 | t-Bu | 4-Cl | C(O)Et | 4,4-diF-c-Hex | t-Bu | S | S | 608 |
| B40 | t-Bu | 4-Cl | | 4,4-diMe-c-Hex | t-Bu | S | S | 629 |
| B41 | t-Bu | 2,4-diF | C(O)NH(CH₂)₂NH₂ | 4,4-diMe-c-Hex | CH₃ | S | R | 590 |

83

Scheme C

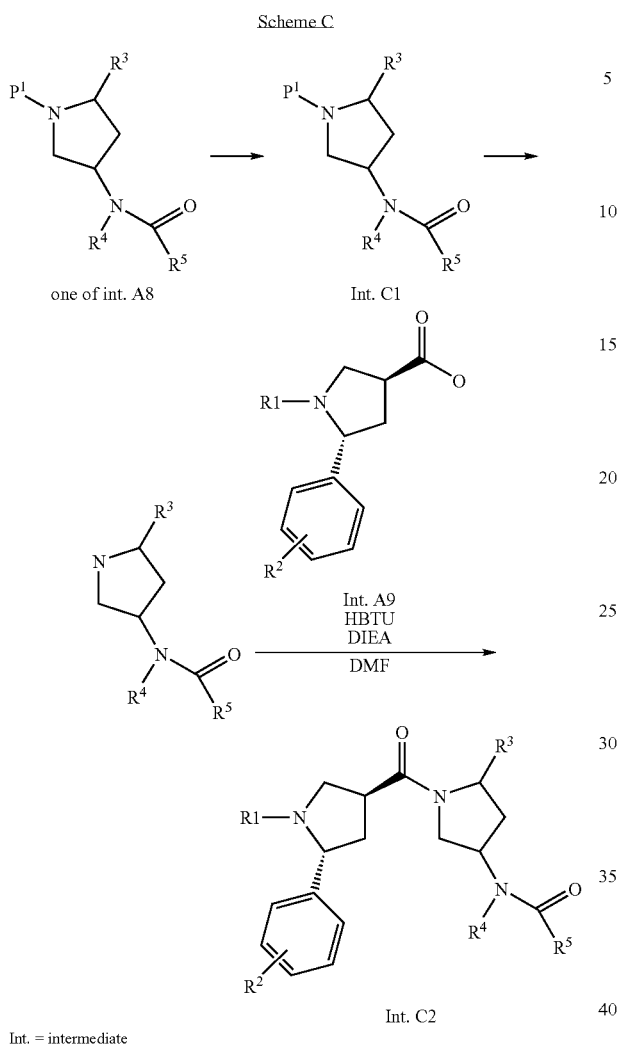

Int. = intermediate

EXAMPLE C1

N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethylmaloneamide TFA salt

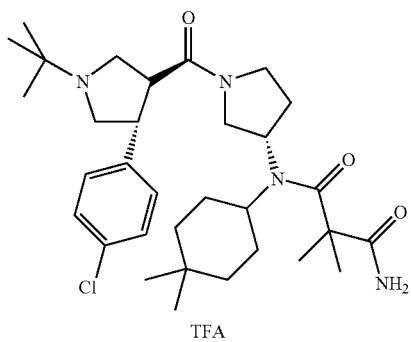

84

Step A: (3S)-1-Boc-[(2-cyano-2-methylpropanoyl)(4,4-dimethylcyclohexyl)amino]pyrrolidine The title compound was prepared according to the procedure described in Step B of Example A1, using (3S)-1-Boc-3-[(4,4-dimethylcyclohexyl)amino]pyrrolidine (1.5 g, 5 mmol) prepared in Step A of Example A8 and 2-cyano-2-methylpropanoyl chloride (2 g, 15 mmol) prepared in Preparation Example A4-3 (1.5 g, 76.6%).

MS[M+H]=392 (M+1)

Step B: (3S)-1-Boc-3-[(3-amino-2,2-dimethyl-3-oxopropanoyl)(4,4-dimethylcyclohexyl)amino]pyrrolidine To a solution of (3S)-1-Boc-[(2-cyano-2-methylpropanoyl)(4,4-dimethylcyclohexyl)amino]pyrrolidine (900 mg, 2.3 mmol) prepared in Step A in methanol (10 ml) was added 10N-NaOH (5 ml), and the solution was stirred at 80° C. for 2 h. After the reaction finished, the solvent was concentrated in vacuo, diluted with water, and extracted with EtOAc. The extracted organic layer was dried over $MgSO_4$, concentrated in vacuo, and purified by column chromatography (eluent: EtOAc/Hex=3/1) to give the title compound (828 mg, 88%).

MS[M+H]=410 (M+1)

Step C: N-(4,4-dimethylcyclohexyl)-2,2-dimethyl-N-[(3S)-pyrrolidine-3-yl]-maloneamide The title compound was prepared according to the procedure described in Step E of Example A1 using (3S)-1-Boc-3-[(3-amino-2,2-dimethyl-3-oxopropanoyl)(4,4-dimethylcyclohexyl)amino]pyrrolidine (192 mg, 0.47 mmol) prepared in Step B (142 mg, 98%).

MS[M+H]=310(M+1)

Step D: N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethylmaloneamide TFA salt The title compound was prepared according to the procedure described in Step F of Example A1, using N-(4,4-dimethylcyclohexyl)-2,2-dimethyl-N-[(3S)-pyrrolidine-3-yl]maloneamide (142 mg, 0.46 mmol) prepared in Step C and (3S,4R)-1-t-butyl-4-(4-chlorophenyl)pyrrolidine-3-carboxylic acid prepared in Preparation Example A9-2 (234 mg, 89%).

MS[M+H]=573(M+1)

1H NMR (500 MHz, CDCl3) 7.29-7.25 (m, 4H), 4.58-4.50 (m, 1H), 4.34-4.26 (m, 1H), 4.20-4.14 (m, 1H), 4.04-3.96 (m, 1H), 3.84-3.75 (m, 1H), 3.69-3.60 (m, 1H), 3.55-3.40 (m, 2H), 3.40-3.32 (m, 1H), 3.19-3.10 (m, 2H), 2.96-2.87 (m, 1H), 2.28-2.17 (m, 1H), 1.87-1.78 (m, 1H), 1.72-1.56 (m, 2H), 1.53-1.38 (m, 3H), 1.43 (s, 9H), 1.40 (s, 3H), 1.36-1.21 (m, 3H), 1.30 (s, 3H), 0.89 (s, 3H), 0.87 (s, 3H)

EXAMPLE C2

N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-methoxy-2,2-dimethylpropaneamide TFA salt

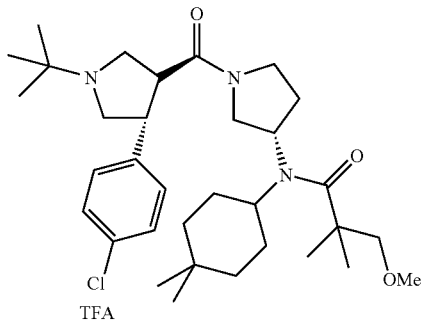

Step A: (3S)-1-Boc-3-{[3-(methoxy)-2,2-dimethylpropanoyl](4,4-dimethylcyclohexyl)amino}pyrrolidine To a solution of (3S)-1-Boc-3-[(4,4-dimethylcyclohexyl)(3-hydroxy-2,2-dimethylpropanoyl)amino]pyrrolidine (800 mg, 2.02 mmol) prepared in Step B of Example A8 in THF was added NaH (73 mg, 3.03 mmol) and iodomethane (430 mg, 3.03 mmol) at 0° C., and the solution was stirred at rt for 2 h. After the reaction finished, the solution was concentrated in vacuo, extracted with 1N-HCl and EtOAc. The organic layer was washed with brine, dried over MgSO$_4$, and concentrated in vacuo. The residue was purified by column chromatography (eluent: EtOAc/Hex=1/2) to give the title compound (784 mg, 94.6%).

MS[M+H]=411 (M+1)

Step B: N-(4,4-dimethylcyclohexyl)-3-methoxy-2,2-dimethyl-N-[(3S)-pyrrolidine-3-yl]propaneamide The title compound was prepared according to the procedure described in Step E of Example A1 using (3S)-1-Boc-3-{[3-(methoxy)-2,2-dimethylpropanoyl](4,4-dimethylcyclohexyl)amino}pyrrolidine (193 mg, 0.47 mmol) prepared in Step A (141 mg, 98%).

MS[M+=311(M+1)

Step C: N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-methoxy-2,2-dimethylpropaneamide TFA salt The title compound was prepared according to the procedure described in Step F of Example A1, using N-(4,4-dimethylcyclohexyl)-3-methoxy-2,2-dimethyl-N-[(3S)-pyrrolidine-3-yl]propaneamide (141 mg, 0.46 mmol) prepared in Step B and (3S,4R)-1-t-butyl-4-(4-chlorophenyl)pyrrolidine-3-carboxylic acid prepared in Preparation Example A9-2 (232 mg, 89%).

MS[M+H]=574 (M+1)

1H NMR (500 MHz, CDCl3) 7.37-7.33 (d, 2H), 7.31-7.25 (d, 2H), 3.91-3.81 (m, 2H), 3.80-3.65 (m, 4H), 3.64-3.55 (m, 2H), 3.54-3.46 (m, 1H), 3.44-3.26 (m, 3H), 3.29 (s, 3H), 3.24-3.17 (m, 1H), 3.08-3.01 (m, 0.3H), 2.94-2.88 (m, 0.7H), 2.42-2.32 (m, 1H), 1.80-1.71 (m, 1H), 1.65-1.50 (m, 2H), 1.49-1.32 (m, 12H), 1.30-1.15 (m, 9H), 0.95-0.85 (m, 6H)

EXAMPLE C3

(3E)-N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-(hydroxyimino)-2,2-dimethylpropaneamide HCl salt

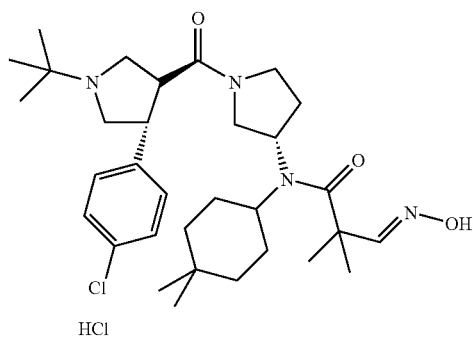

Step A: (3S)-1-Boc-3-[(4,4-dimethylcyclohexyl)(2,2-dimethyl-3-oxopropanoyl)amino]pyrrolidine To a solution of (3S)-1-Boc-3-[(4,4-dimethylcyclohexyl)(3-hydroxy-2,2-dimethylpropanoyl)amino]pyrrolidine (1.05 g, 2.7 mmol) prepared in Step B of Example A8 in DCM was added Dess-Martin periodinane (1.35 g, 3.17 mmol), and stirred at rt for 2 h. After the reaction finished, the solvent was concentrated in vacuo, sodium thiosulfate aqueous solution and EtOAc were added and stirred at rt for 30 min, and extracted with EtOAc. The organic layer was dried over MgSO$_4$, concentrated in vacuo at rt, and purified by column chromatography (eluent: EtOAc/Hex=1/3) to give the title compound (960 mg, 90%).

MS[M+H]=395 (M+1)

Step B: 1-Boc-(3S)-3-[(4,4-dimethylcyclohexyl)(2,2-dimethyl-3-oxopropanoyl)amino]pyrrolidine To a solution of (3S)-1-Boc-3-[(4,4-dimethylcyclohexyl)(2,2-dimethyl-3-oxopropanoyl)amino]pyrrolidine (250 mg, 0.63 mmol) prepared in Step A in methanol (5 ml) was added hydroxyammoniumchloride (49 mg, 1.27 mmol) and TEA (127 mg, 1.26 mmol), and the solution was stirred at 80° C. for 1 h. After the reaction finished, the solvent was concentrated in vacuo, diluted with water (20 ml), and extracted with EtOAc. The organic layer was washed with 1N-HCl, dried over MgSO$_4$, concentrated in vacuo, and purified by column chromatography (eluent: EtOAc/Hex=1/2) to give the title compound (206 mg, 80%).

MS[M+H]=410 (M+1)

Step C: (3E)-N-(4,4-dimethylcyclohexyl)-3-(hydroxyamino)-2,2-dimethyl-N-[(3S)-pyrrolidine-3-yl]propaneamide The title compound was prepared according to the procedure described in Step E of Example A1 using 1-Boc-(3S)-

3-[(4,4-dimethylcyclohexyl)(2,2-dimethyl-3-oxopropanoyl)amino]pyrrolidine (192 mg, 0.47 mmol) prepared in Step B (142 mg, 98%).

MS[M+H]=310(M+1)

Step D: (3E)-N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxyimino)-2,2-dimethylpropaneamide HCl salt The title compound was prepared according to the procedure described in Step F, G of Example A1, using (3E)-N-(4,4-dimethylcyclohexyl)-3-(hydroxyimino)-2,2-methyl-N-[(3S)-pyrrolidine-3-yl]propaneamide (142 mg, 0.46 mmol) prepared in Step C and (3S,4R)-1-t-butyl-4-(4-chlorophenyl)pyrrolidine-3-carboxylic acid prepared in Preparation Example A9-2 (234 mg, 89%).

MS[M+H]=573(M+1)

1H NMR (400 MHz, CDCl3) 7.45-7.39 (m, 2H), 7.37-7.30 (m, 2H), 6.72 (s, 1H), 4.12-3.52 (m, 7H), 3.40-3.19 (m, 3H), 2.77-2.69 (m, 1H), 2.53-2.33 (m, 1H), 1.78-1.57 (m, 8H), 1.55-1.41 (m, 10H), 1.35-1.22 (m, 7H), 0.94 (s, 3H), 0.92 (s, 3H)

EXAMPLE C4

N-[(3S)-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxy-2,2-dimethylbutanamide HCl salt

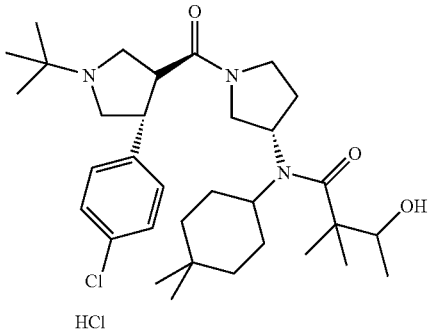

Step A: (3S) 1-Boc-3-[(4,4-dimethylcyclohexyl)(3-hydroxy-2,2-dimethylbutanoyl)amino]pyrrolidine To a solution of (3S)-1-Boc-3-[(4,4-dimethylcyclohexyl)(2,2-dimethyl-3-oxopropanoyl)amino]pyrrolidine (250 mg, 0.63 mmol) prepared in Step A of Example C3 in THF was slowly added dropwise methylmagnesium bromide (in diethylether, 3.0M, 0.25 ml, 0.76 mmol) at 0° C., and the solution was stirred at rt for 2 h. After the reaction finished, to the solution was added 1N-HCl at 0° C., and extracted with EtOAc. The organic layer was dried over MgSO4, concentrated in vacuo, and purified by column chromatography (eluent: EtOAc/Hex=1/2) to give the title compound (238 mg, 92%).

MS[M+H]=425 (M+1)

Step B: 1-(4,4-dimethylcyclohexyl)-3-hydroxy-2,2-dimethyl-N-[(3S)-pyrrolidine-3-yl]butaneamide The title compound was prepared according to the procedure described in Step E of Example A1 using (3S) 1-Boc-3-[(4,4-dimethylcyclohexyl)(3-hydroxy-2,2-dimethylbutanoyl)amino]pyrrolidine (100 mg, 0.23 mmol) prepared in Step A (73 mg, 98%).

MS[M+H]=325 (M+1)

Step C: N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxy-2,2-dimethylbutaneamide HCl salt The title compound was prepared according to the procedure described in Step F, G of Example A1, using N-(4,4-dimethylcyclohexyl)-3-hydroxy-2,2-dimethyl-N-[(3S)-pyrrolidine-3-yl]butaneamide (73 mg, 0.23 mmol) prepared in Step B and (3S,4R)-1-t-butyl-4-(4-chlorophenyl)pyrrolidine-3-carboxylic acid prepared in Preparation Example A9-2 (232 mg, 89%).

MS[M+H]=574 (M+1)

1H NMR (400 MHz, CDCl3) 7.58-7.48 (m, 2H), 7.37-7.29 (m, 2H), 3.92-3.48 (m, 7H), 3.47-3.22 (m, 4H), 2.77-2.69 (m, 1H), 2.53-2.33 (m, 1H), 1.80-1.55 (m, 8H), 1.52-1.38 (m, 10H), 1.32-1.20 (m, 10H), 0.94 (s, 3H), 0.92 (s, 3H)

EXAMPLE C5

N-[(3S)-1-{[(3S,4R)-1-tert butyl-4-(4-chlorophenyl)pyrrolidine-3-yl]carbonyl}pyrrolidine-3-yl]-N-(4,4-dimethylcyclohexyl)-2,2-dimethyl-3-oxobutaneamide HCl salt

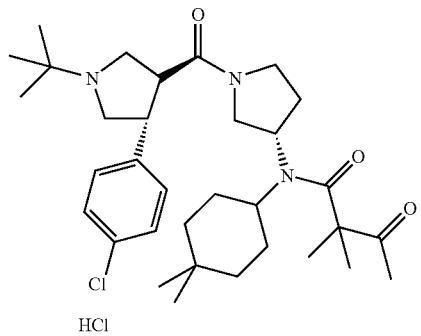

Step A: (3S)-1-Boc-3-[(4,4-dimethylcyclohexyl)(2,2-dimethyl-3-oxobutanoyl)amino]pyrrolidine To a solution of (3S)-1-Boc-3-[(4,4-dimethylcyclohexyl)(3-hydroxy-2,2-dimethylbutanoyl)amino]pyrrolidine (150 mg, 0.36 mmol) prepared in Step A of Example C4 in DCM was added Dess-Martin periodinane (230 mg, 0.54 mmol), and stirred at rt for 2 h. After the reaction finished, the solvent was concentrated in vacuo, sodium thiosulfate aqueous solution and EtOAc were added and stirred at rt for 30 min, and extracted with EtOAc. The organic layer was dried over MgSO4, concentrated in vacuo at rt, and purified by column chromatography (eluent: EtOAc/Hex=1/3) to give the title compound (132 mg, 90%).

MS[M+H]=409 (M+1)

Step B: N-(4,4-dimethylcyclohexyl)-2,2-dimethyl-3-oxo-N-[(3S)-1-pyrrolidine-3-yl]butaneamide The title compound was prepared according to the procedure described in Step E of Example A1 using (3S)-1-Boc-3-[(4,4-dimethylcyclohexyl)(2,2-dimethyl-3-oxobutanoyl)amino]pyrrolidine (50 mg, 0.12 mmol) prepared in Step A (36 mg, 98%).
MS[M+H]=309(M+1)

Step C: N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethyl-3-oxobutaneamide HCl salt The title compound was prepared according to the procedure described in Step F, G of Example A1, using N-(4,4-dimethylcyclohexyl)-2,2-dimethyl-3-oxo-N-[(3S)-pyrrolidine-3-yl]butaneamide (50 mg, 0.11 mmol) prepared in Step B and (3S,4R)-1-t-butyl-4-(4-chlorophenyl)pyrrolidine-3-carboxylic acid prepared in Preparation Example A9-2 (56 mg, 89%).
MS[M+H]=572 (M+1)
1H NMR (500 MHz, CDCl3) 7.60-7.51 (m, 2H), 7.35-7.30 (m, 2H), 3.95-3.48 (m, 7H), 3.47-3.22 (m, 3H), 2.77-2.69 (m, 1H), 2.53-2.33 (m, 1H), 2.11 (s, 3H), 1.78-1.57 (m, 8H), 1.50-1.37 (m, 10H), 1.35-1.25 (m, 7H), 0.94 (s, 3H), 0.92 (s, 3H)

EXAMPLE C6

N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxy-2,2,3-trimethylbutaneamide HCl salt

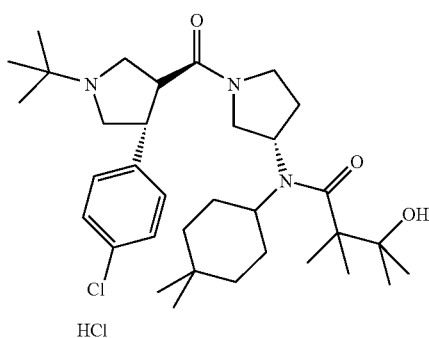

Step A: (3S) 1-Boc-3-[(4,4-dimethylcyclohexyl)(3-hydroxy-2,2,3-trimethylbutanoyl)amino]pyrrolidine To a solution of (3S)-1-Boc-3-[(4,4-dimethylcyclohexyl)(2,2-dimethyl-3-oxobutanoyl)amino]pyrrolidine (100 mg, 0.25 mmol) prepared in Step A of Example C5 in THF was slowly added dropwise methylmagnesium bromide (in diethylether, 3.0M, 0.1 ml, 0.3 mmol) at 0° C., and the solution was stirred at rt for 2 h. After the reaction finished, to the solution was added 1N-HCl at 0° C., and extracted with EtOAc. The organic layer was dried over MgSO4, concentrated in vacuo, and purified by column chromatography (eluent: EtOAc/Hex=1/3) to give the title compound (97 mg, 92%).
MS[M+H]=425 (M+1)

Step B: N-(4,4-dimethylcyclohexyl)-3-hydroxy-2,2,3-trimethyl-N-[(3S)-pyrrolidine-3-yl]butaneamide The title compound was prepared according to the procedure described in Step E of Example A1 using (3S)-1-Boc-3-[(4,4-dimethylcyclohexyl)(3-hydroxy-2,2,3-trimethylbutanoyl)amino]pyrrolidine (80 mg, 0.19 mmol) prepared in Step A (60.5 mg, 98%).
MS[M+H]=325(M+1)

Step C: N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxy-2,2,3-trimethylbutaneamide HCl salt The title compound was prepared according to the procedure described in Step F, G of Example A1, using N-(4,4-dimethylcyclohexyl)-3-hydroxy-2,2,3-trimethyl-N-[(3S)-pyrrolidine-3-yl]butaneamide (62 mg, 0.19 mmol) prepared in Step B and (3S,4R)-1-t-butyl-4-(4-chlorophenyl)pyrrolidine-3-carboxylic acid prepared in Preparation Example A9-2 (99 mg, 89%).
MS[M+H]=588 (M+1)
1H NMR (400 MHz, CDCl3) 7.60-7.49 (m, 2H), 7.39-7.30 (m, 2H), 3.93-3.48 (m, 7H), 3.47-3.21 (m, 3H), 2.77-2.69 (m, 1H), 2.53-2.33 (m, 1H), 1.80-1.55 (m, 8H), 1.52-1.38 (m, 10H), 1.34-1.21 (m, 13H), 0.94 (s, 3H), 0.92 (s, 3H)

EXAMPLE C7

N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-fluoro-2,2-dimethylpropaneamide HCl salt

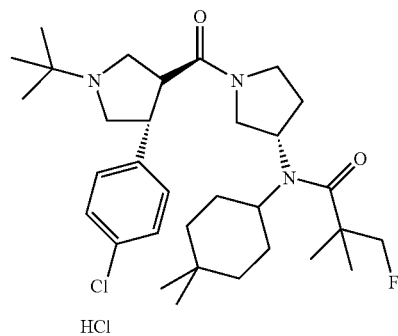

Step A: (3S)-1 Boc-3-[(4,4-dimethylcyclohexyl)(3-fluoro-2,2-dimethylpropanoyl)amino]pyrrolidine To a solution of (3S)-1-Boc-3-[(4,4-dimethylcyclohexyl)(3-hydroxy-2,2-dimethylpropanoyl)amino]pyrrolidine (300 mg, 0.76 mmol) prepared in Step B of Example A8 in DCM was added TEA (192 mg, 1.9 mmol), slowly added dropwise methanesulfonylchloride (104 mg, 0.91 mmol) at 0° C., and the solution was heated to rt, and stirred for 1 h. After the reaction finished, the solvent was concentrated in vacuo, and washed with water and EtOAc. The organic layer was dried over MgSO4, concentrated in vacuo, and purified by column chromatography (eluent: EtOAc/Hex=1/2) to give (3S)-1-Boc-3-[(4,4-dimethylcyclohexyl){2,2-dimethyl-3-[(methylsulfonyl)oxy]propanoyl}amino]pyrrolidine (250 mg, 75%). A solution of this compound (200 mg, 0.42 mmol) in THF was added dropwise TBAF (in THF, 1.0M 0.5 ml, 0.5 mmol), and the solution was stirred at 80° C. for 3 h. After the reaction finished, the solvent was concentrated in vacuo, and extracted with 1N-HCl and EtOAc. The organic layer was dried over MgSO₄, concentrated in vacuo, and purified by column chromatography (eluent: EtOAc/Hex=1/4) to give the title compound (147 mg, 89%).

MS[M+H]=399 (M+1)

Step B: N-(4,4-dimethylcyclohexyl)-3-fluoro-2,2-dimethyl-N-[(3S)-pyrrolidine-3-yl]propaneamide The title compound was prepared according to the procedure described in Step E of Example A1 using (3S)-1-Boc-3-[(4,4-dimethylcyclohexyl)(3-fluoro-2,2-dimethylpropanoyl)amino]pyrrolidine (147 mg, 0.37 mmol) prepared in Step A (108 mg, 98%).

MS[M+H]=299(M+1)

Step C: N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-fluoro-2,2-dimethylpropaneamide HCl salt The title compound was prepared according to the procedure described in Step F, G of Example A1, using N-(4,4-dimethylcyclohexyl)-3-fluoro-2,2-dimethyl-N-[(3S)-pyrrolidine-3-yl]propaneamide (100 mg, 0.47 mmol) prepared in Step B and (3S,4R)-1-t-butyl-4-(4-chlorophenyl)pyrrolidine-3-carboxylic acid prepared in Preparation Example A9-2 (230 mg, 89%).

MS[M+H]=562 (M+1)

1H NMR (400 MHz, CDCl3) 7.58-7.47 (m, 2H), 7.37-7.30 (m, 2H), 4.39-4.28 (m, 2H), 3.92-3.48 (m, 7H), 3.47-3.22 (m, 3H), 2.77-2.69 (m, 1H), 2.53-2.33 (m, 1H), 1.78-1.57 (m, 8H), 1.52-1.38 (m, 10H), 1.35-1.23 (m, 7H), 0.94 (s, 3H), 0.92 (s, 3H)

EXAMPLE C8

N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3,3-difluoro-2,2-dimethylpropaneamide HCl salt

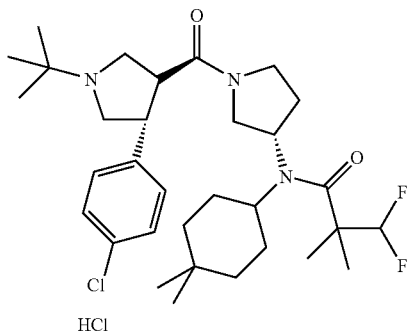

HCl

Step A: (3S)-1-Boc-[(3,3-difluoro-2,2-dimethylpropanoyl)(4,4-dimethylcyclohexyl)amino]pyrrolidine To (3S)-1-Boc-3-[(4,4-dimethylcyclohexyl)(2,2-dimethyl-3-oxopropanoyl)amino]pyrrolidine (1 g, 2.53 mmol) prepared in Step A of Example C3 was added DCM (20 ml), cooled to 78° C., and DAST (0.67 ml, 5.06 mmol) was slowly added dropwise. The mixture was stirred at −78° C. for 1 h, and stirred at rt for 10 h. After the reaction finished, the solvent was concentrated in vacuo, and extracted with water and EtOAc. The organic layer was dried over MgSO₄, concentrated in vacuo, and purified by column chromatography (eluent: EtOAc/Hex=1/1) to give the title compound (630 mg, 60%).

MS[M+H]=417(M+1)

Step B: N-(4,4-dimethylcyclohexyl)-3,3-difluoro-2,2-dimethyl-N-[(3S)-pyrrolidine-3-yl]propaneamide The title compound was prepared according to the procedure described in Step E of Example A1 using (3S)-1-Boc-[(3,3-difluoro-2,2-dimethylpropanoyl)(4,-dimethylcyclohexyl)amino]pyrrolidine (100 mg, 0.24 mmol) prepared in Step A (73 mg, 98%).

MS[M+H]=317(M+1)

Step C: N-[(3S)-1-{[(3S,4R)-1-tert-butyl-4-(4-chlorophenyl)pyrroline-3-yl]carbonyl}pyrrolidine-3-yl]-N-(4,4-dimethylcyclohexyl)-3,3-difluoro-2,2-dimethylpropaneamide HCl salt The title compound was prepared according to the procedure described in Step F, G of Example A1, using N-(4,4-dimethylcyclohexyl)-3,3-difluoro-2,2-dimethyl-N-[(3S)-pyrrolidine-3-yl]propaneamide (73 mg, 0.23 mmol) prepared in Step B and (3S,4R)-1-t-butyl-4-(4-chlorophenyl)pyrrolidine-3-carboxylic acid prepared in Preparation Example A9-2 (118 mg, 89%).

MS[M+H]=580 (M+1)

1H NMR (400 MHz, CDCl3) 7.59-7.49 (m, 2H), 7.38-7.31 (m, 2H), 5.59 (s, 1H), 3.92-3.48 (m, 7H), 3.47-3.22 (m, 3H), 2.77-2.69 (m, 1H), 2.53-2.33 (m, 1H), 1.78-1.57 (m, 8H), 1.52-1.38 (m, 10H), 1.34-1.23 (m, 7H), 0.94 (s, 3H), 0.92 (s, 3H)

EXAMPLE C9

N-[(3S)-1-{[(3S,4R)-1-tert-butyl-4-(4-chlorophenyl)pyrrolidine-3-yl]carbonyl}pyrrolidine-3-yl]-N-[(4,4-difluorocyclohexyl)(3-methoxy-2,2-dimethylpropanoyl)amino]-N-ethyl-N-methyl-L-prolineamide TFA salt

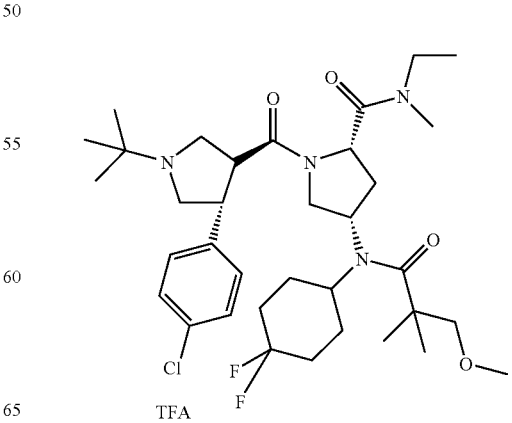

TFA

Step A: 2-methyl-(2S,4S)-1-BOC-4-{[3-(acetyloxy)-2,2-dimethylpropanoyl](4,4-difluorocyclohexyl)amino}pyrrolidine-carboxylate To a solution of 2-methyl-(2S,4S)-1-BOC-4-[(4,4-difluorocyclohexyl)amino]pyrrolidine-carboxylate (1.01 g, 2.84 mmol) prepared in Step A of Example A5 in DCE (5 mL) was added dropwise TEA (5 mL) and DMAP (0.34 g, 2.84 mmol), and added 2,2-dimethyl-3-acetyloxypropionyl chloride (1.01 g, 5.68 mmol) prepared in Preparation Example A4-1. The reaction solution was heated to 90° C., and stirred for 48 h. After the reaction finished, the solvent was removed in vacuo, and to the residue was added a saturated aqueous NaHCO₃ solution, and extracted with EtOAc. The organic extracts were washed with 1N HCl, dried over MgSO₄, concentrated in vacuo, and purified by column chromatography (eluent: EtOAc/Hex=1/4) to give the title compound (0.89 g, 62.9%).
MS[M+H]=505(M+1)

Step B: (4S)-1-BOC-4-[(4,4-difluorocyclohexyl)amino(3-hydroxy-2,2-dimethylpropanoyl)amino]-proline To a solution of 2-methyl-(2S,4S)-1-BOC-4-{[3-(acetyloxy)-2,2-dimethylpropanoyl](4,4-difluorocyclohexyl)amino}pyrrolidine-carboxylate (0.89 g, 1.78 mmol) prepared in Step A in 1N NaOH (5 ml) and water (5 ml), and stirred until the reaction finished. The reaction solution was concentrated in vacuo, acidified with 1N HCl, and extracted with EtOAc. The organic extracts were washed with 1N HCl, dried over MgSO₄, concentrated in vacuo to give the title compound (1.1 g, 90%).
MS[M+H]=449(M+1)

Step C: (2S,4S)-1-BOC-4-[(4,4-difluorocyclohexyl)(3-hydroxy-2,2-dimethylpropanoyl)amino]-2-[(dimethylethylamino)carbonyl]pyrrolidine To a solution of (4S)-1-BOC-4-[(4,4-difluorocyclohexyl)amino(3-hydroxy-2,2-dimethylpropanoyl)amino]-L-proline (1.1 g, 2.6 mmol) prepared in Step B in DMF (5☐) was added dropwise DIPEA (0.08☐, 0.5 mmol), and added dropwise 2M dimethylamine-THF solution (1.8 ml, 3.6 mmol), HOBT (0.5 g, 3.6 mmol) and EDC (0.7 g, 3.6 mmol) were added dropwise in order. After the reaction mixture was stirred at rt for 12 h, the solution was concentrated in vacuo. The residue was diluted with EtOAc, and washed with a saturated NaHCO₃ aqueous solution, water and 1N HCl. The organic solution was dried over MgSO₄, concentrated in vacuo, and the residue was purified by column chromatography (eluent: EtOAc:Hex=1/2) to give the title compound (1.1 g, 93%).
MS[M+H]=490(M+1)

Step D: (2S,4S)-1-BOC-4-[(4,4-difluorocyclohexyl)(3-methoxy-2,2-dimethylpropanoyl)amino]-2-[(dimethylethylamino)carbonyl]pyrrolidine To a solution of (2S,4S)-1-BOC-4-[(4,4-difluorocyclohexyl)(3-hydroxy-2,2-dimethylpropanoyl)amino]-2-[(dimethylamino)carbonyl]pyrrolidine (1.1 g, 2.3 mmol) prepared in Step C in THF was added NaH (83 mg, 3.45 mmol) and iodomethane (490 mg, 3.45 mmol) at 0° C., and the solution was stirred at rt for 2 h. After the reaction finished, the solution was concentrated in vacuo, and extracted with 1N-HCl and EtOAc. The organic layer was washed with brine, dried over MgSO₄, and concentrated in vacuo. The residue was purified by column chromatography (eluent: EtOAc/Hex=1/2) to give the title compound (1.06 mg, 94.6%).
MS[M+H]=504 (M+1

Step E: (4S)-4-[(4,4-difluorocyclohexyl)(3-methoxy-2,2-dimethylpropanol)amino]-N-ethyl-N-methyl-L-prolineamide The title compound was prepared according to the procedure described in Step E of Example A1 using (2S,4S)-1-BOC [(4,4-difluorocyclohexyl)(3-methoxy-2,2-dimethylpropanoyl)amino]-2-[(dimethylethylamino)carbonyl]pyrrolidine (100 mg, 0.20 mmol) prepared in Step D (79 mg, 98%).
MS[M+H]=404(M+1)

Step F: N-[(3S)-1-{[(3S,4R)-1-tert-butyl-4-(4-chlorophenyl)pyrrolidine-3-yl]carbonyl}pyrrolidine-3-yl]-N-[(4,4-difluorocyclohexyl)(3-methoxy-2,2-dimethylpropanoyl)amino]-N-ethyl-N-methyl-L-prolineamide TFA salt The title compound was prepared according to the procedure described in Step F of Example A1, using (4S)-4-[(4,4-difluorocyclohexyl)(3-methoxy-2,2-dimethylpropanoyl)amino]-N-ethyl-N-methyl-L-prolineamide (79 mg, 0.19 mmol) prepared in Step E and (3S,4R)-1-t-butyl-4-(chlorophenyl)pyrrolidine-3-carboxylic acid prepared in Preparation Example A9-2 (112 mg, 89%).
MS[M+H]=667(M+1)
1H NMR (400 MHz, CDCl3) 7.38 (d, 2H), 7.31 (d, 2H), 4.65-4.59 (m, 1H), 4.22-4.02 (m, br, 1H), 4.00-3.93 (m, 1H), 3.86-3.74 (m, 2H), 3.71-3.57 (m, 2H), 3.56-3.19 (m, 9H), 2.96 (d, 3H), 2.86-2.63 (m, br, 1H), 2.33-2.21 (m, 1H), 2.21-2.10 (m, 1H), 2.10-1.96 (m, 1H), 1.86-1.14 (m, 8H), 1.44 (s, 9H), 1.22 (m, 6H), 1.11 (t, 3H)

EXAMPLE C10

(4S)-4-[(3-amino-2,2-dimethylpropanoyl)(4,4-dimethylcyclohexyl)amino]-1-{[(3S,4R)-1-tert-butyl-4-(2,4-difluorophenyl)pyrrolidine-3-yl]carbonyl}-N,N-dimethyl-L-prolineamide HCl salt

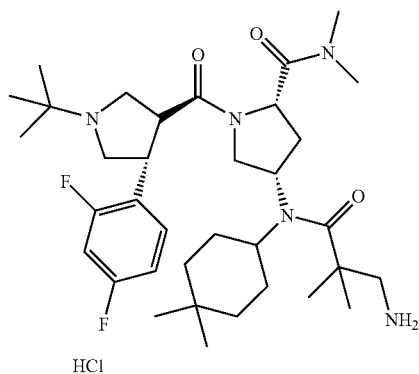

Step A: 1-BOC-(2S,4S)-4-[(2-cyano-2-methylpropanoyl)(4,4-dimethylcyclohexyl)amino]-2-[(dimethylamino)carbonyl]pyrrolidine The title compound was prepared according to the procedure described in Step B~D of Example A1, using methyl-(2S,4S)-1-BOC-4-[(4,4-dimethylcyclohexyl)amino]pyrrolidine-2-carboxylate (1.46 g, 4.14 mmol) prepared in Step A of Example A1 and 2-cyano-2-methylpropanoyl chloride prepared in Preparation Example A4-3 as starting materials (1.07 g, 56%).
MS[M+H]=463 (M+1)

Step B: 1-BOC-(2S,4S)-4-[(3-amino-2,2-dimethyl-propanoyl)(4,4-dimethylcyclohexyl)amino]-2-[(dimethylamino)carbonyl]pyrrolidine To a solution of 1-BOC-(2S,4S)-4-[(2-cyano-2-methyl-propanoyl)(4,4-dimethylcyclohexyl)amino]-2-[(dimethylamino)carbonyl]pyrrolidine (1.07 g, 2.31 mmol) prepared in Step A in methanol was added Pd/C (9 mg), and carried out hydrogen reaction at rt for 10 h. After the reaction finished, the reaction mixture was filtered through Celite, and the filtrate was concentrated in vacuo, and purified by HPLC to give the title compound (0.84 g, 78%).
MS[M+H]=467(M+1)

Step C: 1-BOC-(2S,4S)-4-[(3-{[(benzyloxy)carbonyl]amino}-2,2-dimethylpropanoyl)(4,4-dimethylcyclohexyl)amino]-2-[(dimethylamino)carbonyl]pyrrolidine The title compound was prepared according to the procedure described in Step E of Example B7 using 1-BOC-(2S,4S)-4-[(3-amino-2,2-dimethylpropanoyl)(4,4-dimethylcyclohexyl)amino]-2-[(dimethylamino)carbonyl]pyrrolidine (200 mg, 0.43 mmol) prepared in Step A (201 mg, 80%).
MS[M+H]=601(M+1)

Step D: (4S) [(3-{[(benzyloxy)carbonyl]amino}-2,2-dimethylpropanoyl)(4,4-dimethylcyclohexyl)amino]-N,N-dimethyl-L-prolineamide The title compound was prepared according to the procedure described in Step E of Example A1 using 1-BOC-(2S,4S)-4-[(3-{[(benzyloxy)carbonyl]amino}-2,2-dimethylpropanoyl)(4,4-dimethylcyclohexyl)amino]-2-[(dimethylamino)carbonyl]pyrrolidine (200 mg, 0.33 mmol) prepared in Step C (162 mg, 98%).
MS[M+H]=501(M+1)

Step E: (4S)-4-[(3-{[(benzyloxy)carbonyl]amino}-2,2-dimethylpropanoyl)(4,4-dimethylcyclohexyl)amino]-1-{[(3S,4R)-1-tert-butyl-(2,4-difluorophenyl)pyrrolidine-3-yl]carbonyl}-N,N-dimethyl-L-prolineamide The title compound was prepared according to the procedure described in Step F of Example A1 using (4S)-4-[(3-{[(benzyloxy)carbonyl]amino}-2,2-dimethylpropanoyl)(4,4-dimethylcyclohexyl)amino]-N,N-dimethyl-L-prolineamide (162 mg, 0.32 mmol) prepared in Step D (217 mg, 89%). The reaction proceeded to next step without further purification, and in Step F, HPLC was used for purification.
MS[M+H]=766(M+1)

Step F: (4S)-4-[(3-amino-2,2-dimethylpropanoyl)(4,4-dimethylcyclohexyl)amino]-1-{[(3S,4R)-1-tert-butyl-4-(4-chlorophenyl)pyrrolidine-3-yl]carbonyl}-N,N-dimethyl-L-prolineamide HCl salt The title compound was prepared according to the procedure described in Step E of Preparation Example A1-1 using (4S)-4-[(3-{[(benzyloxy)carbonyl]amino}-2,2-dimethylpropanoyl)(4,4-dimethylcyclohexyl)amino]-1-{[(3S,4R)-1-tert-butyl-4-(2,4-difluorophenyl)pyrrolidine-3-yl]carbonyl}-N,N-diethyl-L-prolineamide (217 mg, 0.28 mmol) prepared in Step E and purification via HPLC (160 mg, 91%).
MS[M+H]=632(M+1)
1H NMR (400 MHz, CDCl3) 8.10-8.04 (m, 1H), 6.97-6.93 (m, 1H), 6.79-6.74 (m, 1H), 4.70 (t, 1H), 4.35-4.22 (m, 2H), 3.95-3.90 (m, 2H), 3.81-3.69 (m, 1H), 3.67-3.54 (m, 2H), 3.42-3.29 (m, 2H), 3.22-3.11 (m, 1H), 2.99 (s, 3H), 2.95 (s, 3H), 2.92-2.70 (m, 3H), 2.19-1.97 (m, 1H), 1.61-1.39 (m, 4H), 1.49 (s, 9H), 1.31-1.15 (m, 4H), 1.27 (s, 6H), 0.95 (s, 3H), 0.91 (s, 3H)

EXAMPLE C11

(4S)-1-{[(3S,4R)-1-tert-butyl-4-(4-chlorophenyl)pyrrolidine-3-yl]carbonyl}-4-{[3-(dimethylamino)-2,2-dimethylpropanoyl](4,4-dimethylcyclohexyl)amino}-N,N-dimethyl-L-prolineamide HCl salt

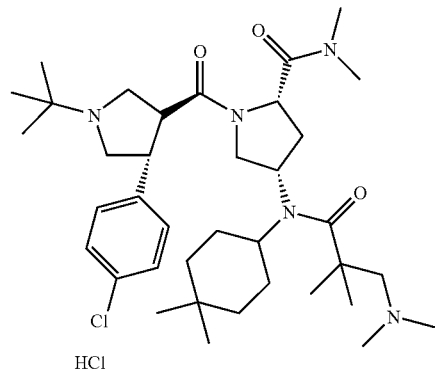

Step A: 1-BOC(2S,4S)-2-[(diethylamino)carbonyl]-4-{[3-(dimethylamino)-2,2-dimethylpropanoyl](4,4-dimethylcyclohexyl)amino}pyrroline The title compound was prepared according to the procedure described in Step A of Example A1 using 1-BOC-(2S,4S)-4-[(3-amino-2,2-dimethylpropanoyl)(4,4-dimethylcyclohexyl)amino]-2-[(dimethylamino)carbonyl]pyrrolidine (142 mg, 0.3 mmol) prepared in Step B of Example C10 and formaldehyde (105 mg, 71%).
MS[M+H]=495(M+1)

Step B: (4S)-4-{[3-(dimethylamino)-2,2-dimethylpropanoyl](4,4-dimethylcyclohexyl)amino}-N,N-dimethyl-prolineamide The title compound was prepared according to the procedure described in Step E of Example A1 using 1-BOC(2S,4S)-2-[(dimethylamino)carbonyl]-4-{[3-(dimethylamino)-2,2-dimethylpropanoyl](4,4-dimethylcyclohexyl)amino}pyrrolidine (105 mg, 0.21 mmol) prepared in Step A (82 mg, 98%).
MS[M+H]=395(M+1)

Step C: (4S)-1-{[(3S,4R)-1-tert-butyl-4-(4-chlorophenyl)pyrrolidine-3-yl]carbonyl}-4-{[3-(dimethylamino)-2,2-dimethylpropanoyl](4,4-dimethylcyclohexyl)amino}-N,N dimethyl-L-prolineamide HCl salt The title compound was prepared according to the procedure described in Step F, G of Example A1, using (4S)-4-

{[3-(dimethylamino)-2,2-dimethylpropanoyl](4,4-dimethylcyclohexyl)amino)}-N,N-dimethyl-L-prolineamide (82 mg, 0.18 mmol) prepared in Step B and (3S,4R)-1-t-butyl-4-(4-chlorophenyl)pyrrolidine-3-carboxylic acid prepared in Preparation Example A9-2 (105 mg, 89%).

MS[M+H]=658(M+1)

1H NMR (400 MHz, CDCl3) 7.50 (d, 2H), 7.32 (d, 2H), 4.70 (t, 1H), 4.35-4.22 (m, 2H), 3.95-3.90 (m, 2H), 3.81-3.69 (m, 1H), 3.67-3.54 (m, 2H), 3.42-3.29 (m, 2H), 3.22-3.11 (m, 1H), 2.99 (s, 3H), 2.95 (s, 3H), 2.88-2.55 (m, 3H), 2.30-2.01 (m, 7H), 1.61-1.39 (m, 4H), 1.49 (s, 9H), 1.31-1.15 (m, 4H), 1.27 (s, 6H), 0.95 (s, 3H), 0.91 (s, 3H)

EXAMPLE C12

N-{(3S,5S)-1-{[(3S,4R)-1-tert-butyl-4-(4-chlorophenyl)pyrrolidine-3-yl]carbonyl}-5-[(dimethylamino)carbonyl]pyrrolidine-3-yl}-N-(4,4-dimethylcyclohexyl)-2,2-dimethylmaloneamide TFA salt

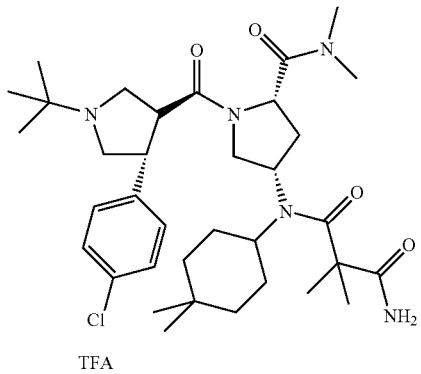

TFA

Step A: 1-BOC-(2S,4S)-4-[(2-cyano-2-methylpropanoyl)(4,4-dimethylcyclohexyl)amino]-2-[(dimethylamino)carbonyl]pyrrolidine The title compound was prepared according to the procedure described in Step B~D of Example A1, using methyl-(2S,4S)-1-BOC-4-[(4,4-dimethylcyclohexyl)amino]pyrrolidine-2-carboxylate (1.77 g, 5 mmol) prepared in Step A of Example A1 and 2-cyano-2-methylpropanoyl chloride prepared in Preparation Example A4-3 as starting materials (1.3 g, 56%).

MS[M+H]=463 (M+1)

Step B: 1-BOC-(2S,4S)-4-[(3-amino-2,2-diethyl-3-oxopropanoyl)(4,4-dimethylcyclohexyl)amino]-2-[(dimethylamino)carbonyl]pyrrolidine To a solution of 1-BOC-(2S,4S)-4-[(2-cyano-2-methylpropanoyl)(4,4-dimethylcyclohexyl)amino]-2-[(dimethylamino)carbonyl]pyrrolidine (1.06 g, 2.3 mmol) prepared in Step A in methanol (10 ml) was added 10N-NaOH (5 ml), and stirred at 80° C. for 2 h. After the reaction finished, the solvent was concentrated in vacuo, diluted with water, and extracted with EtOAc. The extracted organic layer was dried over MgSO4, concentrated in vacuo, and purified by column chromatography (eluent: EtOAc/Hex=3/1) to give the title compound (970 mg, 88%).

MS[M+H]=481 (M+1)

Step C: N-{(3S,5S)-5-[(dimethylamino)carbonyl]pyrrolidine-3-yl}-N-(4,4-dimethylcyclohexyl)-2,2-dimethylmaloneamide The title compound was prepared according to the procedure described in Step E of Example A1 using 1-BOC-(2S,4S)-4-[(3-amino-2,2-dimethyl-3-oxopropanoyl)(4,4-methylcyclohexyl)amino]-2-[(dimethylamino)carbonyl]pyrrolidine (226 mg, 0.47 mmol) prepared in Step B (166 mg, 98%).

MS[M+H]=381 (M+1)

Step D: N-{(3S,5S)-1-{[(3S,4R)-1-tert-butyl-4-(4-chlorophenyl)pyrrolidine-3-yl]carbonyl}-5-[(dimethylamino)carbonyl]pyrrolidine-3-yl}-N-(4,4-dimethylcyclohexyl)-2,2-dimethylmaloneamide TFA salt dried over MgSO4, concentrated F of Example A1, using N-{(3S,5S)-5-[(dimethylamino)carbonyl]pyrrolidine-3-yl}-N-(4,4-dimethylcyclohexyl)-2,2-dimethylmaloneamide (166 mg, 0.53 mmol) prepared in Step C and (3S,4R)-1-t-butyl(4-chlorophenyl)pyrrolidine-3-carboxylic acid prepared in Preparation Example A9-2 (273 mg, 89%).

MS[M+H]=644 (M+1)

1H NMR (500 MHz, CDCl3) 7.36 (d, 21), 7.29 (d, 2H), 4.60 (t, 1H), 4.38-4.25 (m, 1H), 4.25-4.14 (m, 1H), 3.92-3.78 (m, 1H), 3.72-3.27 (m, 6H), 3.19-3.12 (m, 1H), 2.98 (d, 3H), 2.94 (d, 3H), 2.85-2.68 (m, 1H), 2.13-1.99 (m, 1H), 1.62-1.11 (m, 8H), 1.43 (s, 9H), 1.39 (s, 3H), 1.33 (s, 3H), 0.90 (s, 3H), 0.87 (s, 3H)

EXAMPLE C13

S-(3-{[(3S,5S)-1-{[(3S,4R)-1-tert-butyl-4-(2,4-difluorophenyl)pyrrolidine-3-yl]carbonyl}-5-{[ethyl(methyl)amino]carbonyl}pyrrolidine-3-yl](4,4-dimethylcyclohexyl)amino}-2,2-dimethyl-3-oxopropyl) ethanethioate HCl salt

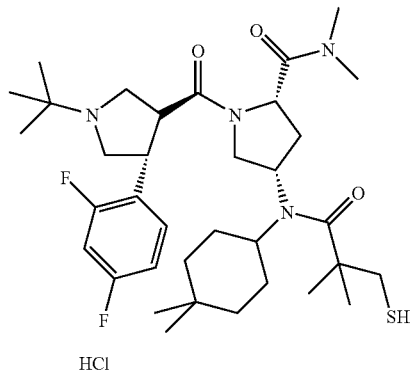

HCl

Step A: 1-BOC-(2S,4S)-4-{[3-(acetylthio)-2,2-dimethylpropanoyl](4,4-dimethylcyclohexyl)amino}-2-{[ethyl(methyl)amino]carbonyl}pyrrolidine The product of Step C of Example A4, BOC-(2S,4S)-4-[(4,4-dimethylcyclohexyl)(3-hydroxy-2,2-dimethylpropanoyl)amino]-2-{[ethyl(methyl)amino]carbonyl}pyrrolidine (1 g, 2.1 mmol) was reacted according to the procedure described in Step C of Preparation Example A1-1 to give 1-BOC-(2S,4S)-4-[(4,4-dimethylcyclohexyl){2,2-dimethyl-3-[(methylsulfonyl)oxy]propanoyl}amino]-2-{[ethyl(methyl)amino]carbonyl}pyrrolidine (0.72 g, 61%). This compound (200 mg, 0.36 mmol) and potassium thioacetate (411 mg, 3.6 mmol) was dissolved in methanol (3.6 mL), and the solution was stirred for 8 h. After the reaction finished, the solution was concentrated in vacuo, and extracted with EtOAc. The organic extracts were washed with water, dried over $MgSO_4$, and concentrated in vacuo to give the title compound (0.14 g, 76%).

MS[M+H]=540 (M+1)

Step B: S-(3-{[(3S,5S)-1-{[(3S,4R)-1-tert-butyl-4-(2,4 difluorophenyl)pyrrolidine-3-yl]carbonyl}-5-{[ethyl(methyl)amino]carbonyl}pyrrolidine-3-yl](4,4-dimethylcyclohexyl)amino}-2,2-dimethyl-3-oxopropyl)ethanethioate HCl salt The title compound was prepared according to the procedure described in Step E-G of Example A1 using 1-BOC-(2S,4S)-4-{[3-(acetylthio)-2,2-dimethylpropanoyl](4,4-methylcyclohexyl)amino}-2-{[ethyl(methyl)amino]carbonyl}pyrrolidine (100 mg, 0.19 mmol) prepared in Step A (60 mg, 44%).

MS[M+H]=705 (M+1)
1H NMR (400 MHz, CDCl3) 8.10-8.03 (m, 1H), 6.9&6.93 (m, 1H), 6.79-6.74 (m, 1H), 4.70 (t, 1H), 4.35-4.22 (m, 2H), 3.95-3.40 (m, 2H), 3.81-3.69 (m, 1H), 3.67-3.54 (m, 2H), 3.42-3.29 (m, 2H), 3.26-3.10 (m, 3H), 2.99 (s, 3H), 2.82-2.63 (m, 3H), 2.19-1.97 (m, 1H), 1.61-1.39 (m, 4H), 1.49 (s, 9H), 1.32-1.15 (m, 7H), 1.27 (s, 6H), 0.95 (s, 3H), 0.91 (s, 3H)

EXAMPLE C14

(4S)-1-{[(3S,4R)-1-tert-butyl-4-(2,4-difluorophenyl)pyrrolidine-3-yl]carbonyl}-4-[(4,4-dimethylcyclohexyl)(3-mercapto-2,2-dimethylpropanoyl)amino]-N-ethyl-N-methyl-L-prolineamide HCl salt

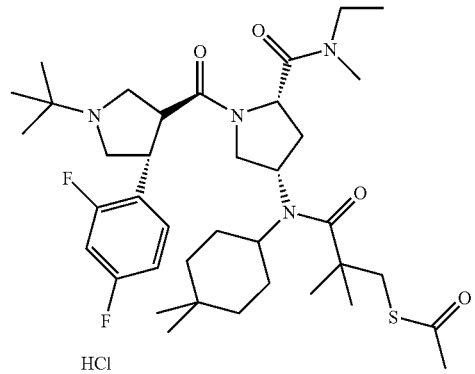

To a solution of S-(3-{[(3S,5S)-1-{[(3S,4R)-1-tert-butyl-4-(2,4-difluorophenyl)pyrrolidine-3-yl]carbonyl}-5-{[ethyl(methyl)amino]carbonyl}pyrrolidine-3-yl](4,4-dimethylcyclohexyl)amino}-2,2-dimethyl-3-oxopropyl)ethanethioate (32 mg, 0.045 mmol) prepared in Example C13 in methanol/water (5:1, 1 mL) was added potassioumcarbonate (38 mg, 0.28 mmol), and the solution was stirred for 5 h. The methanol in the reaction solution was concentrated in vacuo, purified by prep-TLC without further process, and treated according to the procedure described in Step G of Example A1 to give the compound (7 mg, 23%).

MS[M+H]=663 (M+1)
1H NMR (400 MHz, CDCl3) 8.10-8.03 (m, 1H), 6.96-6.93 (m, 1H), 6.79-6.74 (m, 1H), 4.70 (t, 1H), 4.35-4.22 (m, 21), 3.95-3.40 (m, 2H), 3.81-3.69 (m, 1H), 3.67-3.54 (m, 2H), 3.42-3.29 (m, 21), 3.26-3.07 (m, 5H), 2.99 (s, 3H), 2.82-2.30 (m, 4H), 2.19-1.97 (m, 1H), 1.61-1.39 (m, 4H), 1.49 (s, 9H), 1.32-1.15 (m, 7H), 1.27 (s, 6H), 0.95 (s, 3H), 0.91 (s, 3H)

EXAMPLE C15~25

The following Examples were prepared according to the procedure described in Example C1~14, using the intermediates which are prepared in a series of Example A by the reactions between appropriate compounds among Preparation Example A1, A2, A4, A9 and appropriate amines.

TABLE 8

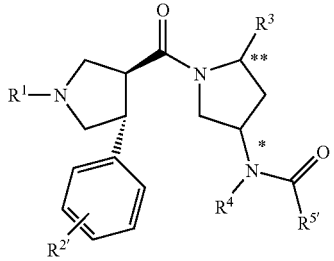

| Example | R¹ | R²' | R³' | R⁴ | R⁵' | * | ** | MS (M + 1) |
|---------|-----|--------|-----|--------------|-------------------------|---|----|-----|
| C15 | t-Bu | 2,4-diF | H | 4,4-diMe-c-Hex | $C(CH_3)_2CH_2NH_2$ | S | | 561 |
| C16 | t-Bu | 4-Cl | H | 4,4-diMe-c-Hex | $N(CH_3)_2$ | S | | 531 |
| C17 | t-Bu | 4-Cl | H | 4,4-diMe-c-Hex | $CH_2CH_2OCH_2CH_3$ | S | | 560 |
| C18 | t-Bu | 4-Cl | H | 4,4-diMe-c-Hex | $C(CH_3)_2CH_2OCH_2$ | S | | 588 |

TABLE 8-continued

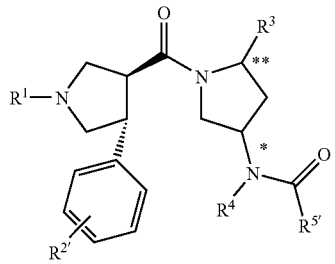

| Example | R¹ | R²' | R³' | R⁴ | R⁵' | * | ** | MS (M + 1) |
|---|---|---|---|---|---|---|---|---|
| C19 | t-Bu | 4-Cl | H | cis-4-Me-c-Hex | $C(CH_3)_2C(O)CH_3$ | S | | 558 |
| C20 | t-Bu | 4-Cl | H | cis-4-Me-c-Hex | $C(CH_3)_2CH(=NOH)$ | S | | 559 |
| C21 | t-Bu | 4-Cl | H | cis-4-Me-c-Hex | $C(CH_3)_2CH_2F$ | S | | 548 |
| C22 | t-Bu | 4-Cl | H | cis-4-Me-c-Hex | $C(CH_3)_2C(O)NH_2$ | S | | 559 |
| C23 | t-Bu | 2,4-diF | H | cis-4-Me-c-Hex | $C(CH_3)_2C(O)NH_2$ | S | | 561 |
| C24 | t-Bu | 4-Cl | $C(O)N(CH_3)_2$ | 4,4-diF-c-Hex | $C(CH_3)_2CH_2OCH_3$ | S | S | 653 |
| C25 | t-Bu | 4-Cl | C(O)NMeEt | 4,4-diF-c-Hex | $C(CH_3)_2CH_2OCH_2CH_3$ | S | S | 681 |

Scheme D

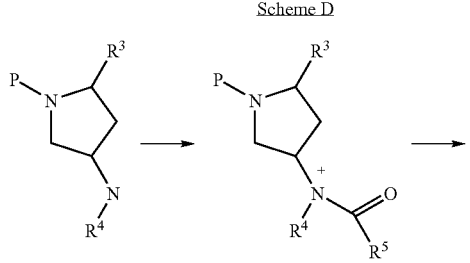

Int. D1

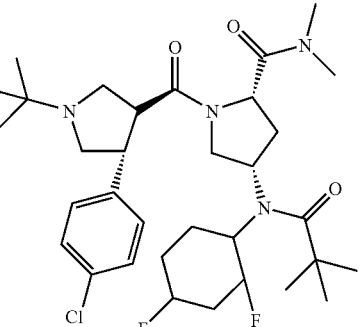

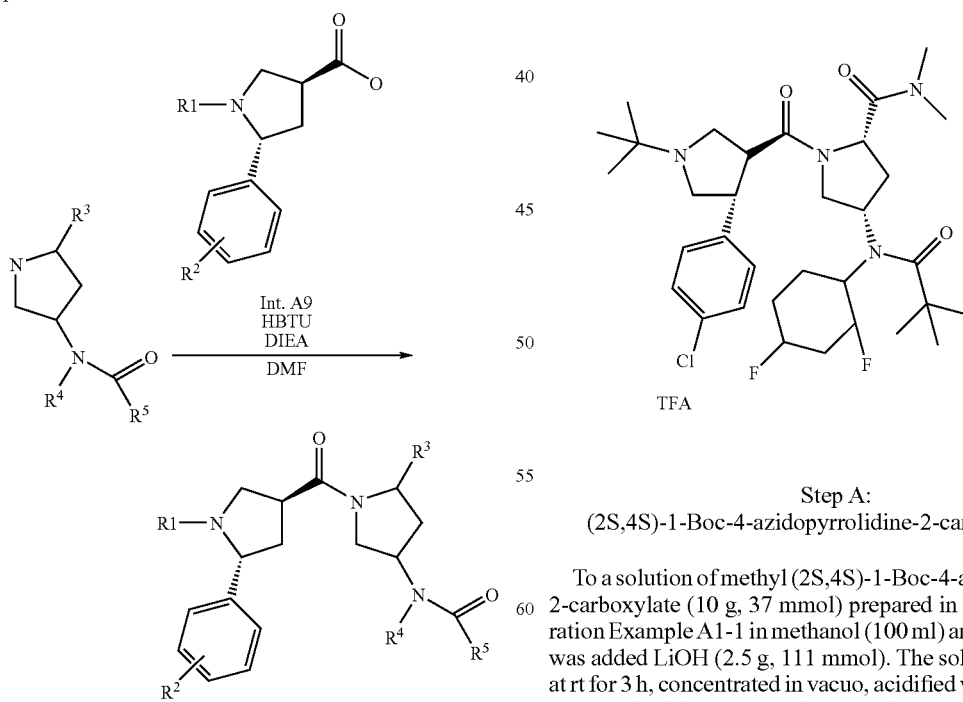

Int. D2

Int. = intermediate

The preparation process of the Intermediate D1 compounds, and the Examples synthesized by the procedure of Scheme D are as follows.

EXAMPLE D1

(4S)-1-{[(3S,4R)-1-tert-butyl-4-(4-chlorophenyl)pyrrolidine-3-yl]carbonyl}-4-[(2,4-difluorophenyl)(2,2-dimethylpropanoyl)amino]-N,N-dimethyl-L-prolineamide TFA salt Step A:
(2S,4S)-1-Boc-4-azidopyrrolidine-2-carboxylic acid To a solution of methyl (2S,4S)-1-Boc-4-azidopyrrolidine-2-carboxylate (10 g, 37 mmol) prepared in Step D of Preparation Example A1-1 in methanol (100 ml) and water (100 ml) was added LiOH (2.5 g, 111 mmol). The solution was stirred at rt for 3 h, concentrated in vacuo, acidified with 1N HCl, and extracted with EtOAC. The organic extracts were washed with brine, dried over MgSO₄, and concentrated in vacuo to give the title compound (9.5 g, 95%).
MS[M+H]=257(M+1)

Step B: (2S,4S) 1-Boc-4-azido[(dimethylamino)carbonyl]pyrrolidine

To a solution of (2S,4S)-1-Boc-4-azidopyrrolidine-2-carboxylic acid (9.5 g, 35 mmol) prepared in Step A in DMF (30☐) was added dropwise DIPEA (1.15☐, 6.70 mmol), and added dropwise 2M dimethylamine-THF solution (26.3 ml, 52.5 mmol), HOBT (7 g, 52.5 mmol) and EDC (10.2 g, 52.5 mmol) in order. The reaction mixture was stirred at rt for 12 h, and concentrated in vacuo. The residue was diluted with EtOAc, and washed with a saturated NaHCO$_3$ aqueous solution, water and 1N HCl. The organic solution was dried over MgSO$_4$, concentrated in vacuo, and the residue was purified by column chromatography (eluent: EtOAc:Hex=1/2) to give the title compound (9.1 g, 93%).
MS[M+H]=284(M+1)

Step C: (2S,4S)-1-Boc-4-amino[(dimethylamino)carbonyl]pyrrolidine

To a solution of (2S,4S)-1-Boc-4-azido[(dimethylamino)carbonyl]pyrrolidine (9 g, 32 mmol) prepared in Step B in dioxane (30 mL) was added dropwise Pd/C (900 mg). The reaction mixture was stirred under hydrogen condition for 24 h, filtered through Celite, and concentrated in vacuo to give the title compound as an oil (8.1 g, 98.5%).
MS[M+H]=258(M+1)

Step D: (2S,4S)-1-Boc-4-[(2,4-difluorophenyl)amino]-2[(dimethylamino)carbonyl]pyrrolidine To a solution of (2S,4S)-1-Boc-4-amino[(dimethylamino)carbonyl]pyrrolidine (8 g, 31.5 mmol) prepared in Step C in toluene (100 ml) was added sodium t-butoxide (3.46 g, 36 mmol), 2-(di-t-butylphosphino)biphenyl (800 mg, 2.68 mmol), tris(dibenzylideneacetone)dipalladium(0) (1.6 g, 1.79 mmol) and 1-bromo-2,4-difluorobenzene (6.94 g, 36 mmol), and the solution was stirred at 110° C. for 10 h. After the reaction finished, the solution was filtered through Celite, and extracted with water and EtOAc. The organic layer was dried over MgSO$_4$, concentrated in vacuo, and purified by column chromatography (eluent, EtOAc/Hex=1/4) to give the title compound (1.5 g, 78%).
MS[M+H]=370 (M+1)

Step E: (4S)-1-{[(3S,4R)-1-tert butyl-4-(4-chlorophenyl)pyrrolidine-3-yl]carbonyl}-4-[(2,4-difluorophenyl)(2,2-dimethylpropanoyl)amino]-N,N-dimethyl-L-prolineamide TEA salt The title compound was prepared according to the procedure described in Step B, E, F, G of Example A1 using (2S,4S)-1-Boc-4-[(2,4-difluorophenyl)amino]-2-[(dimethylamino)carbonyl]pyrrolidine (0.5 g, 1.34 mmol) prepared in Step D as starting material (0.46 g, 55%).
MS[M+H]=617 (M+1)
1H NMR (500 MHz, CDCl3) 7.57 (d, 21), 7.41 (d, 2H), 7.35-7.14 (m, 1H), 7.13-7.00 (m, 1H), 6.99-6.89 (m, 1H), 4.82-4.71 (m, 1H), 4.61-4.53 (m, 1H), 3.92-3.49 (m, 5H), 3.29-3.20 (m, 1H), 3.14-2.85 (m, 2H), 3.04 (d, 3H), 2.93 (d, 3H), 2.59-2.42 (m, 1H), 2.21-2.10 (m, 1H), 1.40 (s, 9H), 0.97 (s, 9H)

EXAMPLE D2~39

The following Examples were prepared according to the procedure described in Example D1, using the intermediates which are prepared in a series of Example A by the reactions between appropriate compounds among Preparation Example A1, A2, A4, A9 and appropriate amines.

TABLE 9

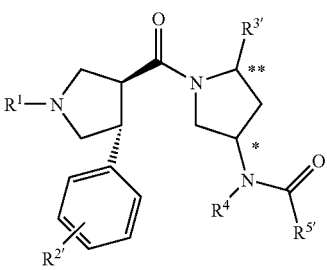

| Example | R$^1$ | R$^{2'}$ | R$^{3'}$ | R$^4$ | R$^{5'}$ | * | ** | MS (M + 1) |
|---|---|---|---|---|---|---|---|---|
| D2 | t-Bu | 4-Cl | H | 2,4-diF-Ph | CH(CH$_3$)$_2$ | S | | 532 |
| D3 | t-Bu | 4-Cl | H | 2,4-diF-Ph | t-Bu | S | | 546 |
| D4 | t-Bu | 4-Cl | H | 2,4-diF-Ph | CF$_3$ | S | | 558 |
| D5 | t-Bu | 4-Cl | H | 2-F-Ph | CH(CH$_3$)$_2$ | S | | 514 |
| D6 | t-Bu | 4-Cl | H | 2,3-diF-Ph | CH(CH$_3$)$_2$ | S | | 532 |
| D7 | t-Bu | 2,4-diF | H | 2,4-diF-Ph | CH(CH$_3$)$_2$ | S | | 534 |
| D8 | t-Bu | 4-Cl | H | 2-F-Ph | t-Bu | S | | 528 |
| D9 | t-Bu | 4-Cl | H | 2,3-diF-Ph | t-Bu | S | | 546 |
| D10 | t-Bu | 4-Cl | H | 3,4-diF-Ph | t-Bu | S | | 546 |
| D11 | t-Bu | 4-Cl | H | 3,5-diF-Ph | t-Bu | S | | 546 |
| D12 | t-Bu | 4-Cl | H | 4-Cl-Ph | t-Bu | S | | 544 |
| D13 | t-Bu | 4-Cl | H | 3-Cl-Ph | t-Bu | S | | 544 |
| D14 | t-Bu | 4-Cl | H | 4-Me-Ph | t-Bu | S | | 524 |
| D15 | t-Bu | 4-Cl | H | 3-Me-Ph | t-Bu | S | | 524 |

TABLE 9-continued

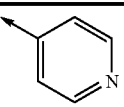

| Example | R¹ | R²′ | R³′ | R⁴ | R⁵′ | * | ** | MS (M + 1) |
|---|---|---|---|---|---|---|---|---|
| D16 | t-Bu | 4-Cl | H | 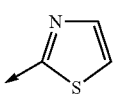 | t-Bu | R | | 511 |
| D17 | t-Bu | 4-Cl | H | 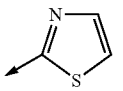 | t-Bu | R | | 517 |
| D18 | t-Bu | 2,4-diF | H |  | t-Bu | R | | 519 |
| D19 | t-Bu | 4-Cl | H | 2,4-diF-Ph | CH(CH₃)₂ | R | | 532 |
| D20 | t-Bu | 4-Cl | H | 2,4-diF-Ph | t-Bu | R | | 546 |
| D21 | t-Bu | 4-Cl | H | 2,4-diF-Ph | 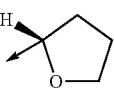 | R | | 556 |
| D22 | t-Bu | 4-Cl | H | Ph | t-Bu | S | | 510 |
| D23 | t-Bu | 4-Cl | C(O)NH₂ | 2,4-diF-Ph | CH(CH₃)₂ | S | S | 575 |
| D24 | t-Bu | 4-Cl | C(O)NH₂ | 4-Cl-Ph | CH(CH₃)₂ | S | S | 573 |
| D25 | t-Bu | 2,4-diF | C(O)N(CH₃)₂ | 2,4-diF-Ph | t-Bu | S | S | 619 |
| D26 | t-Bu | 4-Cl | C(O)N(CH₃)₂ | 2,4-diF-Ph | CH(CH₃)₂ | S | S | 603 |
| D27 | t-Bu | 4-Cl | C(O)N(CH₃)₂ | 4-OMe-Ph | t-Bu | S | S | 611 |
| D28 | t-Bu | 4-Cl | C(O)N(CH₃)₂ | 2,4-diF-Ph | t-Bu | R | S | 617 |
| D29 | t-Bu | 4-Cl | C(O)N(CH₃)₂ | 4-CF₃-Ph | t-Bu | S | S | 650 |
| D30 | t-Bu | 4-Cl | C(O)N(CH₃)₂ | 2,4-diF-Ph | t-Bu | S | R | 617 |
| D31 | t-Bu | 4-Cl | C(O)N(CH₃)₂ | 4-CH₃-Ph | t-Bu | S | S | 595 |
| D32 | t-Bu | 4-Cl | C(O)N(CH₃)₂ | 2,4-diF-Ph | 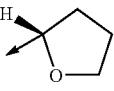 | S | S | 631 |
| D33 | t-Bu | 4-Cl | C(O)N(CH₃)₂ | 4-Cl-Ph | 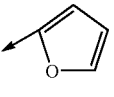 | S | S | 629 |
| D34 | t-Bu | 4-Cl | C(O)N(CH₃)₂ | 2,4-diF-Ph | 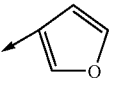 | S | S | 627 |
| D35 | t-Bu | 4-Cl | C(O)N(CH₃)₂ | 2,4-diF-Ph | 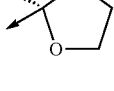 | S | S | 627 |
| D36 | t-Bu | 4-Cl | C(O)N(CH₃)₂ | 2,4-diF-Ph | 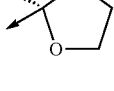 | S | S | 631 |

TABLE 9-continued

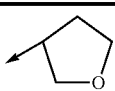

| Example | R¹ | R²' | R³' | R⁴ | R⁵' | * | ** | MS (M + 1) |
|---|---|---|---|---|---|---|---|---|
| D37 | t-Bu | 4-Cl | C(O)N(CH₃)₂ | 2,4-diF-Ph |  | S | S | 631 |
| D38 | t-Bu | 4-Cl | C(O)N(CH₃)₂ | CH₃-(2,4-diF-Ph) | t-Bu | S | S | 631 |
| D39 | t-Bu | 4-Cl | H | 2,4-diF-Ph | 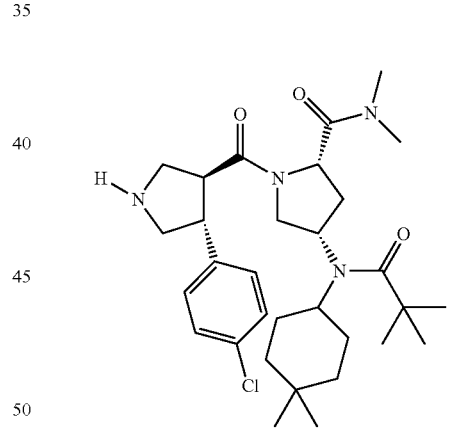 | R | | 575 |

Scheme E

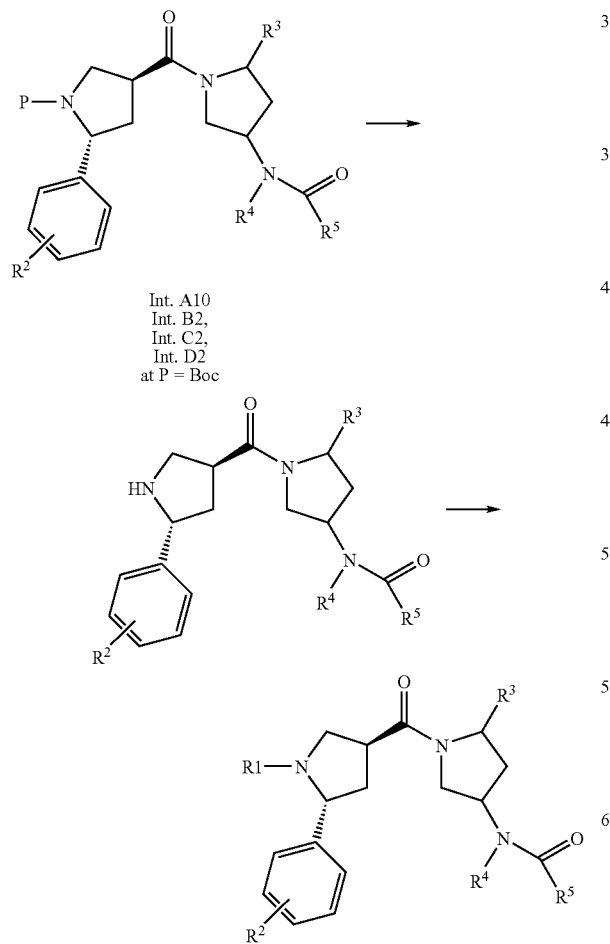

Int. = intermediate

EXAMPLE E1-1

(4S)-1-{[(3S,4R)-4-(4-chlorophenyl)pyrrolidine-3-yl]carbonyl}-4-[(4,4-dimethylcyclohexyl)(2,2-dimethylpropanoyl)amino]-N,N-dimethyl-L-prolineamide Step A 1-BOC-(3R,4S)-3-(4-chlorophenyl)-4-({(2S,4S)-2-[(dimethylamino)carbonyl]-4-[(4,4-dimethylcyclohexyl)(2,2-dimethylpropanoyl)amino]pyrrolidine-1-yl}carbonyl)pyrrolidine The title compound was prepared according to the procedure described in Step F of Example A1, using (4S)-4-[(4,4-dimethylcyclohexyl)(2,2-dimethylpropanoyl)amino]-N,N-dimethyl-L-prolineamide (350 mg, 11.0 mmol) prepared in Step E of Example A1 and (3S,4R)-1-(tert-butoxycarbonyl)-4-(4-chlorophenyl)pyrrolidine-3-carboxylic acid prepared in Preparation Example A9-9 (593 mg, 90%).

MS[M+H]=659(M+1)

Step B: (4S)-1-{[(3S,4R)(4-chlorophenyl)pyrrolidine-3-yl]carbonyl}-4-[(4,4-dimethylcyclohexyl)(2,2-dimethylpropanoyl)amino]-N,N-dimethyl-L-prolineamide 1-BOC-(3R,4S)-3-(4-chlorophenyl)-4-({(2S,4S)-2-[(dimethylamino)carbonyl]-4-[(4,4-dimethylcyclohexyl)(2,2-dimethylpropanoyl)amino]pyrrolidine-1-yl}carbonyl)pyrrolidine (100 mg, 0.15 mmol) prepared in Step A was treated according to the procedure described in Step E of Example A1, and purified by HPLC. This TFA salt of the compound was basified with 1N NaOH, and extracted with EtOAc. The organic layer was dried over MgSO$_4$, and concentrated in vacuo to give the title compound (75 mg, 90%).

MS[M+H]=559(M+1)
1H NMR (500 MHz, CDCl3) 7.30 (d, 2H), 7.24 (d, 2H), 4.71 (t, 1H), 4.29-4.19 (m, 1H), 3.78-3.60 (m, br, 2H), 3.45-3.19 (m, 4H), 3.59-3.50 (m, 1H), 3.06 (s, 3H), 2.96 (s, 3H), 2.96-2.74 (m, 2H), 2.50-2.41 (m, 1H), 2.09-1.95 (m, 1H), 1.63-1.04 (m, 8H), 1.18 (s, 9H), 0.95 (s, 3H), 0.92 (s, 3H)

EXAMPLE E1-2~58

The following Examples were prepared according to the procedure described in Example E1-1, using the intermediates which are prepared in a series of Example A, B, C, D by the reactions between appropriate compounds among Preparation Example A1, A2, A4, A9 and appropriate amines.

TABLE 10

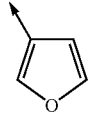

| Example | R$^1$ | R$^{2'}$ | R$^{3'}$ | R$^4$ | R$^{5'}$ | * | ** | MS (M + 1) |
|---|---|---|---|---|---|---|---|---|
| E1-2 | H | 4-Cl | H | Cis-4-Me-c-Hex | CH(CH$_3$)$_2$ | S | | 460 |
| E1-3 | H | 4-Cl | H | 4,4-diMe-c-Hex | CH(CH$_3$)$_2$ | S | | 474 |
| E1-4 | H | 4-Cl | H | 4,4-diMe-c-Hex | t-Bu | S | | 488 |
| E1-5 | H | 4-Cl | H | 4,4-diMe-c-Hex | 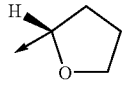 | S | | 498 |
| E1-6 | H | 4-Cl | H | 4,4-diMe-c-Hex | CH$_2$OCH$_2$CH$_3$ | S | | 490 |
| E1-7 | H | 4-Cl | H | 4,4-diMe-c-Hex | CF$_3$ | S | | 500 |
| E1-8 | H | 4-Cl | H | 4,4-diMe-c-Hex | C(CH$_3$)$_2$CN | S | | 499 |
| E1-9 | H | 4-Cl | H | 4,4-diMe-c-Hex | C(CH$_3$)$_2$CH$_2$F | S | | 506 |
| E1-10 | H | 4-Cl | H | 4,4-diMe-c-Hex | C(CH$_3$)$_2$CH$_2$OCH$_2$CH$_3$ | S | | 532 |
| E1-11 | H | 4-Cl | H | 4,4-diMe-c-Hex | 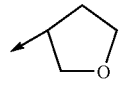 | S | | 502 |
| E1-12 | H | 4-Cl | H | 4,4-diMe-c-Hex | 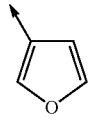 | S | | 502 |
| E1-13 | H | 4-Cl | H | cis-4-Me-c-Hex | t-Bu | S | | 474 |
| E1-14 | H | 4-Cl | H | cis-4-Me-c-Hex | | S | | 484 |
| E1-15 | H | 4-Cl | H | cis-4-Me-c-Hex | C(CH$_3$)$_2$CH(CH$_3$)OH | S | | 504 |
| E1-16 | H | 4-Cl | H | cis-4-Me-c-Hex | C(CH$_3$)$_2$C(CH$_3$)$_2$OH | S | | 518 |
| E1-17 | H | 4-Cl | H | cis-4-Me-c-Hex | C(CH$_3$)$_2$C(O)CH$_3$ | S | | 502 |
| E1-18 | H | 4-Cl | H | cis-4-Me-c-Hex | C(CH$_3$)$_2$C(O)NH$_2$ | S | | 503 |
| E1-19 | H | 2,4-diF | H | cis-4-Me-c-Hex | C(CH$_3$)$_2$C(O)NH$_2$ | S | | 505 |
| E1-20 | H | 4-Cl | H | 4,4-diF-c-Hex | CH(CH$_3$)$_2$ | S | | 482 |

TABLE 10-continued

| Example | R¹ | R²′ | R³′ | R⁴ | R⁵′ | * | ** | MS (M + 1) |
|---|---|---|---|---|---|---|---|---|
| E1-21 | H | 4-Cl | H | 4,4-diF-c-Hex | t-Bu | S | | 496 |
| E1-22 | H | 4-Cl | H | 4,4-diF-c-Hex | CF₃ | S | | 508 |
| E1-23 | H | 4-Cl | H | cis-4-Me-c-Hex | 2,5-dihydrofuran-3-yl | S | | 486 |
| E1-24 | H | 4-Cl | H | 4,4-diF-c-Hex | (S)-tetrahydrofuran-2-yl | S | | 510 |
| E1-25 | H | 2,4-diF | H | 4,4-diMe-c-Hex | furan-3-yl | S | | 500 |
| E1-26 | H | 4-Cl | CONH₂ | cis-4-Me-c-Hex | t-Bu | S | S | 517 |
| E1-27 | H | 4-Cl | Pr | c-Hex | Me | S | S | 460 |
| E1-28 | H | 4-Cl | Pr | c-Hex | t-Bu | S | S | 502 |
| E1-29 | H | 4-Cl | allyl | c-Hex | t-Bu | S | S | 500 |
| E1-30 | H | 2,4-diF | C(O)NH₂ | cis-4-Me-c-Hex | tetrahydrofuran-3-yl | S | S | 533 |
| E1-31 | H | 4-Cl | C(O)NH₂ | cis-4-Me-c-Hex | (S)-tetrahydrofuran-2-yl | S | S | 531 |
| E1-32 | H | 4-Cl | C(O)NH₂ | cis-4-Me-c-Hex | furan-3-yl | S | S | 527 |
| E1-33 | H | 4-Cl | C(O)NH₂ | 4,4-diMe-c-Hex | (S)-tetrahydrofuran-2-yl | S | S | 545 |
| E1-34 | H | 2,4-diF | C(O)NHEt | cis-4-Me-c-Hex | t-Bu | S | S | 547 |
| E1-35 | H | 4-Cl | C(O)NHt-Bu | cis-4-Me-c-Hex | t-Bu | S | R | 573 |
| E1-36 | H | 4-Cl | thiazol-2-yl | c-Hex | Me | S | R | 501 |
| E1-37 | H | 4-Cl | thiazol-2-yl | cis-4-Me-c-Hex | CH(CH₃)₂ | S | R | 543 |
| E1-38 | H | 4-Cl | CH₂NH₂ | 4,4-diMe-c-Hex | t-Bu | S | S | 517 |
| E1-39 | H | 4-Cl | CH₂N(CH₃)₂ | 4,4-diMe-c-Hex | t-Bu | S | S | 545 |

TABLE 10-continued

| Example | R¹ | R²' | R³' | R⁴ | R⁵' | * | ** | MS (M + 1) |
|---|---|---|---|---|---|---|---|---|
| E1-40 | H | 4-Cl | CN | c-Hex | Me | S | R | 443 |
| E1-41 | H | 4-Cl | CN | cis-4-Me-c-Hex | t-Bu | S | R | 499 |
| E1-42 | H | 4-Cl | Ac | c-Hex | Me | S | R | 460 |
| E1-43 | H | 2,4-diF | Ac | cis-4-Me-c-Hex | t-Bu | S | R | 518 |
| E1-44 | H | 4-Cl | Ac | 4,4-diMe-c-Hex | t-Bu | S | R | 530 |
| E1-45 | H | 4-Cl | CH(OH)CH₃ | c-Hex | Me | S | R, S | 462 |
| E1-46 | H | 4-Cl | CH(OH)CH₃ | 4,4-diMe-c-Hex | t-Bu | S | R, S | 532 |
| E1-47 | H | 4-Cl | C(O)NHEt | cis-4-Me-c-Hex | t-Bu | S | S | 545 |
| E1-48 | H | 4-Cl | C(O)NH₂ | cis-4-Me-c-Hex | t-Bu | S | S | 517 |
| E1-49 | H | 2,4-diF | C(O)NH₂ | cis-4-Me-c-Hex | t-Bu | S | S | 519 |
| E1-50 | H | 4-Cl | C(O)N(CH₃)₂ | cis-4-Me-c-Hex | t-Bu | S | S | 545 |
| E1-51 | H | 4-Cl | CH(OH)CH₃ | cis-4-Me-c-Hex | t-Bu | S | R, S | 518 |
| E1-52 | H | 4-Cl | C(O)NH₂ | cis-4-Me-c-Hex | (furan) | S | R | 527 |
| E1-53 | H | 4-Cl | C(O)NH₂ | cis-4-Me-c-Hex | t-Bu | S | R | 517 |
| E1-54 | H | 2,4-diF | C(O)N(CH₃)₂ | 4,4-diMe-c-Hex | t-Bu | S | S | 561 |
| E1-55 | H | 2,4-diF | C(S)N(CH₃)₂ | 4,4-diMe-c-Hex | t-Bu | S | S | 577 |
| E1-56 | H | 4-Cl | C(O)N(CH₃)₂ | 2,4-diF-Ph | CH(CH₃)₂ | S | S | 547 |
| E1-57 | H | 4-Cl | H | 4,4-diMe-c-Hex | C(CH₃)₂CH₂OH | S |  | 504 |

EXAMPLE E2-1

(4S)-1-{[(3S,4R)-1-(aminocarbonyl)-4-(4-chlorophenyl)pyrrolidine-3-yl]carbonyl}-4-[(4,4-dimethylcyclohexyl)(2,2-dimethylpropanoyl)amino]-N,N-dimethyl-L-prolineamide

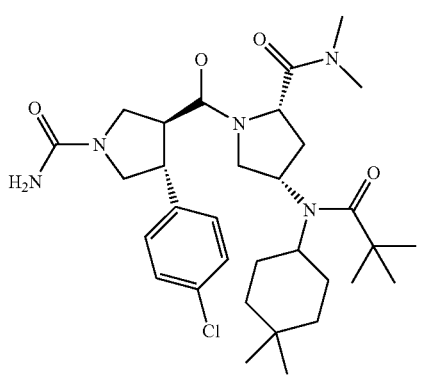

To a solution of (4S)-1-{[(3S,4R)-4-(4-chlorophenyl)pyrrolidine-3-yl]carbonyl}-4-[(4,4-dimethylcyclohexyl)(2,2-dimethylpropanoyl)amino]-N,N-dimethyl-L-prolineamide (84 mg, 0.15 mmol) prepared in Example E1-1 in DMF was added dropwise KOCN (24 mg, 0.3 mmol) and a catalytic amount of acetic acid. The reaction mixture was stirred at rt for 1 h, extracted with EtOAc, washed with excessive amount of water and brine, and the organic solution was dried over MgSO₄. The residue was purified by HPLC to give the title compound.

MS[M+H]=602(M+1)

1H NMR (500 MHz, CDCl3) 7.30 (d, 2H), 7.24 (d, 2H), 4.71 (t, 1H), 4.29-4.19 (m, 1H), 4.05-3.77 (m, 4H), 3.76-3.60 (m, 2H), 3.59-3.50 (m, 1H), 3.06 (s, 3H), 2.96 (s, 3H), 2.99-2.71 (m, 2H), 2.50-2.40 (m, 1H), 2.09-1.95 (m, 1H), 1.63-1.04 (m, 8H), 1.18 (s, 9H), 0.95 (s, 3H), 0.94 (s, 3H)

EXAMPLE E2-2~25

The following Examples were prepared according to the procedure described in Example E2-1, using the intermediates which are prepared in a series of Example A, B, C, D by the reactions between appropriate compounds among Preparation Example A1, A2, A4, A9 and appropriate amines.

TABLE 11

| Example | R¹ | R²' | R³' | R⁴ | R⁵' | * | ** | MS (M + 1) |
|---|---|---|---|---|---|---|---|---|
| E2-2 | NH₂C(O) | 4-Cl | H | 4,4-diMe-c-Hex | C(CH₃)₂CH₂OH | S | | 547 |
| E2-3 | NH₂C(O) | 4-Cl | H | 4,4-diMe-c-Hex | t-Bu | S | | 531 |
| E2-4 | NH₂C(O) | 4-Cl | H | 4,4-diMe-c-Hex | CH(CH₃)₂ | S | | 517 |
| E2-5 | NH₂C(O) | 4-Cl | H | 4,4-diMe-c-Hex | (2S)-tetrahydrofuran-2-yl | S | | 545 |
| E2-6 | NH₂C(O) | 4-Cl | H | 4,4-diMe-c-Hex | tetrahydrofuran-3-yl | S | | 545 |
| E2-7 | NH₂C(O) | 4-Cl | H | 4,4-diMe-c-Hex | C(CH₃)(CH₂OH)₂ | S | | 563 |
| E2-8 | NH₂C(O) | 4-Cl | H | cis-4-Me-c-Hex | CH(CH₃)₂ | S | | 503 |
| E2-9 | NH₂C(O) | 4-Cl | H | cis-4-Me-c-Hex | t-Bu | S | | 517 |
| E2-10 | NH₂C(O) | 4-Cl | H | cis-4-Me-c-Hex | isopropenyl | S | | 501 |
| E2-11 | NH₂C(O) | 4-Cl | H | cis-4-Me-c-Hex | C(CH₃)(CH₂OH)₃ | S | | 549 |
| E2-12 | NH₂C(O) | 2,4-diF | H | 4,4-diMe-c-Hex | t-Bu | S | | 533 |
| E2-13 | NH₂C(O) | 2,4-diF | H | 4,4-diMe-c-Hex | (2S)-tetrahydrofuran-2-yl | S | | 547 |
| E2-14 | NH₂C(O) | 4-Cl | C(O)NH₂ | cis-4-Me-c-Hex | t-Bu | S | S | 560 |
| E2-15 | NH₂C(O) | 4-Cl | C(O)NH₂ | cis-4-Me-c-Hex | CH(CH₃)₂ | S | S | 546 |
| E2-16 | NH₂C(O) | 2,4-diF | C(O)NH₂ | 4,4-diMe-c-Hex | t-Bu | S | S | 576 |
| E2-17 | NH₂C(O) | 2,4-diF | C(O)NH₂ | cis-4-Me-c-Hex | tetrahydrofuran-3-yl | S | S | 576 |
| E2-18 | NH₂C(O) | 4-Cl | C(O)NH₂ | cis-4-Me-c-Hex | (2S)-tetrahydrofuran-2-yl | S | S | 574 |
| E2-19 | NH₂C(O) | 2,4-diF | C(O)NH₂ | cis-4-Me-c-Hex | furan-2-yl | S | S | 572 |
| E2-20 | NH₂C(O) | 2,4-diF | C(O)N(CH₃)₂ | cis-4-Me-c-Hex | tetrahydrofuran-3-yl | S | S | 604 |
| E2-21 | NH₂C(O) | 4-Cl | C(O)N(CH₃)₂ | 4,4-diMe-c-Hex | tetrahydrofuran-3-yl | S | S | 616 |
| E2-22 | NH₂C(O) | 4-Cl | C(O)NH(CH₂)₂NH₂ | cis-4-Me-c-Hex | t-Bu | S | S | 603 |
| E2-23 | NH₂C(O) | 2,4-diF | C(O)NH(CH₂)₂NH₂ | cis-4-Me-c-Hex | t-Bu | S | S | 605 |

TABLE 11-continued

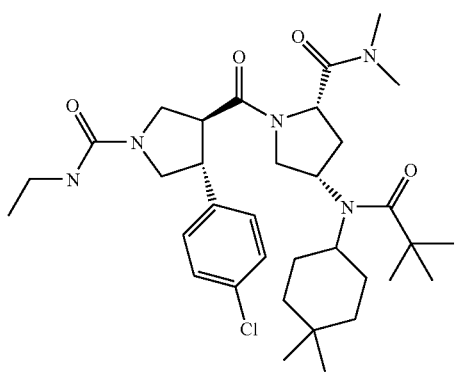

| Example | R¹ | R²' | R³' | R⁴ | R⁵' | * | ** | MS (M + 1) |
|---|---|---|---|---|---|---|---|---|
| E2-24 | NH₂C(O) | 2,4-diF | C(O)NH(CH₂)₃NH₂ | 4,4-diMe-c-Hex | t-Bu | S | S | 633 |
| E2-25 | NH₂C(S) | 2,4-diF | C(O)N(CH₃)₂ | 4,4-diMe-c-Hex | t-Bu | S | S | 620 |

EXAMPLE E3-1

(4S)-1-({[(3S,4R)-4-(4-chlorophenyl)-1-(ethylamino)carbonyl]pyrrolidine-3-yl}carbonyl)-4-[(4,4-dimethylcyclohexyl)(2,2-dimethylpropanoyl)amino]-N,N-dimethyl-L-prolineamide

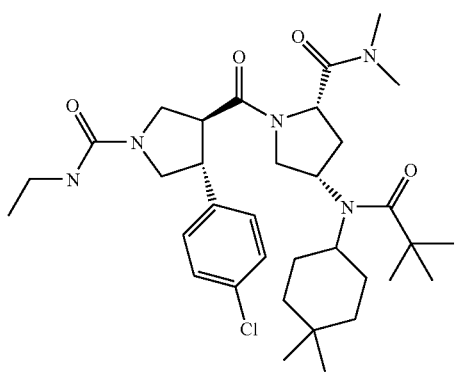

To a solution of (4S)-1-{[(3S,4R)-4-(4-chlorophenyl)pyrrolidine-3-yl]carbonyl}[(4,4-dimethylcyclohexyl)(2,2-methylpropanoyl)amino]-N,N-dimethyl-L-prolineamide (84 mg, 0.15 mmol) prepared in Example E1-1 and TEA (0.04 ml, 0.3 mmol) in DCM, was added dropwise ethylisocyanate (16 mg, 0.22 mmol). The reaction mixture was stirred at rt for 1 h, extracted with EtOAc, washed with excessive amount of water and brine, and the organic solution was dried over MgSO₄. The residue was purified by HPLC to give the title compound.

MS[M+H]=630(M+1)

1H NMR (500 MHz, CDCl3) 7.28 (d, 2H), 7.23 (d, 2H), 4.71 (t, 1H), 4.26-4.13 (m, 1H), 4.08-3.98 (m, 1H), 3.87-3.62 (m, br, 3H), 3.58-3.37 (m, br, 3H), 3.37-3.21 (m, 3H), 3.10-2.96 (m, 1H), 3.05 (s, 3H), 2.94 (s, 3H), 2.74-2.60 (m, 1H), 2.09-1.98 (m, 1H), 1.63-1.04 (m, 8H), 1.18 (s, 9H), 1.14 (t, 3H), 0.95 (s, 3H), 0.93 (s, 3H)

EXAMPLE E3-2

N-[(3S)-1-{[(3S,4R)-4-(4-chlorophenyl)-1-[(ethylamino)carbonothioyl]pyrrolidine-3-yl]carbonyl}pyrrolidine-3-yl]-N-(4,4-difluorocyclohexyl)-3-hydroxy-2,2-dimethylpropaneamide

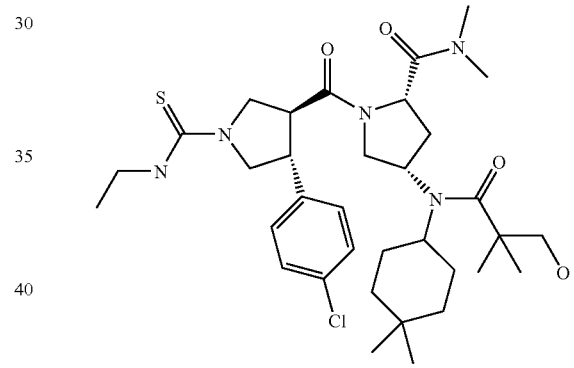

To a solution of N-[(3S)-1-{[(3S,4R)-4-(4-chlorophenyl)pyrrolidine-3-yl)-N-(4,4-dimethylcyclohexyl)-3-hydroxy-2,2-dimethylpropaneamide (93 mg, 0.15 mmol) prepared in Example E1-57 and TEA (0.04 ml, 0.3 mmol) in DCM, was added dropwise ethylisocyanate (19 mg, 0.22 mmol). The reaction mixture was stirred at rt for 1 h, extracted with EtOAc, washed with excessive amount of water and brine, and the organic solution was dried over MgSO₄. The residue was purified by HPLC to give the title compound (74.4 mg, 84%).

MS[M+H]=591(M+1)

1H NMR (500 MHz, CDCl3) 7.55-7.48 (m, 2H), 7.36-7.28 (m, 2H), 3.95-3.20 (m, 12H), 3.12-2.89 (m, 4H), 1.86-1.68 (m, 1H), 1.67-1.53 (m, 6H), 1.52-1.14 (m, 9H), 0.94 (s, 3H), 0.91 (s, 3H), 0.88 (t, 3H)

EXAMPLE E3-3~37

The following Examples were prepared according to the procedure described in Example E3-1,2, using the intermediates which are prepared in a series of Example A, B, C, D by the reactions between appropriate compounds among Preparation Example A1, A2, A4, A9 and appropriate amines.

TABLE 12

| Example | R¹ | R²' | R³' | R⁴ | R⁵' | * | ** | MS (M + 1) |
|---|---|---|---|---|---|---|---|---|
| E3-3 | EtNHC(O) | 4-Cl | H | 4,4-diMe-c-Hex | C(CH₃)₂CH₂OH | S | | 575 |
| E3-4 | EtNHC(O) | 4-Cl | H | 4,4-diMe-c-Hex | CH(CH₃)₂ | S | | 545 |
| E3-5 | EtNHC(O) | 4-Cl | H | 4,4-diMe-c-Hex | (S)-tetrahydrofuran-2-yl | S | | 573 |
| E3-6 | EtNHC(O) | 4-Cl | H | 4,4-diMe-c-Hex | tetrahydrofuran-2-yl | S | | 573 |
| E3-7 | EtNHC(O) | 4-Cl | H | 4,4-diMe-c-Hex | t-Bu | S | | 559 |
| E3-8 | EtNHC(O) | 4-Cl | H | Cis-4-Me-c-Hex | CH(CH₃)₂ | S | | 531 |
| E3-9 | EtNHC(O) | 4-Cl | H | Cis-4-Me-c-Hex | isopropenyl | S | | 529 |
| E3-10 | EtNHC(O) | 4-Cl | H | 2,4-diF-Ph | CH(CH₃)₂ | R | | 547 |
| E3-11 | EtNHC(O) | 4-Cl | H | 2,4-diF-Ph | t-Bu | R | | 561 |
| E3-12 | EtNHC(O) | 2,4-diF | H | 2,4-diF-Ph | t-Bu | R | | 563 |
| E3-13 | t-BuNHC(O) | 4-Cl | H | 4,4-diMe-c-Hex | t-Bu | S | | 587 |
| E3-14 | t-BuNHC(O) | 4-Cl | H | 4,4-diMe-c-Hex | (S)-tetrahydrofuran-2-yl | S | | 601 |
| E3-15 | t-BuNHC(O) | 2,4-diF | H | 4,4-diMe-c-Hex | (S)-tetrahydrofuran-2-yl | S | | 603 |
| E3-16 | n-BuNHC(O) | 4-Cl | H | Cis-4-Me-c-Hex | CH(CH₃)₂ | S | | 559 |
| E3-17 | EtMeNC(O) | 4-Cl | H | Cis-4-Me-c-Hex | CH(CH₃)₂ | S | | 545 |
| E3-18 | EtNHC(S) | 4-Cl | H | 4,4-diMe-c-Hex | CH(CH₃)₂ | S | | 561 |
| E3-19 | EtNHC(S) | 4-Cl | H | Cis-4-Me-c-Hex | CH(CH₃)₂ | S | | 547 |
| E3-20 | MeNHC(S) | 4-Cl | H | Cis-4-Me-c-Hex | CH(CH₃)₂ | S | | 533 |
| E3-21 | EtNHC(O) | 4-Cl | C(O)NH₂ | cis-4-Me-c-Hex | t-Bu | S | S | 588 |
| E3-22 | EtNHC(O) | 2,4-diF | C(O)NH₂ | cis-4-Me-c-Hex | CH(CH₃)₂ | S | S | 576 |
| E3-23 | t-BuNHC(O) | 2,4-diF | C(O)NH₂ | cis-4-Me-c-Hex | CH(CH₃)₂ | S | S | 604 |

TABLE 12-continued

| Example | R¹ | R²' | R³' | R⁴ | R⁵' | * | ** | MS (M + 1) |
|---|---|---|---|---|---|---|---|---|
| E3-24 | PrNHC(O) | 2,4-diF | C(O)NH₂ | cis-4-Me-c-Hex | t-Bu | S | S | 604 |
| E3-25 | EtNHC(O) | 2,4-diF | C(O)NH₂ | 4,4-diMe-c-Hex | | S | S | 618 |
| E3-26 | EtNHC(O) | 2,4-diF | C(O)NH₂ | cis-4-Me-c-Hex | | S | S | 604 |
| E3-27 | EtNHC(O) | 2,4-diF | C(O)NH₂ | cis-4-Me-c-Hex | | S | S | 604 |
| E3-28 | EtNHC(O) | 2,4-diF | C(O)N(CH₃)₂ | cis-4-Me-c-Hex | t-Bu | S | S | 618 |
| E3-29 | EtNHC(O) | 4-Cl | C(O)N(CH₃)₂ | cis-4-Me-c-Hex | t-Bu | S | S | 616 |
| E3-30 | MeNHC(S) | 2,4-diF | C(O)N(CH₃)₂ | cis-4-Me-c-Hex | t-Bu | S | S | 620 |
| E3-31 | EtNHC(S) | 2,4-diF | C(O)N(CH₃)₂ | cis-4-Me-c-Hex | t-Bu | S | S | 634 |
| E3-32 | MeNHC(S) | 4-Cl | C(O)N(CH₃)₂ | 4,4-diMe-c-Hex | t-Bu | S | S | 632 |
| E3-33 | EtNHC(S) | 4-Cl | C(O)N(CH₃)₂ | cis-4-Me-c-Hex | t-Bu | S | S | 632 |
| E3-34 | EtNHC(O) | 2,4-diF | C(O)N(CH₃)₂ | 4,4-diMe-c-Hex | t-Bu | S | S | 632 |
| E3-35 | EtNHC(S) | 2,4-diF | C(O)N(CH₃)₂ | 4,4-diMe-c-Hex | t-Bu | S | S | 648 |
| E3-36 | EtNHC(O) | 2,4-diF | C(O)N(CH₃)₂ | 4,4-diMe-c-Hex | C(CH₃)₂CH₂OH | S | S | 648 |
| E3-37 | EtNHC(O) | 4-Cl | C(O)N(CH₃)₂ | 4,4-diMe-c-Hex | C(CH₃)₂CH₂OH | S | S | 646 |

EXAMPLE E4-1

(4S)-1-({[(3S,4R)-1-acetyl-4-(4-chlorophenyl)pyrrolidine-3-yl]carbonyl}-4-[(4,4-dimethylcyclohexyl)(2,2-dimethylpropanoyl)amino]-N,N-dimethyl-L-prolineamide

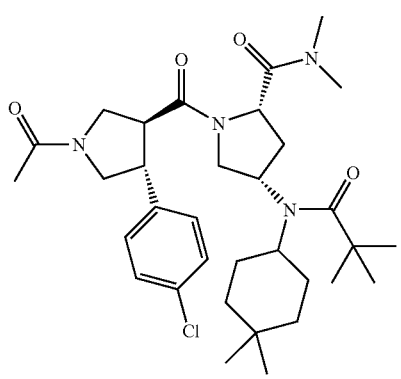

The title compound was prepared according to the procedure described in Step F of Example A1 using (4S)-1-{[(3S,4R)-4-(4-chlorophenyl)pyrrolidine-3-yl]carbonyl}-4-[(4,4-dimethylcyclohexyl)(2,2-dimethylpropanoyl)amino]-N,N-dimethyl-L-prolineamide (84 mg, 0.15 mmol) prepared in Example E1-1 and AcOH via amide coupling reaction.

MS[M+H]=601(M+1)

1H N (500 MHz, CDCl3) 7.30 (d, 2H), 7.24 (d, 2H), 4.71 (t, 1H), 4.29-4.19 (m, 1H), 4.16-4.09 (m, 1H), 4.03-3.79 (m, br, 3H), 3.78-3.60 (m, br, 2H), 3.59-3.50 (m, 1H), 3.37-3.29 (m, 1H), 3.06 (s, 3H), 2.96 (s, 3H), 2.91-2.69 (m, br, 2H), 2.14 (s, 3H), 2.09-1.95 (m, 1H), 1.63-1.04 (m, 8H), 1.18 (s, 9H), 0.95 (s, 3H), 0.94 (s, 3H)

EXAMPLE E4-2~14

The following Examples were prepared according to the procedure described in Example E4-1, using the intermediates which are prepared in a series of Example A, B, C, D by the reactions between appropriate compounds among Preparation Example A1, A2, A4, A9 and appropriate amines.

TABLE 13

![structure]

| Example | $R^1$ | $R^{2'}$ | $R^{3'}$ | $R^4$ | $R^{5'}$ | * | ** | MS (M + 1) |
|---|---|---|---|---|---|---|---|---|
| E4-2 | Ac | 4-Cl | H | 4,4-diMe-c-Hex | $C(CH_3)_2CH_2OH$ | S | | 546 |
| E4-3 | Ac | 4-Cl | H | 4,4-diMe-c-Hex | $CH(CH_3)_2$ | S | | 516 |
| E4-4 | Ac | 4-Cl | H | 4,4-diMe-c-Hex | $C(CH_3)_3$ | S | | 530 |
| E4-5 | Ac | 4-Cl | H | 4,4-diMe-c-Hex | (tetrahydrofuran-2-yl) | S | | 544 |
| E4-6 | Ac | 4-Cl | H | cis-4-Me-c-Hex | $SO_2CH_3$ | S | | 538 |
| E4-7 | $(CH_3)_2CHC(O)$ | 4-Cl | H | 4,4-diMe-c-Hex | $C(CH_3)_3$ | S | | 558 |
| E4-8 | $(CH_3)_2CHC(O)$ | 4-Cl | H | 4,4-diMe-c-Hex | (tetrahydrofuran-2-yl) | S | | 572 |
| E4-9 | $CF_3C(O)$ | 4-Cl | H | 4,4-diMe-c-Hex | $C(CH_3)_3$ | S | | 584 |
| E4-10 | Ac | 4-Cl | $C(O)NH_2$ | cis-4-Me-c-Hex | t-Bu | S | S | 559 |
| E4-11 | $CH(CH_3)_2C(O)$ | 4-Cl | $C(O)NH_2$ | cis-4-Me-c-Hex | $CH(CH_3)_2$ | S | S | 573 |
| E4-12 | $CH_3CH_2C(O)$ | 4-Cl | $C(O)NH_2$ | cis-4-Me-c-Hex | $CH(CH_3)_2$ | S | S | 559 |
| E4-13 | t-BuC(O) | 4-Cl | $C(O)NH_2$ | cis-4-Me-c-Hex | $CH(CH_3)_2$ | S | S | 587 |
| E4-14 | $CH(CH_3)_2C(O)$ | 4-Cl | $C(O)NH_2$ | 4,4-diMe-c-Hex | t-Bu | S | S | 601 |

EXAMPLE E5-1

(4S)-1-({[(3S,4R)-4-(4-chlorophenyl)-1-cyclopropylpyrrolidine-3-yl]carbonyl}-4-[(4,4-dimethylcyclohexyl)(2,2-dimethylpropanoyl)amino]-N,N-dimethyl-L-prolineamide HCl salt

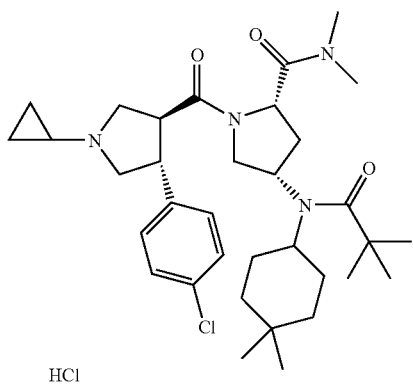

To a solution of (4S)-1-[(3S,4R)-4-(4-chlorophenyl)pyrrolidine-3-yl]carbonyl-4-[(4,4-dimethylcyclohexyl)(2,2-dimethylpropanoyl)amino]-N,N-dimethyl-L-prolineamide (100 mg, 0.18 mmol) prepared in Example E1-1 in DCE (5 ml) was added 1-ethoxycyclopropoxytrimethylsilane (47 mg, 0.27 mmol) and sodium-cyanoborohydride (23 mg, 0.36 mmol), added a catalytic amount of acetic acid, and the solution was stirred at 80° C. for 2 h. After the reaction finished, the solvent was concentrated in vacuo, and extracted with a saturated $NaHCO_3$ aqueous solution and EtOAc. The organic solution was dried over $MgSO_4$, concentrated in vacuo, and the residue was purified by HPLC. This TFA salt of the compound was treated according to the procedure described in Step G of Example A1 to give the title compound.

MS[M+H]=599(M+1)

1H NMR (400 MHz, CDCl3) 7.57 (d, 2H), 7.32 (d, 2H), 4.70 (t, 1H), 4.35-4.22 (m, 2H), 3.95-3.90 (m, 2H), 3.81-3.69 (m, 1H), 3.67-3.54 (m, 2H), 3.42-3.29 (m, 2H), 3.22-3.11 (m, 1H), 2.99 (s, 3H), 2.95 (s, 3H), 2.82-2.68 (m, 1H), 2.15-1.79 (m, 2H), 1.61-1.39 (m, 4H), 1.31-1.15 (m, 4H), 1.22 (s, 9H), 0.95 (s, 3H), 0.91 (s, 3H), 0.82-0.65 (m, 4H),

EXAMPLE E5-2

(4S)-1-{[(3S,4R)-4-(4-chlorophenyl)-1-(tetrahydro-2H-pyran-4-yl)pyrrolidine-3-yl]carbonyl}-4-{(4,4-dimethylcyclohexyl)[(2S)-tetrahydrofuran-2-ylcarbonyl]amino}-N-ethyl-N-methyl-L-prolineamide HCl salt

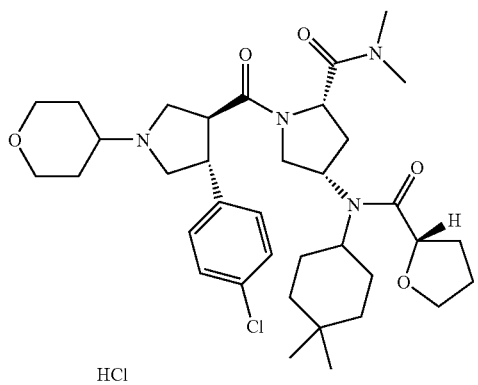

HCl (4S)-4-[(4,4-dimethylcyclohexyl)(tetrahydrofuran-2-yl-carbonyl)amino]-N-ethyl-N-m ethyl-L-prolineamide (100 mg, 0.26 mmol) prepared in Step D of Example A2 and (3S,4R)-1-(tert-butoxycarbonyl)-4-(4-chlorophenyl)pyrrolidine-3-carboxylic acid prepared in Preparation Example A9-9 were reacted according to the procedure described in Step F of Example A1, and then according to that in Step E of Example A1. This compound was reacted with tetrahydro-4H-pyran-4-one via reductive amination as described in Step A of Example A1, and purified by HPLC. This TFA salt of the compound was treated according to the procedure described in Step G of Example A1 to give the title compound (139 mg, 80%).

MS[M+H]=671(M+1)

1H NMR (500 MHz, CDCl3) 7.66-7.52 (m, 2H), 7.37-7.27 (m, 2H), 4.73-4.62 (m, 1H), 4.52-4.39 (m, 1H), 4.32-4.16 (m, 1H), 4.15-3.69 (m, br, 10H), 3.59-3.12 (m, br, 10H), 3.00-2.88 (m, 3H), 2.23-2.80 (m, br, 8H), 1.65-1.04 (m, 11H), 0.98-0.86 (m, 6H)

EXAMPLE E5-3~21

The following Examples were prepared according to the procedure described in Example E5-1,2, using the intermediates which are prepared in a series of Example A, B, C, D by the reactions between appropriate compounds among Preparation Example A1, A2, A4, A9 and appropriate amines.

TABLE 14

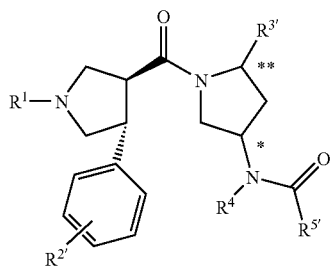

| Example | $R^1$ | $R^{2'}$ | $R^{3'}$ | $R^4$ | $R^{5'}$ | * | ** | MS (M + 1) |
|---|---|---|---|---|---|---|---|---|
| E5-3 | c-Pr | 4-Cl | H | 4,4-diMe-c-Hex | $C(CH_3)_2CH_2OH$ | S | | 544 |
| E5-4 | n-Bu | 4-Cl | H | cis-4-Me-c-Hex | $CH(CH_3)_2$ | S | | 516 |
| E5-5 | i-Pr | 4-Cl | H | 4,4-diMe-c-Hex | t-Bu | S | | 530 |
| E5-6 | $CF_3CH_2$ | 4-Cl | H | 4,4-diMe-c-Hex | t-Bu | S | | 570 |
| E5-7 | c-Pr | 4-Cl | H | 4,4-diMe-c-Hex | $CH(CH_3)_2$ | S | | 514 |
| E5-8 | c-Pr | 4-Cl | H | 4,4-diMe-c-Hex | t-Bu | S | | 528 |
| E5-9 | c-Bu | 4-Cl | H | cis-4-Me-c-Hex | t-Bu | S | | 528 |
| E5-10 | c-Pen | 4-Cl | H | cis-4-Me-c-Hex | $CH(CH_3)_2$ | S | | 528 |
| E5-11 | i-Pr | 2,4-diF | $C(O)N(CH_3)_2$ | 4,4-diF-c-Hex | t-Bu | S | S | 611 |
| E5-12 | i-Pr | 2,4-diF | $C(O)N(CH_3)_2$ | 4,4-diMe-c-Hex | $C(CH_3)_2CH_2OH$ | S | S | 619 |
| E5-13 | c-Bu | 4-Cl | $C(O)N(CH_3)_2$ | 4,4-diMe-c-Hex | $C(CH_3)_2CH_2OH$ | S | S | 629 |
| E5-14 | c-Pen | 4-Cl | $C(O)N(CH_3)_2$ | 4,4-diMe-c-Hex | $C(CH_3)_2CH_2OH$ | S | S | 643 |
| E5-15 | c-Pr | 2,4-diF | $C(O)N(CH_3)_2$ | 4,4-diMe-c-Hex | t-Bu | S | S | 601 |
| E5-16 | c-Pen | 2,4-diF | $C(O)N(CH_3)_2$ | 4,4-diMe-c-Hex | t-Bu | S | S | 629 |
| E5-17 | c-Pr | 2,4-diF | $C(O)N(CH_3)_2$ | 4,4-diMe-c-Hex | $CH(CH_3)_2$ | S | S | 587 |
| E5-18 | c-Pen | 4-Cl | $C(O)N(CH_3)_2$ | 4,4-diMe-c-Hex | t-Bu | S | S | 627 |
| E5-19 | i-Pr | 2,4-diF | $C(O)N(CH_3)_2$ | 4,4-diMe-c-Hex | t-Bu | S | S | 603 |
| E5-20 | c-Pr | 2,4-diF | $C(S)N(CH_3)_2$ | 4,4-diMe-c-Hex | t-Bu | S | S | 617 |
| E5-21 | i-Pr | 2,4-diF | $C(S)N(CH_3)_2$ | 4,4-diMe-c-Hex | t-Bu | S | S | 619 |

EXAMPLE E6

N-[(3S)-1-{[(3S,4R)-4-(4-chlorophenyl)-1-(methylsulfonyl)pyrrolidine-3-yl]carbonyl}pyrrolidine-3-yl]-2-methyl-N-(cis-4-methylcyclohexyl)propaneamide

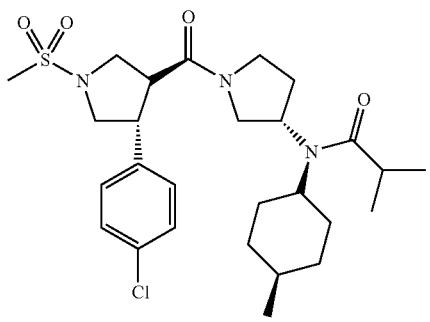

To a solution of N-[(3S)-1{[(3S,4R)-4-(4-chlorophenyl)pyrrolidine-3-yl]-N-(cis-4-methylcyclohexyl)-2-methylpropaneamide TFA salt (124 mg, 0.2 mmol) prepared in Example E1-2 in DCM (3 ml) was added TEA (50 mg, 0.5 mmol), and added methanesulfonylchloride (27.4 mg, 0.24 mmol) at 0° C., and stirred at rt for 30 min. After the reaction finished, the solvent was concentrated in vacuo, the residue extracted with water and EtOAc, and the organic layer was dried over MgSO$_4$. The residue was purified by HPLC to give the title compound (82.8 mg, 77%).

MS[M+H]=538(M+1)

1H NMR (400 MHz, CDCl3) 7.40-7.10 (m, 4H), 3.87-3.50 (m, 6H), 3.47-3.21 (m, 3H), 2.84 (s, 3H), 2.80-2.69 (m, 2H), 2.60-2.33 (m, 2H), 1.78-1.57 (m, 8H), 1.50-1.21 (m, 9H), 0.95 (d, 3H)

EXAMPLE E7-1

(3R,4S)-3-(4-chlorophenyl)-4-({(3S)-3-[(cis-4-methylcyclohexyl)(2-methylpropanoyl)amino]pyrrolidine-1-yl}carbonyl)-N-(2,2,2-trifluoroethyl)pyrrolidine-1-carboxamide

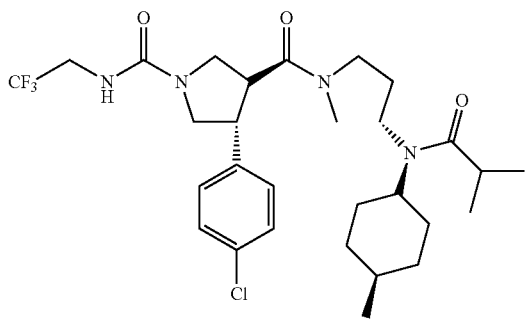

To a solution of phosgene (148 mg, 1.5 mmol) and TEA (30 mg, 0.3 mmol) in DCM (5 ml) was slowly added dropwise N-[(3S)-1-{[(3S,4R)-4-(4-chlorophenyl)pyrrolidine-3-yl]-N-(cis-4-methylcyclohexyl)-2-methylpropaneamide TFA salt (90 mg, 0.15 mmol) prepared in Example E1-2, and stirred at rt for 30 min, and concentrated in vacuo to remove phosgene. To the residue was added DCM (5 ml) and TEA (30 mg, 0.3 mmol), and added dropwise 2,2,2-trifluoroethylamine (20 mg, 0.2 mmol), and stirred at rt for 1 h. After the reaction finished, the solvent was concentrated in vacuo, and the residue was extracted with EtOAc and water, and dried over MgSO$_4$. The residue was purified by HPLC to give the title compound (53.4 mg, 67%).

MS[M+H]=585(M+1)

1H NMR (500 MHz, CDCl3) 7.35-7.28 (m, 2H), 7.22-7.11 (m, 2H), 4.06-3.93 (m, 1H), 3.91-3.71 (m, 5H), 3.70-3.46 (m, 5H), 3.44-3.10 (m, 4H), 2.86-2.66 (m, 2H), 2.55-2.45 (m, 1H), 2.02-1.92 (m, 1H), 1.79-1.56 (m, 5H), 1.51-1.39 (m, 2H), 1.10-1.03 (d, 6H), 1.02-0.96 (m, 3H)

EXAMPLE E7-2~3

The following Examples were prepared according to the procedure described in Example E7-1, using the intermediates which are prepared in a series of Example A, B, C, D by the reactions between appropriate compounds among Preparation Example A1, A2, A4, A9 and appropriate amines.

TABLE 15

| Example | R$^1$ | R$^{2'}$ | R$^4$ | * | MS (M + 1) |
|---|---|---|---|---|---|
| E7-2 | CF$_3$CH$_2$NHC(O) | 4-Cl | 4,4-diMe-c-Hex | S | 613 |
| E7-3 | CF$_3$CH$_2$NHC(O) | 4-Cl | cis-4-Me-c-Hex | S | 599 |

EXAMPLE E8-1 methyl(3R,4S)-3-(4-chlorophenyl)-4-({(3S)-3-[(4,4-dimethylcyclohexyl)(3-hydroxy-2,2-dimethylpropanoyl)amino]pyrrolidine-1-yl}carbonyl)pyrrolidine-1-carboxylate

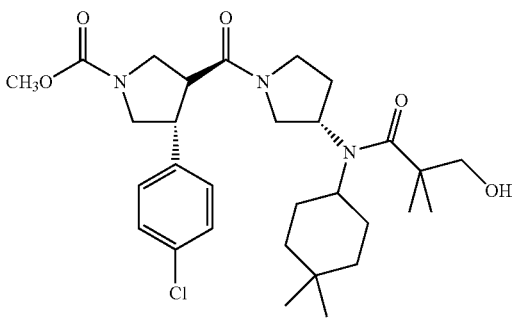

To a solution of N-[(3S)-1-{[(3S,4R))-4-(4-chlorophenyl)pyrrolidine-3-yl]-N-(4,4-dimethylcyclohexyl)-3-hydroxy-2,2-dimethylpropaneamide (93 mg, 0.15 mmol) prepared in Example E1-57 and TEA (0.04 ml, 0.3 mmol) in DCM, was added dropwise methylchloroformate (20 mg, 0.22 mmol). The reaction mixture was stirred at rt for 1 h, extracted with EtOAc, washed with excessive amount of water and brine, and the organic solution was dried over MgSO₄. The residue was purified by HPLC to give the title compound (76 mg, 90%).

MS[M+H]=562(M+1)

1H NMR (500 MHz, CDCl3) 7.30-7.15 (m, 4H), 4.00-3.33 (m, 13H), 3.32-3.22 (m, 1H), 3.21-3.11 (m, 1H), 2.78-2.68 (m, 0.6H), 2.61-2.51 (m, 0.6H), 2.51-2.40 (m, 0.4H), 1.98-1.89 (m, 0.4H), 1.86-1.68 (m, 1H), 1.67-1.35 (m, 7H), 1.32-1.14 (m, 8H), 0.93 (s, 6H)

EXAMPLE E8-2~5

The following Examples were prepared according to the procedure described in Example E8-1, using the intermediates which are prepared in a series of Example A, B, C, D by the reactions between appropriate compounds among Preparation Example A1, A2, A4, A9 and appropriate amines.

TABLE 16

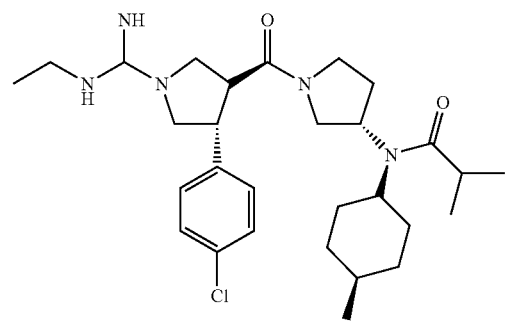

| Example | R¹ | R⁴ | R⁵' | * | MS (M + 1) |
|---|---|---|---|---|---|
| E8-2 | MeOC(O) | 4,4-diMe-c-Hex | CH(CH₃)₂ | S | 532 |
| E8-3 | MeOC(O) | cis-4-Me-c-Hex | t-Bu | S | 532 |
| E8-4 | EtOC(O) | cis-4-Me-c-Hex | CH(CH₃)₂ | S | 532 |
| E8-5 | PhCH₂OC(O) | cis-4-Me-c-Hex | CH(CH₃)₂ | S | 594 |

EXAMPLE E9

N-[(3S)-1-{[(3S,4R)-1-[amino(imino)methyl]-4-(4-chlorophenyl)pyrrolidine-3-yl]carbonyl}pyrrolidine-3-yl]-2-methyl-N-(cis-4-methylcyclohexyl)propaneamide TFA salt

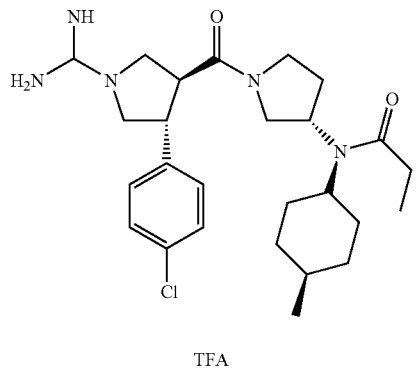

To a solution of N-[(3S)-1-{[(3S,4R)-4-(4-chlorophenyl) pyrrolidine-3-yl]-N-(cis-4-methylcyclohexyl)-2-methylpropaneamide (248 mg, 0.4 mmol) prepared in Example E1-2 in THF (5 ml) was added N,N-bis-Boc-1-guanylpyrazole (186 mg, 0.6 mmol), and stirred at rt for 12 h. After the reaction finished, the solvent was concentrated in vacuo, the residue was extracted with water and EtOAc, and the organic layer was dried over MgSO₄, DCM (3 ml) was added, TFA (1 ml) was added, and stirred at 40° C. for 10 h. The solvent was concentrated in vacuo, and the residue was purified by HPLC to give the title compound (190 mg, 77%).

MS[M+H]=502(M+1)

1H NMR (500 MHz, CDCl3) 7.34-7.28 (m, 2H), 7.25-7.23 (m, 1H), 7.15-7.11 (m, 1H), 4.06-3.93 (m, 1H), 3.91-3.71 (m, 5H), 3.69-3.12 (m, 7H), 2.86-2.66 (m, 2H), 2.55-2.45 (m, 1H), 2.02-1.92 (m, 1H), 1.79-1.56 (m, 5H), 1.51-1.39 (m, 2H), 1.10-1.03 (m, 6H), 1.02-0.96 (m, 3H)

EXAMPLE E10

N-[(3S)-1-({(3S,4R)-4-(4-chlorophenyl)-1-[(ethylamino)(imino)methyl]pyrrolidine-3-yl}carbonyl) pyrrolidine-3-yl]2-methyl-N-(cis-4-methylcyclohexyl)propaneamide TFA salt Step A: N-[(3S)-1-{[(3S,4R)-4-(4-cholorphenyl)-1-cyanopyrrolidine-3-yl]carbonyl}pyrrolidine-3-yl]2-methyl-N-(cis-4-methylcyclohexyl)propaneamide To a solution of N-[(3S)-1-{[(3S,4R)-4-(4-chlorophenyl) pyrrolidine-3-yl]-N-(cis-4-methylcyclohexyl)-2-methylpropaneamide (120 mg, 0.21 mmol) prepared in Example E1-2 in ethanol (5 ml) was added cyanogen bromide (33 mg, 0.31 mmol) and NaHCO₃ (88 mg, 1.05 mmol), and stirred at rt for 1 h. The reaction solution was concentrated in vacuo, extracted with water and EtOAc, and the organic layer was dried over MgSO₄. The organic solution was concentrated to give the title compound, which was used in next step without further purification.

MS[M+H]=485(M+1)

Step B: N-[(3S)-1-({(3S,4R)-4-(4-chlorophenyl)-1-[(ethylamino)(imino)methyl]pyrrolidine-3-yl}carbonyl)pyrrolidine-3-yl]-2-methyl-N-(cis-4-methylcyclohexyl)propaneamide TEA salt To a solution of the compound of Step A in hexafluoroisopropanol (2 ml) was added TEA (1 ml) and excessive amount of ethylamine hydrochloride, and heated to 70° C. The reaction solution was stirred for 5 h, concentrated in vacuo, and purified by HPLC to give the title compound (98.7 mg, 73%).

MS[M+H]=530(M+1)

1H NMR (500 MHz, CDCl3) 7.35-7.28 (m, 2H), 7.25-7.22 (m, 1H), 7.15-7.11 (m, 1H), 4.06-3.93 (m, 1H), 3.91-3.71 (m, 51), 3.70-3.46 (m, 3H), 3.44-3.10 (m, 6H), 2.86-2.66 (m, 2H), 2.55-2.45 (m, 1H), 2.02-1.92 (m, 1H), 1.79-1.56 (m, 5H), 1.51-1.39 (m, 2H), 1.35-1.23 (m, 3H), 1.10-1.03 (m, 6H), 1.02-0.96 (m, 3H)

EXAMPLE E11

N-[(3S)-1-{[(3S,4R)-1-[(acetylamino)(imino)methyl]-4-(4-chlorophenyl)pyrrolidine-3-yl]carbonyl}pyrrolidine-3-yl]-2-methyl-N-(cis-4-methylcyclohexyl)propaneamide

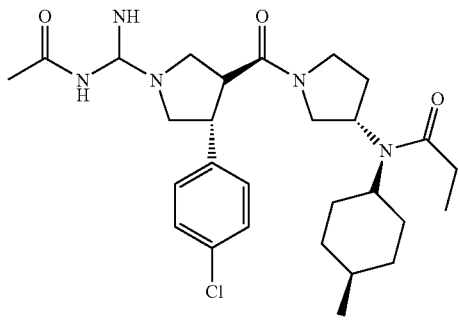

To a solution of N-[(3S)-1-{[(3S,4R)-1-[amino(imino)methyl]-4-(4-chlorophenyl)pyrrolidine-3-yl]carbonyl}pyrrolidine-3-yl]-2-methyl-N-(cis-4-methylcyclohexyl)propaneamide TFA salt (185 mg, 0.3 mmol) prepared in Example E9 in DCM (3 ml) was added acetic acid anhydride (46 mg, 0.45 mmol) and TEA (71 mg, 0.7 mmol), and stirred at rt for 6 h. After the reaction finished, the solvent was concentrated in vacuo, extracted with water and EtOAc, and the organic layer was dried over MgSO$_4$. The organic solution was concentrated in vacuo, and purified by HPLC to give the title compound (139 mg, 85%).

MS[M+H]=544(M+1)

1H NMR (500 MHz, CDCl3) 7.38-7.10 (m, 4I), 4.21-4.05 (m, 1H), 3.95-3.57 (m, 3H), 3.56-3.42 (m, 2H), 3.40-3.04 (m, 3H), 2.75-2.62 (m, 1H), 2.54-2.40 (m, 1H), 2.36-2.21 (m, 2H), 2.01-1.89 (m, 1H), 1.80-1.51 (m, 6H), 1.48-1.34 (m, 3H), 1.33-1.22 (m, 1H), 1.13-0.90 (m, 1H)

EXAMPLE E12-1

N-[(3S)-1-{[(3S,4R)-4-(4-chlorophenyl)-1-phenylpyrrolidine-3-yl]carbonyl}pyrrolidine-3-yl]-N-(4,4-dimethylcyclohexyl)-propaneamide

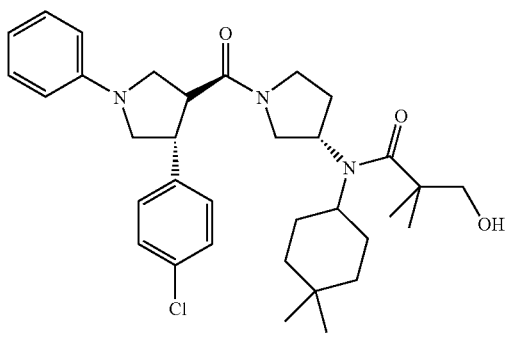

To a solution of N-[(3S)-1-{([(3S,4R)-4-(4-chlorophenyl)pyrrolidine-3-yl]-N-(4,4-dimethylcyclohexyl)-3-hydroxy-2,2-dimethylpropaneamide (124 mg, 0.2 mmol) prepared in Example E1-57 in toluene (5 ml) was added bromobenzene (31 mg, 2 mmol), and carried out the procedure described in Step D of Example D1 to give the title compound (90 mg, 78%).

MS[M+H]=580(M+1)

1H NMR (500 MHz, CDCl3) 7.55-7.47 (m, 2H), 7.41-7.32 (m, 2H), 7.28-7.11 (m, 3H), 3.95-3.20 (m, 12H), 3.01-2.93 (m, 0.4H), 2.75-2.68 (m, 0.6H), 2.48-2.38 (m, 0.6H), 2.18-2.08 (m, 0.4H), 1.86-1.68 (m, 1H), 1.67-1.35 (m, 7H), 1.32-1.14 (m, 8H), 0.94 (s, 3H), 0.91 (s, 3H)

EXAMPLE E12-2~6

The following Examples were prepared according to the procedure described in Example E12-1, using the intermediates which are prepared in a series of Example A, B, C, D by the reactions between appropriate compounds among Preparation Example A1, A2, A4, A9 and appropriate amines.

TABLE 17

| Example | $R^1$ | $R^4$ | $R^{5'}$ | * | MS (M + 1) |
|---|---|---|---|---|---|
| E12-2 | Ph | 4,4-diMe-c-Hex | CH(CH$_3$)$_2$ | S | 550 |
| E12-3 | 2-pyridyl | 4,4-diMe-c-Hex | tetrahydrofuran-2-yl | S | 579 |
| E12-4 | 2-pyridyl | cis-4-Me-c-Hex | t-Bu | S | 551 |
| E12-5 | 2-pyrimidinyl | cis-4-Me-c-Hex | CH(CH$_3$)$_2$ | S | 538 |
| E12-6 | 2-thiazolyl | cis-4-Me-c-Hex | CH(CH$_3$)$_2$ | S | 543 |

EXAMPLE E13-1

N-[(3S)-1-{[(3S,4R)-4-(4-chlorophenyl)-1-(4,5-di-hydro-1H-imidazole-2-yl)pyrrolidine-3-yl]carbonyl}pyrrolidine-3-yl]-N-(4,4-dimethylcyclohexyl)-3-hydroxy-2,2-dimethylpropaneamide TFA salt

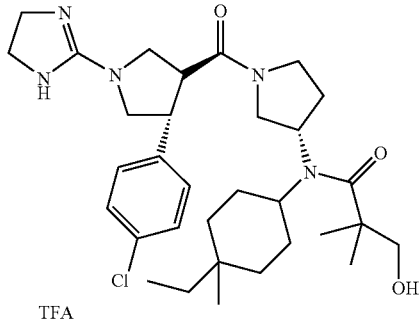

To a solution of N-[(3S)-1-{[(3S,4R) (4-chlorophenyl)pyrrolidine-3-yl]-N-(4,4-dimethylcyclohexyl)-3-hydroxy-2,2-dimethylpropaneamide (124 mg, 0.2 mmol) prepared in Example E1-57 in acetonitrile was added 1-(4,5-dihydro-1H-imidazole-2-yl)-3,5-diethyl-1H-pyrazole hydrobromide (73.5 mg, 0.3 mmol) and TEA (40 mg, 0.4 mmol), and stirred at 90° C. for 5 h. After the reaction finished, the solvent was concentrated in vacuo, extracted with water and EtOAc, and the organic solution was dried over $MgSO_4$. The residue was purified by HPLC to give the title compound (114 mg, 83%).

MS[M+H]=572(M+1)

1H NMR (500 MHz, CDCl3) 7.33-7.15 (m, 4H), 4.01-3.12 (m, 12H), 2.85-2.78 (m, 2H), 2.78-2.71 (m, 0.6H), 2.61-2.53 (m, 0.6H), 2.53-2.43 (m, 0.4H), 2.00-1.91 (m, 0.4H), 1.74-1.65 (m, 3H), 1.58-1.32 (m, 7H), 1.32-1.14 (m, 8H), 0.94 (s, 6H)

EXAMPLE E13-2

N-[(3S)-1-{[(3S,4R)-4-(4-chlorophenyl)-1-(4,5-di-hydro-1H-imidazole-2-yl)pyrrolidine-3-yl]carbonyl}pyrrolidine-3-yl]-N-(4,4-dimethylcyclohexyl)-3-hydroxy-2,2-dimethylpropaneamide TFA salt

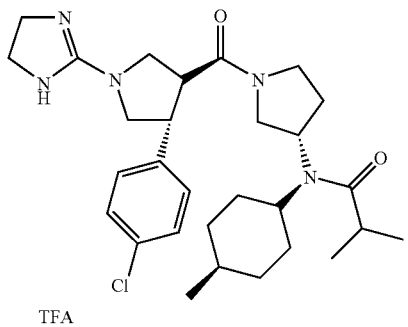

The title compound was prepared according to the procedure described in Example E13-1 using N-[(3S)-1-{[(3S, 4R)-4-(4-chlorophenyl)pyrrolidine-3-yl]-N-(cis-4-methylcyclohexyl)-2-methylpropaneamide prepared in Example E1-2.

MS[M+H]=528(M+1)

Functional Assay

Physiological activity of the compounds of the present invention was assessed by measuring agonistic activity as well as binding activity for melanocortin receptors according to the following assays.

1. Luciferase Assay.

Cell lines expressing human melanocortin receptor 4 (MC4R) were dissociated from tissue culture dishes by rinsing with $Ca^{++}$, $Mg^{++}$ free DPBS, treated with 1× Trypsin/EDTA solution for 1 min at 37° C., and resuspended with DMRM (GIBCO-BRL) supplemented with 10% FBS. The cells were counted and diluted with DMEM supplemented with 10% FBS and 200 ug/ml of Geneticin to 5×110 cells/ml. 90 ul of cell suspension was plated onto each well of 96-well black and clear bottom culture plates (Costar). After the incubation for 24 h in the atmosphere of 6% $CO_2$ at 37° C., 10 ul of NDP-MSH and test compounds diluted in DMSO were added to each well. The final DMSO concentration was 1%. After 4 h of incubation in the atmosphere of 6% $CO_2$ at 37° C., 50 ul of Bright-Glo (Promega) was added to each well. Luciferase activity was measured by using L-Max luminometer (Molecular Device). The amount of luciferase activity induced by treatment with NDP-MSH was defined as 100% to obtain the relative efficacy of test compounds. The $EC_{0.5\ MSH}$ was defined as the concentration of test compounds that results in half maximal activity of NDP-MSH. The $EC_{50}$ was defined as the concentration of test compound that results in half maximal activity of its own.

2. cAMP Accumulation Assay.

Cell lines expressing human melanocortin receptor 4 (MC4R) were grown in F150 mm culture dishes in DMEM (GIBCO-BRL) supplemented with 10% FBS, 200 ug/ml Geneticin (GIBCO-BRL), and antibiotics (penicillin and streptomycin) (GIBCO-BRL) in an atmosphere of 6% $CO_2$ at 37° C. When the cells were fully grown, the cells were washed once with 10 ml of $Ca^{++}$, $Mg^{++}$ free DPBS. The cells were incubated with 8 ml of $Ca^{++}$, $Mg^{++}$ free DPBS for 15 30 min at 37° C. until the cells were easily detached by triturating with pipette. The cells were harvested into 50 ml of conical tubes, and spun at 1500 rpm for 5 min. The supernatant was discarded, and the cells were resuspended in 8 ml of $Ca^{++}$, $Mg^{++}$ free DPBS, and spun at 1500 rpm for 5 min. The supernatant was discarded, and the pellets were resuspended in 3 ml of membrane preparation buffer (10 mM Tris pH 7.4; 0.32M sucrose; 4 ug/ml leupeptin; 10 uM phosphoramidon; 40 ug/ml bacitracin; 5 ug/ml aprotinin). The pellets were homogenized with dounce homogenizer (Bellco with type "B" glass pestle) using 20 strokes. The homogenate was centrifuged at 1300×g at 4° C. for 10 min. The supernatants were collected, and the pellets were resuspended in membrane preparation buffer, and homogenization and centrifugation were repeated. All of the supernatants were collected and centrifuged at 40,000 rpm (Beckman XL-100K Ultracentrifuge, Rotor 45 Ti, 50 ml centrifuge tube) at 4° C. for 15 min. The pellets were resuspended in membrane preparation buffer, and protein was determined by BCA assay kit (PIERCE). Aliquots were placed in tubes and stored at −80° C.

20 ul of NDP-MSH or test compounds diluted in DMSO were added onto each well of 96-well V-plate. 20 ul of 750 ug/ml membrane fraction in MP buffer was added onto each well. After the reaction was performed at rt for 15 min, cAMP was measured using cAMP ($^3H$) assay Kit (Amersham, cat.

No. TRK 432). The amount of cAMP produced by the treatment with test compound was compared to that produced in the response to NDP-MSH which was defined as 100% agonist. The $EC_{50}$ was defined as the concentration of test compound that results in half maximal activity of its own.

INDUSTRIAL APPLICABILITY

As can be seen from the above results, the compounds according to the present invention showed agonistic activity at each MCR. In particular, the compounds according to the present invention showed excellent agonistic activity at MC4R as illustrated in Table shown below.

TABLE 18

| Example | $EC_{50}$(nM) |
|---------|---------------|
| A1  | 13 |
| A2  | 16 |
| A3  | 12 |
| A4  | 3  |
| A5  | 33 |
| A6  | 24 |
| A7  | 24 |
| A9  | 45 |
| A75 | 79 |
| A90 | 30 |
| A96 | 38 |
| A99 | 69 |
| A109 | 54 |
| B4  | 16 |
| B8  | 29 |
| B28 | 14 |
| B33 | 65 |
| C1  | 38 |
| C2  | 11 |
| C3  | 15 |
| C5  | 6  |
| C9  | 41 |
| C12 | 95 |
| C13 | 40 |
| C14 | 66 |
| C24 | 22 |
| D1  | 47 |
| E1-14 | 23 |
| E1-23 | 21 |
| E2-2  | 7  |
| E2-3  | 45 |
| E5-2  | 5  |
| E10   | 4  |

The invention claimed is:

1. A compound of the following formula 1, pharmaceutically acceptable salt or stereoisomer thereof:

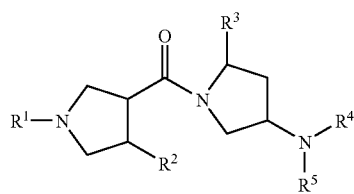

(1)

wherein $R^1$ represents hydrogen, amidino, $C_1$-$C_4$-alkylamidino, $C_1$-$C_4$-alkanoylamidino, $C_1$-$C_{10}$-alkyl, $C_3$-$C_7$-cycloalkyl, $C_6$-$C_{10}$-aryl, heterocycle, heteroaryl, $C_1$-$C_6$-alkylcarbonyl, $C_3$-$C_7$-cycloalkylcarbonyl, $C_1$-$C_4$-alkoxycarbonyl, $C_6$-$C_{10}$-aryl-$C_1$-$C_4$-alkoxycarbonyl, —$SO_2$—$C_1$-$C_4$-alkyl, —C(O)—N($R^6$)($R^7$) or —C(S)—N($R^6$)($R^7$), wherein, $R^6$ and $R^7$ each independently represents hydrogen, $C_1$-$C_6$-alkyl or $C_3$-$C_7$-cycloalkyl, alkyl, cycloalkyl, heterocycle, aryl or heteroaryl is unsubstituted or substituted with one or more substituents independently selected from the group consisting of halogen, amino, $C_1$-$C_4$-alkyl, trifluoromethyl, hydroxy, $C_1$-$C_4$-alkoxy and oxo, $R^2$ represents $C_6$-$C_{10}$-aryl or heteroaryl, each of which is unsubstituted or mono- or di-substituted with a substituent selected from the group consisting of halogen, hydroxy, $C_1$-$C_4$-alkyl, $C_1$-$C_4$-alkoxy, cyano and amino, $R^3$ represents hydrogen, cyano, $C_1$-$C_6$-alkyl, $C_3$-$C_7$-cycloalkyl, $C_2$-$C_6$-alkenyl, monocyclic heterocycle, monocyclic heteroaryl, —C(O)—$R^8$ or —C(S)—$R^8$, wherein, $R^8$ represents hydroxy, $C_1$-$C_4$-alkyl, $C_1$-$C_4$-alkyloxy or N($R^9$)($R^{10}$), $R^9$ and $R^{10}$ each independently represents hydrogen, $C_1$-$C_6$-alkyl, $C_3$-$C_7$-cycloalkyl, $C_1$-$C_4$-alkyloxy, phenyl or heteroaryl, $R^9$ and $R^{10}$ may combine each other to form single ring or two rings, or further comprise oxygen atom or sulfur atom, wherein, alkyl, cycloalkyl, heterocycle, phenyl or heteroaryl is unsubstituted or substituted with a substituent selected from the group consisting of methyl, trifluoromethyl, hydroxy, hydroxyimino, amino, acetylamino, ($C_1$-$C_4$-alkyl)amino and ($C_1$-$C_4$-alkyl)($C_1$-$C_4$-alkyl)amino, $R^4$ represents $C_3$-$C_8$-cycloalkyl, $C_6$-$C_{10}$-aryl, heteroaryl or heterocycle, wherein, $C_6$-$C_{10}$-aryl or heteroaryl is unsubstituted or mono- or poly-substituted with a substituent selected from the group consisting of halogen, hydroxy, $C_1$-$C_4$-alkyl, trifluoromethyl, $C_1$-$C_4$-alkoxy and amino, cycloalkyl or heterocycle is unsubstituted or mono- or poly-substituted with a substituent selected from the group consisting of halogen, hydroxy, $C_1$-$C_4$-alkyl, trifluoromethyl, $C_1$-$C_4$-alkoxy and oxo, $R^5$ represents hydrogen, $C_1$-$C_6$-alkyl, —C(O)—$R^{11}$, $C_1$-$C_6$-alkylsulfonyl, $C_6$-$C_{10}$-arylsulfonyl, —$(CH_2)_p$—$C_6$-$C_{10}$-aryl, —$(CH_2)_p$-heteroaryl or —$(CH_2)_p$—$C_3$-$C_8$-cycloalkyl, wherein, p represents 1 or 2, $R^{11}$ represents $C_1$-$C_{10}$-alkyl, $C_2$-$C_6$-alkenyl, $C_3$-$C_8$-cycloalkyl, $C_3$-$C_8$-cycloalkenyl, amino, $C_1$-$C_4$-alkylamino, ($C_1$-$C_4$-alkyl)($C_1$-$C_4$-alkyl)amino, $C_6$-$C_{10}$-aryl, heteroaryl, or heterocycle, wherein, alkyl is unsubstituted or substituted with one or more substituents independently selected from the group consisting of halogen, hydroxy, mercapto, $C_1$-$C_4$-alkoxy, $C_1$-$C_3$-alkylcarboxy, amino, dimethylamino, $C_1$-$C_4$-alkylcarbonylamino, cyano, carbamoyl, dimethylcarbamoyl, hydroxyimino and oxo, aryl or heteroaryl is unsubstituted or mono- or di-substituted with a substituent selected from the group consisting of halogen, hydroxy, $C_1$-$C_4$-alkyl, trifluoromethyl, $C_1$-$C_4$-alkoxy and amino, cycloalkyl, cycloalkenyl or heterocycle is unsubstituted or mono- or di-substituted with a substituent selected from the group consisting of halogen, hydroxy, amino, $C_1$-$C_4$-alkyl, trifluoromethyl, $C_1$-$C_4$-alkoxy and oxo.

2. The compound of claim 1, wherein
$R^1$ represents hydrogen, amidino, $C_1$-$C_4$-alkylamidino, $C_1$-$C_4$-alkanoylamidino, $C_1$-$C_6$-alkyl; $C_3$-$C_7$-cycloalkyl, phenyl, monocyclic heterocycle, monocyclic heteroaryl, $C_1$-$C_6$-alkylcarbonyl, trifluoroacetyl, $C_1$-$C_4$-alkoxycarbonyl, $C_6$-$C_1$-$C_4$-alkoxycarbonyl, —SO$_2$—$C_1$-$C_4$-alkyl, carbamoyl, $C_1$-$C_6$-alkylcarbamoyl, ($C_1$-$C_6$-alkyl) ($C_1$-$C_6$-alkyl)carbamoyl, thiocarbamoyl, $C_1$-$C_6$-alkylthiocarbamoyl or ($C_1$-$C_6$-alkyl)($C_1$-$C_6$-alkyl)thiocarbamoyl,
wherein, alkyl is unsubstituted or substituted with trifluoromethyl,
pharmaceutically acceptable salt or stereoisomer thereof.
3. The compound of claim 2, wherein
$R^1$ represents hydrogen, amidino, methylamidino, ethylamidino, acetylamidino, methyl, ethyl, trifluoroethyl, propyl, isopropyl, butyl, isobutyl, t-butyl, cyclopropyl, cyclobutyl, cyclopentyl, cyclohexyl, phenyl, oxazolynyl, imidazolynyl, thiazolynyl, piperidinyl, tetrahydropyranyl, imidazolyl, oxazolyl, thiazolyl, pyrazolyl, triazolyl, pyridinyl, acetyl, trifluoroacetyl, propionyl, butyryl, isobutyryl, pivaloyl, methoxycarbonyl, ethoxycarbonyl, benzyloxycarbonyl, methylsulfonyl, carbamoyl, methylcarbamoyl, ethylcarbamoyl, trifluoroethylcarbamoyl, propylcarbamoyl, isopropylcarbamoyl, butylcarbamoyl, t-butylcarbamoyl, thiocarbamoyl, methylthiocarbamoyl, ethylthiocarbamoyl or methylethylcarbamoyl,
pharmaceutically acceptable salt or stereoisomer thereof.
4. The compound of claim 1, wherein
$R^2$ represents phenyl unsubstituted or mono- or di-substituted with a substituent selected from the group consisting of F, Cl and methyl,
pharmaceutically acceptable salt or stereoisomer thereof.
5. The compound of claim 4, wherein
$R^2$ represents phenyl, 4-fluorophenyl, 4-chlorophenyl, 4-methylphenyl or 2,4-difluorophenyl,
pharmaceutically acceptable salt or stereoisomer thereof.
6. The compound of claim 1, wherein
$R^3$ represents hydrogen, cyano, $C_1$-$C_4$-alkyl, $C_2$-$C_4$-alkenyl, —CH$_2$C(CH$_3$)$_2$CH$_2$OH, oxazolyl, thiazolyl, oxazolynyl, thiazolynyl, carboxy, $C_1$-$C_4$-alkylcarbonyl, $C_1$-$C_4$-alkyloxycarbonyl, carbamoyl, thiocarbamoyl, $C_1$-$C_4$-alkylcarbamoyl, ($C_1$-$C_4$-alkyl) ($C_1$-$C_4$-alkyl)carbamoyl, ($C_1$-$C_4$-alkyl) ($C_1$-$C_4$-alkyloxy)carbamoyl, $C_1$-$C_4$-alkylthiocarbamoyl or ($C_1$-$C_4$-alkyl)($C_1$-$C_4$-alkyl)thiocarbamoyl, phenylcarbamoyl, heteroarylcarbamoyl, azetidinecarbonyl, pyrrolidinecarbonyl, piperidinecarbonyl or morpholinecarbonyl,
wherein alkyl is unsubstituted or substituted with a substituent selected from the group consisting of hydroxy, hydroxyimino, amino, ($C_1$-$C_4$-alkyl)amino and ($C_1$-$C_4$-alkyl)($C_1$-$C_4$-alkyl)amino,
pharmaceutically acceptable salt or stereoisomer thereof.
7. The compound of claim 6, wherein
$R^3$ represents hydrogen, cyano, methyl, ethyl, propyl, allyl, —CHNOH, hydroxymethyl, —CH(CH$_3$)OH, aminomethyl, dimethylaminomethyl, oxazolyl, thiazolyl, oxazolynyl, thiazolynyl, carboxy, acetyl, propanoyl, methoxycarbonyl, ethoxycarbonyl, isopropoxycarbonyl, t-butoxycarbonyl, carbamoyl, thiocarbamoyl, ethylcarbamoyl, t-butylcarbamoyl, dimethylcarbamoyl, methylethylcarbamoyl, methylmethoxycarbamoyl, dimethylthiocarbamoyl, phenylcarbamoyl, heteroarylcarbamoyl, —C(O)NH(CH$_2$)$_2$NH$_2$, azetidinecarbonyl, pyrrolidinecarbonyl, piperidinecarbonyl or morpholinecarbonyl,
pharmaceutically acceptable salt or stereoisomer thereof.

8. The compound of claim 1, wherein
$R^4$ represents $C_4$-$C_7$-cycloalkyl or monocyclic heterocycle unsubstituted or mono- or poly-substituted with a substituent selected from the group consisting of halogen, hydroxy, $C_1$-$C_4$-alkyl, trifluoromethyl, $C_1$-$C_4$-alkoxy and oxo; or phenyl or monocyclic heteroaryl unsubstituted or mono- or di-substituted with a substituent selected from the group consisting of halogen, hydroxy, $C_1$-$C_4$-alkyl, trifluoromethyl, $C_1$-$C_4$-alkoxy and amino,
pharmaceutically acceptable salt or stereoisomer thereof.
9. The compound of claim 8, wherein
$R^4$ represents cyclobutyl, cyclopentyl, cyclohexyl, cycloheptyl, 4-methylcyclohexyl, 4,4-dimethylcyclohexyl, 4,4-difluorocyclohexyl, 4-trifluoromethylcyclohexyl, 3,4-tetramethylcyclopentyl, tetrahydropyranyl, pyridinyl, N-methylpyridinyl or phenyl,
wherein, phenyl is unsubstituted or mono- or di-substituted with a substituent selected from the group consisting of F, Cl, methyl and methoxy,
pharmaceutically acceptable salt or stereoisomer thereof.
10. The compound of claim 1, wherein
$R^5$ represents hydrogen, $C_1$-$C_6$-alkyl, —CO—$R^{11}$, $C_1$-$C_6$-alkylsulfonyl, —CH$_2$—$C_6$-$C_{10}$-aryl, —CH$_2$-heteroaryl or —CH$_2$—$C_3$-$C_8$-cycloalkyl,
wherein, $R^{11}$ represents $C_1$-$C_6$-alkyl, difluoromethyl, trifluoromethyl, $C_2$-$C_6$-alkenyl, $C_3$-$C_8$-cycloalkyl, $C_3$-$C_8$-cycloalkenyl, amino, $C_1$-$C_4$-alkylamino or ($C_1$-$C_4$-alkyl)($C_1$-$C_4$-alkyl)amino, phenyl, monocyclic heteroaryl, or monocyclic heterocycle,
wherein, alkyl is unsubstituted or substituted with one or more substituents independently selected from the group consisting of halogen, hydroxy, mercapto, $C_1$-$C_4$-alkoxy, acetoxy, amino, acetylamino, cyano, carbamoyl, dimethylcarbamoyl, hydroxyimino and oxo
phenyl or heteroaryl is unsubstituted or mono- or di-substituted with a substituent selected from the group consisting of F, hydroxy, methyl, trifluoromethyl, methoxy and amino,
cycloalkyl, cycloalkenyl or heterocycle is unsubstituted or mono- or di-substituted with a substituent selected from the group consisting of $C_1$-$C_4$-alkyl, $C_1$-$C_4$-alkoxy and oxo,
pharmaceutically acceptable salt or stereoisomer thereof.
11. The compound of claim 10, wherein
$R^5$ represents hydrogen, $C_1$-$C_5$-alkyl, trifluoromethyl, $C_1$-$C_6$-alkylcarbonyl, trifluoroacetyl, acryloyl, methacryloyl, $C_3$-$C_8$-cycloalkylcarbonyl, $C_3$-$C_8$-cycloalkenylcarbonyl, carbamoyl, $C_1$-$C_4$-alkylcarbamoyl, ($C_1$-$C_4$-alkyl)($C_1$-$C_4$-alkyl)carbamoyl, methanesulfonyl, ethanesulfonyl, propanesulfonyl, benzoyl, hydroxybenzoyl, aminobenzoyl, monocyclic heteroarylcarbonyl, heterocyclecarbonyl, benzyl, —CH$_2$-monocyclic heteroaryl, or —CH$_2$—$C_3$-$C_8$-cycloalkyl,
wherein $C_1$-$C_5$-alkyl, or $C_1$-$C_6$-alkylcarbonyl is unsubstituted or mono- or di-substituted with a substituent selected from the group consisting of F, hydroxy, mercapto, methoxy, ethoxy, acetoxy, amino, methylcarbonylamino, cyano, carbamoyl, hydroxyimino and oxo,
pharmaceutically acceptable salt or stereoisomer thereof.
12. The compound of claim 11, wherein
$R^5$ represents hydrogen, methyl, ethyl, propyl, isobutyl, hydroxyethyl, —CH$_2$C(CH$_3$)$_2$CH$_2$OH, —CH$_2$C(CH$_3$)$_2$CH(CH$_3$)OH, —CH$_2$CH$_2$NHC(O)CH$_3$, aminoethyl, acetyl, trifluoroacetyl, hydroxyacetyl, methoxyacetyl, ethoxyacetyl, propionyl, ethoxypropionyl, isobutyryl, cyanoisobutyryl, hydroxyisobutyryl, carbamoylisobutyryl, 3,3-dimethylbutanoyl, pivaloyl, fluoropivaloyl, difluoropivaloyl, hydroxypivaloyl, mercaptopivaloyl, dihydroxypivaloyl, methoxypivaloyl, ethoxypivaloyl, aminopivaloyl, dimethylaminopivaloyl, hydroxyiminopivaloyl, acetylisobutyryl, —C(O)C(CH$_3$)$_2$CH(CH$_3$)OH, —C(O)C(CH$_3$)$_2$C(CH$_3$)$_2$OH, acryloyl, methacryloyl, cyclopentanecarbonyl, cyclohexylenecarbonyl, carbamoyl, dimethylcarbamoyl, methanesulfonylcarbonyl, benzoyl, thiopenecarbonyl, furoyl, oxazolecarbonyl, thiazolecarbonyl, imidazolecarbonyl, pyrazolecarbonyl, tetrahydrofuroyl, dihydrofuroyl, tetrahydropyrancarbonyl, morpholinecarbonyl, methanesulfonyl, benzyl, furanmethyl, thiazolemethyl or imidazolemethyl, pharmaceutically acceptable salt or stereoisomer thereof.

13. The compound of claim 1, wherein

R$^1$ represents hydrogen, amidino, methylamidino, ethylamidino, acetylamidino, methyl, ethyl, trifluoroethyl, propyl, isopropyl, butyl, isobutyl, t-butyl, cyclopropyl, cyclobutyl, cyclopentyl, cyclohexyl, phenyl, oxazolynyl, imidazolynyl, thiazolynyl, piperidinyl, tetrahydropyranyl, imidazolyl, oxazolyl, thiazolyl, pyrazolyl, triazolyl, pyridinyl, acetyl, trifluoroacetyl, propionyl, butyryl, isobutyryl, pivaloyl, methoxycarbonyl, ethoxycarbonyl, benzyloxycarbonyl, methylsulfonyl, carbamoyl, methylcarbamoyl, ethylcarbamoyl, trifluoroethylcarbamoyl, propylcarbamoyl, isopropylcarbamoyl, butylcarbamoyl, t-butylcarbamoyl, thiocarbamoyl, methylthiocarbamoyl, ethylthiocarbamoyl or methylethylcarbamoyl, R$^2$ represents phenyl, 4-fluorophenyl, 4-chlorophenyl, 4-methylphenyl or 2,4-difluorophenyl, R$^3$ represents hydrogen, cyano, methyl, ethyl, propyl, allyl, —CHNOH, hydroxymethyl, —CH(CH$_3$)OH, aminomethyl, dimethylaminomethyl, oxazolyl, thiazolyl, oxazolynyl, thiazolynyl, carboxy, acetyl, propanoyl, methoxycarbonyl, ethoxycarbonyl, isopropoxycarbonyl, t-butoxycarbonyl, carbamoyl, thiocarbamoyl, ethylcarbamoyl, t-butylcarbamoyl, dimethylcarbamoyl, methylethylcarbamoyl, methylmethoxycarbamoyl, dimethylthiocarbamoyl, phenylcarbamoyl, hetero arylcarbamoyl, —C(O)NH(CH$_2$)$_2$NH$_2$, azetidinecarbonyl, pyrrolidinecarbonyl, piperidinecarbonyl or morpholinecarbonyl, R$^4$ represents cyclobutyl, cyclopentyl, cyclohexyl, cycloheptyl, 4-methylcyclohexyl, 4,4-dimethylcyclohexyl, 4,4-difluorocyclohexyl, 4-trifluoromethylcyclohexyl, 3,4-tetramethylcyclopentyl, tetrahydropyranyl, pyridinyl, N-methylpyridinyl or phenyl, wherein, phenyl is unsubstituted or mono- or di-substituted with a substituent selected from the group consisting of F, Cl, methyl and methoxy, R$^5$ hydrogen, methyl, ethyl, propyl, isobutyl, hydroxyethyl, —CH$_2$C(CH$_3$)$_2$CH$_2$OH, —CH$_2$C(CH$_3$)$_2$CH(CH$_3$)OH, —CH$_2$CH$_2$NHC(O)CH$_3$, aminoethyl, acetyl, trifluoroacetyl, hydroxyacetyl, methoxyacetyl, ethoxyacetyl, propionyl, ethoxypropionyl, isobutyryl, cyanoisobutyryl, hydroxyisobutyryl, carbamoylisobutyryl, 3,3-dimethylbutanoyl, pivaloyl, fluoropivaloyl, difluoropivaloyl, hydroxypivaloyl, mercaptopivaloyl, dihydroxypivaloyl, methoxypivaloyl, ethoxypivaloyl, aminopivaloyl, dimethylaminopivaloyl, hydroxyiminopivaloyl, acetylisobutyryl, —C(O)C(CH$_3$)$_2$CH(CH$_3$)OH, —C(O)C(CH$_3$)$_2$C(CH$_3$)$_2$OH, acryloyl, methacryloyl, cyclopentanecarbonyl, cyclohexylenecarbonyl, carbamoyl, dimethylcarbamoyl, methanesulfonylcarbonyl, benzoyl, thiopenecarbonyl, furoyl, oxazolecarbonyl, thiazolecarbonyl, imidazolecarbonyl, pyrazolecarbonyl, tetrahydrofuroyl, dihydrofuroyl, tetrahydropyrancarbonyl, morpholinecarbonyl, methanesulfonyl, benzyl, furanmethyl, thiazolemethyl or imidazolemethyl, pharmaceutically acceptable salt or stereoisomer thereof.

14. The compound of claim 13, which is selected from the following group:

(4S)-1-{[(3S,4R)-1-tert-butyl-4-(2,4-difluorophenyl)pyrrolidine-3-yl]carbonyl}-4-[(4,4-dimethylcyclohexyl)(2,2-dimethylpropanoyl)amino]-N,N-dimethyl-L-prolineamide (4S)-1-{[(3S,4R)-1-tert-butyl-4-(4-chlorophenyl)pyrrolidine-3-yl]carbonyl}-4-{(4,4-dimethylcyclohexyl)[(2S)-tetrahydrofuran-2-ylcarbonyl]amino}-N,N-ethylmethyl-L-prolineamide (4S)-1-{[(3S,4R)-1-tert-butyl-4-(4-chlorophenyl)pyrrolidine-3-yl]carbonyl}-4-{(4,4-dimethylcyclohexyl)[(2S)-tetrahydrofuran-2-ylcarbonyl]amino}-N-ethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(3-hydroxy-2,2-dimethylpropanoyl)amino]-N-ethyl-N-methyl-L-prolineamide (4S)-1-{[(3S,4R)-1-tert-butyl-4-(4-chlorophenyl)pyrrolidine-3-yl]carbonyl}-4-[(4,4-difluorocyclohexyl)(2,2-dimethylpropanoyl)amino]-N,N-dimethyl-L-prolineamide (4S)-1-{[(3S,4R)-1-tert-butyl-4-(4-chlorophenyl)pyrrolidine-3-yl]carbonyl}-4-[(4,4-difluorocyclohexyl)(2,2-dimethylpropanoyl)amino]-N-ethyl-L-prolineamide (4S)-1-{[(3S,4R)-4-(4-chlorophenyl)-1-methylpyrrolidine-3-yl]carbonyl}-4-[(2,2-dimethylpropanoyl)(cis-4-methylcyclohexyl)amino]-L-prolineamide N-[(3S)-1-{[(3S,4R)-1-t-butyl-4-(4-chlorophenyl)pyrrolidine-3-yl]carbonyl}pyrrolidine-3-yl]-N-(4,4-dimethylcyclohexyl)-3-hydroxy-2,2-dimethylpropaneamide N-[(3S)-1-{[(3S,4R)-1-t-butyl-4-(4-chlorophenyl)pyrrolidine-3-yl]carbonyl}pyrrolidine-3-yl]-N-(4,4-dimethylcyclohexyl)-2,2-dimethylpropaneamide (4S)-1-{[(3S,4R)-1-tert-butyl-4-(2,4-difluorophenyl)pyrrolidine-3-yl]carbonyl}-4-[(4,4-dimethylcyclohexyl)(methylsulfonyl)amino]-N,N-dimethyl-L-prolineamide N-[(3S)-1-{[(3S,4R)-1-t-butyl-4-(4-chlorophenyl)pyrrolidine-3-yl]carbonyl}pyrrolidine-3-yl] (4,4-dimethylcyclohexyl)amino}-2,2-dimethylpropane-1-ol (3S)-1-{[(3S,4R)-1-tert-butyl-4-(4-chlorophenyl)pyrrolidine-3-yl]carbonyl}-N-isobutyl-N-(cis-4-methylcyclohexyl)pyrrolidine-3-amine (4S)-1-{[(3S,4R)-1-tert-butyl-4-(4-chlorophenyl)pyrrolidine-3-yl]carbonyl}-4-[(cis-4-methylcyclohexyl)(tetrahydro-2H-pyran-4-ylcarbonyl)amino]-L-prolineamide (4S)-1-{[(3S,4R)-1-tert-butyl-4-(2,4-difluorophenylpyrrolidine-3-yl]carbonyl}-4-[(4,4-dimethylcyclohexyl)(3-thienylcarbonyl)amino]-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(isobutyryl)amino]-N,N-dimethyl-L-prolineamide (4S)-1-{[(3S,4R)-1-tert-butyl-4-(4-chlorophenyl)pyrrolidine-3-yl]carbonyl}-4-[(4,4-dimethylcyclohexyl)(2,2,-dimethylpropanoyl)amino]-N,N-dimethyl-L-prolineamide (4S)-1-{[(3S,4R)-1-tert-butyl-4-(2,4-difluorophenyl)pyrrolidine-3-yl]carbonyl}-4-[(2,2,-dimethylpropanoyl)(cis-4-methylcyclohexyl)amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(2,2,-dimethylpropanoyl)amino]-N-ethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(2,2,-dimethylpropanoyl)amino]-N-ethyl-N-methyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(2,2,-dimethylpropanoyl)amino]-N-isopropyl-L-prolineamide N-[(3S,5S)-5-(azetidine-1-ylcarbonyl)-1-[(3S,4R)-1-tert-butyl-4-(2,4-difluorophenyepyrrolidine-3-yl]carbonyl}pyrrolidine-3-yl]-N-(4,4-dimethylcyclohexyl)-2,2-dimethylpropaneamide (4S)-1-{[(3S,4R)-1-tert-butyl-4-(2,4-difluorophenyl)pyrrolidine-3-yl]carbonyl}-4-[(2,5-dihydrofuran-3-ylcarbonyl)(4,4-dimethylcyclohexyl)amino]-N,N-dimethyl-L-prolineamide (4S)-1-{[(3S,4R)-1-tert-butyl-4-(4-chlorophenyl)pyrrolidine-3-yl]carbonyl}-4-[(4,4-dimethylcyclohexyl)(3-hydroxy-2,2,-dimethylpropanoyl)amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)[(2S)-tetrahydrofuran-2-ylcarbonyl]amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-difluorocyclohexyl)(3-hydroxy-2,2,-dimethylpropanoyl)amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(3-hydroxy-2,2,-dimethylpropanoyl)amino]-N-ethyl-N-methyl-L-prolineamide (4S)-1-{[(3S,4R)-1-tert-butyl-4-(4-chlorophenyl)pyrrolidine-3-yl]carbonyl}-4-[(4,4-dimethylcyclohexyl)(3-furoyl)amino]-N,N-dimethyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)(3-furoyl)amino]-N-ethyl-N-methyl-L-prolineamide N-[(3S)-1-{[(3S,4R)-1-tert-butyl-4-(4-chlorophenyl)pyrrolidine-3-yl]carbonyl}pyrrolidine-3-yl]-N-[(4,4-difluorocyclohexyl)(3-hydroxy-2,2-dimethylpropanoyl)amino]-N-ethyl-N-methyl-L-prolineamide (4S)-1-{[(3S,4R)-1-tert-butyl-4-(2,4-difluorophenyl)pyrrolidine-3-yl]carbonyl}-4-[(4,4-dimethylcyclohexyl)[(2S)-tetrahydrofuran-2-ylcarbonyl]amino]-N-ethyl-N-methyl-L-prolineamide (4S)-1-{[(3S,4R)-1-tert-butyl-4-(4-chlorophenyl)pyrrolidine-3-yl]carbonyl}-4-[(4,4-difluorocyclohexyl)(2,2,-dimethylpropanoyl)amino]-N-ethyl-N-methyl-L-prolineamide (4S)-1-{[(3S,4R)-1-tert-butyl-4-(4-chlorophenyl)pyrrolidine-3-yl]carbonyl}-N-ethyl-4-[(3-hydroxy-2,2,-dimethylpropanoyl)(cis 4-methylcyclohexylamino]-N-methyl-L-prolineamide N-[(3S,5S)-1-{[(3S,4R)-1-tert-butyl-4-(4-chlorophenyl)pyrrolidine-3-yl]carbonyl}-5-{[ethyl(methyl)amino]carbonyl}pyrrolidine-3-yl]-N-(4,4-dimethylcyclohexyl)-2,2-dimethylpropaneamide N-[(3S,5S-1-{[(3S,4R)-1-tert-butyl-4-(4-chlorophenyl)pyrrolidine-3-yl]carbonyl}-5-(pyrrolidine-1-ylcarbonyl)pyrrolidine-3-yl]-N-(4,4-difluorocyclohexyl)-2,2-dimethylpropaneamide (4S)-1-{[(3S,4R)-1-tert-butyl-4-(4-chlorophenyl)pyrrolidine-3-yl]carbonyl}-N-ethyl-N-methyl-4-{spiro[2,5]oct-6-yl[(2S)-tetrahydrofuran-2-ylcarbonyl]amino}-L-prolineamide N-[(3S,5S-1-{[(3S,4R)-1-tert-butyl-4-(4-chlorophenyl)pyrrolidine-3-yl]carbonyl}-5-(morpholine-4-ylcarbonyl)pyrrolidine-3-yl]-N-(4,4-dimethylcyclohexyl)acetamide (4S)-1-{[(3S,4R)-1-tert-butyl-4-(4-chlorophenyl)pyrrolidine-3-yl]carbonyl}-4-[(4,4-dimethylcyclohexyl)[(2R)-tetrahydrofuran-2-ylcarbonyl]amino]-N-ethyl-N-methyl-L-prolineamide (4S)-1-{[(3S,4R)-1-tert-butyl-4-(4-chlorophenyl)pyrrolidine-3-yl]carbonyl}-4-[(4,4-dimethylcyclohexyl)(3-hydroxy-2,2,-dimethylpropanoyl)amino]-N-ethyl-L-prolineamide (4S)-1-{[(3S,4R)-1-tert-butyl-4-(4-chlorophenyl)pyrrolidine-3-yl]carbonyl}-4-[(4,4-dimethylcyclohexyl)(2,2,-dimethylpropanoyl)amino]-N-phenyl-L-prolineamide (2S)—N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)tetrahydrofuran-2-carboxamide N-[(3S)-1-{[(3S,4R)-1-tert-butyl-4-[(4-chlorophenyl)pyrrolidine-3-yl]carbonyl}pyrrolidine-3-yl]-2-methyl-N-(cis-4-(trifluoromethyl)cyclohexyl]propaneamide (2S)—N-[(3S)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)tetrahydrofuran-2-carboxamide N-[(35)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)tetrahydrofuran-3-carboxamide N-[(3S)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)-3-hydroxy-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-cycloheptyl-3-hydroxy-2,2-dimethylpropaneamide (4S)-1-{[(3S,4R)-1-tert-butyl-4-(4-chlorophenyl)pyrrolidine-3-yl]carbonyl}-4-{(4,4-dimethylcyclohexyl)(methylsulfonyl)amino}-N-ethyl-N-methyl-L-prolineamide (3S)-1-{[(3S,4R)-1-tert-butyl-4-(4-chlorophenyl)pyrrolidine-3-yl]carbonyl}-N-(4,4-dimethylcyclohexyl)-N-3-furylpyrrolidine-3-amine N-[(3S,5S)-1-{[(3S,4R)-1-tert-butyl-4-(4-chlorophenyl)pyrrolidine-3-yl]carbonyl}-5-(4,5-dihydro-1,3-oxazole-2-yl)pyrrolidine-3-yl]-N-(4,4-dimethylcyclohexyl)-2,2-dimethylpropaneamide N-(3S,5S)-1-{[(3S,4R)-1-tert-butyl-4-(4-chlorophenyl)pyrrolidine-3 carbonyl-5-[(dimethylamino)carbonothionyl]pyrrolidine-3-yl}-N-(4,4-dimethylcyclohexyl)-2-methylpropaneamide N-[(3S,5R)-1-{[(3S,4R)-1-tert-butyl-4-(2,4-difluorophenyl)pyrrolidine-3-yl]carbonyl}-5-(1,3-thiazole-2-yl)pyrrolidine-3-yl]-N-(4,4-dimethylcyclohexyl)-2,2-dimethylpropaneamide N-[(3S,5S)-1-{[(3S,4R)-1-tert-butyl-4-(4-chlorophenyl)pyrrolidine-3-yl]carbonyl}-5-(hydroxymethyl)pyrrolidine-3-yl]-N-(4,4-dimethylcyclohexyl)-2,2-dimethylpropaneamide N-[(3S,5S)-1-{[(3S,4R)-1-tert-butyl-4-(4-chlorophenyl)pyrrolidine-3-yl]carbonyl}-5-methylpyrrolidine-3-yl]-N-(4,4-dimethylcyclohexyl)-2,2-dimethylpropaneamide N-{(3S,5S)-1-{[(3S,4R)-1-tert-butyl-4-(2,4-difluorophenyl)pyrrolidine-3-yl]carbonyl}-5-[(E)-(hydroxyimino)methyl]pyrrolidine-3-yl}-N-(4,4-dimethylcyclohexyl)-2,2-dimethylpropaneamide N-[(3S,5S)-5-(aminoethyl)-1-{[(3S,4R)-1-tert-butyl-4-(2,4-difluorophenyl)pyrrolidine-3-yl]carbonyl}pyrrolidine-3-yl]-N-(4,4-dimethylcyclohexyl)-2,2-dimethylpropaneamide N-[(3S,5S)-5-[(acetylamino)methyl]-1-{[(3S,4R)-1-tert-butyl-4-(2,4-dichlorophenyl)pyrrolidine-3-yl]carbonyl}pyrrolidine-3-yl]-N-(4,4-dimethylcyclohexyl)-2,2-dimethylpropaneamide N-[(3S,5S)-1-{[(3S,4R)-1-tert-butyl-4-(2,4-dichlorophenyl)pyrrolidine-3-yl]carbonyl}-5-[(dimethylamino)methyl]pyrrolidine-3-yl]-]-N-(4,4-dimethylcyclohexyl)-2,2-dimethylpropaneamide N-[(3S,5S)-1-{[(3S,4R)-1-tert-butyl-4-(2,4-difluorophenyl)pyrrolidine-3-yl]carbonyl}-5-cyanopyrrolidine-3-yl]-2,2-dimethyl-N-(cis-4-methylcyclohexyl)propaneamide N-[(3S,5R)-5-acetyl-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethylpropaneamide N-[(3S)-1-{[(3S,4R)-1-tert-butyl-4-(4-chlorophenyl)pyrrolidine-3-yl]carbonyl}-5-(1-hydroxymethyl)pyrrolidine-3-yl]-N-(4,4-dimethylcyclohexyl)-2,2-dimethylpropaneamide (4S)-4-[acetyl(4,4-dimethylcyclohexyl)amino]-N-(2-aminoethyl)-1-{[(3S,4R)-1-tert-butyl-4-(2,4-difluorophenyl)pyrrolidine-3-yl]carbonyl}-L-prolineamide methyl (4S)-1-{[(3S,4R)-1-tert-butyl-4-(4-chlorophenyl)pyrrolidine-3-yl]carbonyl}-4-[(4,4-dimethylcyclohexyl)(2,2-dimethylpropanoyl)amino]-L-prolinate (4S)-1-{[(3S,4R)-1-tert-butyl-4-(4-chlorophenyl)pyrrolidine-3-yl]carbonyl}-4-[(4,4-dimethylcyclohexyl)(2,2-dimethylpropanoyl)amino]-L-proline N-[(3S,5R)-5-(aminocarbothioyl-1-{[(3S,4R)-1-tert-butyl-4-(2,4-difluorophenyl)pyrrolidine-3-yl]carbonyl}pyrrolidine-3-yl]-N-(4,4-dimethylcyclohexyl)-2,2-dimethylpropaneamide N-{(3S,5R)-1-{[(3S,4R)-1-tert-butyl-4-(2,4-difluorophenyl)pyrrolidine-3-yl]carbonyl}-5-[(dimethylamino)carbonothionyl]pyrrolidine-3-yl]-N-(4,4-dimethylcyclohexyl)-2,2-dimethylpropaneamide N-[(3S,5R)-1-{[(3S,4R)-1-tert-butyl-4-(2,4-difluorophenyl)pyrrolidine-3-yl]carbonyl}-5-propionylpyrrolidine-3-yl]-N-(4,4-dimethylcyclohexyl)-2,2-dimethylpropaneamide N-[(3S,5S)-1-{[(3S,4R)-1-tert-butyl-4-(4-chlorophenyl)pyrrolidine-3-yl]carbonyl}-5-propionylpyrrolidine-3-yl]-N-(4,4-difluorocyclohexyl)-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethylmalonamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-methoxy-2,2-dimethylpropaneamide (3E)-N-[(3S)-1-[(3S,4R)-1-tert-butyl-4-(4-chlorophenyl)pyrrolidine-3-yl]carbonyl}pyrrolidine-3-yl]-N-(4,4-dimethylcyclohexyl)-3-(hydroxyimino)-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxy-2,2-dimethylbutanamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-2,2-dimethyl-3-oxobutanamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-hydroxy-2,2,3-trimethylbutanamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3-fluoro-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-(4,4-dimethylcyclohexyl)-3,3-difluoro-2,2-dimethylpropaneamide N-[(3S)-1-{[(3S,4R)-1-tert-butyl-4-(4-chlorophenyl)pyrrolidine-3-yl]carbonyl}pyrrolidine-3-yl]-N-[(4,4-difluorocyclohexyl)(3-methoxy-2,2-dimethylpropanoyl)amino]-N-ethyl-N-methyl-L-prolineamide (4S)-4-[(3-amino-2,2-dimethylpropanoyl)(4,4-dimethylcyclohexyl)amino]-1-{(3S,4R)-1-tert-butyl-4-(2,4-difluorophenyl)pyrrolidine-3-yl]carbonyl}-N,N-dimethyl-L-prolineamide (4S)-1-{[(3S,4R)-1-tert-butyl-4-(4-chlorophenyl)pyrrolidine-3-yl]carbonyl}-4-{[3-(dimethylamino)-2,2-dimethylpropanoyl] (4,4-dimethylcyclohexyl)amino}-N,N-dimethyl-L-prolineamide N-{(3S,5S)-1-{[(3S,4R)-1-tert-butyl-4-(4-chlorophenyl)pyrrolidine-3-yl]carbonyl}-5-[(dimethylamino)carbonyl]pyrrolidine-3-yl}-N-(4,4-dimethylcyclohexyl)-2,2-dimethylmalonamide S-(3-{[(3S,5S)-1-{[(3S,4R)-1-tert-butyl-4-(2,4-difluorophenyl)pyrrolidine-3-yl]carbonyl}-5-{[ethyl(methyl)amino]carbonyl}pyrrolidine-3-yl] (4,4-dimethylcyclohexyl)amino}-2,2-dimethyl-3-oxopropyl)ethanethioate (4S)-1-{[(3S,4R)-1-tert-butyl-4-(2,4-difluorophenyl)pyrrolidine-3-yl]carbonyl}-4-[(4,4-dimethylcyclohexyl)(3-mercapto-2,2-dimethylpropanoyl)amino]-N-ethyl-N-methyl-L-prolineamide (4S)-1-{[(3S,4R)-1-text-butyl-4-(4-chlorophenyl)pyrrolidine-3-yl]carbonyl}-4-[(4,4-difluoro cyclohexyl)(3-methoxy-2,2,-dimethylpropanoyl)amino]-N,N-dimethyl-L-prolineamide (4S)-1-{[(3S,4R)-1-tert-butyl-4-(4-chlorophenyl)pyrrolidine-3-yl]carbonyl}-4-[(4,4-difluorocyclohexyl)(3-ethoxy-2,2,-dimethylpropanoyl)amino]-N-ethyl-N-methyl-L-prolineamide (4S)-1-{[(3S,4R)-1-tert-butyl-4-(4-chlorophenyl)pyrrolidine-3-yl]carbonyl}-4-[(2,4-difluorophenyl)(2,2-dimethylpropanoyl)amino]-N,N-dimethyl-L-prolineamide (4S)-1-{[(3S,4R)-1-tert-butyl-4-(4-chlorophenyl)pyrrolidine-3-yl]carbonyl}-4-[(2,2,-dimethylpropanoyl)(4-methoxyphenyl)amino]-N,N-dimethyl-L-prolineamide (4S)-1-{[(3S,4R)-1-tert-butyl-4-(4-chlorophenyl)pyrrolidine-3-yl]carbonyl}-4-{(2,2,-dimethylpropanoyl) [4-(trifluoromethyl)phenyl]amino}-N,N-dimethyl-L-prolineamide (4S)-1-{[(3S,4R)-1-tert-butyl-4-(4-chlorophenyl)pyrrolidine-3-yl]carbonyl}-4-[(2,2-dimethylpropanoyl)(4-methylphenyl)amino]-N,N-dimethyl-L-prolineamide (4S)-1-{[(3S,4R)-1-tert-butyl-4-(4-chlorophenyl)pyrrolidine-3-yl]carbonyl}-4-{(2,4-difluorophenyl)[(2S)-tetrahydrofuran-2-ylcarbonyl]amino}-N—N-dimethyl-L-prolineamide (4S)-1-[(3S,4R)-4-(4-chlorophenyl)pyrolidine-3-yl]carbonyl}-4-[(4,4-dimethylcyclohexyl)(2,2-dimethylpropanoyl)amino]-N,N-dimethyl-L-prolineamide (2S)—N-[(3S)-1-{[(3S,4R)-4-(4-chlorophenyl)pyrrolidine-3-yl]carbonyl}pyrrolidine-3-yl]-N-(4,4-dimethylcyclohexyl)tetrahydrofuran-2-carboxamide N-[(3S)-1-{[(3S,4R)-4-(4-chlorophenyl)pyrrolidine-3-yl]carbonyl}pyrrolidine-3-yl]-N-(cis-4-methyl cyclohexyl)-3-furamide N-[(3S)-1-{[(3S,4R)-4-(4-chlorophenyl)pyrrolidine-3-yl]carbonyl}pyrrolidine-3-yl]-N-(cis-4-methylcyclohexyl)-2,5-dihydrofuran-3-carboxamide (4S)—N-1-{[(3S,4R)-4-(4-chlorophenyl)pyrrolidine-3-yl]carbonyl}-4-[(2,2,-dimethylpropanoyl) (cis-4-methylcyclohexyl)amino]-D-prolineamide N-[(3S)-1-{[(3S,4R)-4-(4-chlorophenyl)pyrrolidine-3-yl]carbonyl}-5-(1-hydroxymethyl)pyrrolidine-3-yl]-N-(4,4-dimethylcyclohexyl)-2,2-dimethylpropaneamide (4S)-1-{[(3S,4R)-1-(aminocarbonyl)-4-(4-chlorophenyl)pyrrolidine-3-yl]carbonyl}-4-[(4,4-dimethylcyclohexyl)(2,2-dimethylpropanoyl)amino]-N,N-dimethyl-L-prolineamide (3R,4S)-3-(4-chlorophenyl)-4-({(3S)-3-[(4,4-dimethylcyclohexyl)(3-hydroxy-2,2-dimethylpropanoyl)amino]pyrrolidine-1-yl}carbonyl)pyrrolidine-1-carboxamide (3R,4S)-3-(4-chlorophenyl)-4-({(3S)-3-[(4,4-dimethylcyclohexyl)(2,2-dimethylpropanoyl)amino]pyrrolidine-1-yl}carbonyl)pyrrolidine-1-carboxamide (4S)-1-({[(3S,4R)-4-(4-chlorophenyl)-1-(ethylamino)carbonyl]pyrrolidine-3-yl}carbonyl)-4-[(4,4-dimethyl cyclohexyl)(2,2-dimethylpropanoyl)amino]-N,N-dimethyl-L-prolineamide N-[(3S)-1-{[(3S,4R)-4-(4-chlorophenyl)-1-[(ethylamino)carbonothionyl]pyrrolidine-3-yl]carbonyl}pyrrolidine-3-yl]-N-(4,4-difluorocyclohexyl)-3-hydroxy-2,2-dimethylpropaneamide (3R,4S)-3-(4-chlorophenyl)-4-({(3S)-3-[(4,4-dimethylcyclohexyl)(3-hydroxy-2,2-dimethylpropanoyl)amino]pyrrolidine-1-yl}carbonyl)-N-ethylpyrrolidine-1-carboxamide (3R,4S)-3-(4-chlorophenyl)-4-({(3S)-3-[(4,4-dimethylcyclohexyl)(2,2-dimethylpropanoyl)amino]pyrrolidine-1-yl}carbonyl)-N-ethylpyrrolidine-1-carboxamide (3R,4S)-3-(4-chlorophenyl)-4-({(3S)-3-[(2,4-difluorophenyl)(2,2-dimethylpropanoyl)amino]pyrrolidine-1-yl}carbonyl)-N-ethylpyrrolidine-1-carboxamide (3R,4S)-3-(4-chlorophenyl)-N-ethyl-4-({(3S)-3-[isobutyryl(cis-4-methylcyclohexyl)amino]pyrrolidine-1-yl}carbonyl)-N-methylpyrrolidine-1-carboxamide (4S)-1-({[(3S,4R)-1-acetyl-4-(4-chlorophenyl)pyrrolidine-3-yl]carbonyl}-4-[(4,4-dimethylcyclohexyl)(2,2-dimethylpropanoyl)amino]-N,N-dimethyl-L-prolineamide N-[(3S)-1-{[(3S,4R)-4-(4-chlorophenyl)-1-isobutyrylpyrrolidine-3-yl]carbonyl}pyrrolidine-3-yl]-N-(4,4-dimethyl cyclohexyl)-2,2-dimethylpropaneamide (4S)-1-{[(3S,4R)-4-(4-chlorophenyl)-1-isobutyrylpyrrolidine-3-yl]carbonyl}-4-[(4,4-dimethylcyclohexyl)(2,2-dimethylpropanoyl)amino]-L-prolineamide (4S)-1-([(3S,4R)-4-(4-chlorophenyl)1-cyclopropylpyrrolidine-3-yl]carbonyl}-4-[(4,4-dimethylcyclohexyl)(2,2-dimethylpropanoyl)amino]-N,N-dimethyl-L-prolineamide (4S)-1-{[(3S,4R)-4-(4-chlorophenyl)-1-(tetrahydro-2H-pyran-4-yl)pyrrolidine-3-yl]carbonyl}-4-{(4,4-dimethylcyclohexyl) [(2S)-tetrahydrofuran-2-ylcarbonyl]amino}-N-ethyl-N-methyl-L-prolineamide N-[(3S)-1-{[(3S,4R)-4-(4-chlorophenyl)-1-(2,2,2-trifluoroethyl)pyrrolidine-3-yl]carbonyl}pyrrolidine-3-yl]-N-(4,4-dimethylcyclohexyl)-2,2-dimethylpropaneamide (4S)-1-{[(3S,4R)-4-(2,4-difluorophenyl)-1-isobutyrylpyrrolidine-3-yl]carbonyl}-4-[(4,4-dimethylcyclohexyl)(3-hydroxy-2,2-dimethylpropanoyl)amino]-N,N-dimethyl-L-prolineamide (4S)-1-{[(3S,4R)-4-(4-chlorophenyl)-1-cyclobutylpyrrolidine-3-yl]carbonyl}-4-[(4,4-dimethylcyclohexyl)(3-hydroxy-2,2-dimethylpropanoyl)amino]-N,N-dimethyl-L-prolineamide (4S)-1-{[(3S,4R)-1-cyclopentyl-4-(2,4-difluorophenyl)pyrrolidine-3-yl]carbonyl}-4-[(4,4-dimethylcyclohexyl)(2,2-dimethylpropanoyl)amino]-N,N-dimethyl-L-prolineamide N-{(3S,5S)-1-{[(3S,4R)-4-(2,4-difluorophenyl)-1-isobutyrylpyrrolidine-3-yl]carbonyl}-5-[(dimethylamino)carbonothio]pyrrolidine-3-yl}-N-(4,4-dimethylcyclohexyl)-2,2-dimethylpropaneamide N-[(3S)-1-{[(3S,4R)-4-(4-chlorophenyl)-1-(methylsulfonyl)pyrrolidine-3-yl]carbonyl}pyrrolidine-3-yl]-2-methyl-N-(cis-4-methylcyclohexyl)propaneamide (3R,4S)-3-(4-chlorophenyl)-4-({(3S)-3-[(cis-4-methylcyclohexyl)(2-methylpropanoyl)amino]pyrrolidine-1-yl}carbonyl)-N-(2,2,2-trifluoroethyl)pyrrolidine-1-carboxamide (3R,4S)-3-(4-chlorophenyl)-4-({(3S)-3-[(4,4-dimethylcyclohexyl)(2,2-dimethylpropanoyl)amino]pyrrolidine-1-yl}carbonyl)-N-(2,2,2-trifluoromethyl)pyrrolidine-1-carboxamide methyl(3R,4S)-3-(4-chlorophenyl)-4-({(3S)-3-[(4,4-dimethylcyclohexyl)(3-hydroxy-2,2-dimethylpropanoyl)amino]pyrrolidine-1-yl}carbonyl)pyrrolidine-1-carboxylate N-[(3S)-1-{[(3S,4R)-1-[amino(imino)methyl]-4-(4-chlorophenyl)pyrrolidine-3-yl]carbonyl}pyrrolidine-3-yl]-2-methyl-N-(cis-4-methylcyclohexyl)propaneamide N-[(3S)-1-({(3S,4R)-4-(4-chlorophenyl)-1-[(ethylamino)(imino)methyl]pyrrolidine-3-yl}carbonyl)pyrrolidine-3-yl]2-methyl-N-(cis-4-methylcyclohexyl)propaneamide N-[(3S)-1-{[(3S,4R)-1-[acetylamino)(imino)methyl]-4-(4-chlorophenyl)pyrrolidine-3-yl]carbonyl}pyrrolidine-3-yl]-2-methyl-N-(cis-4-methylcyclohexyl)propaneamide N-[(3S)-1-{[(3S,4R)-4-(4-chlorophenyl)-1-phenylpyrrolidine-3-yl]carbonyl}pyrrolidine-3-yl]-N-(4,4-dimethylcyclohexyl)-propaneamide N-[(3S)-1-{[(3S,4R)-4-(4-chlorophenyl)-1-pyridine-2-ylpyrrolidine-3-yl]carbonyl}pyrrolidine-3-yl]-2,2-dimethyl-N-(cis-4-methylcyclohexyl)propaneamide N-[(3S)-1-{[(3S,4R)-4-(4-chlorophenyl)-1-(4,5-dihydro-1H-imidazole-2-yl)pyrrolidine-3-yl]carbonyl}pyrrolidine-3-yl]-N-(4,4-dimethylcyclohexyl)-3-hydroxy-2,2-dimethylpropaneamide N-[(3S)-1-{[(3S,4R)-4-(4-chlorophenyl)-1-(4,5-dihydro-1H-imidazole-2-yl)pyrrolidine-3-yl]carbonyl}pyrrolidine-3-yl]-N-(4,4-dimethylcyclohexyl)-3-hydroxy-2,2-dimethylpropaneamide, pharmaceutically acceptable salt or stereoisomer thereof.

15. A melanocortin receptor agonistic composition comprising the compound of formula 1 as defined in claim 1, pharmaceutically acceptable salt or stereoisomer thereof as active ingredient, together with pharmaceutically acceptable carrier.

16. The composition of claim 15 for the treatment of obesity.

17. The composition of claim 15 for the treatment of diabetes.

18. The composition of claim 15 for the treatment of inflammation.

19. The composition of claim 15 for the treatment of erectile dysfunction.

* * * * *